(12) United States Patent
Fales et al.

(10) Patent No.: US 7,935,722 B2
(45) Date of Patent: May 3, 2011

(54) TETRAHYDROCARBAZOLE DERIVATIVES USEFUL AS ANDROGEN RECEPTOR MODULATORS

(75) Inventors: Kevin Robert Fales, Avon, IN (US); Jonathan Edward Green, Avon, IN (US); Prabhakar Kondaji Jadhav, Zionsville, IN (US); Donald Paul Matthews, Indianapolis, IN (US); David Andrew Neel, Zionsville, IN (US); Edward C R Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 522 days.

(21) Appl. No.: 11/917,398

(22) PCT Filed: Jun. 21, 2006

(86) PCT No.: PCT/US2006/024122
§ 371 (c)(1),
(2), (4) Date: Dec. 13, 2007

(87) PCT Pub. No.: WO2007/002181
PCT Pub. Date: Jan. 4, 2007

(65) Prior Publication Data
US 2010/0022550 A1    Jan. 28, 2010

Related U.S. Application Data

(60) Provisional application No. 60/693,604, filed on Jun. 24, 2005.

(51) Int. Cl.
*A61K 31/403* (2006.01)
*A61K 31/4439* (2006.01)
*A61K 31/427* (2006.01)
*C07D 209/82* (2006.01)

(52) U.S. Cl. ............. 514/411; 514/410; 540/1; 548/400; 548/416; 548/418; 548/427; 548/439

(58) Field of Classification Search ............. 514/252.06, 514/255.05, 256, 339, 370, 410, 411, 238, 514/333, 405, 276.7, 198, 421, 439; 540/1; 548/400, 416, 418, 427, 439
See application file for complete search history.

(56) References Cited

U.S. PATENT DOCUMENTS

| 3,959,309 | A | * | 5/1976 | Mooradian ............ 548/439 |
| 4,988,820 | A | | 1/1991 | Boshagen et al. |
| 5,204,374 | A | | 4/1993 | Muller et al. |
| 5,223,517 | A | | 6/1993 | Muller et al. |
| 5,374,647 | A | | 12/1994 | Bohagen et al. |
| 7,122,570 | B2 | | 10/2006 | Koppitz et al. |
| 2005/0171143 | A1 | | 8/2005 | Tanimoto et al. |

FOREIGN PATENT DOCUMENTS

| WO | WO 94/27989 | 12/1994 |
| WO | WO 2004/041782 | 5/2004 |
| WO | WO 2005/056527 | 6/2005 |
| WO | WO 2006/065480 | 6/2006 |

OTHER PUBLICATIONS

Golob, et al., "Antiestrogenic Activities of 3,8-Dihydroxy-6,11-Dihydrobenzocarbazoles with Sulfur-Containing Side Chains," Arch. Pharm. Med. Chem., vol. 333, No. 9, pp. 305-311 (2000).

* cited by examiner

*Primary Examiner* — Sreeni Padmanabhan
*Assistant Examiner* — Sahar Javanmard
(74) *Attorney, Agent, or Firm* — Dan L. Wood; Alexander Wilson

(57) ABSTRACT

The present invention provides a compound of the formula: Formula (I) or a pharmaceutically acceptable salt thereof; pharmaceutical compositions comprising an effective amount of a compound of Formula (I) in combination with a suitable carrier, diluent, or excipient; and methods for treating physiological disorders, particularly frailty, osteoporosis, osteopenia, and male and female sexual dysfunction comprising administering to a patient in need thereof an effective amount of a compound of formula (I).

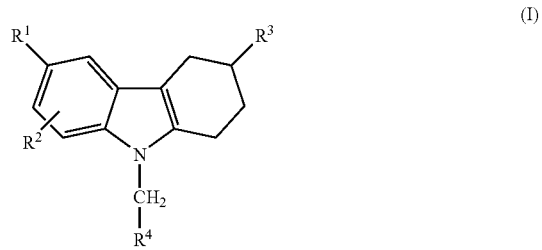

(I)

19 Claims, No Drawings

TETRAHYDROCARBAZOLE DERIVATIVES USEFUL AS ANDROGEN RECEPTOR MODULATORS

This application is the U.S. National stage filing of PCT Application Ser. No. PCT/US2006/024122, filed Jun. 21, 2006, which claims the benefit of priority under 35 USC 119(e) of U.S. Provisional Application No. 60/693,604, filed Jun. 24, 2005.

TECHNICAL FIELD OF INVENTION

The present invention relates to tetrahydrocarbazole compounds that are useful as therapeutic agents, to pharmaceutical compositions comprising the compounds, to methods of using the compounds to treat disorders in patients, and to intermediates and processes useful in the synthesis of the compounds.

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995); Nature Rev. Drug Discovery, 3: 950-964 (November 2004). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12):1325-1341(1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (hsps) in the cytoplasm. Following entry of circulating hormone into the cell, binding elicits a conformational change in the receptor, dissociating the receptor from the hsp. The ligand bound receptors translocate to the nucleus, where they act as monomers as well as hetero-and homodimers in binding to particular hormone response elements (HREs) in the promoter regions of target genes. The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of hsps and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Androgens exert profound influences on a multitude of physiological functions by virtue of their diverse roles in inter alia male sexual development and function, maintenance of muscle mass and strength in both males and females, maintenance of bone mass, erythropoeisis, memory and cognition, and maintenance of sexual behaviour (e.g. libido and potency). The actions of androgens (testosterone and 5α-dihydrotestosterone (DHT)) are mediated by the AR which, upon androgen binding, translocates to the cell nucleus where it binds to specific DNA sequences termed androgen respone elements (AREs) to initiate or repress transcription of target genes. The effects of androgens can be generally characterized as anabolic or androgenic in nature. Anabolic (i.e. tissue building) effects of androgens include increasing muscle mass and strength and bone mass, whereas androgenic (i.e. masculinizing) effects include the development of male secondary sexual characteristics such as the internal reproductive tissues (i.e. prostate and seminal vesicle), the external genetalia (penis and scrotum), libido, and hair growth patterns.

Reductions in bioavailable serum androgen levels that occur with aging can have serious physiological effects in both males and females. In males, for example, decreases in androgen levels are associated with loss of libido, erectile dysfunction, depression, decreased cognitive ability, lethargy, osteoporosis, and loss of muscle mass and strength. Rajfer (2003), *Rev. Urol.,* 5 (Suppl. 1): S1-S2. In addition, as men age and testosterone levels decline, bones weaken, diabetes and cardiovascular disease rates increase, and the ratio of muscle mass to fat decreases. Vastag, B. (2003), *JAMA;* 289: 971-972. In females, low plasma levels of circulating testosterone are associated with diminished libido, unexplained fatigue, and general lack of well being. Davis, S. R. (1999), *Medical J. Australia;* 170: 545-549. Clinically, the principal application of androgen therapy has been in the treatment of hypogonadism in men. Significantly, androgen replacement therapy in hypogonadal men has also been shown to decrease bone resorption and increase bone mass. Katznelon, L., et al., *J. Clin. Endocrinol Metab.;* 81: 4358 (1996). Other indications for which androgens have been used clinically include treatment of delayed puberty in boys, anemia, primary osteoporosis, and muscle wasting diseases. In addition, androgen replacement therapy has been used recently in aging men and for the regulation of male fertility. T. R. Brown, *Endocrinology;* 145(12): 5417-5419 (2004). In females, androgen therapy has been used clinically for the treatment of sexual dysfunction or diminished libido. W. Arlt, *Euro. J. Endocrinol.;* 154(1) 1-11 (2006).

However, activation of AR in certain tissues is also associated with serious deleterious consequences. For example, unwanted side effects of steroidal androgen therapy include growth stiumulation of the prostate and seminal vesicles. Feldkorn et al., *J. Steroid Bichem and Mol. Biol.;* 94(5): 481-487 (2005). Prostate cancers, for example, depend on AR for growth and development. Gegory, C. W. et al. (2001), *Cancer Res.,* June 1; 61(11):4315-4319; and Jenster, G. (1999), *Semin. Oncol.,* August; 26(4): 407-421. Androgen therapy has also been associated with sleep apnea, stimulation of prostate tumors and elevations in prostate specific antigen (PSA), an indication of increased prostate cancer risk. Vastag, B. (2003), *JAMA;* 289: 971-972. In addition, use of androgen agonists have specifically been associated with liver damage, adverse effects on male sexual function, adverse effects associated with cardiovascular and erythropoetic function, prostate enlargement, hisutism, and virilization. (see Published International Patent Applications WO 03/011824 and WO 03/034987). Furthermore, preparations of unmodified and modified steroidal androgens have been found to suffer from rapid degradation in the liver leading to poor oral bioavailability and short duration of activity following parenteral administration, variations in plasma levels, hepatotoxicity, or cross reactivity with other steroid hormone receptors (e.g. the glucocorticoid receptor (GR), the mineralocorticoid receptor (MR), and the progesterone receptor (PR) which have ligand binding domains homologous to AR) Yin et al., *JPET;* 304(3): 1323-1333 (2003). Furthermore, in females, the use of steroidal androgens may lead to hirsutism or virilization.

Thus, there remains a need in the art for alternatives to classical steroidal androgen therapy which possess the beneficial pharmacological properties of steroidal androgens, but with a reduced likelihood or incidence of the typical limitations associated with steroidal androgen therapy. Recent efforts to identify suitable replacements for steroidal androgens have focused on identifying tissue selective androgen receptor modulators (SARMs) which display a differentiated profile of activity in androgenic tissues. In particular, such agents preferably display androgen agonist activity in anabolic tissues such as muscle or bone, yet are only partial agonists or even antagonists in androgenic tissues such as the prostate or seminal vesicles.

Ligands used to modulate (i.e., agonize, partially agonize, partially antagonize, or antagonize) the transcriptional activity of AR display androgenic or antiandrogenic activity (or anabolic or antianabolic activity) and, further, may be steroidal or nonsteroidal in structure. Androgenic agents (AR Agonists or partial AR agonists) mimic the effects of natural androgens in either activating or repressing the transcriptional activity of AR, whereas antiandrogenic agents (AR antagonists or partial AR antagonists) block androgen mediated transactivation or transrepression of AR. Further, the AR ligand-AR complex has also been reported to influence the recruitment of cofactor proteins to the enhancer and or promoter sites. Shang et al. (March 2002), *Mol. Cell.* 9(3): 601-610. In addition to their effects on target gene transcription, ligands for AR may also induce "non-genotropic" effects. For example, ligands can bind to AR localized in non-nuclear compartments such as the endoplasmic reticulum, outer cell membrane, or cytoplasm and induce biochemical changes that are mediated by adaptor proteins such as phosphatidylinositol-3-kinase (PI3K), extracellular regulated kinases (ERKs), mitogen activated protein kinases (MAPKs), or p38/stress activated protein kinase/c-Jun N-terminal kinases (p38/SAP/JNK). These "non-genotropic" effects encompass a wide array of physiological changes including the triggering of antiapoptotic and survival pathways. (see Bowen, R. L. (2001), *JAMA* 286(7): 790-1; Gouras, G. K., H. Xu, et at. (2000), *Proc. Natl. Acad. Sci. USA* 97(3): 1202-5; Kousteni, S., T. Bellido, et al. (2001), *Cell* 104(5): 719-30; and Kousteni, S., L. Han, et al. (2003) [comment] *Journal of Clinical Investigation* 111(11): 1651-64.)

Thus, it is clear that a ligand which has affinity for AR could be used to modulate receptor activity and thereby influence a multitude of physiological effects related to alterations in androgen levels and/or AR activity. Furthermore, the effects of such agents can be accomplished by both classical conventional HRE-mediated (e.g. "genotropic") or non-genotropic mechanisms. Preferably such agents function as selective androgen receptor modulators (SARMs) displaying androgenic effects in tissues such as muscle and/or bone, while concomitantly displaying antiandrogenic properties in tissues such as the prostate, liver, and those responsible for virilization in females. Alternatively, SARMs may display tissue selectivity with regard to their androgenic effects functioning as, for example, agonists in anabolic tissue such as muscle or bone but only partial agonists or antagonists in tissues such as the prostate or seminal vesicles. In addition, such ligands are preferably non-steroidal in nature thus avoiding many of the undesired pharmacological, physiochemical and pharmacokinetic properties of their steroidal counterparts, including poor oral bioavailability, rapid hepatic metabolism, and cross activation of other steroid receptors. He, Y, et al. (2002), *Eur. J. Med. Chem.;* 37: 619-634.

Several physiological disorders are believed to be susceptible to AR modulation, and in particular, modulation by SARMs. Frailty represents one such disorder. Frailty is a geriatric condition which results in a reduction in one's reserve capacity to the extent that multiple physiological systems are close to, or past the threshold of symptomatic clinical failure. As a consequence, the frail person is at an increased risk of disability and death from minor external stresses (e.g. disease or life events). Campbell, A. J., et al. (1997), Age and Ageing; 26(4): 315-318. Frailty represents a complex syndrome characterized by numerous musculoskeletal symptoms including declines in muscle mass and strength, decreased range of motion, slowness and paucity of movement, balance and gait abnormalities, weight loss and reduced food intake, weakness and fatigue, decreased exercise tolerance, and sarcopenia (loss of lean body mass). Brown, M., et al. (2000), *J. of Gerontology;* 55(6): M350-M355; and Fried, L. and Watson, J. (1999), *Principles of Geriatric Medicine and Gerontolgy,* 1387-1402, New York: McGraw Hill. As such, an agent with androgenic properties in tissues such as muscle and bone would be expected to have utility in treating the frail patient.

Other physiological disorders are also suitable for AR modulation. For example, it is now well known that hypogonadism is associated with osteoporosis in men. Kaufman, J. M., et al., *Ann. Rheum. Dis.;* October; 59(10): 765-772 (2000). Furthermore, In men with prostate cancer, androgen deprivation therapy increased the rate of bone mineral density loss. Preston, D. M., et al., *Prostate Cancer Prostatic Dis.;* 5(4): 304-310 (2002). In addition, androgen replacement therapy in hypogonadal men decreases bone resorption and increases bone mass. Katznelon, L., et al., *J. Clin. Endocrinol Metab.;* 81: 4358 (1996). As such, AR modulators are believed to be useful in the treatment of osteoporosis (either as a monotherapy or in combination with other inhibitors of bone resorption including, but not limited to estrogens, bisphosphonates, and selective estrogen receptor modulators). In fact, small clinical trials have in fact shown that testosterone replacement therapy in older men may help delay or reverse osteoporosis, possibly preventing hip and vertebral fractures. Vastag, B., *JAMA;* 289: 971-972 (2003).

Moreover, AR modulators, can be used to enhance performance in the treatment of male and female sexual dysfunction (see Morley, J. E. and Perry, H. M., *J. Steroid Biochem. Mol. Biol.*; June; 85(2-5): 367-373 (2003) and *Medical J. Australia;* 170: 545-549 (1999), supra). Other indications or physiological disorders or for which an AR modulator is believed to have utility include maintenance of muscle mass, strength and function; as bone anabolic agents in the treatment of osteoporosis or osteopenia; restoration of bone either independently or as an adjunct to androgen deprivation therapy in the treatment of prostate or pancreatic cancer; as an agent to accelerate bone repair (e.g. bone fractures); as a treatment for sarcopenia or Age Related Functional Decline (ARFD); as an agent to increase energy (e.g. reduce lethargy) and libido; or as a treatment for hypogonadism. In addition, AR modulators can be used for the treatment of prostate cancer.

Thus, it is an object of the present invention to provide nonsteroidal AR ligands which possess androgen receptor modulating activity. In particular, it is an object of the present invention to provide nonsteroidal AR ligands which possess androgen receptor agonist activity. More particularly, it is a preferred embodiment of the present invention to provide nonsteroidal androgen agonists which bind to AR with greater affinity relative to the other steroid hormone receptors. Even more particularly, it is a preferred embodiment of the present invention to provide tissue selective androgen receptor modulators (SARMs) which display androgen agonist activity in muscle or bone, but only partial agonist, partial antagonist or antagonist activity in other androgenic tissues such as the prostate or seminal vesicle.

The following references provide some examples of the state of the art as it relates to the present invention.

He et al., Eur. J. Med. Chem.; 37: 619-634 (2002) discloses bicalutamide analogs as nonsteroidal Androgen receptor ligands.

Published International PCT Application WO 03/051837 discloses tricyclic derivatives as gonodotropin-releasing hormone antagonists.

Published International PCT Application WO 03/011302 A1 discloses androstene derivative compounds as androgen receptor modulators.

Published International PCT Application WO 03/077919 A1 discloses azasteroid derivative compounds as androgen receptor modulators.

Published International PCT Application WO 02/16310 A1 discloses bicalutamide analogs as nonsteroidal Androgen receptor ligands.

Published International PCT Application WO 03/034987 A2 discloses tricyclic derivatives as androgen receptor modulators.

Published International PCT Application WO 03/011824 A1 discloses bicyclic modulators of the androgen receptor.

Published International PCT Application WO 04/041782 discloses indole derivative molecules as modulators of the androgen receptor.

Published International PCT Application WO 03/0114420 discloses fused heterocyclic derivative molecules as modulators of the androgen receptor.

Published International PCT Application WO 03/096980 discloses N-aryl hydantoin derivative molecules as modulators of the androgen receptor.

Published International PCT Application 03/011824 discloses N-naphthyl hydantoin derivative molecules as modulators of the androgen receptor.

Published International PCT Application 04/016576 discloses N-naphthyl pyrrolidine derivative molecules as modulators of the androgen receptor.

Published International PCT Application 05/000795 discloses aniline derivative molecules as modulators of the androgen receptor.

SUMMARY OF THE INVENTION

The present invention is directed to the discovery that certain tetrahydocarbazole derivative compounds, as defined below, are modulators of the androgen receptor. Accordingly, the present invention provides a compound of the formula:

Formula I wherein, $R^1$ represents hydrogen, hydroxy, cyano, halo, nito, $(C_1$-$C_4)$alkyl, halo$(C_1$-$C_4)$alkyl, halo$(C_1$-$C_4)$alkoxy, $SCH_3$, $C(=S)NH_2$, $CH=NOCH_3$, $CH=NOCH_2CH_3$, $C(NOCH_3)CH_3$, $C(NOCH_2CH_3)CH_3$, $CH=NOH$, $COR^{1a}$, $OR^{1b}$, $SO_2R^{1c}$, $NHCOR^{1d}$, or a 5 to 6 membered heteroalyl group optionally substituted with 1 or 2 substituents selected from the group consisting of amino, cyano, $(C_1$-$C_4)$alkyl, $(C_1$-$C_4)$alkoxy, halo, halo$(C_1$-$C_4)$alkyl, or halo$(C_1$-$C_4)$alkoxy;

$R^{1a}$ represents hydrogen, amino, hydroxy, $(C_1$-$C_4)$alkyl, $(C_1$-$C_4)$alkoxy, or halo$(C_1$-$C_4)$alkyl;

$R^{1b}$ represents $(C_1$-$C_4)$alkyl, cyclopropyl, or cyclopropylmethyl;

$R^{1c}$ represents amino or $(C_1$-$C_4)$alkyl;

$R^{1d}$ represents $(C_1$-$C_4)$alkoxy;

$R^2$ represents hydrogen, halo, $(C_1$-$C_4)$alkyl, or $(C_1$-$C_4)$alkoxy, or $R^1$ and $R^2$ together form a group of the formula $R^3$ represents $NHCOR^{3a}$ or $NHSO_2R^{3b}$;

$R^{3a}$ and $R^{3b}$ each independently represent at each occurrence $(C_1$-$C_6)$alkyl, halo$(C_1$-$C_4)$alkyl, $(C_1$-$C_4)$alkoxy, cyclopropyl, cyclobutyl, NH—$(C_1$-$C_4)$alkylamine, N,N—$(C_1$-$C_6)$dialkylamine, or $N(CH_3)OCH_3$; and $R^4$ represents a phenyl group optionally substituted with 1 or 2 substituents selected from the group consisting of amino, hydroxy, cyano, halo, nitro, $(C_1$-$C_4)$alkyl, $(C_1$-$C_4)$alkoxy, halo$(C_1$-$C_4)$alkyl, halo$(C_1$-$C_4)$alkoxy, NH—$(C_1$-$C_4)$alkylamine, N,N—$(C_1$-$C_6)$dialkylamine, $NHSO_2CH_3$, or $COOCH_3$; or a 5 to 6 memebered heteroaryl group optionally substituted with 1 or 2 substituents independently selected from the group consisting of amino, $(C_1$-$C_4)$alkyl, halo, or hydroxy or a pharmaceutically acceptable salt thereof.

In another embodiment, the present invention provides a method of treating a disorder or condition susceptible to androgen receptor modulation, comprising administering to a patient in need thereof an effective amount of a compound of Formula I, or a pharmaceutically acceptable salt thereof. More particularly, the present invention provides a method of treating reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy, comprising administereing to a patient in need thereof an effective amount of a compound of Formula I, or a pharmaceutically acceptable salt thereof. As a more particular aspect, the present invention provides a method for treating frailty, osteoporosis, osteopenia, prostate cancer, and male or female sexual dysfunction comprising administereing to a patient in need thereof an effective amount of a compound of Formula I, or a pharmaceutically acceptable salt thereof.

Further, the present invention provides the use of a compound of Formula I, or a pharmaceutically acceptable salt thereof, as an agent for the treatment of reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy. More particularly, the invention provides the use of a compound of Formula I, or a pharmaceutically acceptable salt thereof, as an agent for the treatment of frailty, osteoporosis, osteopenia, or male or female sexual dysfunction.

In another embodiment, the present invention provides the use of a compound of Formula I, or a pharmaceutically acceptable salt thereof, for the manufacture of a medicament for the treatment of a disorder or condition susceptible to androgen receptor modulation. In particular, the present invention provides the use of a compound of Formula I, or a pharmaceutically acceptable salt thereof, for the manufacture of a medicament for the treatment of reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy. More particularly, the present invention provides the use of a compound of Formula I, or a pharmaceutically acceptable salt thereof, for the manufacture of a medicament for the treatment of frailty, osteoporosis, osteopenia, or male or female sexual dysfunction.

In addition, the present invention provides pharmaceutical compositions comprising a compound of Formula I, or a pharmaceutically acceptable salt thereof, in combination with a pharmaceutically acceptable carrier, diluent or excipient. More particularly, the present invention provides pharmaceutical compositions for the treatment of frailty, osteoporosis, osteopenia, or male or female sexual dysfunction, comprising a compound of Formula I, or a pharmaceutically acceptable salt thereof, in combination with a pharmaceutically acceptable carrier, diluent or excipient.

The present invention also encompasses novel intermediates, reagents, and processes useful for the synthesis of the compounds of Formula I as well as a compound of Formula I for use in therapy.

DETAILED DESCRIPTION OF THE INVENTION

The present invention provides compounds with affinity for AR, which could be used to modulate (i.e., agonize, partially agonize, partially antagonize, or antagonize) receptor activity and gene expression, thereby influencing physiological functions related to Androgen hormone levels and/or AR activity. In particular, compounds of Formula (I) are potent AR ligands, which preferably agonize the androgen receptor. In addition, particularly preferred compounds of Formula (I) selectively bind to AR with greater affinity relative to the other steroid hormone receptors. More particularly, the compounds of the present invention are selective androgen receptor modulators (SARMs) which display both androgenic and antiandrogenic properties, acting as agonists of AR in some tissues while antagonizing AR in yet other tissues. Alternatively, the present invention provides as a more partiuclar embodiment SARMs which display agonist activity in tissues such as muscle or bone, yet only partial agonist activity in tissues such as the prostate or seminal vesicles. In this regard, such ligands are believed to be useful in treating or preventing a multitude of disorders and conditions susceptible to AR modulation. Thus, methods for the treatment or prevention of disorders or conditions susceptible to AR modulation constitute an important embodiment of the present invention. As a particularly preferred aspect, the present invention provides compounds useful as SARMs.

It is also understood that many of the compounds of the present invention may exist as pharmaceutically acceptable salts and, as such, pharmaceutically acceptable salts are therefore included within the scope of the present invention. The term "pharmaceutically acceptable salt" as used herein, refers to salts of the compounds of the present invention, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of the present invention are capable of forming salts, the pharmaceutically acceptable salts and isoforms thereof are encompassed in the names or structures provided herein. Acids and bases suitable for the preparation of pharmaceutically acceptable salts, as well as procedures for preparing such salts, are well within the knowledge of those skilled in the art. See for example, Stahl et al., "Handbook of Pharmaceutical Salts: Properties, Selection and Use," VCHA/Wiley-VCH, (2002); Gould, P. L., "Salt selection for basic drugs," *International Journal of Pharmaceutics*, 33: 201-217 (1986); Berge et al., "Pharmaceutical Salts," *Journal of Pharmaceutical Sciences*, 66, No. 1, (January 1977); Bastin et al. "Salt Selection and Optimization Procedures for Pharmaceutical New Chemical Entities," *Organic Process Research and Development*, 4: 427-435 (2000).

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to one of two stereoisomers whose molecules are non-superimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981. The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of the present invention can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second is enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

Where used herein, the term "Pg" refers to a suitable oxygen or nitrogen protecting group. Suitable oxygen or nitrogen protecting groups, as used herein, refers to those groups intended to protect or block the oxygen or nitrogen group against undesirable reactions during synthetic procedures. Whether the term "Pg", as used herein, represents an oxygen protecting group or a nitrogen protecting group will be readily apparent to the ordinarily skilled artisan. The suitability of the oxygen or nitrogen protecting group used will depend upon the conditions that will be employed in subsequent reaction steps wherein protection is required, and is well within the knowledge of one of ordinary skill in the art. Commonly used nitrogen and oxygen protecting groups are disclosed in Greene, "Protective Groups In Organic Synthesis, $3^{rd}$ Edition" (John Wiley & Sons, New York (1999)).

As used herein, the following terms have the meanings indicated: "i.v." refers to intravenously; "p.o." refers to orally; "i.p." refers to intraperitoneally; "s.c." refers to subcutaneously; "eq" or "equiv." refers to equivalents; "g" refers to grams; "Kg" refers to kilograms; "mg" refers to milligrams; "µg" refers to micrograms; "L" refers to liters; "mL" refers to milliliters; "µL" refers to microliters; "mol" refers to moles; "mmol" refers to millimoles; "M" refers to molar; "mM" refers to millimolar; "nM" refers to nanomolar; "µM" refers to micromolar; "N" refers to normal; "psi" refers to pounds per square inch; "mm Hg" refers to millimeters of mercury; "min" refers to minutes; "h" or "hr" or "hrs." refers to hours; "° C." refers to degrees Celsius; "δ" refers to part per million down-field from tetramethylsilane; "MHz" refers to megahertz; "TLC" refers to thin layer chromatography; "HPLC" refers to high performance liquid chromatography; "$R_t$" refers to retention time; "UV" refers to ultraviolet; "nm" refers to nanometer; "Anal" refers to analytical; "Calcd" refers to calculated; "mp" or "m.p." refers to melting point; "$CDCl_3$" refers to chloroform-d; "THF" refers to tetrahydrofuran; "DMF" refers to N,N-dimethylformamide; "DMSO" refers to dimethyl sulfoxide; "DMSO-$d_6$" refers to dimethyl-$d_6$-sulfoxide; "EtOAc" refers to ethyl acetate; "MeOH" refers to methanol; "EtOH" refers to ethanol; "i-PrOH" refers to isopropanol; "$Et_2O$" refers to diethyl ether; "MTBE" refers to tert-butyl methyl ether; "DMEA" refers to N,N-dimethylethylamine; "$Na_2SO_4$" refers to sodium sulfate; "$MgSO_4$" refers to magnesium sulfate; "$Na_2CO_3$" refers to sodium carbonate; "$K_2CO_3$" refers to potassium carbonate; "$NaHCO_3$" refers to sodium bicarbonate; $Na_2S_2O_3$ refers to sodium thiosulfate; "NaOH" refers to sodium hydroxide; "HCl" refers to hydrogen chloride or hydrochloric acid; "$H_2O_2$" refers to hydrogen peroxide; "NaH" refers to sodium hydride; "LDA" refers to lithium diisopropylamide; "$CH_2Cl_2$" refers to dichloromethane; "$NH_4OH$" refers to ammonium hydroxide; "$NH_4Cl$" refers to ammonium chloride; "$NH_3$" refers to ammonia; and "Al—Ni" refers to aluminum-nickel.

Also as used herein, "$K_d$" refers to the equilibrium dissociation constant for a ligand-receptor complex; "$K_i$" refers to the equilibrium dissociation constant for drug-receptor complex, and is an indication of concentration of drug that will bind to half the binding sites at equilibrium; "IC50" refers to the concentration of an agent which produces 50% of the maximal inhibitory response possible for that agent; "IC50" also refers to the concentration of an agent which produces 50% displacement of ligand binding to the receptor; "EC50" refers to the concentration of an agent which produces 50% of the maximal response possible for that agent; and "ED50"

refers to the dose of an administered therapeutic agent which produces 50% the maximal response for that agent.

As used herein the term "$(C_1-C_4)$alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$(C_1-C_6)$alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "$(C_1-C_4)$alkyl" is included within the definition of "$(C_1-C_6)$alkyl".

As used herein, the terms "Me", "Et", "Pr", "i-Pr", "Bu" and "t-Bu" refer to methyl, ethyl, propyl, isopropyl, butyl and tert-butyl respectively.

As used herein, the term "$(C_1-C_4)$alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "$(C_1-C_6)$alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "$(C_1-C_4)$alkoxy" is included within the definition of "$(C_1-C_6)$alkoxy".

As used herein, the terms "halo", "halide" or "hal" or "Hal" refer to a chlorine, bromine, iodine or fluorine atom, unless otherwise specified herein.

As used herein, the term "halo$(C_1-C_4)$alkyl" refers to a straight or branched, monovalent, saturated aliphatic chain of 1 to 4 carbon atoms bearing one or more halo groups attached to one or more of the carbon atoms. As used herein, the term "halo$(C_1-C_6)$alkyl" refers to a straight or branched, monovalent, saturated aliphatic chain of 1 to 6 carbon atoms bearing one or more halo groups attached to one or more of the carbon atoms. It is understood that the term "halo$(C_1-C_4)$alkyl" is included within the definition of "halo$(C_1-C_6)$alkyl". Typical examples of "halo$(C_1-C_4)$alkyl" or "halo$(C_1-C_6)$alkyl" include $CF_3$, $CHF_2$, $CH_2F$, and the like. As used herein, the term "halo$(C_1-C_4)$alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo$(C_1-C_6)$alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo$(C_1-C_4)$alkoxy" is included within the definition of "halo$(C_1-C_6)$alkoxy". Typical examples of "halo$(C_1-C_4)$alkoxy" or "halo$(C_1-C_6)$alkoxy" include $OCF_3$, $OCHF_2$, $OCH_2F$, and the like.

As used herein, the term "aryl" refers to a monovalent aromatic carbocyclic radical and includes groups such as phenyl, naphthyl and the like.

As used herein, the term "heteroaryl" refers to a 5 to 6 membered monovalent monocyclic aromatic radical containing one to four heteroatoms each independently selected from the group consisting of oxygen, sulfur, and nitrogen. It is understood that the remaining atoms of the radical are carbon and that the radical may be attached, for example to the structure of Formula I, through any atom of the cyclic system which provides for a stable structure. Examples of typical heterocyclic groups include furanyl, thiophenyl, pyrrolyl, tetrazolyl, thiazolyl, isothiazolyl, oxadiazolyl, triazolyl, thiadiazolyl, oxazolyl, isoxazolyl, imidazolyl, pyrazolyl, pyridinyl, pyradazinyl, pyrimidinyl, pyrazinlyl, and triazinyl, and the like.

As used herein the term "N,N—$(C_1-C_4)$dialkylamine" refers to a nitrogen atom substituted with two straight or branched, monovalent, saturated aliphatic chains of 1 to 4 carbon atoms. Included within the term "N,N—$(C_1-C_6)$dialkylamine" are —$N(CH_3)_2$, —$N(CH_3)CH_2CH_3$, —$N(CH_2CH_3)_2$, —$N(CH_2CH_2CH_3)_2$, —$N(CH_2CH_2CH_2CH_3)_2$, and the like. The term "NH—$(C_1-C_4)$ alkylamine" refers to a nitrogen atom substituted with a single straight or branched, monovalent, saturated aliphatic chains of 1 to 4 carbon atoms.

As will be appreciated by one of ordinary skill in the art, some of the heterocyclic moieties of the compounds of Formula I may exist as positional isomers and as tautomeric forms. For example, tetrazole is known to exist as tautomeric structures:

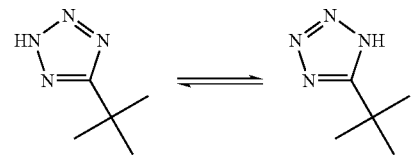

Similarly, triazoles exist in two positional isomeric forms, the 1,2,4-triazole and the 1,2,3-triazole. Each form of which may exist as tautomeric structures. The present invention contemplates all positional isomers, individual tautomeric forms, as well as any combination thereof.

The designation "⎯▬" refers to a bond that protrudes forward out of the plane of the page.

The designation "⋯⋯" refers to a bond that protrudes backward out of the plane of the page.

As used herein the term "androgen receptor" or "AR" refers to the androgen receptor subtype, of the larger class of nuclear hormone receptors, which binds the androgen hormone testosterone, as its cognate ligand. The term "androgen receptor modulator" or "androgen modulator" or "AR modulator" as used herein, refers to those nuclear hormone receptor ligands which bind to the AR subtype and modulate (i.e. agonize, partially agonize, partially antagonize, antagonize) the receptor activity. As a particular embodiment, the present invention provides selective androgen receptor modulators (SARMs) which display androgenic properties in certain tissues (e.g. muscle and/or bone) while concomitantly displaying antiandrogenic effects in other tissues such as the prostate or liver. Alternatively, SARMs of the present invention may display agonist activity in anabolic tissues such as muscle or bone, yet display only parital agonist activity or antagonist activity in tissues such as the prostate or seminal vesicles.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of pathological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder or condition. As such, the methods of treatment provided by this invention encompass both therapeutic and prophylactic administration.

As used herein the term "effective amount" refers to the amount or dose of the compound, upon single or multiple dose administration to the patient, which provides the desired effect in the patient undergoing diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain as an effective amount about 0.001 mg/kg to about 100 mg/kg of an active compound of the present invention. Preferably, the daily dose will contain as an effective amount about 0.05 mg/kg to about 50 mg/kg of the compound of the present invention.

Oral administration is a preferred route of administering the compounds employed in the present invention whether administered alone, or in combination with other therapeutic agents. Oral administration, however, is not the only route, nor even the only preferred route. Other preferred routes of administration include transdermal, percutaneous or subcutaneous, pulmonary, intravenous, intramuscular, intranasal, intraperitoneal, buccal, sublingual, or intrarectal routes. Where the AR modulator is administered in combination with other compounds, one of the compounds may be administered by one route, such as oral, and the other may be administered by the transdermal, percutaneous or subcutaneous, pulmonary, intravenous, intramuscular, intranasal, intraperitoneal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of the present invention are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given.

The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired doses and the type of composition to be used. The amount of the compound, however, is best defined as the "effective amount", that is, the amount or dose of each compound which provides the desired effect to the patient in need of such treatment. The activity of the compounds employed in the present invention does not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating disorders susceptible to androgen receptor modulation, and particularly frailty, osteoporosis, osteopenia, and male or female sexual dysfunction.

When used in conjunction with the methods and uses of the present invention, the compounds and compositions of the present invention may be administered either alone, or in combination with conventional therapeutic agents used to treat the particular disorder or condition. Where the compounds or compositions of the present invention are used as part of a combination, the compound or composition comprising Formula I may be administered separately or as part of a formulation comprising the therapeutic agent with which it is to be combined.

Combination Therapy for Osteoporosis:

Conventional therapeutic agents for the treatment of osteoporosis may advantageously be combined with the compounds of Formula I, or compositions comprising a compound of Formula I. Conventional agents for the treatment of osteoporosis include hormone replacement therapies such as conjugated equine estrogen (Premarin®), synthetic conjugated estrogen (Cenestin®), esterified estrogen (Estratab® or Menest®), estropiate (Ogen® or Ortho-est®); as well as transdermal estradiol preparations such as Alora®, Climara®, Estraderm®, and Vivelle®. Combination estrogen-progestin formulations are also available for the treatment of osteoporosis including Prempro® (conjugated equine estrogen and medroxyprogesterone acetate), Premphase® (conjugated equine estrogen and norgestimate), Ortho-Prefest® (estradiol and norgestimate), Femhrt® (ethinyl estradiol and norethindrone acetate), and Combipatch (transdermal estradiol and norethindrone acetate). Other conventional osteoporosis treatments which may be combined with the compounds or compositions of the present invention include bisphosphonates such as alendronate (Fosamax®), risedronate (Actonel®), and pamidronate (Aredia®); selective estrogen receptor modulators (SERMs) such as raloxifene (Evista®); calcitonin (Calcimar® or Miacalcin®); parathyroid hormone (Forteo®); calcium; Vitamin D; diuretics (to reduce $Ca^{2+}$ excretion); fluoride; and androgens (testosterone or 5α-dihydrotestosterone).

Thus, a formulation for combination therapy in treating osteoporosis 15 comprises:

Ingredient (A1): a compound of formula I;

Ingredient (A2): one or more co-agents that are conventional for the treatment of osteoporosis selected from the group consisting of Premarin®, Cenestin®, Estratab®, Menest®, Ogen®, Ortho-est®, Alora®, Climara®, Estraderm®, Vivelle®, Prempro®, Premphase®, Ortho-Prefest®, Femhrt®, Combipatch®, Fosamax®, Actonel®, Aredia®); Evista®; Calcimar®, Miacalcin®, Forteo®, calcium, Vitamin D, diuretics, fluoride, testosterone, and 5α-dihydrotestosterone;

and optionally

Ingredient (A3): a pharmaceutically acceptable carrier, diluent or excipient.

Particular Aspects of the Invention

The following lists set out several groupings of particular substituents and particular variables for compounds of Formula I. It will be understood that compounds of Formula I having such particular substituents or variables, as well as methods and uses employing such compounds, represent particular aspects of the present invention. It will be further understood that each of these groupings of particular substituents and particular variables may be combined with other provided groupings, to create still additional particular aspects of the compounds, methods and uses of the present invention.

Thus, a particular aspect of the present invention is one wherein the compound of Formula I, is one wherein (a) $R^1$ represents cyano, halo, $(C_1$-$C_4)$alkyl, halo$(C_1$-$C_4)$ alkyl, halo$(C_1$-$C_4)$alkoxy, C(=S)$NH_2$, CH=$NOCH_3$, CH=$NOCH_2CH_3$, C($NOCH_3$)$CH_3$, C($NOCH_2CH_3$) $CH_3$, $COR^{1a}$, $OR^{1b}$, $SO_2R^{1c}$, $NHCOR^{1d}$, or a 5 to 6 membered heteroaryl group optionally substituted with 1 or 2 substituents independently selected from the group consisting of amino, cyano, $(C_1$-$C_4)$alkyl, $(C_1$-$C_4)$ alkoxy, halo, halo$(C_1$-$C_4)$alkyl, or halo$(C_1$-$C_4)$alkoxy;

(b) $R^1$ represents cyano, halo, $(C_1$-$C_4)$alkyl, $CF_3$, $OCF_3$, $CHF_2$, $OCHF_2$, CH=$NOCH_3$, CH=$NOCH_2CH_3$, C($NOCH_3$)$CH_3$, C($NOCH_2CH_3$)$CH_3$, $COR^{1a}$, $OR^{1b}$, $SO_2R^{1c}$, $NHCOR^{1d}$, or a 5 to 6 membered heteroaryl group optionally substituted with 1 or 2 substituents independently selected from the group consisting of amino, cyano, $(C_1$-$C_4)$alkyl, $(C_1$-$C_4)$alkoxy, halo, halo $(C_1$-$C_4)$alkyl, or halo$(C_1$-$C_4)$alkoxy;

(c) $R^1$ represents cyano, halo, $(C_1$-$C_4)$alkyl, $CF_3$, $OCF_3$, $CHF_2$, $OCHF_2$, CH=$NOCH_3$, CH=$NOCH_2CH_3$, C($NOCH_3$)$CH_3$, C($NOCH_2CH_3$)$CH_3$, $COR^{1a}$ wherein $R^{1a}$ represents hydrogen, hydroxyl, methyl, methoxy, ethoxy, amino, or trifluoromethyl; $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl or ethyl; $NHCOR^{1d}$ wherein $R^{1d}$ represents methoxy or ethoxy; or a 5 to 6 membered heteroaryl group optionally substituted with 1 or 2 substituents independently selected from the group consisting of amino, cyano, $(C_1-C_4)$alkyl, $(C_1-C_4)$alkoxy, halo, halo$(C_1-C_4)$alkyl, or halo$(C_1-C_4)$alkoxy;

(d) $R^1$ represents cyano, halo, $(C_1-C_4)$alkyl, $CF_3$, $OCF_3$, $CHF_2$, $OCHF_2$, $CH=NOCH_3$, $CH=NOCH_2CH_3$, $C(NOCH_3)CH_3$, $C(NOCH_2CH_3)CH_3$, $COR^{1a}$ wherein $R^{1a}$ represents hydrogen, hydroxyl, methyl, methoxy, ethoxy, amino, or trifluoromethyl; $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl or ethyl; $NHCOR^{1d}$ wherein $R^{1d}$ represents methoxy or ethoxy; or a 5 to 6 membered heteroaryl group selected from the group consisting of furanyl, thiophenyl, pyrrolyl, tetrazolyl, thiazolyl, isothiazolyl, oxadiazolyl, triazolyl, thiadiazolyl, oxazolyl, isoxazolyl, imidazolyl, pyrazolyl, pyridinyl, pyradazinyl, pyrimidinyl, pyrazinlyl, and triazinyl, each optionally substituted with 1 or 2 substituents independently selected from the group consisting of amino, cyano, $(C_1-C_4)$alkyl, $(C_1-C_4)$alkoxy, halo, halo$(C_1-C_4)$alkyl, or halo$(C_1-C_4)$alkoxy;

(e) $R^1$ represents cyano, halo, $(C_1-C_4)$alkyl, $CF_3$, $OCF_3$, $CHF_2$, $OCHF_2$, $CH=NOCH_3$, $CH=NOCH_2CH_3$, $C(NOCH_3)CH_3$, $C(NOCH_2CH_3)CH_3$, $COR^{1a}$ wherein $R^{1a}$ represents hydrogen, hydroxyl, methyl, methoxy, ethoxy, amino, or trifluoromethyl; $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl or ethyl; $NHCOR^{1d}$ wherein $R^{1d}$ represents methoxy or ethoxy; or a 5 to 6 membered heteroaryl group selected from the group consisting of thiazolyl, thiadiazolyl, isoxazolyl, pyridinyl, pyradazinyl, pyrimidinyl, each optionally substituted with 1 or 2 substituents independently selected from the group consisting of amino cyano, $(C_1-C_4)$alkyl, $(C_1-C_4)$alkoxy, halo, halo$(C_1-C_4)$alkyl, or halo$(C_1-C_4)$alkoxy;

(f) $R^1$ represents cyano, bromo, chloro, fluoro, methyl, $CF_3$, $OCF_3$, $CHF_2$, $OCHF_2$, $CH=NOCH_3$, $CH=NOCH_2CH_3$, $C(NOCH_3)CH_3$, $C(NOCH_2CH_3)CH_3$, $COR^{1a}$ wherein $R^{1a}$ represents hydrogen, hydroxyl, methyl, methoxy, ethoxy, amino, or trifluoromethyl; $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl or ethyl; $NHCOR^{1d}$ wherein $R^{1d}$ represents methoxy or ethoxy; or a 5 to 6 membered heteroaryl group selected from the group consisting of thiazolyl, thiadiazolyl, isoxazolyl, pyridinyl, pyradazinyl, pyrimidinyl, each optionally substituted with a first substituent selected from the group consisting of cyano, amino, $(C_1-C_4)$alkyl, or halo and a second substituent that is $(C_1-C_4)$alkyl;

(g) $R^1$ represents cyano, bromo, chloro, fluoro, methyl, $CF_3$, $OCF_3$, $CHF_2$, $OCHF_2$, $CH=NOCH_3$, $CH=NOCH_2CH_3$, $C(NOCH_3)CH_3$, $C(NOCH_2CH_3)CH_3$, $COR^{1a}$ wherein $R^{1a}$ represents hydrogen, hydroxyl, methyl, methoxy, ethoxy, amino, or trifluoromethyl; $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl or ethyl; $NHCOR^{1d}$ wherein $R^{1d}$ represents methoxy or ethoxy; or a 5 to 6 membered heteroaryl group selected from the group consisting of thiazolyl, thiadiazolyl, isoxazolyl, pyridinyl, pyradazinyl, pyrimidinyl, each optionally substituted with a first substituent selected from the group consisting of amino, methyl, or fluoro and a second substituent that is methyl;

Additional particular aspects of the present invention are provided by compounds of Formula I wherein:

(a) $R^2$ represents hydrogen, methyl, ethyl, propyl, isopropyl, methoxy, ethoxy, fluoro, bromo, chloro, or $R^1$ and $R^2$ together to form a group of the formula a group of the formula

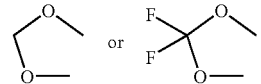

(b) $R^2$ represents hydrogen, methyl, fluoro, bromo, chloro, or $R^1$ and $R^2$ together to form a group of the formula a group of the formula

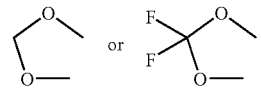

(c) $R^2$ represents hydrogen, methyl, ethyl, propyl, isopropyl, methoxy, ethoxy, fluoro, bromo, or chloro; or (d) $R^2$ represents hydrogen, methyl, fluoro, bromo, or chloro;

Yet Additional particular aspects of the present invention are provided by compounds of Formula I wherein:

(a) $R^3$ represents $NHCOR^{3a}$ or $NHSO_2R^{3b}$, wherein $R^{3a}$ and $R^{3b}$ each independently represent at each occurrence methyl, ethyl, isopropyl, $CH(C_2H_5)_2$, $CH(CH_3)CH_2CH_3$, $CF_3$, $CHF_2$, methoxy, ethoxy, cyclopropyl, cyclobutyl, $NH(CH_3)$, $N(CH_3)_2$, or $N(CH_3)OCH_3$;

(b) $R^3$ represents $NHCOR^{3a}$ wherein $R^{3a}$ represents at each occurrence methyl, ethyl, isopropyl, $CH(C_2H_5)_2$, $CH(CH_3)CH_2CH_3$, $CF_3$, methoxy, ethoxy, cyclopropyl, cyclobutyl, $NH(CH_3)$, or $N(CH_3)_2$; or $R^3$ represents $NHSO_2R^{3b}$, wherein $R^{3b}$ represents at each occurrence cyclopropyl, $NH(CH_3)$, $N(CH_3)_2$, or $N(CH_3)OCH_3$; or (c) $R^3$ represents $NHCOR^{3a}$ wherein $R^{3a}$ represents isopropyl;

Still additional particular aspects of the present invention are provided by compounds of Formula I wherein:

(a) $R^4$ represents a phenyl group optionally substituted with 1 or 2 substituents independently selected from the group consisting of amino, hydroxy, cyano, halo, nitro, methyl, methoxy, $CF_3$, $OCF_3$, $CHF_2$, $OCHF_2$, $NH(CH_3)$, $NH(C_2H_5)$, $N(CH_3)_2$, $NHSO_2CH_3$, or $COOCH_3$; or a 5 to 6 membered heteroaryl group optionally substituted with 1 or 2 substituents independently selected from the group consisting of amino, $(C_1-C_4)$alkyl, or halo;

(b) $R^4$ represents a phenyl group optionally substituted with 1 or 2 substituents independently selected from the group consisting of amino, hydroxy, cyano, halo, nitro, methyl, methoxy, $CF_3$, $OCF_3$, $CHF_2$, $OCHF_2$, $NH(CH_3)$, $NH(C_2H_5)$, $N(CH_3)_2$, $NHSO_2CH_3$, or $COOCH_3$; or a 5 to 6 membered heteroaryl group selected from the group consisting of furanyl, thiophenyl, pyrrolyl, tetrazolyl, thiazolyl, isothiazolyl, oxadiazolyl, triazolyl, thiadiazolyl, oxazolyl, isoxazolyl, imidazolyl, pyrazolyl, pyridinyl, pyradazinyl, pyrimidinyl, pyrazinlyl, and triazinyl, optionally substituted with one or two substituents independently selected from the group consisting of amino, $(C_1-C_4)$alkyl, or halo;

(c) $R^4$ represents a phenyl group optionally substituted with 1 or 2 substituents independently selected from the group consisting of amino, hydroxy, cyano, halo, nitro, methyl, methoxy, $CF_3$, $OCF_3$, $CHF_2$, $OCHF_2$, $NH(CH_3)$, $NH(C_2H_5)$, $N(CH_3)_2$, $NHSO_2CH_3$, or $COOCH_3$; or a 5 to 6 membered heteroaryl group selected from the group consisting of thiophenyl, thiazolyl, pyridinyl, or pyrazinyl, each optionally substituted with one or two substituents independently selected from the group consisting of amino, $(C_1-C_4)$alkyl, or halo;

(d) $R^4$ represents a phenyl group optionally substituted with 1 or 2 substituents independently selected from the group consisting of amino, hydroxy, cyano, halo, nitro, methyl, methoxy, $CF_3$, $OCF_3$, $CHF_2$, $OCHF_2$, $NH(CH_3)$, $NH(C_2H_5)$, $N(CH_3)_2$, $NHSO_2CH_3$, or $COOCH_3$; or a 5 to 6 membered heteroaryl group selected from the group consisting of thiophenyl, thiazolyl, pyridinyl, or pyrazinyl, each optionally substituted with one or two substituents independently selected from the group consisting of amino, methyl, fluoro, or chloro;

(e) $R^4$ represents a phenyl group optionally substituted with 1 or 2 substituents independently selected from the group consisting of amino, hydroxy, cyano, halo, nitro, methyl, methoxy, $CF_3$, $OCF_3$, $CHF_2$, $OCHF_2$, $NH(CH_3)$, $NH(C_2H_5)$, $N(CH_3)_2$, $NHSO_2CH_3$, or $COOCH_3$; or a 5 to 6 membered heteroaryl group selected from the group consisting of thiophenyl, thiazolyl, pyridinyl, or pyrazinyl, each optionally substituted with a substituent independently selected from the group consisting of amino, methyl, fluoro, or chloro;

Even more particular embodiments of the present invention are provided by the compounds of Formula I(a), I(b), and I(c), below:

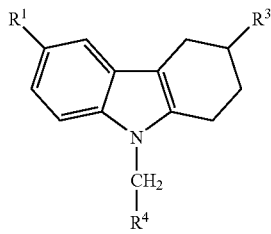

Formula I(a)

wherein,
$R^1$ represents cyano, halo, $(C_1-C_4)$alkoxy, halo$(C_1-C_4)$alkoxy, $CH=NOCH_3$, $CH=NOCH_2CH_3$, $C(NOCH_3)CH_3$, $C(NOCH_2CH_3)CH_3$, or COH;
$R^3$ represents $NHCOR^{3a}$;
$R^{3a}$ represents $(C_1-C_6)$alkyl, $(C_1-C_6)$alkoxy, cyclopropyl, cyclobutyl, $NH-(C_1-C_4)$alkylamine, or $N,N-(C_1-C_6)$dialkylamine; and
$R^4$ represents a 5 to 6 membered heteroaryl group optionally substituted with 1 or 2 substituents independently selected from the group consisting of amino, $(C_1-C_4)$alkyl, or halo, or a pharmaceutically acceptable salt thereof.

More particular aspects of the compound Formula I(a) are provided by compounds wherein:
(a) $R^1$ represents cyano, fluoro, bromo, chloro, methoxy, $OCF_3$, $OCHF_2$, $CH=NOCH_3$, $CH=NOCH_2CH_3$, $C(NOCH_3)CH_3$, $C(NOCH_2CH_3)CH_3$, or COH;
(b) $R^1$ represents cyano, fluoro, bromo, chloro, methoxy, $OCF_3$, $CH=NOCH_3$, or COH;
(c) $R^1$ represents cyano, bromo, methoxy, $OCF_3$, $CH=NOCH_3$, or COH;
(d) $R^1$ represents cyano, methoxy, $OCF_3$, $CH=NOCH_3$, or COH;
(e) $R^1$ represents cyano;
(f) $R^1$ represents methoxy;
(g) $R^1$ represents $OCF_3$;
(h) $R^1$ represents $CH=NOCH_3$; or
(i) $R^1$ represents COH.

Additional particular aspects of the compound Formula I(a) are provided by compounds wherein:
(a) $R^3$ represents $NHCOR^{3a}$, wherein $R^{3a}$ represents $(C_1-C_6)$alkyl, $(C_1-C_6)$alkoxy, cyclopropyl, or $N,N-(C_1-C_6)$dialkylamine;
(b) $R^3$ represents $NHCOR^{3a}$, wherein $R^{3a}$ represents isopropyl, methoxy, cyclopropyl, or $N(CH_3)_2$;
(c) $R^3$ represents $NHCOR^{3a}$, wherein $R^{3a}$ represents isopropyl;
(d) $R^3$ represents $NHCOR^{3a}$, wherein $R^{3a}$ represents methoxy;
(e) $R^3$ represents $NHCOR^{3a}$, wherein $R^{3a}$ represents cyclopropyl; or
(f) $R^3$ represents $NHCOR^{3a}$, wherein $R^{3a}$ represents $N(CH_3)_2$ Yet additional particular aspects of the compound Formula I(a) are provided by compounds wherein:
(a) $R^4$ represents a 5 to 6 membered heteroaryl group seleceted from the group consisting of furanyl, thiophenyl, pyrrolyl, tetrazolyl, thiazolyl, isothiazolyl, oxadiazolyl, triazolyl, thiadiazolyl, oxazolyl, isoxazolyl, imidazolyl, pyrazolyl, pyridinyl, pyradazinyl, pyrimidinyl, pyrazinlyl, and triazinyl, each optionally substituted with 1 or 2 substituents independently selected from the group consisting of amino, $(C_1-C_4)$alkyl, or halo;
(b) $R^4$ represents a 5 to 6 membered heteroaryl group seleceted from the group consisting of thiophenyl, thiazolyl, pyridinyl, or pyrazinyl each optionally substituted with 1 or 2 substituents independently selected from the group consisting of amino, $(C_1-C_4)$alkyl, or halo;
(c) $R^4$ represents a 5 to 6 membered heteroaryl group seleceted from the group consisting of thiophenyl, thiazolyl, pyridinyl, or pyrazinyl, each optionally substituted with 1 or 2 substituents independently selected from the group consisting of amino, methyl, chloro, or fluoro;
(d) $R^4$ represents a 5 to 6 membered heteroaryl group seleceted from the group consisting of thiophenyl, thiazolyl, pyridinyl, or pyrazinyl, each optionally substituted with a substituent selected from the group consisting of amino, methyl, chloro, or fluoro;
(e) $R^4$ represents a group of the following

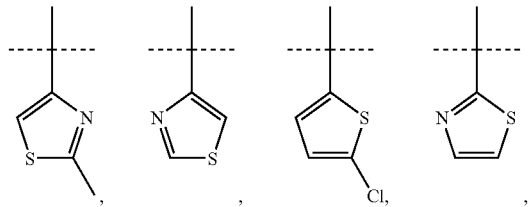

-continued

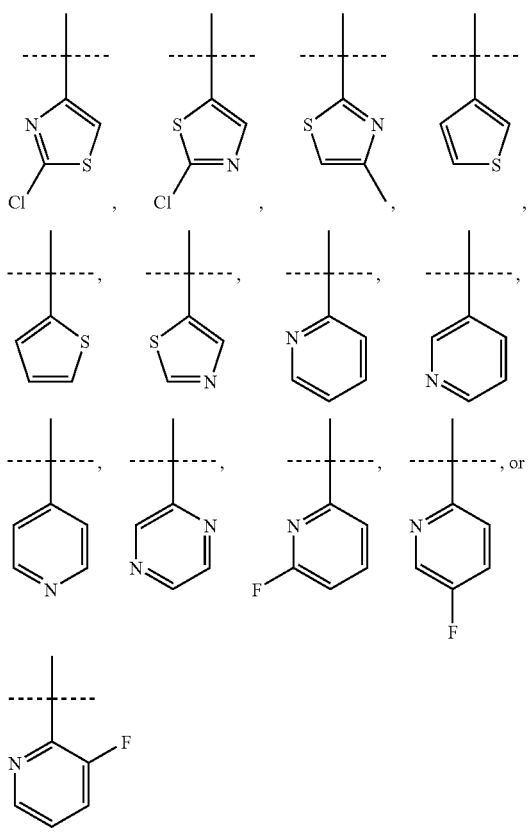

Even more particular embodiments of the present invention are provided by the compounds of Formula I(b), below:
wherein,

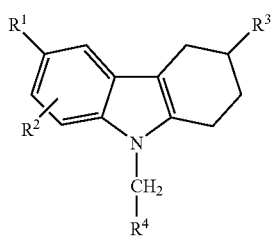

Formula I(b)

$R^1$ represents hydrogen, hydroxy, cyano, halo, nitro, $(C_1\text{-}C_4)$alkyl, halo$(C_1\text{-}C_4)$alkyl, halo$(C_1\text{-}C_4)$alkoxy, C(=S)NH$_2$, CH=NOCH$_3$, CH=NOH, COR$^{1a}$, OR$^{1b}$, SO$_2$R$^{1c}$, NHCOR$^{1d}$;

$R^{1a}$ represents hydrogen, amino, hydroxy, $(C_1\text{-}C_4)$alkyl, $(C_1\text{-}C_4)$alkoxy, or halo$(C_1\text{-}C_4)$alkyl;

$R^{1b}$ represents $(C_1\text{-}C_4)$alkyl, cyclopropyl, or cyclopropylmethyl;

$R^{1c}$ represents $(C_1\text{-}C_4)$alkyl;

$R^{1d}$ represents $(C_1\text{-}C_4)$alkoxy;

$R^2$ represents hydrogen halo, $(C_1\text{-}C_4)$alkyl, or $(C_1\text{-}C_4)$alkoxy, or $R^1$ and $R^2$ together represent a group of the formula

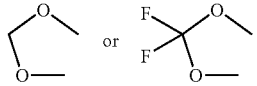

$R^3$ represents NHCOR$^{3a}$ or NHSO$_2$R$^{3b}$;

$R^{3a}$ and $R^{3b}$ each independently represent at each occurrence $(C_1\text{-}C_6)$alkyl, halo$(C_1\text{-}C_4)$alkyl, $(C_1\text{-}C_4)$alkoxy, cyclopropyl, cyclobutyl, NH—$(C_1\text{-}C_4)$alkylamine, N,N—$(C_1\text{-}C_6)$dialkylamine, or N(CH$_3$)OCH$_3$; and $R^4$ represents a phenyl group optionally substituted with 1 or 2 substituents independently selected from the group consisting of amino, hydroxy, cyano, halo, nitro, $(C_1\text{-}C_4)$alkyl, $(C_1\text{-}C_4)$alkoxy, halo$(C_1\text{-}C_4)$alkyl, halo$(C_1\text{-}C_4)$alkoxy, NH—$(C_1\text{-}C_4)$alkylamine, N,N—$(C_1\text{-}C_6)$dialkylamine, NHSO$_2$CH$_3$, or COOCH$_3$;

Additional particular aspects of the compound Formula I(b) are provided by compounds wherein:

(a) $R^1$ represents hydroxy, cyano, halo, nitro, $(C_1\text{-}C_4)$alkyl, halo$(C_1\text{-}C_4)$alkyl, halo$(C_1\text{-}C_4)$alkoxy, CH=NOCH$_3$, CH=NOCH$_2$CH$_3$, C(NOCH$_3$)CH$_3$, C(NOCH$_2$CH$_3$)CH$_3$, COR$^{1a}$, OR$^{1b}$, SO$_2$R$^{1c}$, or NHCOR$^{1d}$;

(b) $R^1$ represents hydroxy, cyano, fluoro, chloro, bromo, nitro, methyl, CF$_3$, CHF$_2$, OCF$_3$, OCHF$_2$, CH=NOCH$_3$, CH=NOCH$_2$CH$_3$, C(NOCH$_3$)CH$_3$, C(NOCH$_2$CH$_3$)CH$_3$, COR$^{1a}$, OR$^{1b}$, SO$_2$R$^{1c}$, or NHCOR$^{1d}$;

(c) $R^1$ represents hydroxy, cyano, fluoro, chloro, bromo, nitro, methyl, CF$_3$, CHF$_2$, OCF$_3$, OCHF$_2$, CH=NOCH$_3$, CH=NOCH$_2$CH$_3$, C(NOCH$_3$)CH$_3$, C(NOCH$_2$CH$_3$)CH$_3$, COR$^{1a}$ wherein R$^{1a}$ represents hydrogen, hydroxyl, amino, methyl, methoxy, ethoxy, or CF$_3$; OR$^{1b}$ wherein R$^{1b}$ represents methyl, ethyl, propyl, isopropyl, cyclopropyl, or cyclopropylmethyl; SO$_2$R$^{1c}$ wherein R$^{1c}$ represents methyl; or NHCOR$^{1d}$ wherein R$^{1d}$ represents methoxy or ethoxy;

(d) $R^1$ represents cyano, fluoro, chloro, bromo, methyl, CF$_3$, CHF$_2$, OCF$_3$, OCHF$_2$, CH=NOCH$_3$, CH=NOCH$_2$CH$_3$, C(NOCH$_3$)CH$_3$, C(NOCH$_2$CH$_3$)CH$_3$, COR$^{1a}$ wherein R$^{1a}$ represents hydrogen, hydroxyl, amino, methyl, methoxy, ethoxy, or CF$_3$; OR$^{1b}$ wherein R$^{1b}$ represents methyl, ethyl, propyl, isopropyl, cyclopropyl, or cyclopropylmethyl; SO$_2$R$^{1c}$ wherein R$^{1c}$ represents methyl; or NHCOR$^{1d}$ wherein R$^{1d}$ represents methoxy or ethoxy;

(e) $R^1$ represents cyano, fluoro, chloro, bromo, CH=NOCH$_3$, CH=NOCH$_2$CH$_3$, C(NOCH$_3$)CH$_3$, C(NOCH$_2$CH$_3$)CH$_3$, or OR$^{1b}$ wherein R$^{1b}$ represents methyl, ethyl, propyl, isopropyl, cyclopropyl, or cyclopropylmethyl;

(f) $R^1$ represents cyano;

(g) $R^1$ represents fluoro, bromo, or chloro;

(h) $R^1$ represents CH=NOCH$_3$, CH=NOCH$_2$CH$_3$, C(NOCH$_3$)CH$_3$, or C(NOCH$_2$CH$_3$)CH$_3$;

(i) $R^1$ represents OR$^{1b}$ wherein R$^{1b}$ represents methyl, ethyl, propyl, isopropyl, cyclopropyl, or cyclopropylmethyl;

Yet Additional particular aspects of the compounds of Formula I(b) are provided by compounds wherein:

(a) $R^2$ represents hydrogen bromo, chloro, fluoro, methyl, or methoxy, or $R^1$ and $R^2$ together represent a group of the formula

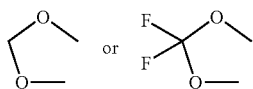

(b) $R^2$ represents hydrogen, bromo, chloro, or fluoro;
(c) $R^2$ represents hydrogen, methyl or methoxy;
(d) $R^2$ represents hydrogen or $R^1$ and $R^2$ together represent a group of the formula

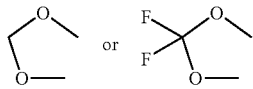

(e) $R^2$ represents hydrogen.

Yet Additional particular aspects of the compounds of Formula I(b) are provided by compounds wherein:

(a) $R^3$ represents $NHCOR^{3a}$ or $NHSO_2R^{3b}$, wherein $R^{3a}$ and $R^{3b}$ each independently represent at each occurrence methyl, ethyl, isopropyl, $CH(C_2H_5)_2$, $CH(CH_3)CH_2CH_3$, $CF_3$, $CHF_2$, methoxy, ethoxy, cyclopropyl, cyclobutyl, $NH(CH_3)$, $N(CH_3)_2$, or $N(CH_3)OCH_3$;

(b) $R^3$ represents $NHCOR^{3a}$ wherein $R^{3a}$ represents at each occurrence methyl, ethyl, isopropyl, $CH(C_2H_5)_2$, $CH(CH_3)CH_2CH_3$, $CF_3$, methoxy, ethoxy, cyclopropyl, cyclobutyl, $NH(CH_3)$, or $N(CH_3)_2$; or $R^3$ represents $NHSO_2R^{3b}$, wherein $R^{3b}$ represents at each occurrence cyclopropyl, $NH(CH_3)$, $N(CH_3)_2$, or $N(CH_3)OCH_3$;

(c) $R^3$ represents $NHCOR^{3a}$ wherein $R^{3a}$ represents methyl, ethyl, isopropyl, cyclopropyl, or cyclobutyl;

(d) $R^3$ represents $NHCOR^{3a}$ wherein $R^{3a}$ isopropyl;

Further particular aspects of the compound of formula I(b) are provided by compounds whererin:

(a) $R^4$ represents a phenyl group optionally substituted with 1 or 2 substituents independently selected from the group consisting of amino, hydroxy, cyano, bromo, chloro, fluoro, nitro, methyl, methoxy, $CF_3$, $CHF_2$, $OCF_3$, $OCHF_2$, $NH(C_2H_5)$, $N(CH_3)_2$, $NHSO_2CH_3$, or $COOCH_3$;

(b) $R^4$ represents a phenyl group optionally substituted with a first subsitutent selected from the group consisting of amino, hydroxy, cyano, bromo, chloro, fluoro, nitro, methyl, methoxy, $CF_3$, $CHF_2$, $OCF_3$, $OCHF_2$, $NH(C_2H_5)$, $N(CH_3)_2$, $NHSO_2CH_3$, or $COOCH_3$ and a second subsitutent selected from the group consisting of bromo, chloro, fluoro, or methyl;

(c) $R^4$ represents a phenyl group optionally substituted with a first subsitutent selected from the group consisting of cyano, bromo, chloro, fluoro, methyl, or methoxy, and a second subsitutent that is fluoro;

(d) $R^4$ represents a phenyl group optionally substituted with a subsitutent selected from the group consisting of cyano, bromo, chloro, fluoro, methyl, or methoxy, (e) $R^4$ represents a phenyl group optionally substituted with a cyano group;

(f) $R^4$ represents a phenyl group optionally substituted with a fluoro group;

(g) $R^4$ represents a phenyl group optionally substituted with a methyl group; or (h) $R^4$ represents a phenyl group optionally substituted with a methoxy group;

Additonal particular aspects of the present invention are provided by compounds of Formula I(c)

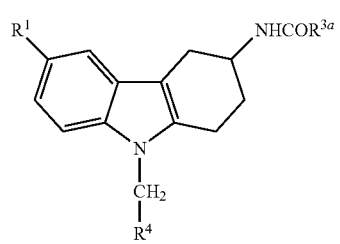

Formula I(c)

wherein, $R^1$ represents a 5 to 6 membered heteroaryl group optionally substituted with 1 or 2 substituents independently selected from the group consisting of amino, $(C_1-C_4)$alkyl, or halo;

$R^{3a}$ represents $(C_1-C_6)$alkyl, halo$(C_1-C_4)$alkyl, $(C_1-C_4)$alkoxy, cyclopropyl, cyclobutyl, $NH-(C_1-C_4)$alkylamine, $N,N-(C_1-C_6)$dialkylamine, or $N(CH_3)OCH_3$; and $R^4$ represents a phenyl group optionally substituted with 1 or 2 substituents independently selected from the group consisting of amino, hydroxy, cyano, halo, nitro, $(C_1-C_4)$alkyl, $(C_1-C_4)$alkoxy, halo$(C_1-C_4)$alkyl, halo$(C_1-C_4)$alkoxy, $NH-(C_1-C_4)$alkylamine, $N,N-(C_1-C_6)$dialkylamine, $NHSO_2CH_3$, or $COOCH_3$;

or a pharmaceutically acceptable salt thereof

Other particular aspects of the compound of Formula I(c) are provided by compounds whererin:

(a) $R^1$ represents a 5 to 6 membered heteroaryl selected from the group consisting of furanyl, thiophenyl, pyrrolyl, tetrazolyl, thiazolyl, isothiazolyl, oxadiazolyl, triazolyl, thiadiazolyl, oxazolyl, isoxazolyl, imidazolyl, pyrazolyl, pyridinyl, pyradazinyl, pyrimidinyl, pyrazinlyl, and triazinyl, each optionally substituted with 1 or 2 substituents independently selected from the group consisting of amino, cyano, $(C_1-C_4)$alkyl, $(C_1-C_4)$alkoxy, halo, halo$(C_1-C_4)$alkyl, or halo$(C_1-C_4)$alkoxy;

(b) $R^1$ represents a 5 to 6 membered heteroaryl selected from the group consisting of thiazolyl, thiadiazolyl, isoxazolyl, pyridinyl, pyradazinyl, pyrimidinyl, each optionally substituted with 1 or 2 substituents independently selected from the group consisting of amino, cyano, $(C_1-C_4)$alkyl, $(C_1-C_4)$alkoxy, halo, $CF_3$, $CHF_2$, $OCF_3$, or $OCHF_2$;

(c) $R^1$ represents a 5 to 6 membered heteroaryl selected from the group consisting of thiazolyl, thiadiazolyl, isoxazolyl, pyridinyl, pyradazinyl, pyrimidinyl, each optionally substituted with 1 or 2 substituents independently selected from the group consisting of amino, methyl, or fluoro;

(d) $R^1$ represents a 5 to 6 membered heteroaryl selected from the group consisting of thiazolyl, thiadiazolyl, isoxazolyl, pyridinyl, pyradazinyl, pyrimidinyl, each optionally substituted with a first substituent selected from the group consisting of amino, methyl, or fluoro, and a second substituent that is methyl;

(e) $R^1$ represents a group of the formula

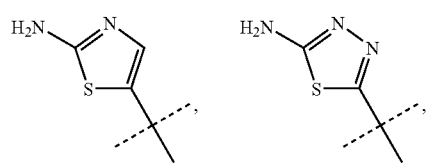

-continued

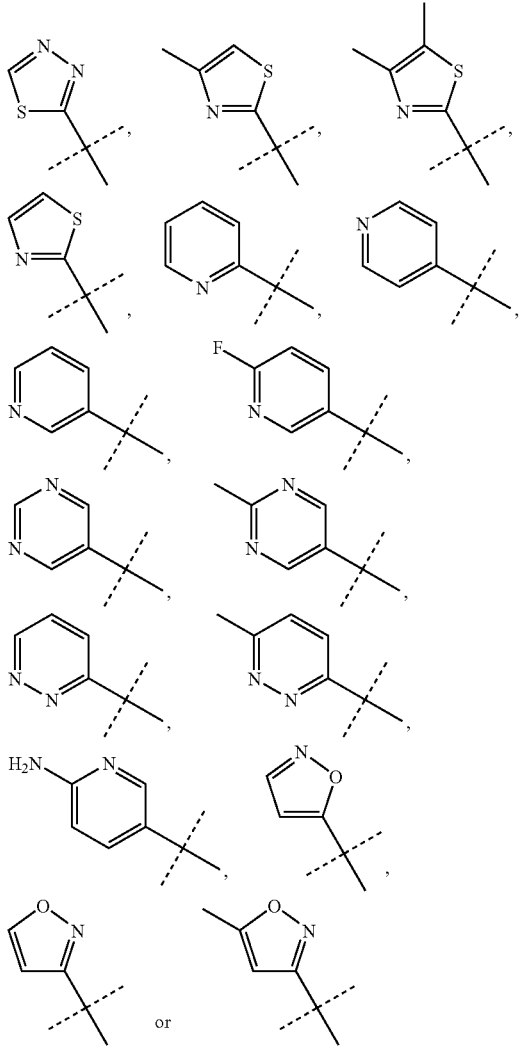

More particular aspects of the compound of Formula I(c) are provided by compounds whererin:
(a) $R^{3a}$ represents $(C_1-C_6)$alkyl, cyclopropyl, or cyclobutyl;
(b) $R^{3a}$ represents methyl, ethyl, propyl, isopropyl, cyclopropyl, or cyclobutyl;
(c) $R^{3a}$ represents isopropyl, cyclopropyl, or cyclobutyl; or
(d) $R^{3a}$ represents isopropyl More particular aspects of the compound of Formula I(c) are provided by compounds whererin:
(a) $R^4$ represents a phenyl group optionally substituted with 1 or 2 substituents independently selected from the group consisting of amino, hydroxy, cyano, halo, nitro, $(C_1-C_4)$alkyl, $(C_1-C_4)$alkoxy, halo$(C_1-C_4)$alkyl, halo $(C_1-C_4)$alkoxy, NH—$(C_1-C_4)$alkylamine, N,N—$(C_1-C_6)$dialkylamine, $NHSO_2CH_3$, or $COOCH_3$;
(b) $R^4$ represents a phenyl group optionally substituted with 1 or 2 substituents independently selected from the group consisting of cyano, halo, $(C_1-C_4)$alkyl, or $(C_1-C_4)$alkoxy;
(c) $R^4$ represents a phenyl group optionally substituted with 1 or 2 substituents independently selected from the group consisting of cyano, fluoro, methyl, or methoxy;
(d) $R^4$ represents a phenyl group optionally substituted with a substituent selected from the group consisting of cyano, fluoro, methyl, or methoxy;
(e) $R^4$ represents a phenyl group optionally substituted with a cyano group;
(f) $R^4$ represents a phenyl group optionally substituted with a fluoro group;
(g) $R^4$ represents a phenyl group optionally substituted with a methyl group; or
(h) $R^4$ represents a phenyl group optionally substituted with a methoxy group.

As an especially particular aspect, the present invention provides the compound of Formula I(a), wherein $R^1$ represents cyano, halo, or CH=$NOCH_3$;

$R^3$ represents $NHCOR^{3a}$;

$R^{3a}$ represents $(C_1-C_6)$alkyl, $(C_1-C_6)$alkoxy, cyclopropyl, or NH—$(C_1-C_4)$alkylamine; and $R^4$ represents a 5 to 6 membered heteroaryl group optionally substituted with a substituent selected from the group consisting of amino, methyl, ethyl, isopropyl, and fluoro, or a pharmaceutically acceptable salt thereof.

As a most particular aspect, the present invention provides the compound of Formula I(a), wherein $R^1$ represents cyano or CH=$NOCH_3$;

$R^3$ represents $NHCOR^{3a}$;

$R^{3a}$ represents methyl, ethyl, isopropyl, or cyclopropyl; and $R^4$ represents a pyridine, thiazole, or pyrazine group optionally substituted with a substituent selected from the group consisting of amino, methyl and fluoro, or a pharmaceutically acceptable salt thereof.

As yet an additional especially particular aspect, the present invention provides the compound of Formula I(b), wherein $R^1$ represents cyano, halo, or CH=$NOCH_3$;

$R^2$ represents hydrogen;

$R^3$ represents $NHCOR^{3a}$;

$R^{3a}$ represents $(C_1-C_6)$alkyl, $(C_1-C_6)$alkoxy, cyclopropyl, or NH—$(C_1-C_4)$alkylamine; and $R^4$ represents a phenyl group optionally substituted with 1 or 2 substituents selected from the group consisting of amino, hydroxyl, cyano, methyl, fluoro, and chloro, or a pharmaceutically acceptable salt thereof.

As a most especially particular aspect, the present invention provides the compound of Formula I(b), wherein $R^1$ represents cyano or CH=$NOCH_3$;

$R^2$ represents hydrogen;

$R^3$ represents $NHCOR^{3a}$;

$R^{3a}$ represents methyl, ethyl, isopropyl, or cyclopropyl; and $R^4$ represents a phenyl group optionally substituted with a substituent selected from the group consisting of cyano, methyl, and fluoro, or a pharmaceutically acceptable salt thereof.

As yet an additional especially particular aspect, the present invention provides the compound of Formula I(c), wherein $R^1$ represents a 5 to 6 membered heteroaryl selected from the group consisting of thiazolyl, thiadiazolyl, isoxazolyl, pyridinyl, pyradazinyl, and pyrimidinyl, each optionally substituted with 1 or 2 substituents independently selected from the group consisting of amino, methyl, and fluoro;

$R^{3a}$ represents $(C_1-C_6)$alkyl, $(C_1-C_6)$alkoxy, cyclopropyl, or NH—$(C_1-C_4)$alkylamine; and $R^4$ represents a phenyl group optionally substituted with 1 or 2 substituents independently selected from the group consisting of amino, hydroxyl, cyano, methyl, fluoro, and chloro, or a pharmaceutically acceptable salt thereof.

As a most particular aspect, the present invention provides the compound of Formula I(c) wherein $R^1$ represents a 5 to 6 membered heteroaryl selected from the group consisting of thiazolyl, thiadiazolyl, isoxazolyl, pyridinyl, pyradazinyl, and pyrimidinyl, each optionally substituted with a substituent selected from the group consisting of amino, methyl, and fluoro;

$R^{3a}$ represents methyl, ethyl, isopropyl, or cyclopropyl; and $R^4$ represents a phenyl group optionally substituted with a substituent selected from the group consisting of cyano, methyl, and fluoro, or a pharmaceutically acceptable salt thereof.

In addition, it will be understood a most particular aspect of the present invention is provided by those compounds of Formula I, Formula I(a), Formula I(b), and Formula I(c) exemplified herein. Furthermore, the methods, uses, and compositions comprising the herein exemplified compounds of Formula I, Formula I(a), Formula I(b), and Formula I(c), are also a most particular aspect of the present invention.

All of the compounds of the present invention can be chemically prepared, for example, by following the synthetic routes set forth in the Schemes and/or the Preparations and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula I.

All substituents, unless otherwise indicated, are as previously defined. The reagents and starting materials are readily available to one of ordinary skill in the art. For example, certain reagents or starting materials can be prepared by one of ordinary skill in the art following procedures disclosed in Khanna, I. K., et al., *J. Med. Chem.* (2000) 43, 3168-3185; Erlenmeyer, H., et al. *Helv. Chim. Acta* (1944), 27, 1437-1438; McElhinney, R. S., et al., *J. Med. Chem.* (1998) 41, 5265-5271; Yang, L., et al., *Bioorg. Med. Chem. Lett.* (1999) 9, 1761-1766; Hermitage, S. A, Cardwell, K. S., Chapman, T., Cooke, J. W. B., Newton, R., *Org. Process Res. Dev.*, (2001) 5(1), 37-44; R Frenette et al, *Bioorg. Med. Chem. Lett.*, (1999) 9(16) 2391-2396; Campaigne, E., Thompson, R. L., Van Werth, J. E., *Journal of Medicinal & Pharmaceutical Chemistry*, (1959) 1, 577-600; Kikelj, D. and Urleb, U., *Science of Synthesis*, (2002) 11, 627-833; Tsunoda, T., et al., *Tetrahedron Lett.* (1996) 37, 2459-2462. Tetrahydrocarbazoles can be prepared by one of ordinary skill in the art using the Fischer indole synthesis as reviewed by Hughes, OPPI (1993), 25(6), 607-32. Additional reagents, starting materials, or useful procedures may be found in WO99/55302. Other necessary reagents and starting materials may be made by procedures which are selected from standard techniques of organic and heterocyclic chemistry, techniques which are analogous to the syntheses of known structurally similar compounds and the procedures described in the Examples below, including any novel procedures.

Scheme I

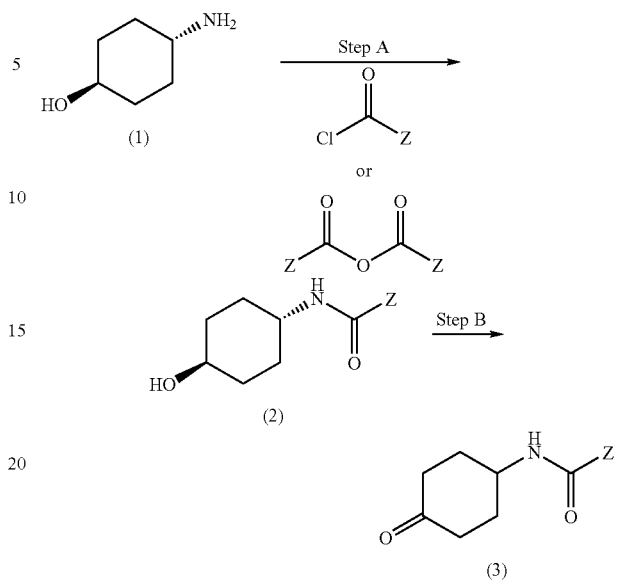

In Scheme I, Step A, an acid chloride or anhydride, such as isobutyric anhydride is reacted with a substituted or unsubstituted trans-4-aminocyclohexanol (1) and triethylamine in an inert solvent such as tetrahydrofuran or dioxane at about 0 to 50° C. for about 10 to 48 hours. The amide product of formula (2) (wherein Z represents for example a small alkyl, such as isopropyl, or cycloalkyl, O-Bn, or alkoxy) may be isolated by diluting with water, and washing with diethyl ether to remove by-products. The amide (2) may then be salted out by adding sodium chloride and extracted with dichloromethane. In addition, amide (2) that precipitates out of the aqueous can also be isolated by filtration.

Another preferred method of performing Step A, uses an inorganic base such as potassium carbonate in a protic solvent such as methanol with an acid chloride, with cyclopropylcarbonyl chloride being preferred. The reaction is conducted at about 0 to 50° C. for about 10 to 48 hours. The product may be isolated by concentration of the reaction and resuspension in methanol/dichloromethane chloride to remove the inorganic salts.

In Scheme I, Step A, wherein the product (2) has Z=O-benzyl, the preferred method is that of Janda, K. D. and Ashley, J. A. *Synth. Comm.* (1990) 20, 1073-1082.

In Scheme I, Step B, a derivative of formula (2) is oxidized to a ketone of formula (3) using an oxidizing agent such as pyridinium chlorochromate in an inert solvent such as dichloromethane and strring at about 0 to 50° C. for about 10 to 48 hours. The reaction is mixed with a large amount of silica and filtered over a silica pad eluting with an appropriate solvent such as dichloromethane and ethyl acetate/hexane to obtain a cyclic keto amide of formula (3).

Alternatively, particulary wherein Z=O-benzyl, a Swern oxidation is the preferred method to obtain the ketone of formula (3). The Swern oxidation uses conditions well known to those skilled in the art, such as treatment with oxalyl chloride in the presence of DMSO in an inert solvent such as dichloromethane at a temperature of about −80 to −60° C. for about 1 to 2 hours, followed by treatment with triethylamine at −80° C. to room temperature for about 1 to 24 hours. The product is isolated using standard extraction techniques.

Scheme II

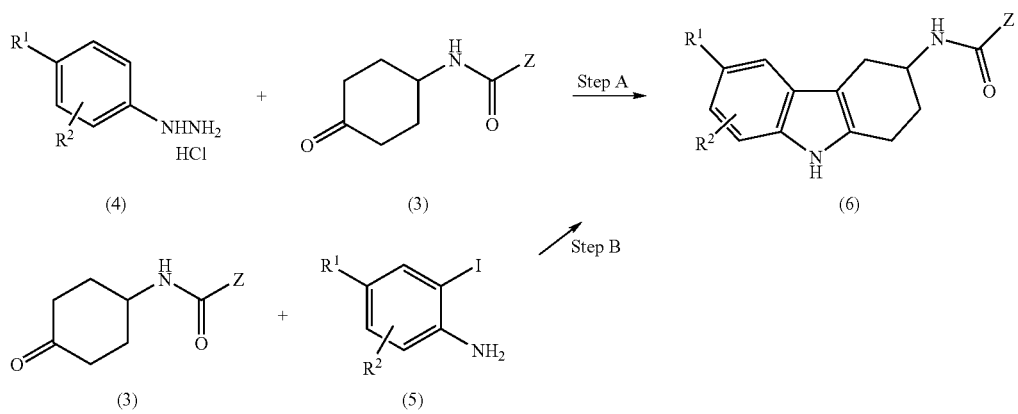

In Scheme II, Step A, a phenylhydrazine salt (for example the hydrochloride salt) of formula (4), is reacted with a cyclic ketone of formula (3) in a Fischer indole synthesis to provide a tetrahydrocarbazole of formula (5). The hydrazine and ketone are reacted in ethanol saturated with hydrogen chloride gas at reflux for about 10 to 48 hours and isolated using standard aqueous workup techniques. Alternatively the reaction can be accomplished without the hydrogen chloride gas simply by using a phenyl hydrazine hydrochloride salt of formula (4) with a ketone of formula (3) in ethanol at about 50 to 85° C. for about 10 to 72 hours. In yet another procedure a phenylhydrazine hydrochloride salt of formula (4) and a ketone of formula (3) can be reacted as a vigorously stirred heterogeneous mixture in water and concentrated hydrochloric acid at about 80 to 100° C. for about 4 to 8 hours as essentially described in U.S. Pat. No. 6,359,146B1. The tetrahydrocarbazole can then be isolated by filtration. Using yet another variation, acetyl chloride and absolute ethanol are stirred at 0° C. to room temperature for about 1 to 2 hours. A phenylhydrazine hydrochloride salt of formula (4) and a ketone of formula (3) are then added to the ethanol/HCl and refluxed for about 10 to 72 hours.

It will be recognized by one skilled in the art that phenyl hydrazines of formula (4) can be obtained from the corresponding aniline by treatment with nitrous acid to form the diazonium salt, followed by reduction with tin(II) chloride.

Isolation of the tetrahydrocarbazole derivative of formula (6) is accomplished by adding water directly and filtering the resulting precipitate or by using standard techniques of an aqueous workup and extraction with an organic solvent. The (R) and (S) enantiomers of tetrahydrocarbazoles of formula (6) are obtained by chiral chromatography using standard techniques common to one skilled in the art. The enantiomers are used in subsequent reactions as described in Scheme III through Scheme VIII.

In Scheme II, Step B, tetrahydrocarbazoles of formula (6) can be obtained by a palladium-catalyzed annulation reaction between a cyclic ketone of formula (3) and an iodoaniline of formula (5) as generally described in Chen, C., et. al., *J. Org. Chem.* (1997), 62, 2676-2677. The ketone and iodoaniline are reacted in an inert solvent such as dimethylformamide in the presence of a palladium catalyst such as palladium acetate and an amine base such as 1,4-diazobicyclo[2.2.2]octane (DABCO). The reaction is heated under anhydrous conditions at a temperature of about 80 to 150° C. for 6 to 48 hours. The product can be isolated by common extractive techniques and purified by silica gel chromatography.

Scheme III

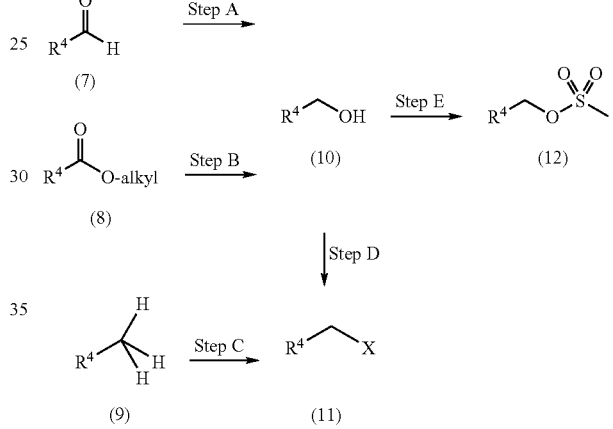

In Scheme III, Step A, an aldehyde of formula (7), is reduced to an alcohol of formula (10). A vast array of methods for reducing aldehydes are well known to those skilled in the art and can be found in the text of R. C. Larock in "Comprehensive Organic Transformations", VCH Publishers, 1989, p. 528-534. The preferred method is reduction with sodium borohydride in ethanol or methanol at room temperature to 60° C. for about 30 min to 24 hours.

Alternatively, as shown in Scheme III, Step B, the alcohol is obtained by reducing an ester of formula (8). Numerous methods for reducing carboxylic esters to alcohols are well known to those skilled in the art and can be found in the text of R. C. Larock in "Comprehensive Organic Transformations", VCH Publishers, 1989, p. 549-551. The preferred method is reduction with lithium borohydride in an aprotic solvent such as tetrahydrofuran or dioxane at room temperature to reflux temperature for about 1 to 48 hours.

In Scheme III, Step C, a compound of formula (9), wherein $R^4$ is aryl or heteroaryl, is halogenated to provide an alkyl halide of formula (11). The compound of formul (9) is treated with a free radical initiator such as benzoyl peroxide or 1,1'-azobisisobutyronitrile or 1,1'-azobis(cyclohexanecarbonitrile) in carbon tetrachloride with N-chlorosuccinimide or N-bromosuccinimide under irradiation from a UV light. The preferred method is treatment with 1,1'-azobis(cyclohexanecarbonitrile) and N-bromosuccinimide at about room temperature to the refluxing temperature of carbon tetrachloride, for about 4 to 48 hours. The product may then be purified using standard techniques such as filtration of insoluable components, followed by silica gel chromatography.

In Scheme III, Step D, An alcohol of formula (10) is converted to an alkyl halide of formula (11), wherein X represents, for example, Br or Cl, with Br being preferred. A variety of methods for this transformation are known to those skilled in the art such as the following: 47% hydrogen bromide in acetic acid, dibromotriphenylphosphorane with triethylamine, thionyl chloride, phosphorous tribromide, N-chlorosuccinimide or N-bromosuccinimide with methyl sulfide, or acetyl bromide. The preferred method is treatment with acetyl bromide at −78° C. to 50° C. with the preferred temperature at 0° C. to room temperature, for about 1 to 48 hours. The product is isolated using an ethyl acetate, sodium bicarbonate workup and may be purified by standard techniques such as silica gel chromatography. Another preferred method is treatment of the alcohol with thionyl chloride at about 0° C. for 30 minutes to 4 hours to give an alkyl halide of formula (II), wherein X represents Cl.

Alternatively, in Scheme III, Step E, an alcohol of formula (10) is converted to a methylsulfonic acid ester of formula (12). The alcohol is combined with an organic base such as triethylamine or diisopropylethylamine and treated with methanesulfonylchloride in an inert solvent such as dichloromethane. The reaction is maintained at 0° C. to room temperature for 15 minutes to 4 hours. The product is isolated by extractive techniques known to one skilled in the art.

In Scheme IV, Step A, a tetrahydrocarbazole of formula (6) is alkylated with a alkylating agent of formula (11) wherein X is bromide or chloride, or with an agent of formula (12) to give a N-substituted tetrahydrocarbazole of formula (14). The anion of the tetrahydrocarbazole is generated in an inert solvent such as dimethylformamide, N-methylpyrrolidinone, tetrahydrofuran, dioxane, or toluene with a base such as sodium hydride, potassium hydride, potassium or sodium bis(trimethylsilyl)amide, or cesium carbonate. Preferred solvents are dimethylformamide and tetrahydrofuran with sodium hydride and potassium bis(trimethylsilyl)amide being the preferred bases. After about 10 to 60 minutes treatment with base, the anion is treated with a benzyl halide, at about −78 to 23° C. and continuing for about 4 to 48 hours. When using cesium carbonate the base and benzyl halide can be added directly and the reaction heated for about 50 to 100° C. for about 10 to 72 hours.

In Scheme IV, Step B, a tetrahydrocarbazole of formula (6), is reacted with an alcohol of formula (10), in a Mitsunobu reaction to provide a tetrahydrocarbazole of formula (14). Common redox systems, known to those skilled in the art, such as diethyl azodicarboxylate (DEAD)/triphenylphosphine, N,N,N',N'-tetramethylazodicarboxamide (TMAD)/tributylphosphine or 1,1'-(azodicarbonyl)dipiperidine (ADDP)/tributylphosphine are used to effect the transformation, with the latter being the preferred redox system. The product is isolated by solvent evaporation and dissolution of the crude material in ethyl acetate/water. The mixture is eluted over a solid-phase extraction cartridge with ethyl Scheme IV

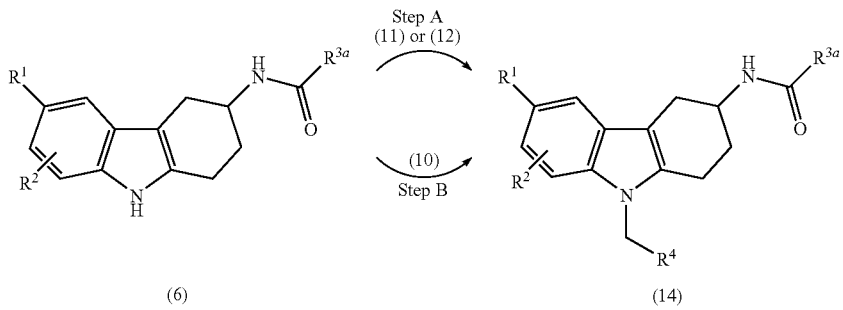

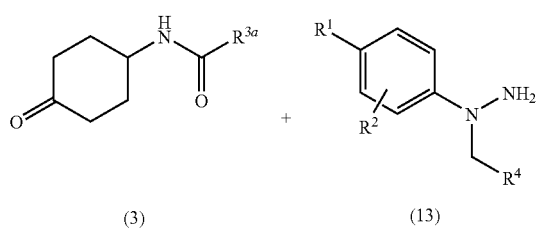

acetate and may then be purified using standard techniques such as silica gel chromatography.

Alternatively, stabilized trialkylphosphoranes, such as (cyano-methylene)tributylphosphorane (CMBP) or (cyano-methylene)trimethylphosphorane (CMMP) (prepared as described in Tsunoda, T., et al., *Tetrahedron Lett.* (1996) 37, 2459-2462) can be used with alcohols of formula (6) to prepare a tetrahydrocarbazole of formula (11) (see Bobrun, A. and Casi, G., *Tetrahedron Lett.* (2002)43, 2187-2190).

In Scheme IV, Step C, is provided yet an additional route to obtain tetrahydrocarbazoles of formula (14), wherein the tetrahydrocarbazole is constructed with the benzyl group attached to the phenyl hydrazine as in formula (13). N-benzyl-N-phenylhydrazines are obtained as described by Audrieth, L. F., Weisiger, J. R., Carter, H. E., *J. Org. Chem.* (1941) 6, 417-420. The ketone of formula (3) and the N-benzyl-N-phenylhydrazine of formula (13) are stirred in acetic acid at 50° C. to reflux temperature for about 1 to 24 hours. The product is isolated by dilution with water and extraction with benzene or toluene and then purified by recrystillization.

variety of methods known to those skilled in the art. These include: sodium ethanethiolate in DMF, 48% HBr in acetic acid, neat pyridine hydrochloride at high temperature, and boron tribromide. The methoxy tetrahydrocarbazole is preferably treated with boron tribromide in an inert solvent such as dichloromethane at a temperature of 0 to 40° C. for about 4 to 48 hours. The product is isolated by solvent evaporation in the presence of methanol and may be purified by silica gel chromatography.

In Scheme V, Step B, a phenol of formula (16) is alkylated to give a tetrahydrocarbazole of formula (17) using an alkyl halide and an inorganic base such as potassium carbonate, cesium carbonate or sodium hydride in an inert solvent such as acetone, dimethylformamide or N-methylpyrrolidinone. Preferred conditions use cesium carbonate or sodium hydride in dimethylformamide at room temperature to 50° C. for about 4 to 48 hours. The product is isolated by extractive techniques and may be purified by silica gel chromatography.

Scheme V

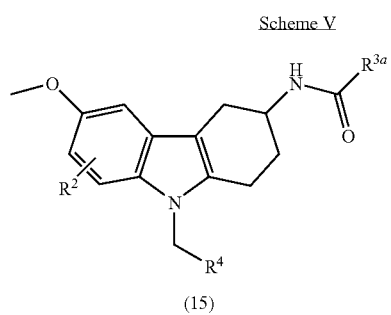

(15)

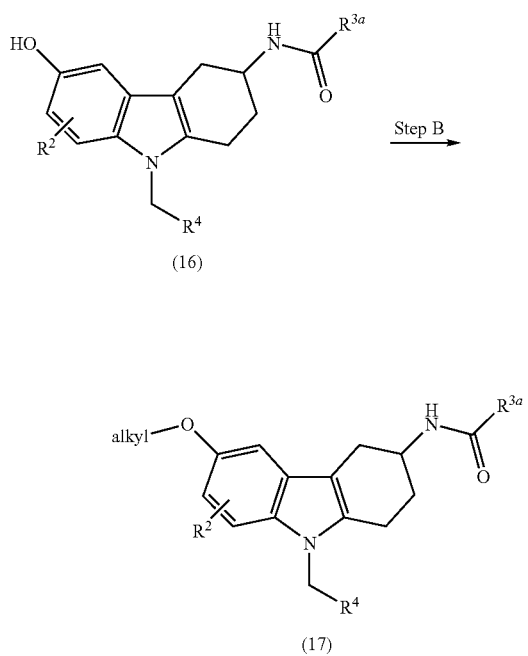

(16)

(17)

In Scheme V, a methoxy tetrahydrocarbazole of formula (15) is demethylated to give a phenol of formula (16). Conversion of a methoxy aryl to a phenol is accomplished by a Scheme VI

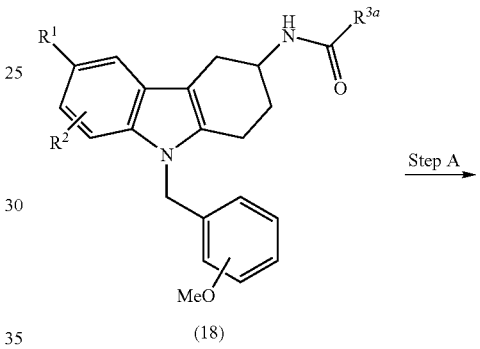

(18)

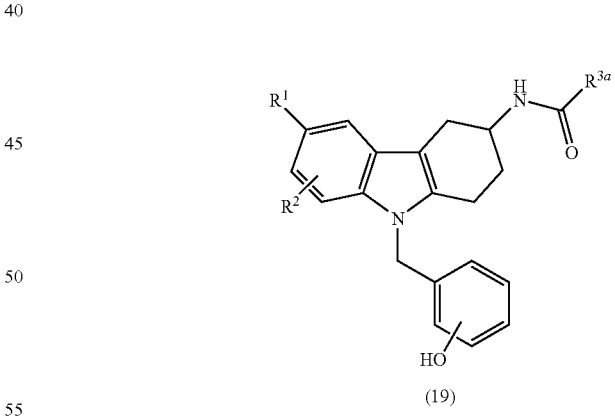

(19)

In Scheme VI, a methoxybenzyl tetrahydrocarbazole of formula (18), is converted to a phenol of formula (19), a reaction which can be accomplished by a variety of methods well-known to those skilled in the art, as described in Scheme V, Step A. The preferred method is treatment with boron tribromide in an inert solvent such as dichloromethane at a temperature of 0 to 40° C. for about 4 to 48 hours. The product is isolated by solvent evaporation in the presence of methanol or by common extractive tenchniques using water and an organic solvent. Purification is accomplished by silica gel chromatography.

Scheme VII

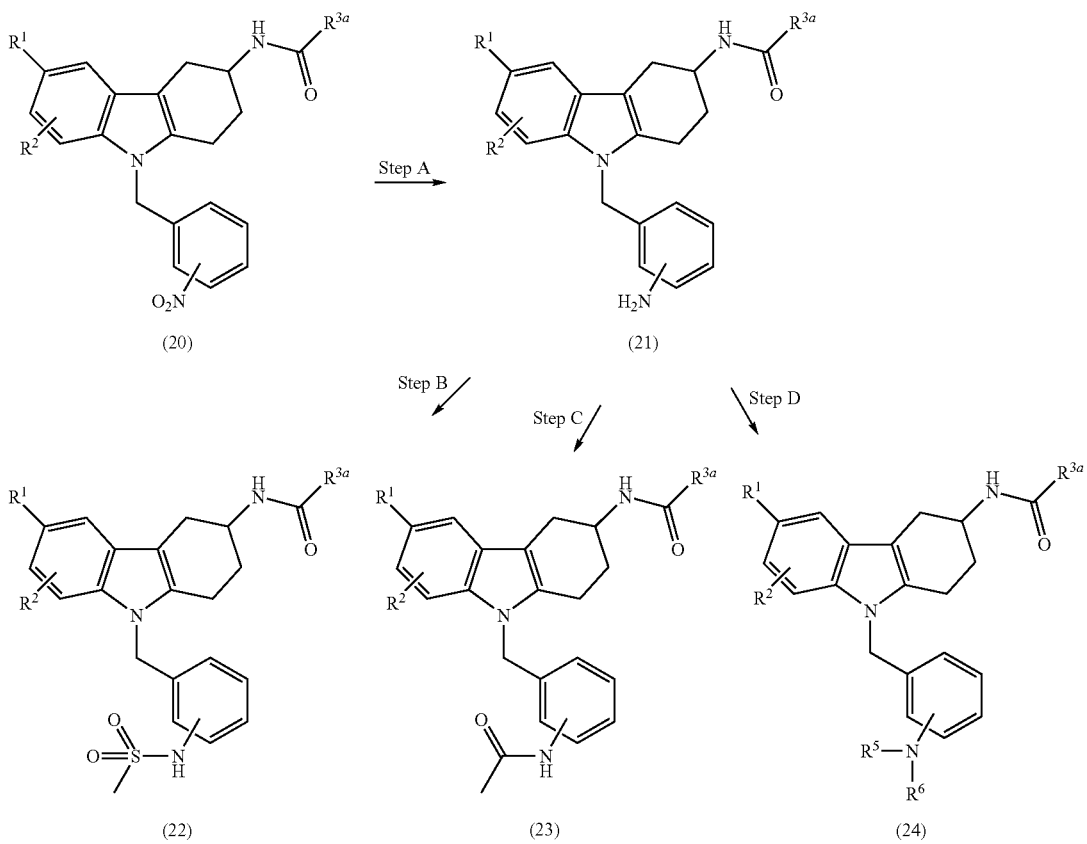

In Scheme VII, the nitro group is further elaborated to amines and amine derivatives using chemistry well known to those skilled in the art. Thus in Scheme VII, Step A, a nitro benzyl tetrahydrocarbazole of formula (20) is reduced to an aniline of formula (21). There are a variety of methods for reducing arylnitro groups which are well known to those skilled in the art and can be found in the text of R. C. Larock in "Comprehensive Organic Transformations", VCH Publishers, 1989, p. 412-415. The preferred method is reduction with tin(II)chloride dihydrate in a mixture of a protic solvent, such as ethanol, and concentrated hydrochloric acid at a temperature of 40 to 80° C. for about 30 minutes to 24 hours. The product is isolated by taking the reaction alkaline with sodium hydroxide and extracting with an organic solvent. The product is purified by silica gel chromatography.

Alternatively, another preferred method for doing the reduction is with sulfided platinum, 5% wt. on carbon in a solvent such as methanol or ethanol, on a Parr shaker under 55 psi hydrogen. The hydrogenation is preformed at room temperature for about 4 to 24 hours. The product is isolated by filtration techniques common to those skilled in the art and purified by silica gel chromatography.

In Scheme VII, Step B, the aniline of formula (21) can be converted to other derivatives, such as the sulfonamide of formula (22). The aniline is reacted with a sulfonyl chloride in an inert solvent such as dichloromethane or dimethylformamide with an organic base such as pyridine. The reaction is performed at a temperature of 0 to 40° C. for about 4 to 48 hours. The product can be isolated by common extractive techniques and purified by silica gel chromatography.

In Scheme VII, Step C, an aniline of formula (21) is acylated to form an amide of formula (23). The aniline is reacted with an acid chloride in an inert solvent such as dichloromethane or tetrahydrofuran in the presence of an organic base such as triethyl amine or diisopropylethylamine. The reaction is performed at a temperature of 0 to 40° C. for about 4 to 48 hours. The product can be isolated by common extractive techniques and purified by silica gel chromatography.

In Scheme VII, Step D, an aniline of formula (21) is converted to an alkyl amine of formula (24) (one or both of $R^5$ and $R^6$ represent an alkyl group) in a reductive amination. Methods for reductive amination are well known to those skilled in the art and are and can be found in the text of R. C. Larock in "Comprehensive Organic Transformations", VCH Publishers, 1989, p. 421-423. A preferred method to obtain an alkylamine of formula (24) is reaction with an aldehyde in an inert solvent such as tetrahydrofuran or dimethylformamide in the presence of sodium triacetoxyborohydride and acetic acid. The reaction is heated 40 to 100° C. for 4 to 48 hours with additional amounts of reagents as needed. The product can be isolated by common extractive techniques and purified by silica gel chromatography.

Alternatively the reduction can be accomplished with sodium cyanoborohydride in an inert solvent such as acetonitrile, dimethylformamide, or tetrahydrofuran. An alkyl aldehyde such as formaldehyde can be used in excess to obtain a dimethyl aniline of formula (24) ($R^5$ and $R^6$ each represent methyl). The reaction is accomplished at room temperture to the reflux temperature of the solvent for about 4 to 48 hours. The product can be isolated by common extractive techniques and purified by silica gel chromatography.

Scheme VIII

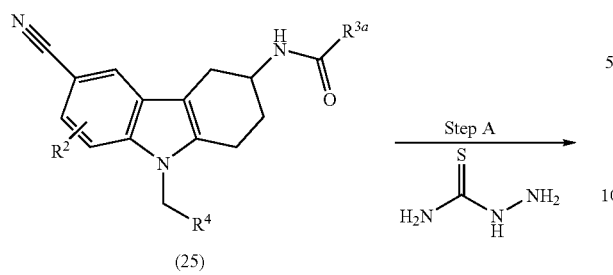

(25)

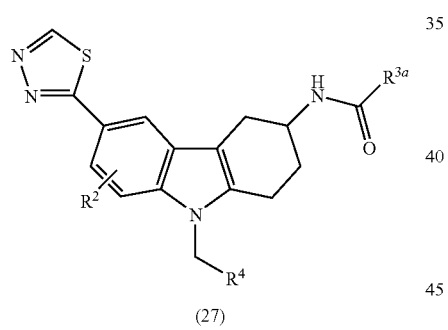

(26)

(27)

Scheme IX

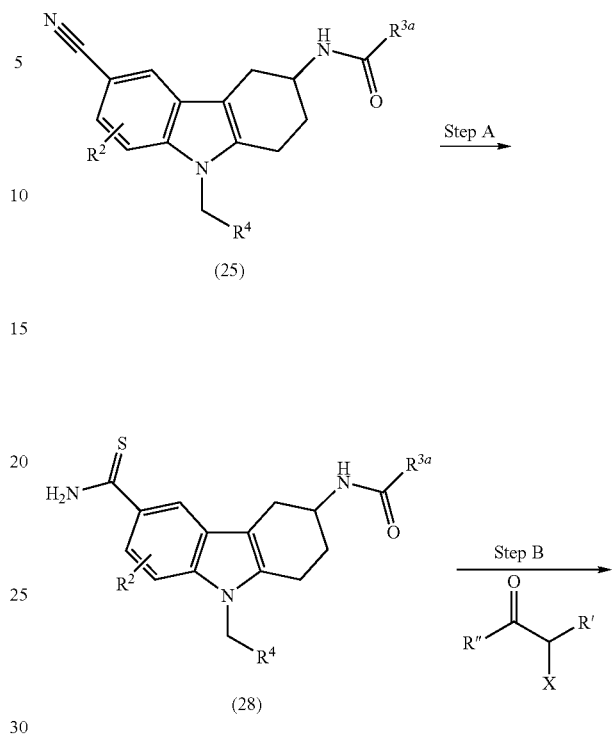

(25)

(28)

(29)

In Scheme VIII, Step A, a nitrile tetrahydrocarbazole, of formula (25) is cyclized with thiosemicarbazide to give an aminothiadiazole of formula (26). The nitrile and thiosemicarbazide are heated at about 40 to 120° C. for about 4 to 48 hours in an organic acid such as trifluoroacetic acid. The reaction mixture is poured onto dilute ammonium hydroxide and the precipitate filtered to obtain the product (26). Alternatively the product (26) is isolated by standard extractive techniques and may then be purified by silica gel chromatography.

In Scheme IV, Step B, the aminothiadiazole may be deaminated using isoamylnitrite to give an unsubstituted thiadiazole derivative of formula (27). The aminothiadiazole (26) is treated with isoamylnitrite in a solvent such as dimethylformamide or N-methylpyrrolidinone at ambient temperature to 100° C. for about 0.5 to 16 hours. The product is isolated using standard extractive techniques with water and ethyl acetate and may be purified by silica gel chromatography.

In Scheme IX, Step A, a nitrile tetrahydrocarbazole of formula (25) is converted to a primary thioamide of formula (28). The nitrile is treated with thioacetamide in refluxing 4 N hydrochloric acid in dioxane for about 4 to 48 hours. The product mixture is neutralized with sodium bicarbonate and the product (28) isolated by standard techniques, such as filtration.

In Scheme V, Step B, a primary thioamide of formula (28) is reacted with an alpha haloketone wherein X represents Cl or Br and R' and R" each independently represent, for example, H or alkyl, to provide a thiazole of formula (29). The thioamide is treated with the alpha haloketone in a solvent such as dimethylformamide, N-methylpyrrolidinone, tetrahydrofuran, dioxane, toluene, ethanol, or isopropanol at about 50 to 120° C. for about 4 to 48 hours. Upon cooling the reaction is mixed with water and the precipitate collected. Alternatively, the product (29) can be isolated by standard extractive techniques and purified by silica gel chromatography.

Scheme X

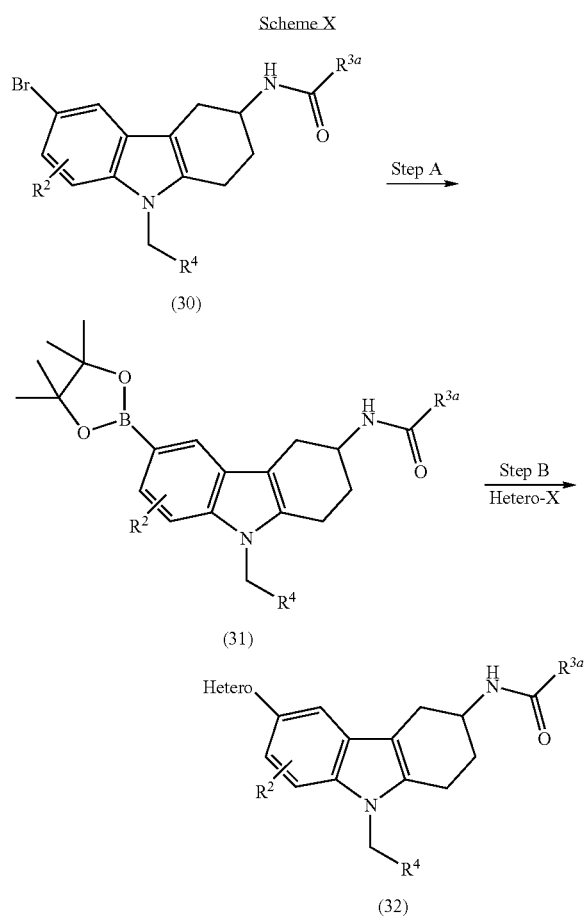

In Scheme X, Step A, a bromotetrahydrocarbazole of formula (30), prepared for example, as described in Schemes II-IV, is reacted with a boronate ester such as bis(pinacoloto) borane, a phosphine ligand, such as tricyclohexylphosphine, a palladium catalyst such as tris(benzylideneacetone)dipalladium, and a base such as potassium acetate. An inert solvent such as dimethyl sulfoxide or dimethyl formamide is used and the reaction heated under argon or nitrogen at 50 to 120° C. for 4 to 48 hours. The reaction is poured into water and isolated using standard extractive techniques. The product may then be purified by eluting over neutral alumina to provide a boronate ester of formula (31).

In Scheme X, Step B, the boronate ester of formula (31) is coupled to a unsubstituted or substituted haloheteroaryl (Hetero-X, where X represents a halo group and Hetero represents unsubstituted or substituted heteroaryl) using a Suzuki reaction with a palladium catalyst such as tetrakis(triphenylphosphine)palladium (0), and a base such as 2M potassium carbonate. An inert solvent is used such as tetrahydrofuran, dioxane, dimethylformamide, N-methylpyrrolidinone, or ethylene glycol dimethyl ether, with dioxane being preferred. The reaction is heated under an inert atmosphere of argon or nitrogen at 50 to 120° C. for 4 to 48 hours. The reaction is poured into water and isolated using standard extractive techniques. The product may then be purified by silica gel chromatography to provide a heterocyclic-substituted tetrahydrocarbazole of formula (32).

Scheme XI

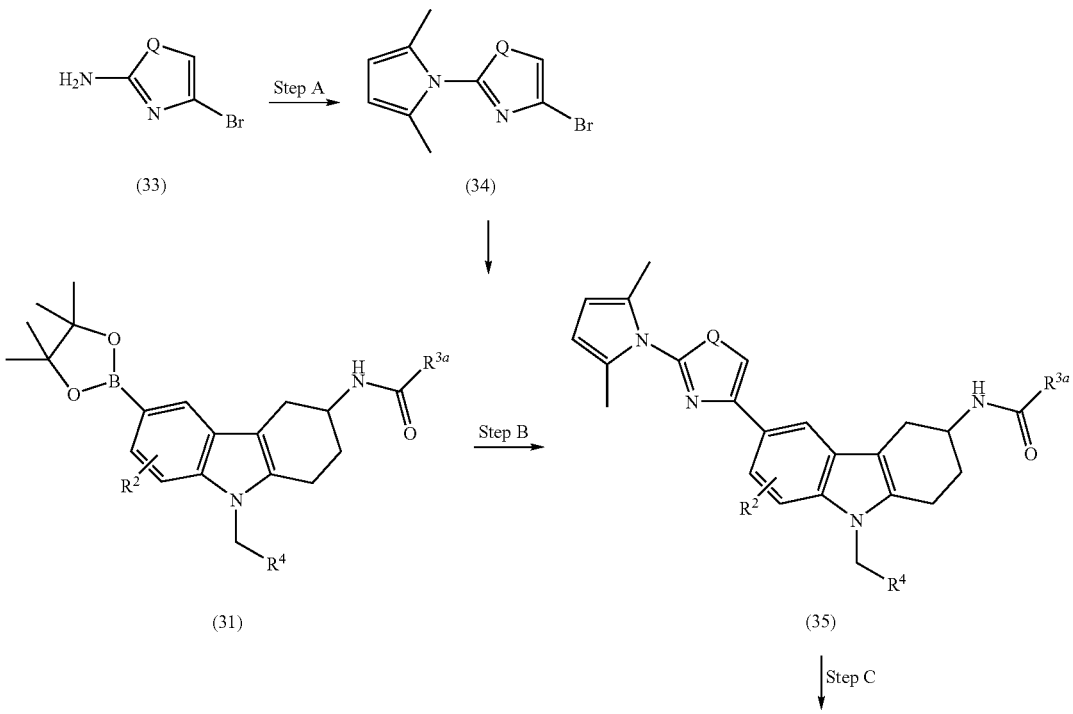

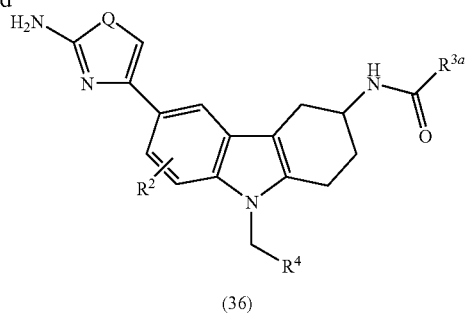

(36)

In Scheme XI, Step A, an aminohaloheteroaryl of formula (33), wherein Q represents O, S, N, or CH=CH, is reacted with hexane-2,5-dione with sodium carbonate and acetic acid in an inert solvent such as benzene. The reaction is refluxed with a Dean-Stark trap for 4 to 48 hours according to a procedure similar to that described by Macor, J. E., Chenard, B. L., Post, R. J. *J. Org. Chem.*(1994) 59, 7496-7498. The reaction is concentrated and the product may then be purified by silica gel chromatography to give the amino protected heteroaryl of formula (34).

In Scheme XI, Step B, the protected aminobeteroaryl of formula (34) is coupled to the boronate ester of formula (31) using conditions as essentially described for Scheme X, Step B, above to give a heteroaryl-substituted tetrahydrocarbazole of formula (35). A preferred palladium catalyst for this reaction is dichloro[1,1'-bis(diphenylphosphino)ferrocene]palladium (II) dichloromethane adduct using 2M sodium carbonate in dioxane.

In Scheme XI, Step C, the protected heteroaryl of formula (35) is deprotected using about a ten fold excess of hydroxylamine hydrochloride, triethylamine and 1 molar sodium hydroxide in refluxing ethanol for about 4 to 48 hours. The product is isolated using standard extractive techniques to give the aminoheteroaryl-substituted tetrahydrocarbazole of formula (36).

Scheme XII

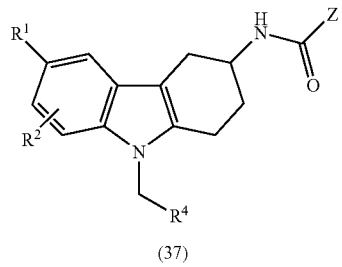

(37)

Step A, where Z = OBn
or
Step B, where Z = O-tBu
or
Step C, where Z = Me

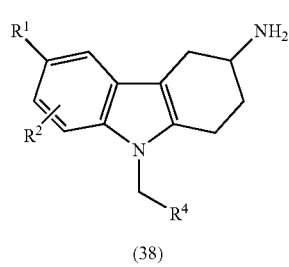 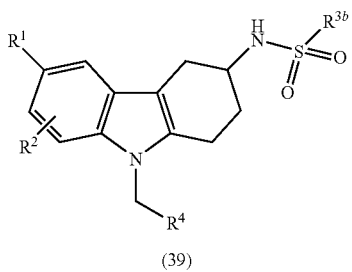

(38)        Step D        (39)
ClSO$_2$R$^{3b}$

Step E
(42)

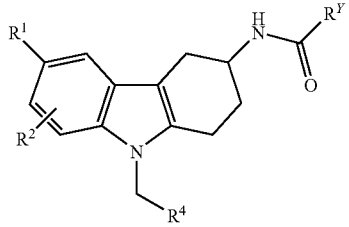

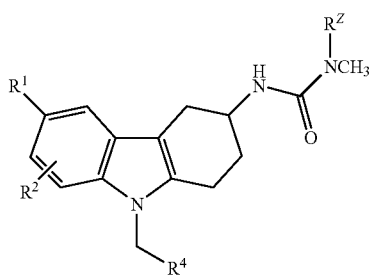

In Scheme XII, Step A, a substituted tetrahydrocarbazole of formula (37), where Z=OBn is deprotected to provide the amine substituted tetrahydrocarbazole of formula (38). Common deprotection conditions for removing a carboxybenzyl (CBZ) group are well know by those skilled in the art and can be found in the text of T. W. Green and P. G. M. Wuts in "Protective Groups in Organic Synthesis", John Wiley & Sons, Inc., 1991, 335-338. Preferred conditions use a solvent mixture of ethanol and tetrahydrofuran at room temperature with 5% or 10% palladium on carbon under hydrogen gas at normal atmospheric pressure.

In Scheme XII, Step B, a tetrahydrocarbazole of formula (37), wherein the amide is protected as a tert-butyl carbamate (BOC) (Z=O-t-butyl), is deprotected to give a provide the amine substituted tetrahydrocarbazole of formula (38). Common deprotection conditions for removing a BOC group are well know by those skilled in the art and can be found in the text of T. W. Green and P. G. M.

Wuts in "Protective Groups in Organic Synthesis", John Wiley & Sons, Inc., 1991, 328-330. Preferred conditions use 4N hydrogen chloride in dioxane at a temperature of about 0° C. to room temperature for about 10 minutes to 24 hours. The product can be isolated as the HCl salt by filtration.

In Scheme XII, Step C, a tetrahydrocarbazole of formula (37) wherein Z=Me is hydrolyzed to an amino substituted tetrahydrocarbazole of formula (38) as the maleic acid salt. The amide is treated with potassium hydroxide pellets in a mixture of 2-methoxyethanol and water and heated at 90° C. to reflux temperature for about 4 to 48 hours. The product is isolated by removal of solvent in vacuo and extraction with water and an organic solvent. The product is purified by recrystillization with maleic acid to give a compound of formula (38) as the maleic acid salt.

In Scheme XII, Step D, a tetrahydrocarbazole amine of formula (38) is sulfonylated to give a sulfonamide of formula (39) by reaction with a sulfonyl halide or a sulfamoyl chloride. The free amine or the salt of the amine is combined with an excess of an amine base such as triethylamine or diisopropylethylamine in an inert solvent such as tetrahydrofuran, dichloroethane or dichloromethane. The reaction is stirred at a temperature of 0 to 40° C. for 1 to 24 hours. The product is isolated by common extractive techniques and may be purified by recrystallization or by silica gel chromatography.

In Scheme XII, Step E, a tetrahydrocarbazole amine of formula (38) is acylated with a compound of structure (42) (wherein X represents halogen and $R^Y$ represents, for example, $R^{3a}$ or OPh-p-$NO_2$) to give an amide of formula (40). It is recognized by one skilled in the art that there are an immense number of methods for acylating amines using carboxylic acids. Such methods are well known to those skilled in the art and can be found in the text of R. C. Larock in "Comprehensive Organic Transformations", VCH Publishers, 1989, p. 972-976. The preferred method to obtain a tetrahydrocarbazole of formula (40) is by acylation with an acid chloride (X represents, for example Cl), a carbamoyl chloride, or a chloroformate using conditions well known to those skilled in the art. The free amine or a salt of the amine is combined with an excess of an organic amine base such as triethylamine or diisopropylethylamine in an inert solvent such as tetrahydrofuran, dichloroethane or dichloromethane, N-methylpyrrolidinone, or N,N-dimethylformamide, or a mixture thereof. The reaction is stirred at a temperature of 0 to 40° C. for 1 to 72 hours. The product is isolated by common extractive techniques and may be purified by recrystillization or by silica gel chromatography.

In Scheme XI, Step F, a tetrahydrocarbazole amine of formula (39), wherein $R^Y$ represents O-Ph-p-$NO_2$ (p-nitrophenyloxy) is reacted with an alkyl amine or an N,O-dialkylhydroxyamine to give tetrahydrocarbazole ureas of formula (41). The p-nitrophenylcarbamate is combined with an excess of an organic amine base such as triethylamine or diisopropylethylamine in a inert aprotic solvent such as tetrahydrofuran, dioxane, N-methylpyrrolidinone, or N,N-dimethylformamide. The preferred method uses tetrahydrofuran with the hydrochloride salt of methylamine of N,O-dimethylhydroxylamine at a temperature of 0 to 60° C. for about 1 to 48. The product is isolated by common extractive techniques and may be purified by recrystillization or by silica gel chromatography.

Scheme XIII

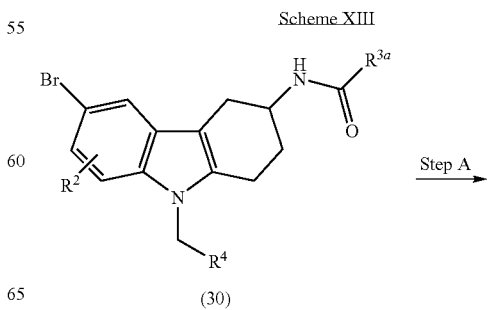

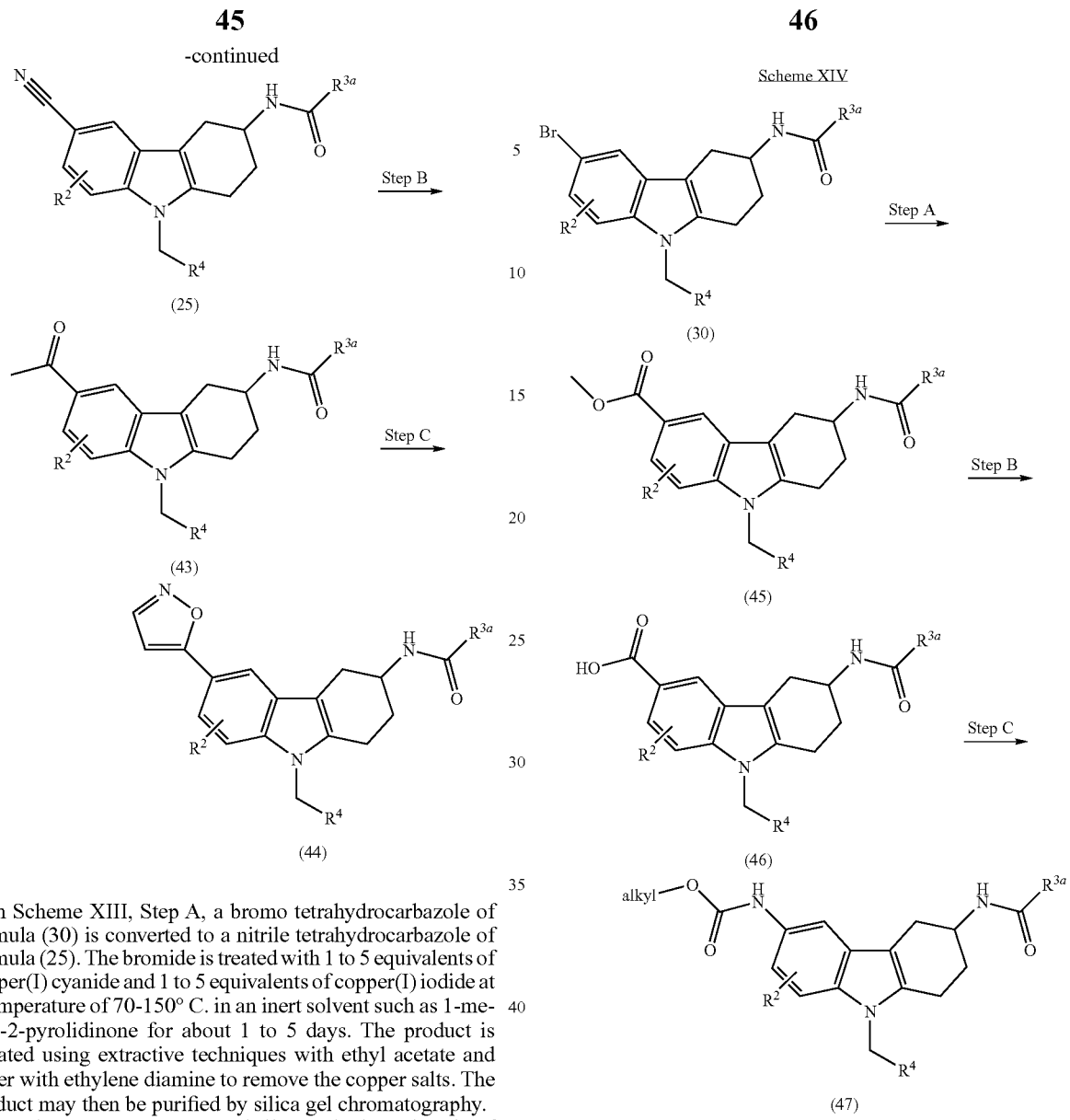

In Scheme XIII, Step A, a bromo tetrahydrocarbazole of formula (30) is converted to a nitrile tetrahydrocarbazole of formula (25). The bromide is treated with 1 to 5 equivalents of copper(I) cyanide and 1 to 5 equivalents of copper(I) iodide at a temperature of 70-150° C. in an inert solvent such as 1-methyl-2-pyrolidinone for about 1 to 5 days. The product is isolated using extractive techniques with ethyl acetate and water with ethylene diamine to remove the copper salts. The product may then be purified by silica gel chromatography.

In Scheme XIII, Step B, a nitrile tetrahydrocarbazole of formula (25) is converted to an acetyl tetrahydrocarbazole of formula (43) by a Grignard reaction with methyl magnesium halide. The nitrile is treated, preferably with methyl maganesium bromide in an inert solvent such as diethyl ether or tetrahydrofuran. The preferred method uses tetrahydrofuran at a temperature of 0 to 50° C. for about 1 to 24 hours. The reaction is quenched with an alcohol, such as methanol, the solids removed and the filtrate concentrated. The material is treated with refluxing 1N hydrochloric acid/tetrahydrofuran for about 1 to 5 hours. A water immiscible organic solvent, such as ethyl acetate, is added and the resulting precipitate discarded to leave the product.

In Scheme XIII, Step C, an acetyl tetrahydrocarbazole of formula (43) is converted to the isoxazole substituted tetrahydrocarbazole of formula (44). The acetyl is treated neat with dimethylformamide dimethylacetal at a temperature of 80 to 100° C. for about 12 hours to 4 days. After concentrating, the intermediate enamine is treated with bydroxylamine hydrochloride in an inert solvent such as dioxane or THF at a temperature of room temperature to 50° C. for about 30 min to 12 hours. Water is added and the isoxazole of formula (44) collected by filtration.

In Scheme XIV, Step A, a bromo tetrahydrocarbazole of formula (30) is carbonylated to provide an ester substituted tetrabydrocarbazole of formula (45). The bromide is combined with an acetate salt such as sodium acetate in an alcoholic solvent such as methanol in the presence of a palladium catalyst under an atmosphere of carbon monoxide. The preferred method uses dichloro[1,1'-bis(diphenyl-phosphino) ferrocene]palladium (II) dichloromethane adduct on a Parr reactor with the reaction vessel charged with 55 psi of carbon monoxide at a temperature of 50 to 100° C. for about 4 to 48 hours. The product can be isolated directly by silica gel chromotagraphy.

In Scheme XIV, Step B, an ester substituted tetrahydrocarbazole of formula (45) is hydrolyzed to an acid of formula (46). It will be recognized by one skilled in the art that ester hydrolysis is a common organic transformation and that there are numerous methods for effecting this reaction such as various aqueous inorganic bases. Specific methods for methyl ester hydrolysis can be found in T. W. Green and P. G. M. Nuts, "Protective Groups in Organic Chemistry" John Wiley & Sons, Inc.,$2^{nd}$ edition, 1991, p. 231-234. The preferred method uses an excess of lithium hydroxide in a solvent mixture of water, a protic solvent, such as methanol, and an inert water miscible organic solvent such as tetrahydrofuran. The reaction is preformed at a temperature of 0° C. to the reflux temperature of the solvent for a period of about 1 to 48 hours. The product is isolated by common extractive techniques, such as acidification followed by extraction with an organic solvent.

In Scheme XIV, Step C, the acid substituted tetrahydrocarbazole of formula (46) is converted to a carbamate of formula (47) using a Curtius rearrangement. Curtius rearrangements are well-known to those skilled in the art and there are numerous protocols to effect this transformation as found in the text of R. C. Larock in "Comprehensive Organic Transformations", VCH Publishers, 1989, p. 431-432. The preferred method uses an azide transfer reagent, such as diphenylphosphorylazide and an organic amine base, such as triethylamine in an inert aromatic solvent, such as benzene or toluene. The reaction is preformed at a temperature of 50° C. to the reflux temperature of the solvent for about 4 to 24 hours to effect rearrangement to the isocyanate. The isocyanate is reacted in situ with an alcohol, such as methanol or ethanol to provide compounds of formula (47). The product is isolated and purified using common extractive techniques and silica gel chromatography.

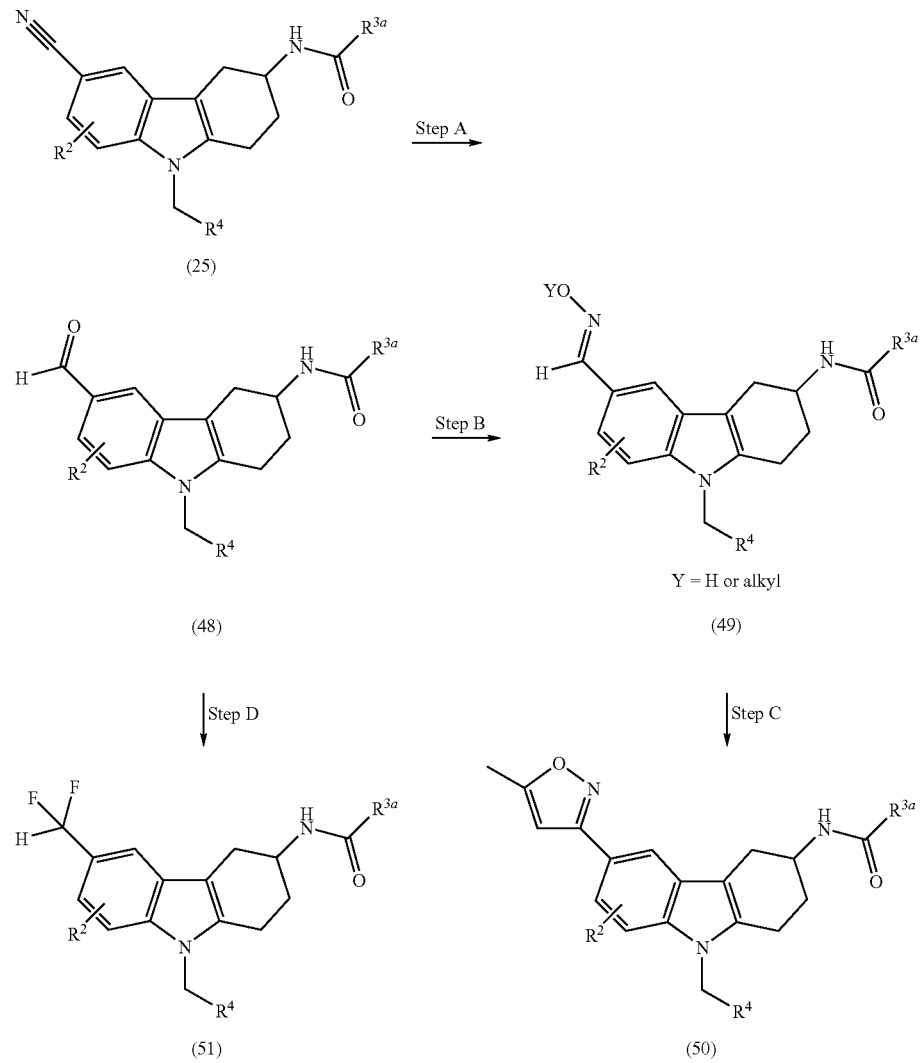

In Scheme XV, Step A, a nitrile tetrahydrocarbazole or formula (25), is reduced to a formyl tetrahydrocarbazole of formula (48). The nitrile is treated with aluminum-nickel catalyst in 90 to 95% formic acid at room to reflux temperature for about 2 to 48 hour. The product is isolated by addition of a protic solvent such as methanol, followed by filtration and concentration of the filtrate. The residue is further purified by common extractive techniques such as with sodium bicarbonate solution and ethyl acetate to provide the aldehyde of formula (48).

In Scheme XV, Step B, a formyl tetrahydrocarbazole of formula (48) is converted by addition of hydroxylamine or alkoxyamine to give an oxime tetrahydrocarbazole of formula (49). The aldehyde is treated with the hydrochloride salt of hydroxylamine or methoxyamine in pyridine at 0 to 100° C. for about 2 to 48 hour. The product is isolated using common isolation and extractive techniques known to those skilled in the art.

Alternatively, Step B, is accomplished in the presence of an inorganic base such as sodium or potassium hydroxide. The aldehyde of formula (48) is treated with hydroxylamine or alkoxyamine with sodium hydroxide in a protic solvent such as aqueous methanol or ethanol, with aqueous ethanol being preferred, at about room temperature to 50° C. for a period of about 2 to 48 hours. The product is isolated by common extractive techniques and purified over silica gel.

In Scheme XV, Step C, an oxime of formula (49), wherein Y=H, is oxidized to a nitrile oxide and then reacted in situ in a 1,3-dipolar cycloaddition a with an alkyne dipolarophile such as propyne to give an isoxazole tetrahydrocarbazole of formula (50). It will be recognized by one skilled in the art that there are various reagents used for effecting the conversion of oximes to nitrile oxides. Such reagents include chlorine, N-chlorosuccinimide, N-bromosuccinimide, nitrosyl chloride or sodium hypochlorite. The preferred method uses propyne gas in a solution with a solvent such as dichloromethane with a solution of sodium hypochlorite or bleach. The reaction is preferably preformed in a sealed tube at −30 to 50° C., with 23° C. being preferred for a time of about 1 to 48 hours. The product can be isolated and purified by common techniques such as extraction and silica gel chromatography.

In Scheme XV, Step D, a formyl tetrahydrocarbazole of formula (48) is converted via deoxo-fluorination to a difluoromethyl tetrahydrocarbazole of formula (51) using a nucleophilic fluorinating reagent. It will be recognized by one skilled in the art that dialklylaminosulfur trifluoride reagents, such as diethylaminosulfur trifluoride (DAST) or [bis(2-methoxyethyl)amino]sulfur trifluoride (Deoxofluor) are routinely used for introducing fluorine into organic molecules. The preferred conditions use 5 to 25 equivalents of Deoxofluor in an aprotic halogenated solvent, such as dichloroethane, but preferably dichloromethane, at a temperature of 0 to 80° C. for 1 to 48 hours. The product can be isolated and purified by common techniques such as neutralization with an inorganic base and extraction, followed by silica gel chromatography.

Scheme XVI

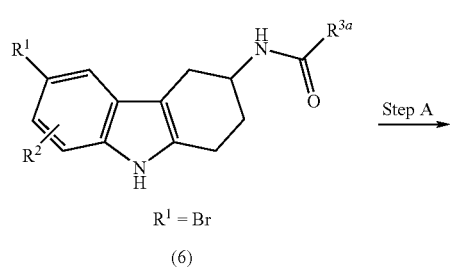

(6)

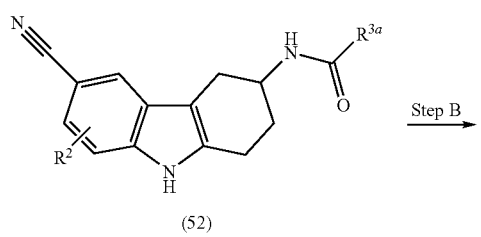

(52)

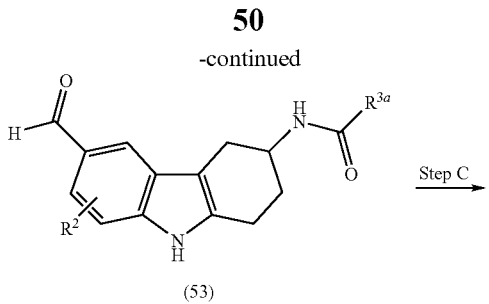

(53)

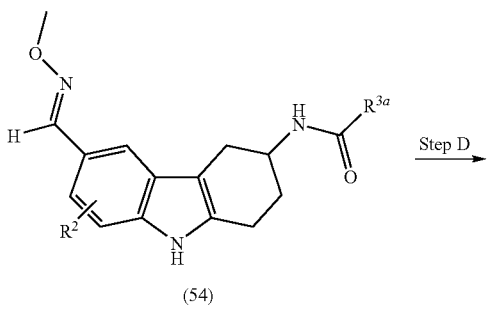

(54)

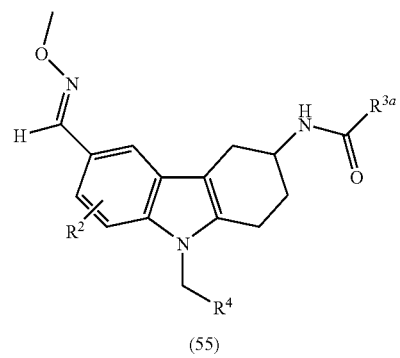

(55)

Scheme XVI describes syntheses wherein functionalization at R1 occurs prior to alkylation at the indole nitrogen with X—CH$_2$R$^4$. In Step A, a compound of formula (6), wherein R1=Br is converted to a nitrile tetrahydrocarbazole of formula (52) using conditions as essentially described for Scheme XIII, Step A.

In Scheme XVI, Step B, a nitrile of formula (52) is reduced to a formyl tetrahydrocarbazole of formula (53), using conditions as essentially described in Scheme XV, Step A.

In Scheme XVI, Step C, a formyl tetrahydrocarbazole of formula (53) is converted by addition of methoxyamine, to give a methoxime tetrahydrocarbazole of formula (54), using conditions as essentially described for Scheme XV, Step B.

In Scheme XVI, Step D, a methoxime tetrahydrocarbazole of formula (54), is alkylated to give a tetrahydrocarbazole of formula (55), using alkylating agents prepared as described in Scheme III, and using alkylating conditions as essentially described in Scheme IV, Step A or alternatively using Mitsunobu conditions as described in Scheme IV, Step B.

Scheme XVII

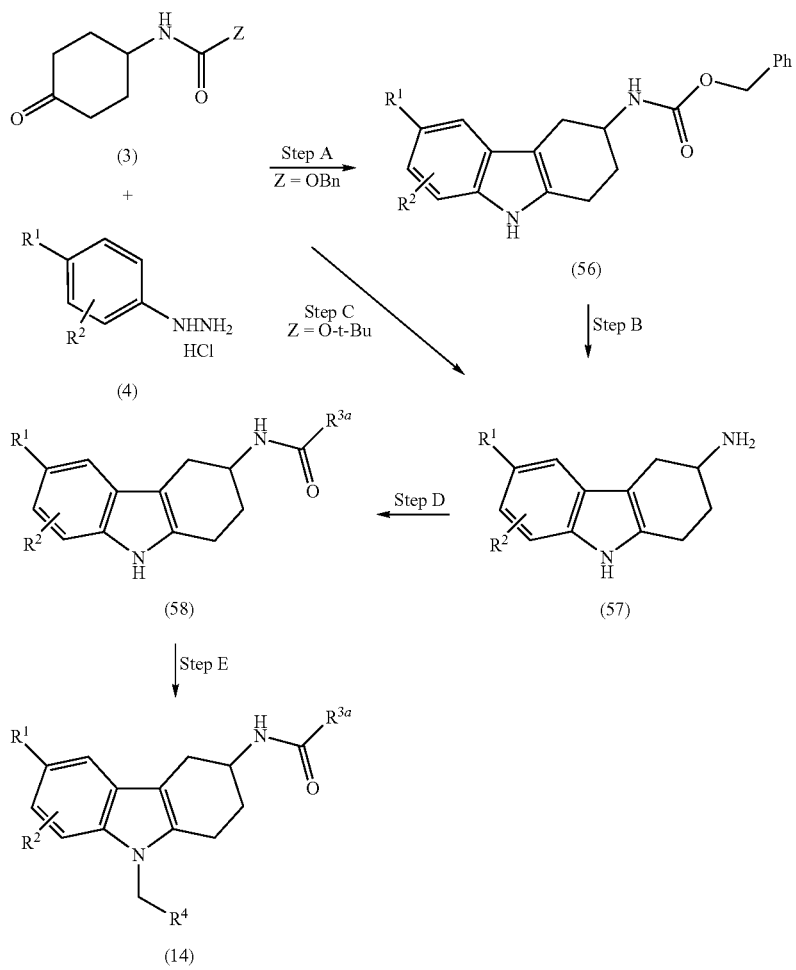

Scheme XVII describes syntheses wherein the Fisher-Indole reaction is performed with protecting groups on the amine functionality to provide versatility in the synthetic sequence.

In Scheme XVII, Step A, a phenylhydrazine salt (for example the hydrochloride salt) of formula (4), is reacted with a cyclic ketone of formula (3), wherein Z=OBn, in a Fischer indole reaction to provide a tetrahydrocarbazole of formula (5). The hydrazine and ketone are reacted in acetic acid and heated at about 60 to 110° C., for about 4 to 48 hours. The product is isolated by removal of the acetic acid under reduced pressure and trituration of the material in an inert solvent, preferably dichloromethane. After filtration, the filtrate is concentrated and the resulting material purified using standard techniques such as recrystillization or silica gel chromatography.

In Scheme XVII, Step B, a benzyl carbamate tetrahydrocarbazole of formula (56) is deprotected to provide the amine tetrahydrocarbazole of formula (57) using conditions essentially as described for Scheme XII, Step A.

Alternatively, in Scheme XVII, Step C, an amine tetrahydrocarbazole of formula (57) is obtained directly from the Fisher-Indole reaction of a substituted phenyl hydrazine of formula (4) with a ketone of formula (3), wherein Z=O-t-butyl. The tert-butoxycarbonyl (BOC) protecting group is cleaved under the acidic reaction conditions. The preferred method uses 1 volume of concentrated hydrochloric acid and 2 volumes of water at a temperature of 50° C. to the reflux temperature of the solvent for a period of about 4 to 48 hours. The product can be isolated by cooling the reaction and collecting the precipitate. The solid precipitate is washed with an inorganic aqueous base such as potassium carbonate or sodium carbonate and then azeotroped sequentially with chloroform, ethanol and then chloroform.

In yet another method, the BOC protecting group is employed by reacting a ketone of formula (3), wherein Z=O-t-butyl, with an iodoaniline of formula (5,) as previously described in Scheme II, Step B. The BOC group is then removed in a subsequent reaction as previously described in Scheme XII, Step B.

In Scheme XVII, Step D, an amine tetrahydrocarbazole of formula (57) is acylated essentially as described in Scheme XII, Step B with an acid chloride, a carbamoyl chloride, or a chloroformate using conditions well known to those skilled in the art which will allow selective reaction at the more nucleophilic amine verses the indole nitrogen. The preferred conditions use an insert solvent such as dimethylformamide or DMSO with an organic base such as diisopropylethylamine or triethylamine and the reaction stirred at a temperature of 0 to 50° C. for a period of 5 minutes to 1 hour.

In Scheme XVII, Step E, a tetrahydrocarbazole of formula (58) is alkylated with an alkylating agent of formula (10), (11), or (12) as described in Scheme IV, Steps A or B to give a tetrahydrocarbazole of formula (14).

Determination of Biological Activity

To demonstrate that compounds of the present invention have affinity for the androgen receptor, and thus have the capacity to modulate androgen receptor activity, nuclear hormone receptor binding assays are first performed. All ligands, radioligands, solvents, and reagents employed in the binding assays are readily available from commercial sources, or can be readily synthesized by the ordinarily skilled artisan.

Steroid Hormone Nuclear Receptor Binding Assay:

Cell lysates from 293 cells overexpressing human GR (glucocorticoid receptor), AR (androgen receptor), MR (mineralocorticoid receptor) or PR (progesterone receptor) are used for competition binding assays to determine Ki values for test compounds. Briefly, competition binding assays are run in a buffer containing 20 mM Hepes, pH 7.6, 0.2 mM EDTA, 75 mM NaCl, 1.5 mM MgCl2, 20% glycerol, 20 mM sodium molybdate, 0.2 mM DTT, 20 ug/inl aprotinin and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added at various concentrations ranging from about 0.01 nM to 10 µM. Nonspecific binding is determined in the presence of 500 nM dexamethasone for GR binding, 500 nM aldosterone for MR binding, or 500 nM methyltrienolone for AR and PR binding. The binding reaction (140 µl) is incubated for overnight at 4° C., then 70 µl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 µl of the mix is transferred to another 96-well plate and 175 µl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an $IC_{50}$ and % Inhibition at 10 µM. The $K_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The $IC_{50}$ values for test compounds are converted to $K_i$ using Cheng-Prusoff equation and the $K_d$ determined by saturation binding assay.

Binding assay protocols for steroid hormone nuclear receptors similar to those described above can be readily designed by the ordinarily skilled artisan. Representative compounds of the present invention have a Ki in the AR binding assay of ≦5 µM. Furthermore, exemplified compounds of the present invention have a Ki in the AR binding assay of ≦1.5 µM. More particularly, preferred compounds of the present invention have a Ki in the AR binding assay of ≦1 µM. Even more particularly, more preferred compounds of the present invention have a Ki in the AR binding assay of ≦500 nM. More particular still, especially preferred compounds of the present invention have a Ki in the AR binding assay of ≦100 nM. Table I (see below) provides AR binding data for a representative sample of the exemplified compounds of the present invention. In addition, the most particularly preferred compounds of the present invention selectively bind to the androgen receptor with greater affinity relative to the other steroid hormone receptors (MR, GR, and PR)

To demonstrate the ability of compounds of the present invention to modulate the activity of the androgen receptor (i.e. either agonize, partially agonize, partially antagonize, or antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Steroid Hormone Nuclear Receptor Modulation:

Human embryonic kidney hEK293 cells are co-transfected using FuGEN™. Briefly, the reporter plasmid containing two copies of probasin ARE (androgen response element $^5$'GGT-TCTTGGAGTACT$^{3'}$) (SEQ ID NO:1) and TK promoter upstream of the luciferase reporter cDNA, is transfected with a plasmid constitutively expressing human androgen receptor (AR) using viral CMV promoter. The reporter plasmid containing two copies of GRE (glucocorticoid response element $^5$'TGTACAGGATGTTCT$^3$) (SEQ ID NO:2) and TK promoter upstream of the luciferase reporter cDNA, is transfected with a plasmid constitutively expressing either human glucocorticoid receptor (GR), human mineralocorticoid receptor (MR), or human progesterone receptor (PR), using viral CMV promoter. Cells are transfected in T150 cm$^2$ flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 h and then exposed to various concentrations of test compounds ranging from about 0.01 nM to 10 µM. In the antagonist assays low concentrations of agonist for each respective receptor are added to the media (0.25 nM dexamethosone for GR, 0.3 nM of methyltrienolone for AR, 0.05 nM of promegestone for PR and 0.05 nM aldosterone for MR). After 24 h of incubations with compounds, cells are lysed and luciferase activity is determined.

Data are fitted to a four parameter-fit logistic curve fit to determine EC50 values The percentage efficacy (compounds with saturated maximum responses) or the percent maximum stimulations (compounds with maximum responses that do not saturate) are determined relative to maximum stimulation obtained with the following reference agonists: 100 nM methyltrienolone for AR assay, with 30 nM promegestone for PR assay, with 30 nM aldosterone for MR assay and with 100 nM dexamethasone for GR assay. IC50 values may be determined similarly using antagonist mode assay data. In the antagonist mode, percent inhibitions are determined by comparing test compound activity in the presence of low concentration of agonist (0.25 nM dexamethasone for GR, 0.3 nM of methyltrienolone for AR, 0.05 nM of promegestone for PR and 0.05 nM aldosterone for MR) to the response produced by the same low concentration of agonist in the absence of test compound.

C2C12 AR/ARE Reporter Assay:

As an indicator of agonist activity in muscle tissue, the C2C12 AR/ARE reporter assay is performed. Briefly, mouse myoblast C2C12 cells are co-transfected using FuGENE™. A reporter plasmid containing a GRE/ARE (glucocorticoid response element/androgen response element $^5$'TGTACAG-GATGTTCT$^3$) (SEQ ID NO:3) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% or 10% Fetal Bovine Serum (PBS). After a 5 hour incubation, transfected cells are trypsinized, plated in 96 well dishes in DMEM media containing 10% charcoal-stripped FBS, incubated for 2 h and then exposed to various concentrations of test compounds ranging from about 0.01 nM to 10 µM. After 48 h of incubations with compounds, cells are lysed and luciferase activity is determined using standard techniques. Data is fit to a 4 parameter-fit logistics to determine EC50 values. The % efficacy is determined versus maximum stimulation obtained with 10 nM methyltrienolone.

Functional assays of nuclear hormone receptor modulation similar to those described above can be readily designed by the ordinarily skilled artisan. Table I (see below) provides average EC50 and % Efficacy data in the C2C12 AR/ARE reporter assay for a representative sample of the exemplified compounds of the present invention.

In vivo Mouse Model of Efficacy and Selectivity:

Male ICR mice (8 weeks old) are castrated according to approved procedures (Taconic, N.Y.) and allowed to waste for eight weeks. Age-matched sham-operated mice are also prepared. (Sham-operated mice are animals that have been exposed to the same surgical procedures as castrated animals except their testes are not removed.) Animals are housed in a temperature-controlled room (24° C.) with a reversed 12 hour light/dark cycle (dark 10:00/22:00) and water and food are available ad libitum.

In order to demonstrate in vivo efficacy, compounds of the present invention are administered daily by oral gavage or subcutaneous injection to the castrated sixteen week old mice (body weight about 48-50 g). Test compounds are administered to the animals using conventional vehicles. For example, for oral dosing 1% Sodium Carboxymethylcellulose (CMC)+0.25% Tween 80 in sterile $H_2O$ can be used for oral formulation and 6% Ethyl-alcohol (EtOH)+94% cyclodexitrane (CDX) can be used for subcutaneous injections. Castrated mice treated with Testosteron Enanthate (TE) (10 mg/kg/d) are used as a treatment positive control whereas castrated mice treated only with vehicle are used as treatment negative control. In addition, sham-operated mice treated with vehicle only are used as control for the surgical method.

Test animals are dosed over a two week timeframe, orally or subcutaneously, with, for example, 0.3, 1, 3, 10 or 30 mg/kg/day of a compound of the present invention. After the two-week treatment, as an indicator of activity the wet weight of the Levator Ani muscle in the test group is determined and compared to the weight in the castrated, vehicle only control group. The percent efficacy is then calculated as follows:

(Wet weight in treatment group/Wet weight in control group)×100

As an indicator of tissue selective activity, the wet weight of the seminal vesicle from test animals is similarly compared to the weight of the seminal vesicles from the castrated, vehicle-only group. In addition, a comparison of the wet weight of the prostate glands from the drug-treated group, to the wet weight of the prostate glands removed from the castrated, vehicle-only group, may also be used as an indicator of tissue selective activity.

Table II (see below) provides % efficacy data for a select sample of exemplified compounds of the present invention. Animal models of efficacy and selectivity similar to those described above can be readily designed and performed by the ordinarily skilled artisan, for example, Eisenberg and Gilbert, *J Pharmacol Exp Ther.* 1950, 99(1), 38-44, provides an alternative rat model that may be employed to show in vivo efficacy.

In Vivo Models of Disorders Associated with Bone Loss:

To demonstrate that compounds of the present invention have the capacity to treat disorders associated with bone loss, such as osteoporosis or osteopenia, animal models well known to those in the art may be employed. Examples of such models are provided in Y. L. Ma et al., *Japanese Journal of Bone and Mineral Metabolism* 23 (Suppl.): 62-68 (2005); Y. L. Ma et al., *Endocrinology* 144: 2008-2015 (2003); and K. Hanada et al., *Biol. Pharm. Bull.* 26(11): 1563-1569 (2003). As will be appreciated by one of ordinary skill in the art, the animal model protocols described in the references above may be readily adapted for use in conjunction with the compounds and methods of the present invention.

The following preparations and examples further illustrate the invention and represent typical synthesis of the compounds of Formula I, including any novel compounds, as described generally above. The reagents and starting materials are readily available to, or may be readily synthesized by, one of ordinary skill in the art. Where the synthesis of the compound is not explicitly stated, a reference to a previous Example or representative Scheme describing procedures for the synthesis of the compound is provided. It should be understood that the Preparations and Examples are set forth by way of illustration and not limitation, and that various modifications may be made by one of ordinary skill in the art.

Proton nuclear magnetic resonance ($^1$H NMR) spectra are collected on a Bruker Avance 300 MHz or a Varian 400 MHz spectrometer. Chemical shift values are reported in parts per million (ppm) δ values, relative to TMS as the internal standard (bs, broad singlet; s, singlet; d, doublet; t, triplet; q, quartet). Melting points are determined on a MelTemp II, model 1001, or a Mettler Toledo FP62 melting point apparatus and are uncorrected. All products are a racemic mixture of R and S stereoisomers unless indicated otherwise.

HPLC analysis is preformed using the following methods: Agilent Zorbax SB-C18, 5 µm column (4.6×250 mm). Method A: Elution system consists of an isocratic elution of acetonitrile: 0.03 M phosphate buffer (80:20) for 10 minutes. The flow rate is 1.5 mL/min. UV detection is performed at 220 nm. Method B: Elution system consists of an isocratic elution of acetonitrile: 0.03 M phosphate buffer (60:40) for 10 minutes. The flow rate is 1.5 mL/min. UV detection is performed at 220 nm. HPLC analyses are performed using Method A if not otherwise noted.

Mass spectral analyses are conducted on one of the following: 1) ThermoFinnigen aQa using electrospray ionization (ESI); 2) Applied Biosystems API150EX mass spectrometer using atmospheric chemical ionization (APCI); 3) Micromass ZMD equipped with a Waters autosampler and using electrospray ionization (ES); 4) LCMS-APCI analysis is preformed on a Hewlett Packard LC/MSD using an Agilent Eclipse Zorbax SDB-C8, 5.0 µm column (4.6×150 mm). The flow rate is 0.5 mL/min. UV detection is performed at 254 nm. On of the following methods was utilized. Method C: An isocratic elution of 70:30 methanol/10 mM ammonium acetate buffer (pH 5.5) for 10 min. Method D: An isocratic elution of 80:20 methanol/10 mM ammonium acetate buffer (pH 5.5) for 10 min. Method E: A gradient elution beginning with 80:20 methanol/1 mM ammonium acetate buffer (pH 6.0), for 1 min, adjusting the solvent composition in even gradient to 100% methanol over 2 min, then holding at 100% methanol for 7 min.; or 5) Agilent 1100 series LCMSD with atmospheric pressure electrospray (APES) using the following method: Waters Exterra C18, 3.5 µm column (2.1×50 mm). The elution system consists of solvent A=0.2% aqueous ammonium formate, B=ammonium formate in 50% methanol/acetonitrile solution. The elution system consists of a gradient elution beginning with 5% B for 1 min, adjusting the solvent composition in even gradient to 100% B over 6 min, then holding at 100% B for 1 min. The flow rate is 1.0 mL/min. UV detection is performed at 214 nm.

PREPARATIONS AND EXAMPLES

Preparation 1

N-(4-Hydroxycyclohexyl)isobutyramide

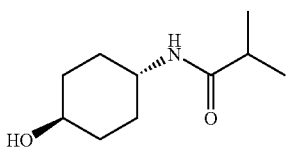

Add isobutyric anhydride (317.3 g, 2.01 mol) dropwise over three hours to trans-4-aminocyclohexanol (210.0 g, 1.82 mol) and triethylamine (279 mL, 2.01 mol) in tetrahydrofuran (4500 mL) in a twelve liter mechanically stirred flask. Stir at 23-30° C. under nitrogen for 18 h. Dilute with water (4500 mL) and wash with diethyl ether (2×2000 mL) to remove by-products. Add sodium chloride (700 g) and wash with $CH_2Cl_2$ (5000 mL) to extract out product. Remove organic portion and filter the aqueous to collect precipitated solids. Add the filtrate to water and extract with additional $CH_2Cl_2$ (2×2500 mL). Dry the organic portion ($Na_2SO_4$), filter, concentrate in vacuo and combine with the collected precipitate to give 219.5 g of a white solid (65%). MS (ES): m/z 186 (M+1); $^1$H NMR(DMSO-$d_6$): δ 5.23 (by s, 1H, NH), 3.75 (m, 1H), 3.59 (m, 1H), 2.27 (septet, 1H), 2.00 (m, 5H), 1.40 (m, 2H), 1.22 (m, 2H), 1.07 (d, 6H).

Preparation 2

N-(4-Oxocyclohexyl)isobutyramide

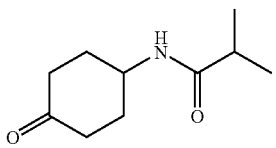

Add pyridinium chlorochromate (561.6 g, 2.61 mol) to N-(4-hydroxycyclohexyl)isobutyramide (321.8 g, 1.74 mol) in $CH_2Cl_2$ (8000 mL) and stir mechanically for 24 h under nitrogen. Add silica gel (2000 g), stir, and filter through a silica pad (6000 g). Elute with $CH_2Cl_2$ followed by 75-100% EtOAc/hexanes to obtain 210 g of a light brown solid (66%/ o). MS (ES): m/z 184 (M+1); $^1$H NMR(DMSO-$d_6$): δ 5.54 (br s, NH), 4.27 (septet, 1H), 2.20-2.60 (m, 7H), 1.78 (m, 2H), 1.15 (d, 6H).

Preparation 3

N-(6-Cyano-2,3,4,9-tetrahydro-1H-carbazol-3-yl)isobutyramide

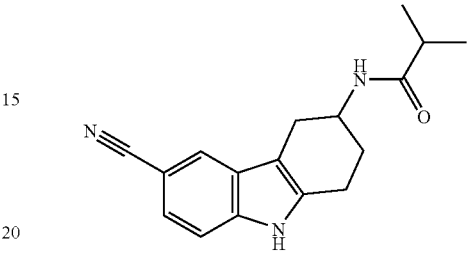

Method 1. Combine p-cyanophenylhydrazine hydrochloride (38.00 g, 224 mmol) and N-(4-oxo-cyclohexyl)isobutyramide (41.06 g, 224 mmol) in absolute ethanol (500 mL) and heat at 70-85° C. under nitrogen for 48-64 h. Concentrate in vacuo and partition between $CH_2Cl_2$/i-PrOH and water. Dry the organic portion ($Na_2SO_4$), filter, and evaporate to give 55.7 g (88%) of a yellow solid. MS (ES): m/z 282 (M+1). Alternatively, the titled compound can be prepared as described below.

Method 2. Combine 4-cyanophenylhydrazine hydrochloride (51.95 g, 306.3 mmol) and N-(4-oxo-cyclohexyl)-isobutyramide (56.13 g, 306.3 mmol) in water (100 mL) and concentrated hydrochloric acid (140 mL). Vigorously stir the thick suspension at 90° C. for 5.5 h. Allow to cool to room temperature and then cool to 5° C. with continued stirring for 30 min. Filter and dry at 45° C. for 18 h on house vacuum. Suspend the resulting solid powder in water/THF (200 mL/100 mL) and take alkaline with 1N NaOH (10 mL). Stir for 2 h and filter, washing liberally with water. Dry under house vacuum at 45° C. for 3 days to obtain 71.97 g (83%) of a light brown powder. MS (ES): m/z 282 (M+1), 280 (M−1); $^1$H NMR(DMSO-$d_6$): δ 11.39 (s, 1H), 7.88 (m, 2H), 7.42 (d, 1H, J=8.4 Hz), 7.37 (dd, 1H, J=8.4, 1.3 Hz), 4.06 (m, 1H), 2.96 (dd, 1H, J=15.4, 5.3 Hz), 2.83 (m, 2H), 2.50 (m, 1H), 2.41 (m, 1H), 1.98 (m, 1H), 1.81 (m, 1H), 1.04 (d, 3H, J=2.2 Hz), 1.02 (d, 3H, J=1.8 Hz).

Preparation 4

N-(6-Bromo-2,3,4,9-tetrahydro-1H-carbazol-3-yl)isobutyramide

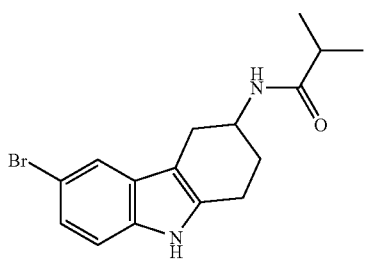

Combine p-bromophenylhydrazine hydrochloride (10.0 g, 44.7 mmol) and N-(4-oxo-cyclohexyl)isobutyramide (8.20g, 44.7 mmol) in saturated ethanolic HCl (180 mL) and heat at reflux under nitrogen for 18 h. Concentrate in vacuo to remove about ½ of the EtOH, then dilute with water (300 mL). Collect the resulting solid, slurry in EtOAc and recollect to give 11.5 g (77%) of a beige solid. MS (ES): 335 (M+1), 337 (M+H+2). $^1$H NMR(DMSO-$d_6$): δ 10.93 (s, 1H, NH), 7.80 (d, 1H, J=7.9 Hz), 7.48 (s, 1H), 7.19 (d, 1H, J=8.8 Hz), 7.07 (d, 1H, J=8.4 Hz), 4.00 (m, 1H), 2.86 (dd, 1H, J=15.2, 5.1 Hz), 2.77 (m, 2H), 2.46-2.32 (m, 2H), 1.93 (m, 1H), 1.75 (m, 1H), 0.99 (d, 6H, J=6.6 Hz).

Preparation 4a

N-(6-Fluoro-2,3,4,9-tetrahydro-1H-carbazol-3-yl) isobutyramide

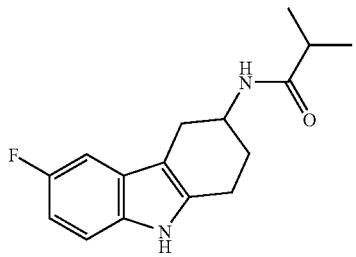

Combine p-fluorophenylhydrazine hydrochloride (5.00 g, 30.7 mmol) and N-(4-oxo-cyclohexyl)isobutyramide (5.64 g, 30.7 mmol) in ethanolic HCl (125 mL) and heat at reflux under nitrogen for 18 h. Concentrate the reaction in vacuo to remove most of the EtOH, dilute with water and extract with EtOAc. Wash the EtOAc extracts with water and brine, dry over $Na_2SO_4$, and evaporate to give 7.1 g (56%) of a beige solid. MS (ES): m/z 275 (M+1); $^1$H NMR(DMSO-$d_6$): δ 10.79 (s, 1H, NH), 7.81 (d, 1H, J=7.5 Hz), 7.19 (dd, 1H, J=8.6, 4.6 Hz), 7.07 (d, 1H, J=10.1 Hz), 6.79 (dt, 1H, J=8.9, 1.8 Hz), 4.00 (m, 1H), 2.85 (dd, 1H, J=15.0, 5.3 Hz), 2.76 (m, 2H), 2.39 (m, 2H), 1.93 (m, 1H), 1.75 (m, 1H), 0.99 (d, 6H, J=6.6 Hz).

Example 1

N-[9-(3-Fluorobenzyl)-6-bromo-2,3,4,9-tetrahydro-1H-carbazol-3-yl]isobutyramide

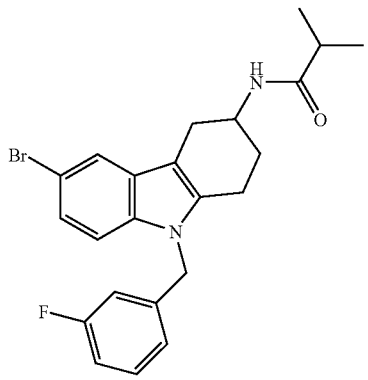

Add N-(6-bromo-2,3,4,9-tetrahydro-1H-carbazol-3-yl) isobutyramide (0.25 g, 0.75 mmol) to a suspension of sodium hydride (0.036 g, 0.90 mmol of a 60% dispersion in mineral oil) in DMF (3 mL) and stir for 15 min. Add 3-fluorobenzyl-bromide (0.10 mL, 0.90 mmol) and stir for 18-72 h. Dilute with water and collect the precipitate by filtration. Purify by silica gel chromatography eluting with 20-100% EtOAc/hexanes gradient to give 0.23 g of a white solid (71%). MS (ES): m/z 443 (M+1), 445 (M+H+2); HPLC: $R_t$=3.71 min (97.1%); m.p.=177-179° C.

Using the appropriate tetrahydrocarbazole derivative, prepared essentially as described in Preparations 3, 4, or 4a above, Examples 2-60, in the Table below, are prepared by alkylating the tetrahydrocarbazole with the appropriate benzylhalide essentially as described in Example 1.

| Ex | $R^1$ | $R^2$ | $R^a$ | $R^b$ | MS (ES) m/z | HPLC ($R_t$, %) | MP ° C. |
|---|---|---|---|---|---|---|---|
| 2 | H | H | H | H | 347 (M + 1) | 2.87 min, (100%) | 191-193 |
| 3 | H | H | 3-F | H | 365 (M + 1) | 2.82 min, (100%) | 170-172 |
| 4 | 6-F | H | 2-F | H | 383 (M + 1) | 2.86 min, (100%) | 156-158 |
| 5 | 6-F | H | 2-Cl | H | 399 (M + 1) | 3.69 min, (100%) | 155-157 |
| 6 | 6-F | H | 2-OMe | H | 395 (M + 1) | 3.15 min, (95.6%) | 196-198 |
| 7 | 6-F | H | 2-CN | H | 390 (M + 1) | 2.48 min, (100%) | 164-167 |
| 8 | 6-F | H | 3-F | H | 383 (M + 1) | 2.81 min, (100%) | 181-184 |
| 9 | 6-F | H | 3-Cl | H | 399 (M + 1) | 3.32 min, (99.4%) | 177-179 |
| 10 | 6-F | H | 3-OMe | H | 395 (M + 1) | 2.77 min, (98.3%) | 191-193 |
| 11 | 6-F | H | 3-CN | H | 390 (M + 1) | 2.39 min, (97.3%) | 184-186 |
| 12 | 6-F | H | 4-F | H | 383 (M + 1) | 2.81 min, (100%) | 166-168 |
| 13 | 6-F | H | 4-Cl | H | 399 (M + 1) | 3.38 min, (99.9%) | 188-190 |
| 14 | 6-F | H | 4-CN | H | 390 (M + 1) | 2.37 min, (85.6%) | 181-184 |
| 15 | 6-F | H | 4-OMe | H | 395 (M + 1) | 2.76 min, (98.4%) | 178-181 |
| 16 | 6-Cl | H | H | H | 381 (M + 1) | 3.53 min, (99.7%) | 174-176 |
| 17 | 6-Cl | H | 2-F | H | 399 (M + 1) | 3.62 min, (99.0%) | 190-193 |
| 18 | 6-Cl | H | 2-Cl | H | 415 (M + 1) | 4.73 min, (100%) | 197-199 |
| 19 | 6-Cl | H | 2-OMe | H | 411 (M + 1) | 3.94 min, (99.5%) | 141-149 |
| 20 | 6-Cl | H | 2-CN | H | 405 (M + 1) | 2.96 min, (100%) | 238-240 |
| 21 | 6-Cl | H | 3-F | H | 399 (M + 1) | 2.86 min, (99.3%) | 187-189 |

-continued

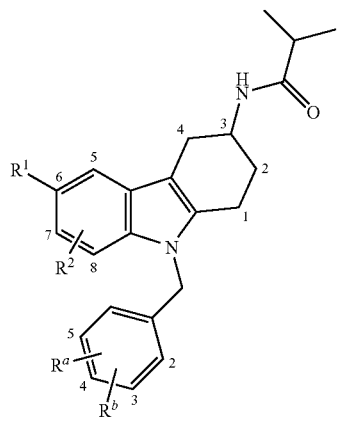

| Ex | R¹ | R² | Rᵃ | Rᵇ | MS (ES) m/z | HPLC (R_t, %) | MP °C. |
|---|---|---|---|---|---|---|---|
| 22 | 6-Cl | H | 3-Cl | H | 415 (M + 1) | 4.17 min, (100%) | 187-189 |
| 23 | 6-Cl | H | 3-OMe | H | 411 (M + 1) | 2.82 min, (99.5%) | 178-181 |
| 24 | 6-Cl | H | 3-CN | H | 406 (M + 1) | 2.79 min, (97.3%) | 225-228 d |
| 25 | 6-Cl | H | 4-F | H | 399 (M + 1) | 3.42 min, (100%) | 175-178 |
| 26 | 6-Cl | H | 4-Cl | H | 415 (M + 1) | 4.25 min, (98.6%) | 176-178 |
| 27 | 6-Cl | H | 4-OMe | H | 411 (M + 1) | 3.33 min, (100%) | 182-184 |
| 28 | 6-Cl | H | 4-CN | H | 406 (M + 1) | 2.77 min, (100%) | 158-162 compaction at 141 |
| 29 | 6-Cl | H | 3-F | 5-F | 417 (M + 1) | 3.64 min, (100%) | 207-210 |
| 30 | 6-Br | H | H | H | 425 (M + H), 427 (M + H + 2) | 3.82 min, (100%) | 173-177 |
| 31 | 6-Br | H | 2-F | H | 443 (M + H), 445 (M + H + 2) | 3.93 min, (100%) | 194-197 |
| 32 | 6-Br | H | 2-Cl | H | 459 (M + 1), 461 (M + 1 + 2) | 5.22 min, (96.5%) | 196-198 |
| 33 | 6-Br | H | 2-CN | H | 450 (M + 1), 452 (M + 1 + 2) | 3.18 min, (100%) | 240-241.5 |
| 34 | 6-Br | H | 2-OMe | H | 455 (M + 1), 457 (M + 1 + 2) | 4.32 min, (100%) | 108-111 |
| 35 | 6-Br | H | 3-F | H | 443 (M + 1), 445 (M + 1 + 2) | 3.71 min, (97.1%) | 177-179 |
| 36 | 6-Br | H | 3-Cl | H | 459 (M + 1), 461 (M + 1 + 2) | 4.55 min, (100%) | 186-188 |
| 37 | 6-Br | H | 3-OMe | H | 455 (M + 1), 457 (M + 1 + 2) | 3.66 min, (100%) | 176-180 |
| 38 | 6-Br | H | 3-CN | H | 450 (M + 1), 452 (M + 1 + 2) | 2.99 min, (98.3%) | 228-230 |
| 39 | 6-Br | H | 4-F | H | 443 (M + 1), 445 (M + 1 + 2) | 3.69 min, (100%) | 165-170 |
| 40 | 6-Br | H | 4-Cl | H | 459 (M + 1), 461 (M + 1 + 2) | 4.65 min, (98.9%) | 142-149 |
| 41 | 6-Br | H | 4-OMe | H | 455 (M + 1) 457 (M + 1 + 2) | 3.64 min, (100%) | 120-125 |
| 42 | 6-CH3 | H | H | H | 361 (M + 1) | 2.94 min, (98.6%) | 197-199 |

-continued

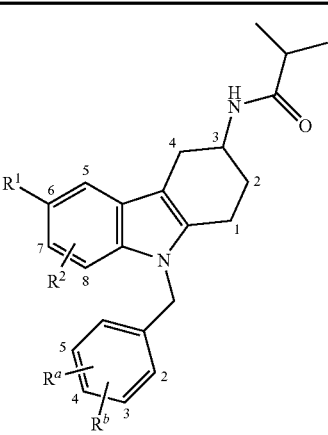

| Ex | R¹ | R² | Rᵃ | Rᵇ | MS (ES) m/z | HPLC (R_t, %) | MP °C. |
|---|---|---|---|---|---|---|---|
| 43 | 6-CH3 | H | 2-F | H | 379 (M + 1) | 3.00 min, (95.4%) | 174-176 |
| 44 | 6-CH3 | H | 2-Cl | H | 395 (M + 1), 397 (M + 1 + 2) | 3.79 min, (99.4%) | 194-194 |
| 45 | 6-CH3 | H | 2-OMe | H | 390 (M + 1) | 3.18 min, (98.4%) | 178-180 |
| 46 | 6-CH3 | H | 2-CN | H | 386 (M + 1) | 2.96 min, (100%) | 218-220 |
| 47 | 6-CH3 | H | 3-F | H | 379 (M + 1) | 2.87 min, (98.5%) | 215-217 |
| 48 | 6-CH3 | H | 3-Cl | H | 395 (M + 1) | 3.35 min, (99.3%) | 190-192 |
| 49 | 6-CH3 | H | 3-OMe | H | 390 (M + 1) | 2.82 min, (99.3%) | 197-199 |
| 50 | 6-CH3 | H | 3-CN | H | 386 (M + 1) | 2.44 min, (100%) | 209-211 |
| 51 | 6-CN | H | 3-F | H | 390 (M + 1) | 2.41 min, (100%) | 195-199 |
| 52 | 6-CO2Et | H | 3-F | H | 437 (M + 1) | 2.83 min, (100%) | 226-228 |
| 53 | 6-SO2Me | H | 3-F | H | 443 (M + 1) | 1.95 min, (100%) | 205-207 |
| 54 | 6-OCF3 | H | 3-F | H | 449 (M + 1) | 2.94 min, (100%) | 160-162 |
| 55 | 6-CF3 | H | 3-F | H | 433 (M + 1) | 3.49 min, (100%) | 131-138 |
| 56 | H | 7-Cl | 3-F | H | 399 (M + 1), 401 (M + 1 + 2) | 3.46 min, (99.6%) | 233-235 |
| 57 | H | 8-Cl | 3-F | H | 399 (M + 1), 401 (M + 1 + 2) | 3.56 min, (99.6%) | 205-207 |
| 58 | H | 8-F | 3-F | H | 383 (M + 1) | 3.56 min, (99.6%) | 185-188 |
| 59 | 6-OMe, | 7-Cl | 3-F | H | 429 (M + 1) | 2.76 min (98%) | 212-215 |
| 60 | H | 8-Me | 3-F | H | 379 (M + 1) | 3.40 min (80%) | 188-191 |

Example 61

N-[9-(3-Fluorobenzyl)-6-nitro-2,3,4,9-tetrahydro-1H-carbazol-3-yl]isobutyramide

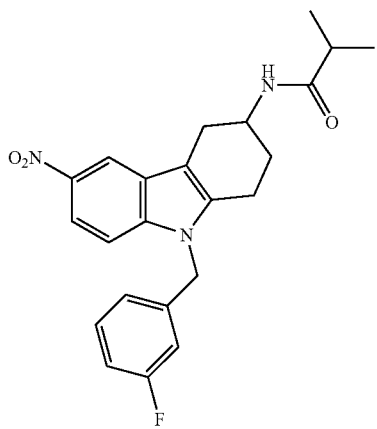

Heat p-nitrophenylhydrazine hydrochloride (5.00 g, 26.4 mmol) and N-(4-oxo-cyclohexyl)isobutyramide (5.31 g, 29.0 mmol) in absolute EtOH (105 mL) at 70° C. for 2 h. Collect the yellow hydrazone product by filtration and rinse with EtOH to yield 7.2 g (86%). Transfer the hydrazone to a solution of benzene and treat with p-toluenesulfonic acid (2 equiv) at reflux for 18 h to afford the tetrahydrocarbazole. Alkylate with 3-fluorobenzylbromide using cesium carbonate (1.2 eq) as base at 23° C. for 18 h. Pour the reaction mixture onto water and filter the precipitate. Purify the material by silica gel chromatography, eluting with 20-80% EtOAc/hexanes gradient to obtain the title compound. MS (ES): m/z 410 (M+1); HPLC: $R_t$=2.60 min, (100%).

Example 62

N-[6-Dimethylamino-9-(3-fluoro-benzyl)-2,3,4,9-tetrahydro-1H-carbazol-3-yl]-isobutyramide

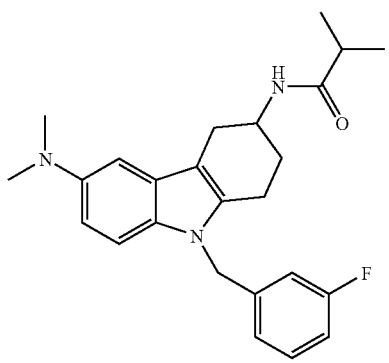

In a sealed tube, heat N-[6-bromo-9-(3-fluoro-benzyl)-2,3,4,9-tetrahydro-1H-carbazol-3-yl]-isobutyramide (Example 35) (200 mg, 0.45 mmol), dimethyl amine (2.0 M in tetrahydrofuran, 0.45 mL, 0.90 mmol), palladium acetate (5 mg, 0.002 mmol), sodium tert-butoxide (133 mg, 1.38 mmol), and 1,2,3,4,5-pentaphenyl-1'-(di-t-butylphosphino)ferrocene ligand (60 mg, 0.008 mmol) in toluene (5 mL) at 70° C. overnight. Cool to room temperature, dilute with ethyl acetate/10% potassium carbonate, and filter off the red suspension. Wash the organic portion with 10% aqueous potassium carbonate (2×), dry over anhydrous sodium sulfate, filter, and concentrate. Purify the residue by silica gel column chromatography eluting with 40 to 100% ethyl acetate/hexanes to obtain the title compound (135 mg, 74%). MS (ES): m/z 408 (M+1); $^1$H NMR (CD$_3$OD): δ 7.25 (m, 1H), 7.18 (d, 1H), 7.01 (s, 1H), 6.96 (t, 1H), 6.89 (d, 1H), 6.81 (d, 1H), 6.65 (d, 1H), 5.30 (s, 2H), 4.19 (m, 1H), 3.08 (dd, 1H), 2.88 (s, 6H), 2.77 (m, 2H), 2.63 (m, 1H), 2.50 (m, 1H), 2.12 (m, 1H), 1.97 (m, 1H), 1.18 (m, 6H).

Example 63

9-(3-Fluorobenzyl)-6-isobutyrylamino-6,7,8,9-tetrahydro-5H-carbazole-3-carboxylic acid amide

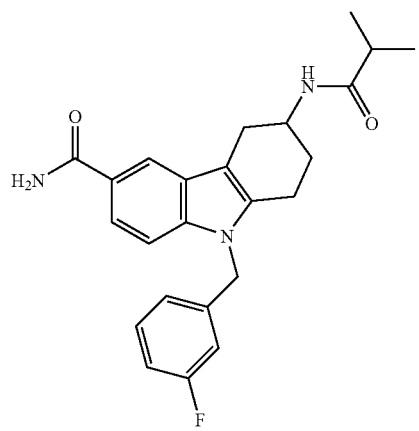

Add K$_2$CO$_3$ (0.26 g, 1.93 mmol) and 30% H$_2$O$_2$ (2.0 mL) portionwise to N-(6-cyano-9-(3-fluorobenzyl)-2,3,4,9-tetrahydro-1H-carbazol-3-yl)isobutyramide (Example 51) (1.50 g, 3.85 mmol) in DMSO while cooling in an ice bath. Stir for 18 h and add more H$_2$O$_2$ with warming to 50° C. if needed to facilitate complete reaction. Dilute with water and collect the precipitate by filtration (1.45 g, 92%). Recrystallize from EtOAc to yield a white solid. MS (ES): m/z 408 (M+1); m.p.=192-194° C.

Example 64

N-(9-(3-Fluorobenzyl)-6-thiocarbamoyl-2,3,4,9-tetrahydro-1H-carbazol-3-yl)isobutyramide

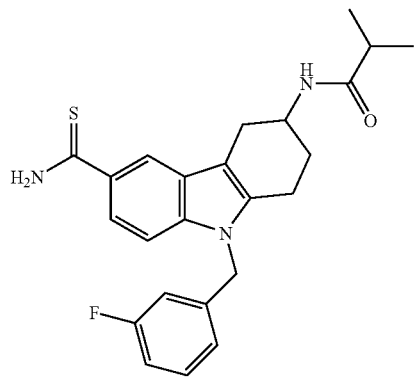

Heat N-(6-cyano-9-(3-fluorobenzyl)-2,3,4,9-tetrahydro-1H-carbazol-3-yl)isobutyramide (Example 51) (1.00 g, 2.57 mmol) with thioacetamide (0.386 g, 5.14 mmol) at reflux temperature in 4N HCl in dioxane (30 mL) for 4 h. Allow to cool, pour onto water and neutralize with $NaHCO_3$. Collect 0.98 g (90%) of a precipitate. Purify a portion of the material by silica gel chromatography (25-80% EtOAc/hexanes gradient) to give a yellow solid. MS (ES): m/z 424 (M+1); HPLC: $R_t$=1.90 min, (95%).

Example 65

N-(9-Benzyl-6-methoxy-2,3-4,9-tetrahydro-1H-carbazol-3-yl)-acetamide

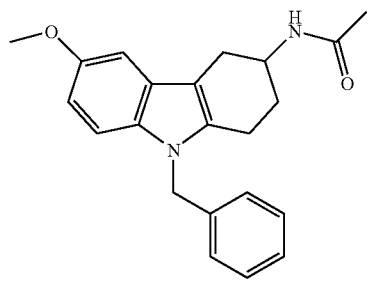

Add N-benzyl-N-(4-methoxy-phenyl)-hydrazine (9.1 g, 0.04 mol) (prepare as in Shaw, E., *J. Am. Chem. Soc.* (1955), 77, 4319-4324) to N-(4-oxo-cyclohexyl)-acetamide (6.2 g, 0.04 mol) (prepare as in Dionne, G., Hymbe, L. G., Asselin, A., McQuillan, J. and Treasureywala, A. M., *J. Med. Chem.*, (1986), 29, 1452-1457) in acetic acid (60 mL) and reflux for 2 h. Pour in water, extract with hot benzene and remove the solvent in vacuo. Recrystillize the resulting solid from benzene/cyclohexane to give 10.4 g of a crystalline solid. m.p=184-185° C. Recrystillize from the same solvents to obtain an analytically pure sample. Anal. Calcd for $C_{22}H_{24}N_2O_2$: C, 75.83; H, 6.94; N, 8.04. Found: C, 75.71; H, 7.01; N 7.89.

Preparation 5

9-Benzyl-6-methoxy-2,34,9-tetrahydro-1H-carbazol-3-ylamine maleic acid salt

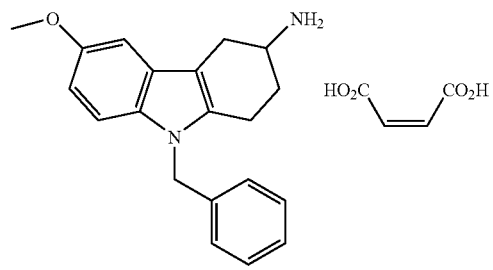

Add N-(9-benzyl-6-methoxy-2,3-4,9-tetrahydro-1H-carbazol-3-yl)-acetamide (6.5 g 0.020 mol) and potassium hydroxide pellets (35 g, 0.62 mol) to 2-methoxyethanol (130 mL) and water (35 mL). Reflux for 18 h. Remove the solvent in vacuo and dilute the resulting residue with water and extract with hot benzene. Combine the organic portions and wash with water until the wash is neutral, then dry ($MgSO_4$), and concentrate in vacuo to obtain 6.25 g of a viscous oil. Dissolve the residue in warm methanol (25 mL) and add a solution of maleic acid (2.5 g, 0.0215 mol) in absolute methanol (7 mL). Cool and filter to obtain 6.2 g fine crystalline needles. m.p.=167-168.5° C. Obtained a second crop from the mother liquor of 0.35 g to give a combined yield of 80.5%. m.p.=163-165° C. Obtain an analytical sample by recrystillization from absolute methanol. Anal. Calcd for $C_{24}H_{26}N_2O_5$: C, 68.23; H, 6.20; N, 6.63. Found: C, 68.07; H, 6.04; N, 6.92.

Example 66

N-(9-Benzyl-6-methoxy-2,3,4,9-tetrahydro-1H-carbazol-3-yl)-propionamide

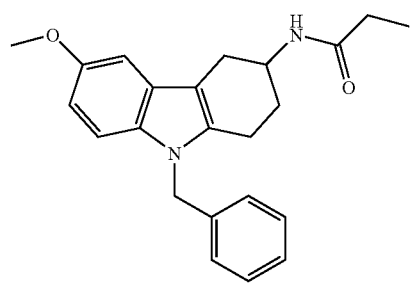

Suspend 9-benzyl-6-methoxy-2,34,9-tetrahydro-1H-carbazol-3-ylamine maleic acid salt (100 mg, 0.237 mmol) in dichloromethane (2 mL) under nitrogen and add triethylamine (0.099 mL, 0.711 mmol) followed by propionyl chloride (0.021 mL, 0.237 mmol). Stir the reaction at room temperature for 16 h. Concentrate in vacuo and purify the residue directly by silica gel chromatography, eluting with 25% ethyl acetate/hexanes followed by 60% ethyl acetate/hexanes to obtain 61 mg (71%) of a solid. MS (ES): m/z 363 (M+1), 361

(M−1); ¹H NMR(DMSO-d₆): δ 7.90 (d, 1H, J=7.5 Hz), 7.33-7.20 (m, 4H), 7.02 (d, 2H, J=7.0 Hz), 6.92 (d, 1H, J=2.2 Hz), 6.67 (dd, 1H, J=8.8, 2.2 Hz), 5.29 (s, 2H), (m, 1H), 3.72 (s, 3H), 2.95 (dd, 1H, J=15.0, 5.3 Hz), 2.80 (m, 1H), 2.79 (m, 1H), 2.42 (m, 2H), 2.11 (q, 2H, J=7.6 Hz), 1.99 (m, 1H), 1.79 (m, 1H), 1.02 (t, 3H, J=7.5 Hz).

Prepare Examples 67 and 68, below, as essentially described in Example 66, using isobutryl chloride and cyclopropane carbonyl chloride respectively with 9-benzyl-6-methoxy-2,34,9-tetrahydro-1H-carbazol-3-ylamine maleic acid salt.

Example 67

N-(9-Benzyl-6-methoxy-2,3,4,9-tetrahydro-1H-carbazol-3-yl)-isobutyramide

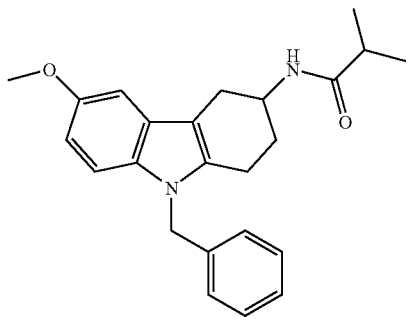

MS (ES): m/z 377 (M+1); ¹H NMR(DMSO-d₆): δ 7.84 (d, 1H, J=7.5 Hz), 7.32-7.19 (m, 4H), 7.02 (d, 2H, J=7.0 Hz), 6.92 (d, 1H, J=2.2 Hz), 6.67 (dd, 1H, J=8.8, 2.2 Hz), 5.29 (s, 2H), 4.00 (m, 1H), 3.75 (s, 3H), 2.95 (dd, 1H, J=15.2, 5.1 Hz), 2.83-2.63 (m, 2H), 2.52-2.36 (m, 2H), 1.97 (m, 1H), 1.80 (m, 1H), 1.02 (m, 6H).

Example 68

Cyclopropanecarboxylic acid (9-benzyl-6-methoxy-2,3,4,9-tetrahydro-1H-carbazol-3-yl)-amide

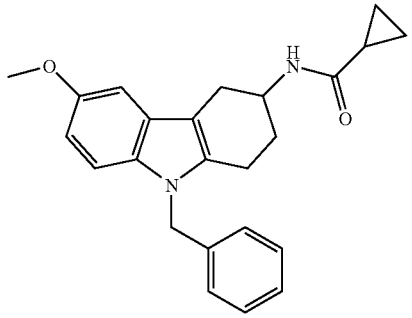

MS (ES): m/z 375 (M+1); ¹H NMR(DMSO-d₆): δ 8.21 (d, 1H, J=7.5 Hz), 7.32-7.20 (m, 4H), 7.03 (d, 2H, J=7.5 Hz), 6.92 (d, 1H, J=2.2 Hz), 6.67 (dd, 1H, J=8.8, 2.2 Hz), 5.29 (s, 2H), 4.03 (m, 1H), 3.75 (s, 3H), 2.96 (dd, 1H, J=15.2, 5.1 Hz), 2.86-2.77 (m, 1H), 2.74-2.63 (m, 1H), 2.00 (m, 1H), 1.80 (m, 1H), 1.60 (m, 1H), 0.66 (m, 4H).

Preparation 6

N-(6-methoxy-2,3,4,9-tetrahydro-1H-carbazol-3-yl)-isobutyramide

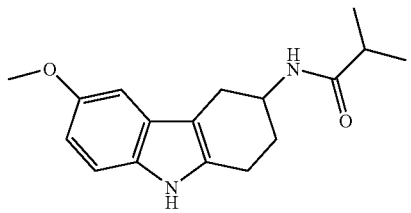

Add acetyl chloride (8.5 mL, 120 mmol) to absolute ethanol (30 mL) and stir for 1 h. Add 4-methoxyphenylhydrazine hydrochloride (1.74 g, 10 mmol) and N-(4-oxo-cyclohexyl)-isobutyramide (Preparation 2) (1.83 g, 120 mmol) and reflux with stirring for 56 h. Cool to room temperature, dilute with ethyl acetate (100 mL) and wash with sodium bicarbonate solution (2×50 mL), brine, dry (MgSO₄), filter and concentrate in vacuo. Dissolve the residue in dichloromethane and pass over a silica pad, eluting with 20% ethyl acetate/dichloromethane to obtain 2.32 g of a solid. Triturate the solid in diethyl ether with a small amount of dichloromethane, filter and dry under house vacuum to obtain 2.14 g (75%) of an off-white solid. MS (ES): m/z 287 (M+1), 285 (M−1); ¹H NMR(DMSO-d₆): δ 10.52 (s, 1H), 7.83 (d, 1H, J=7.5 Hz), 7.13 (d, 1H, J=8.8 Hz), 6.85 (s, 1H), 6.64 (dd, 1H, J=8.8, 2.2 Hz), 4.02 (m, 1H), 3.75 (m, 3H), 2.90 (dd, 1H, J=15.0, 5.3 Hz), 2.78 (m, 2H), 2.42 (m, 2H), 1.96 (m, 1H), 1.79 (m, 1H), 1.03 (d, 6H, J=6.6 Hz).

Preparation 7

N-(8-methoxy-2,3,4,9-tetrahydro-1H-carbazol-3-yl)-isobutyramide

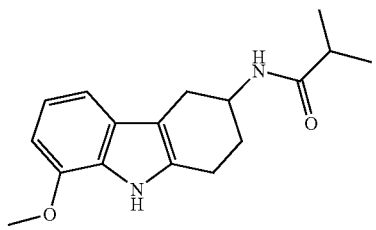

Add acetyl chloride (34.1 mL, 480 mmol) portionwise to absolute ethanol (120 mL) cooled in an ice bath and stir for 2 h. Add 4-methoxyphenylhydrazine hydrochloride (1.74 g, 10 mmol) and N-(4-oxo-cyclohexyl)-isobutyramide (Preparation 2) (1.83 g, 120 mmol) and reflux with stirring for 18 h. Follow the procedures essentially as described in Preparation 6, above, to give 6.0 g green gum after workup. Pass over a silica pad eluting with dichloromethane/25% ethyl acetate to provide 1.29 g of a brown foam. Further purify the residue by flash chromatography, eluting with dichloromethane, dichloromethane/25% ethyl acetate and then a gradient up to dichloromethane/40% ethyl acetate to obtain a pale tan solid. Triturate in diethyl ether with a bit of hexane to give 421 mg (4%) of an off-white solid. MS (ES): m/z 287 (M+1), 285 (M−1); $^1$H NMR(DMSO-d$_6$): δ 10.77 (s, 1H), 7.83 (d, 1H, J=7.5 Hz), 6.95 (d, 1H, J=7.9 Hz), 6.86 (t, 1H, J=7.7 Hz), 6.61 (d, 1H, J=7.5 Hz), 4.02 (m, 1H), 3.90 (s, 3H), 2.89 (dd, 1H, J=15.0, 5.3 Hz), 2.76 (m, 2H), 2.50-2.34 (m, 3H), 1.95 (m, 1H), 1.76 (m, 1H), 1.03 (d, 6H, J=7.0 Hz).

Preparation 8

N-(7-methoxy-2,3,4,9-tetrahydro-1H-carbazol-3-yl)-isobutyramide

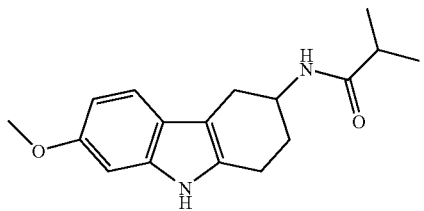

Follow the procedures essentially as described in Preparation 6, above, using acetyl chloride (26 mL, 360 mmol) and absolute ethanol (90 mL) with 3-methoxyphenylhydrazine hydrochloride (5.24 g, 30 mmol) and N-(4-oxo-cyclohexyl)-isobutyramide (5.50 g, 30 mmol). When complete, dilute the reaction with ethyl acetate (200 mL) and wash with 0.5N NaOH and sodium bicarbonate solution. Filter the solids in the organic phase, triturate in dichloromethane and filter to give 2.67 g (31%) gray solid. MS (ES): m/z 287 (M+1), 285 (M−1); $^1$H NMR(DMSO-d$_6$): δ 10.52 (s, 1H), 7.83 (d, 1H, J=7.5 Hz), 7.21 (d, 1H, J=8.4 Hz), 6.78 (s, 1H), 6.60 (d, 1H, J=8.4 Hz), 4.00 (m, 1H), 3.75 (s, 3H), 2.87 (dd, 1H, J=14.8, 5.1 Hz), 2.76 (m, 2H), 2.48-2.36 (m, 2H), 2.48-2.36 (m, 2H), 1.76 (m, 1H), 1.03 (d, 6H, J=6.6 Hz).

Example 69

N-[9-(2-Chloro-benzyl)-6-methoxy-2,3,4,9-tetrahydro-1H-carbazol-3-yl]-isobutyramide

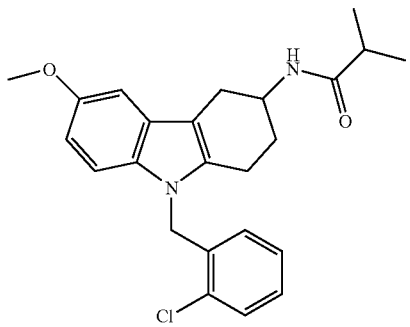

Dissolve N-(6-methoxy-2,3,4,9-tetrahydro-1H-carbazol-3-yl)-isobutyramide (Preparation 6) (100 mg, 0.35 mmol) in anhydrous tetrahydrofuran (4 mL) under nitrogen. Add dropwise potassium bis(trimethylsilyl)amide (0.77 mL, 0.385 mmol, 0.5N in toluene) and stir 25 min. Add slowly 2-chlorobenzylbromide (0.050 mL, 0.385 mmol) and stir at ambient temperature for 18 h. Quench with saturated ammonium chloride solution (0.5 mL) and dilute with a volume of dichloromethane and water (1 mL). Pass over a Varian Chem Elut column to remove aqueous portion and concentrate in vacuo. Alternatively, workup with ethyl acetate/water and dry over MgSO$_4$. Purify the resulting residue by flash chromatography, eluting with dichloromethane with a gradient up to 10% ethyl acetate/dichloromethane to obtain 99 mg (69%) of a white solid. MS (ES): m/z 411, 413 (M+1); $^1$H NMR(DMSO-d$_6$): δ 7.86 (d, 1H, J=7.5 Hz), 7.52 (d, 1H, J=8.4 Hz), 7.28 (t, 1H, J=7.7 Hz), 7.17 (m, 2H), 6.97 (d, 1H, J=2.2 Hz), 6.68 (dd, 1H, J=8.8, 2.2 Hz), 6.24 (d, 1H, J=7.9 Hz), 5.36 (s, 2H), 4.02 (m, 1H), 3.77 (s, 3H), 2.98 (dd, 1H, J=15.2, 5.1 Hz), 2.75-2.61 (m, 2H), 2.41 (m, 1H), 1.96 (m, 1H), 1.81 (m, 1H), 2.52 (m, 1H).

Using the appropriate tetrahydrocarbazole derivative from Preparations 3, 6, 7, or 8 above or as prepared essentially as described in Preparations 4 or 4a above, Examples 70-89, in the Table below, are prepared by alkylating the tetrahydrocarbazole with the appropriate benzylhalide essentially as described in Example 69.

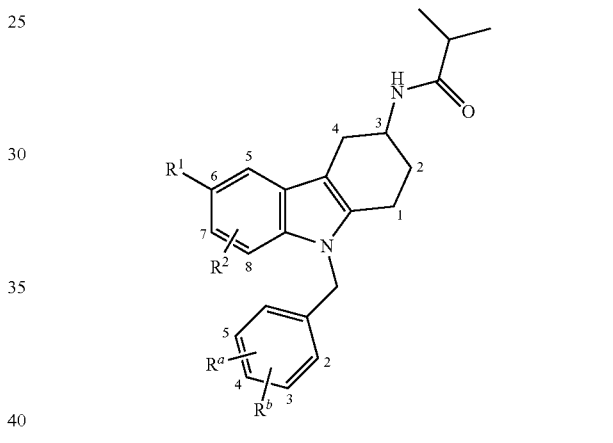

| Ex. | R$^1$ | R$^2$ | R$^a$ | R$^b$ | MS (ES) m/z | HPLC (R$_t$, %) |
|---|---|---|---|---|---|---|
| 70 | 6-OMe | H | 3-Cl | H | 411 (M + 1) | 2.85 min, (100%) |
| 71 | 6-OMe | H | 4-Cl | H | 411, 413 (M + 1) | 2.91 min, (100%) |
| 72 | 6-OMe | H | 2-OMe | H | 407 (M + 1) | 2.77 min, (99.3%) |
| 73 | 6-OMe | H | 3-OMe | H | 407 (M + 1) | 2.58 min, (100%) |
| 74 | 6-OMe | H | 4-OMe | H | 407 (M + 1) | 2.59 min, (98.3%) |
| 75 | 6-OMe | H | H | H | 377 (M + 1) | 2.69 min, (96.3%) |
| 76 | H | 8-OMe | H | H | 377 (M + 1) | 3.21 min, (97.2%) |
| 77 | H | 7-OMe | H | H | 377 (M + 1) | 2.72 min, (100%) |
| 78 | 6-OMe | H | 2-F | H | 395 (M + 1) | 2.77 min, (98.6%) |
| 79 | 6-OMe | H | 3-F | H | 395 (M + 1) | 2.65 min, (99.5%) |
| 80 | 6-OMe | H | 4-F | H | 395 (M + 1) | 2.63 min, (100%) |
| 81 | 6-Cl | H | 3-Br | H | 459, 461 (M + 1), 517, 519 (M + AcO)$^−$ | 4.34 min, (100%) |
| 82 | 6-Cl | H | 3-Me | H | 395, 397 (M + 1) | 4.22 min, (100%) |

-continued

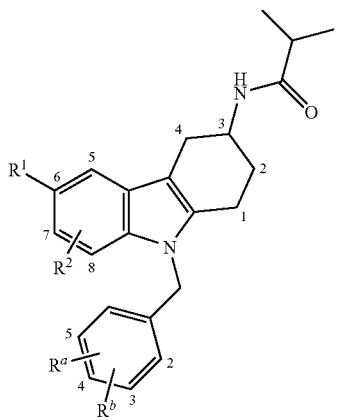

| Ex. | R¹ | R² | Rᵃ | Rᵇ | MS (ES) m/z | HPLC (R$_t$, %) |
|---|---|---|---|---|---|---|
| 83 | 6-Cl | H | 3-CF3 | H | 449, 451 (M + 1), 447, 449 (M − 1) | 4.00 min, (100%) |
| 84 | 6-Cl | H | 3-CO2Me | H | 439, 441 (M + 1), 447 (M − 1)⁻ | 3.18 min, (100%) |
| 85 | 6-CN | H | H | H | 372 (M + 1; APCI-pos) | LCMS (Method C) 4.86 min, (98%) |
| 86 | 6-CN | H | 3-Br | H | 450, 452 (M + 1; APCI-pos) | LCMS (Method C) 7.03 min, (96%) |
| 87 | 6-CN | H | 4-OMe | H | 402 (M + 1; APCI-pos) | LCMS (Method D) 2.27 min, (92%) |
| 88 | 6-CN | H | 3-NO2 | H | 417 (M + 1; APCI-pos) | LCMS (Method E) 2.0 min, (95%) |
| 89 | 6-CN | H | 3-F | 5-F | 408 (M + 1; APCI-pos) | LCMS (Method C) 5.3 min, (98%) |

Example 90

N-[9-(3-Amino-benzyl)-6-cyano-2,3,4,9-tetrahydro-1H-carbazol-3-yl]-isobutyramide

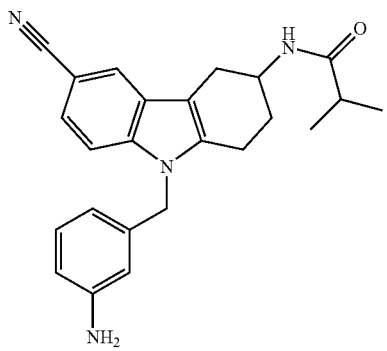

Add sulfided platinum (5 wt % on carbon) (120 mg) to a solution of N-[6-cyano-9-(3-nitro-benzyl)2,3,4,9-tetrahydro-1H-carbazol-3-yl]-isobutyramide (Example 88) (470 mg, 1.1 mmol) and methanol (50 mL). Purge and fill the reaction vessel with nitrogen (3×), then with hydrogen (3×, 55 psi). Seal the reaction vessel at about 55 psi, and stir the mixture at room temperature overnight. Filter the reaction mixture through a Celite® pad, and wash the filter cake with methanol. Concentrate under reduced pressure and purify the crude residue by flash chromatography (2.5% methanol/methylene chloride) to give the title compound. LCMS (Method D): m/z 387.1 (M+1, APCI); ¹H NMR (DMSO-d₆): δ 7.97 (d, 1H), 7.88 (d, 1H), 7.57 (d, 1H), 7.42 (dd, 1H), 6.94 (t, 1H), 6.24 (d, 1H), 6.20 (m, 1H), 5.26 (s, 2H), 5.07 (s, 2H), 4.03-4.06 (m, 1H), 3.01 (dd, 1H), 2.72-2.86 (m, 2H), 2.55 (dd, 1H), 2.38-2.46 (m, 1H), 1.98-2.02 (m, 2H), 1.79-1.87 (m, 1H), 1.04 (d, 3H), 1.02 (d, 3H).

Example 91

N-[9-(3-Fluoro-benzyl)-6-hydroxy-2,3,4,9-tetrahydro-1H-carbazol-3-yl]-isobutyramide

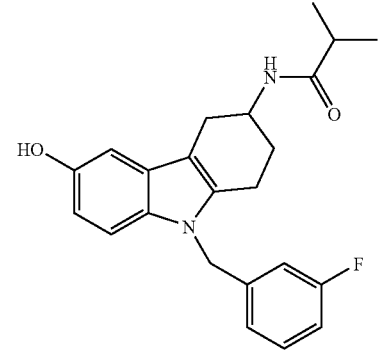

Add a solution of boron tribromide in dichloromethane (1.0M, 33 mL, 33 mmol) to N-[9-(3-fluoro-benzyl)-methoxy-2,3,4,9-tetrahydro-1H-carbazol-3-yl]-isobutyramide (Example 79) (2.60 g, 6.59 mmol) and stir at room temperature overnight. Quench slowly with methanol and concentrate under high vacuum. Purify the residue by silica chromatography (15% methanol in ethyl acetate) to obtain the title compound as a yellow solid (1.34 g, 53%). MS (ES): m/z 381(M+1); ¹H NMR (CD₃OD): δ 7.28 (m, 1H), 7.07 (d, 1H), 6.97 (m, 1H), 6.78-6.85 (m, 2H), 6.65 (d, 1H), 5.28 (s, 2H), 4.18 (m, 1H), 3.05 (dd, 1H), 2.76 (m, 2H), 2.47-2.67 (m, 2H), 2.13 (m, 1H), 1.92 (m, 1H), 1.17 (d, 6H).

Example 92

N-[6-Cyclopropylmetboxy-9-(3-fluoro-benzyl)-2,3,4,9-tetrahydro-1H-carbazol-3-yl]-isobutyramide

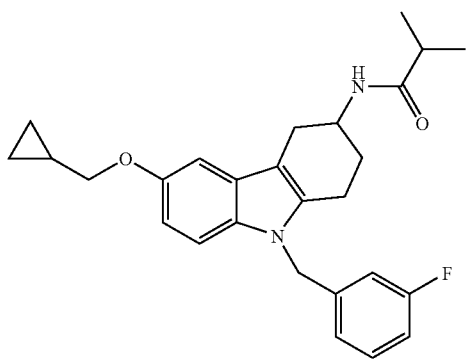

Stir N-[9-(3-fluoro-benzyl)-6-hydroxy-2,3,4,9-tetrahydro-1H-carbazol-3-yl]-isobutyramide (167 mg, 0.44 mmol), cyclopropylmethyl bromide (59 mg, 0.44 mmol), and cesium carbonate (172 mg, 0.53 mmol) in dimethylformamide (1.5 mL) at room temperature under nitrogen overnight. Dilute the reaction with ethyl acetate, wash with water (2×), dry over sodium sulfate, filter, and concentrate. Purify the residue by silica chromatography eluting with 10 to 100% ethyl acetateihexanes to obtain the title compound (101 mg, 53%). MS (ES): m/z 435 (M+1); $^1$H NMR (CDCl$_3$): δ 7.28 (m, 1H), 7.13 (d, 1H), 6.98 (s, 1H), 6.95 (m, 1H), 6.85 (d, 1H), 6.79 (d, 1H), 6.65 (d, 1H), 5.60 (broad s, 1H, NH), 5.22 (s, 2H), 4.43 (m, 1H), 3.87 (d, 2H), 3.15 (dd, 1H), 2.60-2.81 (m, 3H), 2.34 (m, 1H), 2.18 (m, 2H), 1.34 (m, 1H), 1.18 (m, 6H), 0.65 (d, 2H), 0.39 (d, 2H).

Example 93

N-[6-Ethoxy-9-(3-fluoro-benzyl)-2,3,4,9-tetrahydro-1H-carbazol-3-yl]-isobutyramide

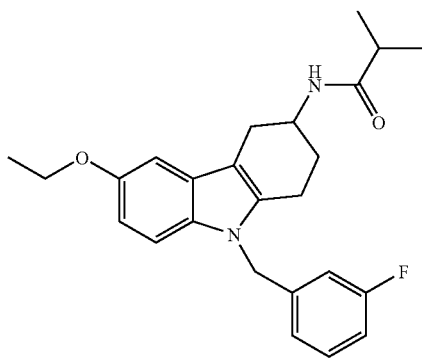

Add N-[9-(3-fluoro-benzyl)-6-hydroxy-2,3,4,9-tetrahydro-1H-carbazol-3-yl]-isobutyramide (175 mg, 0.46 mmol), ethyl iodide (72 mg 0.46 mmol), and sodium hydride (60% suspension in mineral oil, 37 mg, 0.92 mmol) to dimethylformamide (1 mL) and stir at room temperature overnight. Dilute the reaction with ethyl acetate, wash with water (2×), dry over sodium sulfate, and concentrate. Recrystallize from ethyl acetate/hexanes to obtain the title compound (107 mg, 57%): MS (ES): m/z (M+1); 1H NMR (CDCl3): δ 7.28 (m, 1H), 7.11 (d, 1H), 6.98 (s, 1H), 6.97 (m, 1H), 6.82 (d, 1H), 6.79 (d, 1H), 6.65 (d, 1H), 5.58 (broad s, 1H, NH), 5.22 (s, 2H), 4.44 (m, 1H), 4.09 (q, 2H), 3.15 (dd, 1H), 2.60-2.81 (m, 3H), 2.33 (m, 1H), 2.15 (m, 2H), 1.45 (t, 1H), 1.18 (m, 6H).

Prepare Examples 94 and 95, below, by essentially following the procedures as described in Example 93 using the appropriate alkyl halide and N-[9-(3-fluoro-benzyl)-6-hydroxy-2,3,4,9-tetrahydro-1H-carbazol-3-yl]-isobutyramide.

Example 94

N-[9-(3-Fluoro-benzyl)-6-isopropoxy-2,3,4,9-tetrahydro-1H-carbazol-3-yl]-isobutyramide

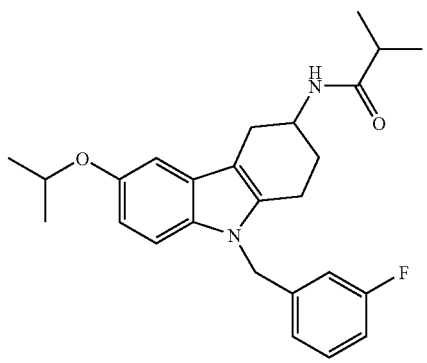

MS (ES): m/z 423 (M+1); $^1$H NMR (CDCl$_3$): δ 7.23 (m, 1H), 7.11 (d, 1H), 7.00 (s, 1H), 6.96 (m, 1H), 6.82 (m, 2H), 6.68 (d, 1H), 5.58 (broad s, 1H, NH), 5.22 (s, 2H), 4.54 (m, 1H), 4.44 (m, 1H), 3.15 (dd, 1H), 2.60-2.81 (m, 3H), 2.35 (m, 1H), 2.17 (m, 2H), 1.39 (d, 6H), 1.18 (m, 6H).

Example 95

N-[9-(3-Fluoro-benzyl)-6-propoxy-2,3,4,9-tetrahydro-1H-carbazol-3-yl]-isobutyramide

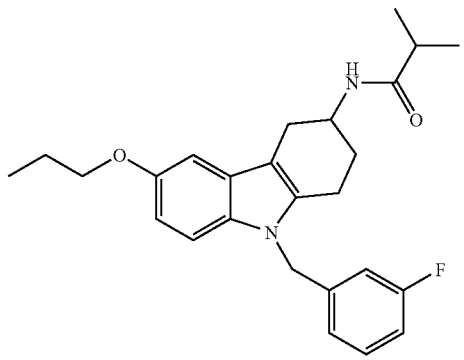

MS (ES): m/z 423(M+1); $^1$H NMR (CD$_3$OD): δ 7.99 (s,1H, NH), 7.26 (m, 1H), 7.11 (d, 1H), 6.96 (m, 2H), 6.81 (d, 1H), 6.77 (d, 1H), 6.65 (d, 1H), 5.27 (s, 2H), 4.18 (m, 1H), 3.96 (t, 2H), 3.08 (dd, 1H), 2.75 (m, 2H), 2.62 (m, 1H), 2.50 (m, 1H), 2.10 (m, 2H), 1.79-1.97 (m, 3H), 1.18 (m, 6H), 1.09 (t, 3H).

Preparation 9

N-(6,7,8,9-Tetrahydro-5H-1,3-dioxa-9-aza-cyclopenta[b]fluoren-6-yl)-isobutyramide

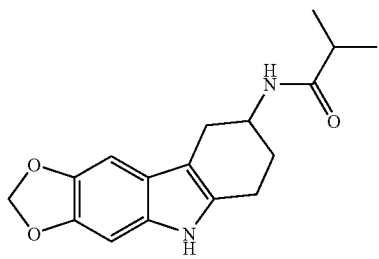

Add N-(4-oxo-cyclohexyl)-isobutyramide (974 mg, 5.32 mmol) a suspension of benzo[1,3]dioxol-5-yl-hydrazine hydrochloride salt (Clemo, G. R.; Weiss, J. *J. Chem. Soc.* (1945), 702.) (1.00 g, 5.32 mmol) to water (7 mL) and concentrated hydrochloric acid (3 mL). Heat the reaction to 90° C. for 12 h and cool to ambient temperature. Collect the resultant solid by vacuum filtration, rinse with water and place under high vacuum for 12 h to afford the titled compound (1.20 g, 75%) as a dark brown solid. m.p.=198-200° C.; $^1$H NMR (300 MHz, CDCl$_3$): δ 7.77 (br s, 1H), 6.81 (s, 1H), 6.78 (s, 1), 5.91 (s, 2H), 5.57 (br s, 1H), 4.40 (br s, 1H), 3.00 (dd, J=15.4, 5.1 Hz, 1H), 2.80-2.69 (m, 2H), 2.50 (dd, J=15.4, 6.5 Hz, 11H), 2.30 (septet, J=6.9 Hz, 1H), 2.05-1.96 (m, 2H), 1.14 (d, J=6.9 Hz, 6H).

Preparation 10

(2,2-Difluoro-benzo[1,3]dioxol-5-yl)-hydrazine hydrochloride salt

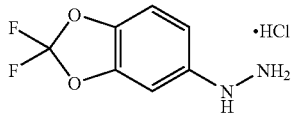

Add slowly a solution of sodium nitrite (1.40 g, 20.3 mmol) in water (11 mL) to a flask containing 2,2-difluoro-benzo[1, 3]dioxol-5-ylamine (3.41 g, 19.7 mmol), water (14 mL), and concentrated hydrochloric acid (5 mL) at −5° C. Cool the reaction to −10° C. then add tin(II) chloride (11.20 g, 49.6 mmol) in concentrated hydrochloric acid (9 mL). Stir the reaction for one hour and collect the resultant solid by filtration. Dissolve the solid in methylene chloride (20 mL) and treat with acetone (5 mL). Wash the resultant organic solution with water (50 mL), dry over magnesium sulfate, filter, and evaporate under reduced pressure. Stir the resultant oil with 2N hydrochloric acid (100 mL) for 12 h. Collect a solid by filtration, wash with water and dry in a vacuum oven at 40° C. overnight to give the subtitled compound (1.14 g, 26%) as a red powder. $^1$H NMR (300 MHz, DMSO-d$_6$): δ 10.32 (br s, 3H), 8.45 (br s, 1H), 7.34 (d, J=8.7 Hz, 1H), 7.11 (d, J=2.3 Hz, 1H), 6.79 (dd, J=8.7, 2.3 Hz, 1H).

Preparation 11

N-(2,2-Difluoro-6,7,8,9-tetrahydro-5H-1,3-dioxa-9-aza-cyclopenta[b]fluoren-6-yl)-isobutyramide

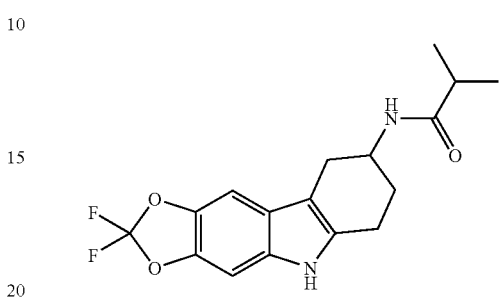

Add N-(4oxo-cyclohexyl)-isobutyramide (933 mg, 5.09 mmol) to a suspension of (2,2-difluoro-benzo[1,3]dioxol-5-yl)-hydrazine hydrochloride salt (1.14 g, 5.09 mmol), water (7 mL) and concentrated hydrochloric acid (3 mL). Heat the reaction to 90° C. for 12 h with stirring and cool to ambient temperature. Collect the resultant solid by vacuum filtration, rinse with water and place in a vacuum oven for 5 h to afford the subtitled compound (732 mg, 43%) as a tan solid. $^1$H NMR (300 MHz, CDCl$_3$): δ 7.96 (br s, 1H), 7.00 (s, 1H), 6.98 (s, 1H), 5.54 (br d, J=7.5 Hz, 1H), 4.40 (br s, 1H), 3.03 (dd, J=15.3, 5.1 Hz, 1H), 2.88-2.71 (m, 2H), 2.51 (dd, J=15.3, 7.0 Hz, 1H), 2.33 (pentet, J=6.9 Hz, 1H), 2.12-1.91 (m, 2H), 1.16 (d, J=6.9 Hz, 6H).

Example 96

N-[6-Cyano-9-(2-trifluoromethyl-benzyl)-2,3,4,9-tetrahydro-1H-carbazol-3-yl]-isobutyramide

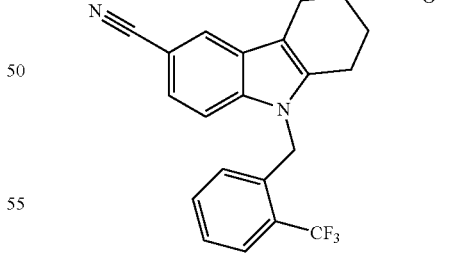

Suspend sodium hydride (60% in oil, 48 mg, 1.20 mmol) in N,N-dimethylformamide (2.5 mL) and chill to 0° C. Add slowly a solution of N-(6-cyano-2,3,4,9-tetrahydro-1H-carbazol-3-yl)-isobutyramide (281 mg, 1.00 mmol) in N,N-dimethylformamide (2.5 mL) via syringe, and stir 10 min before warming to ambient temperature for 30 min. Add 2-(trifluoromethyl)benzyl bromide (263 mg, 1.10 mmol) and stir approximately 16 h. Add ethyl acetate (75 mL), wash with water (50 mL) and brine (2×50 mL). Dry the organic phase over magnesium sulfate, filter, and evaporate under reduced pressure. Triturate the residue with 2:1 hexanes:methylene chloride to afford the title compound (333 mg, 76%). MS (ES): m/z 440 (M+1); ¹H NMR (300 MHz, CDCl₃): δ 7.83 (s, 1H), 7.73 (d, J=7.2 Hz, 1H), 7.39-7.29 (m, 3H), 7.16 (d, J=8.4 Hz, 1H), 6.27 (d, J=7.4 Hz, 1H), 5.53-5.51 (m, 1H), 5.46 (s, 2H), 4.47-4.30 (m, 1H), 3.21-3.15 (m, 1H), 2.67-2.59 (m, 3H), 2.33 (septet, J=6.8 Hz, 1H), 2.16-2.11 (m, 1H), 2.03-1.93 (m, 1H), 1.16 (d, J=6.8 Hz, 3H), 1.15 (d, J=6.8 Hz, 3H); m.p.=222-225° C.

Prepare Examples 97 to 100 below using tetrahydrocarbazoles as prepared in Preparations 3, 9, and 11, and the appropriate benzylhalide, by essentially following the procedures as described in Example 96, above.

Example 97

N-[6-Cyano-9-(2-difluoromethoxy-benzyl)-2,3,4,9-tetrahydro-1H-carbazol-3-yl]-isobutyramide

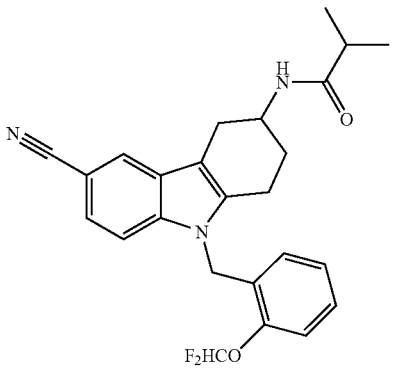

MS (ES): m/z 438 (M+1); ¹H NMR (300 MHz, CDCl₃): δ 7.81 (s, 1H), 7.37-7.15 (m, 4H), 7.03 (t, J=7.5 Hz, 1H), 6.62 (t, J=73.4 Hz, 1H), 6.38 (d, J=8.1 Hz, 1H), 5.52 (br d, J=7.8 Hz, 1H), 5.32 (s, 2H), 4.38 (br t, J=8.2 Hz, 1H), 3.16 (dd, J=15.4, 5.1 Hz, 1H), 2.74-2.59 (m, 3H), 2.33 (septet, J=6.9 Hz, 1H), 2.17-1.97 (m, 2H), 1.15 (d, J=6.9 Hz, 6H); m.p.=217-219° C.

Example 98

N-[9-(3-Fluoro-benzyl)-6,7,8,9-tetrahydro-5H-1,3-dioxa-9-aza-cyclopenta[b]fluoren-6-yl]-isobutyramide

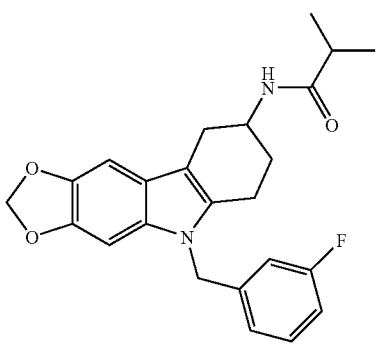

MS (ES): m/z 409 (M+1); ¹H NMR (300 MHz, CDCl₃): δ 7.28-7.20 (m, 1H), 6.95-6.86 (m, 2H), 6.75 (d, J=7.7 Hz, 1M), 6.65-6.60 (m, 2H), 5.90 (s, 2H), 5.51 (br d, J=7.7 Hz, 1H), 5.14 (s, 2H), 4.40 (br s, 1H), 3.05 (dd, J=15.4, 5.0 Hz, 1H), 2.95-2.53 (m, 3H), 2.32 (septet, J=6.9 Hz, 1H), 2.17-1.98 (m, 2H), 1.15 (d, J=6.9 Hz, 3H), 1.13 (d, J=6.9 Hz, 3H); m.p.=250-255° C.

Example 99

N-[2,2-Difluoro-9-(3-fluoro-benzyl)-6,7,8,9-tetrahydro-5H-1,3-dioxa-9-aza-cyclopenta[b]fluoren-6-yl]-isobutyramide

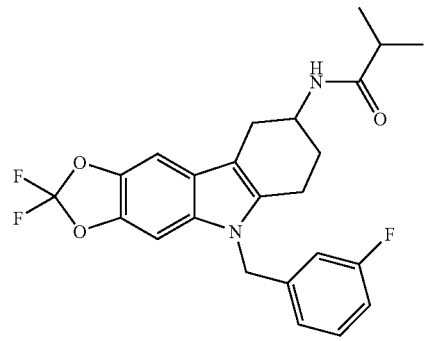

MS (ES): m/z 445 (M+1); ¹H NMR (300 MHz, CDCl₃): δ 7.29-7.22 (m, 1H), 7.07 (s, 1H), 6.94 (t, J=8.3 Hz, 1H), 6.83 (s, 1H), 6.73 (d, J=7.8 Hz, 1H), 6.60 (d, J=9.3 Hz, 1H), 5.50 (br d, J=7.7 Hz, 1H), 5.19 (s, 2H), 4.40 (br s, 1H), 3.09 (dd, J=15.3, 5.0 Hz, 1H), 2.75-2.54 (m, 3H), 2.32 (septet, J=6.9 Hz, 1H), 2.12-1.97 (m, 2H), 1.14 (d, J=6.9 Hz, 3H), 1.12 (d, J=6.9 Hz, 3H); m.p.=197-199° C.

Example 100

N-[6-Cyano-9-(2-trifluoromethoxy-benzyl)-2,3,4,9-tetrahydro-1H-carbazol-3-yl]-isobutyramide

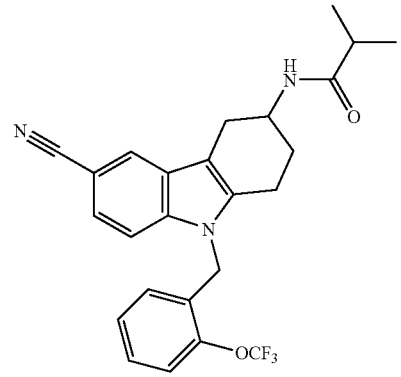

MS (ES): m/z 456 (M+1); ¹H NMR (300 MHz, CDCl₃): δ 7.81 (d, J=1.0 Hz, 1H), 7.36 (dd, J=8.5, 1.5 Hz, 1H), 7.32-7.30 (m, 2H), 7.18 (d, J=8.5 Hz, 1H), 7.13-7.07 (m, 1H), 6.36 (d, J=7.7 Hz, 1H), 5.58-5.51 (m, 1H), 5.34 (s, 2H), 4.46-4.33 (m, 1H), 3.22-3.10 (m, 1H), 2.78-2.57 (m, 3H), 2.33 (septet, J=6.9 Hz 1H), 2.19-2.07 (m, 1H), 2.05-1.90 (m, 1H), 1.16 (d, J=6.9 Hz, 3H), 1.15 (d, J=6.9 Hz, 3H); m.p.=224-225° C.

Example 101

N-[6-Chloro-9-(2-hydroxy-benzyl)-2,3,4,9-tetrahydro-1H-carbazol-3-yl]-isobutyramide

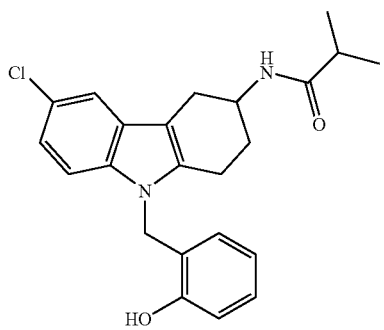

Dissolve N-[6-chloro-9-(2-methoxy-benzyl)-2,3,4,9-tetrahydro-1H-carbazol-3-yl]-isobutyramide (Example 19) (100 mg, 0.24 mmol) in anhydrous dichloromethane (3 mL) under nitrogen and cool in a brine/ice bath to 0° C. Slowly add boron tribromide (1M in dichloromethane, 1.22 mL, 1.22 mmol). After 30 min remove the ice bath and allow to warm to ambient temperature over 4 h. Dilute with ethyl acetate (12 mL) and wash with water. Extract aqueous portion with ethyl acetate (3×). Combine all organic portions, wash with water, brine, dry (MgSO$_4$), and concentrate in vacuo to obtain a residue. Elute the residue over a silica pad with 25% ethyl acetate/dichloromethane to obtain 93 mg (96%) of a tan solid. MS (ES): m/z 397, 399 (M+1), 395, 397 (M−1); $^1$H NMR (DMSO-d$_6$): δ 9.83 (s, 1H), 7.85 (d, 1H, J=7.9 Hz), 7.45 (s, 1H), 7.33 (d, 1H, J=8.4 Hz), 7.04 (m, 2H), 6.86 (d, 1H, J=7.9 Hz), 6.63 (t, 1H, J=7.3 Hz), 6.32 (d, 1H, J=7.5 Hz), 5.23 (s, 2H), 4.02 (m, 1H), 2.95 (dd, 1H, J=15.2, 5.1 Hz), 2.84-2.66 (m, 2H), 2.52 (m, 1H), 2.40 (m, 1H), 1.97 (m, 1H), 1.80 (m, 1H), 1.02 (m, 7H).

Prepare Examples 102 and 103, using the appropriate methoxybenzyl precursor from Examples 23 and 27, by essentially following procedures as described in Example 101.

Example 102

N-[$^6$-Chloro-9-(3-hydroxy-benzyl)-2,3,4,9-tetrahydro-1H-carbazol-3-yl]-isobutyramide

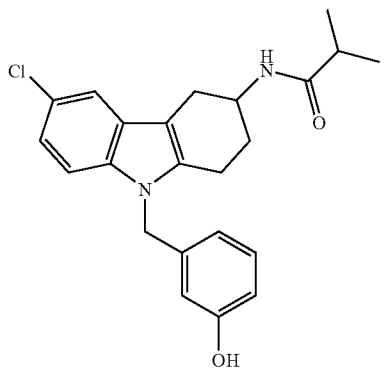

MS (ES): m/z 397, 399 (M+1), 395, 397 (M−1); $^1$H NMR (DMSO-d$_6$): δ 9.36 (s, 1H), 7.85 (d, 1H, J=7.9 Hz), 7.46 (d, 1H, J=1.8 Hz), 7.38 (d, 1H, J=8.4 Hz), 7.12-7.03 (m, 2H), 6.62 (m, 1H), 6.50 (d, 1H, J=7.5 Hz), 6.35 (s, 1H), 5.27 (s, 2H), 4.01 (m, 1H), 2.95 (dd, 1H, J=15.0, 4.8 Hz), 2.85-2.64 (m, 2H), 2.51 (m, 1H), 2.40 (m, 1H), 1.98 (m, 1H), 1.80 (m, 1H), 1.02 (m, 6H).

Example 103

N-[6-Chloro-9-(4-hydioxy-benzyl)-2,3,4,9-tetrahydro-1H-carbazol-3-yl]-isobutyramide

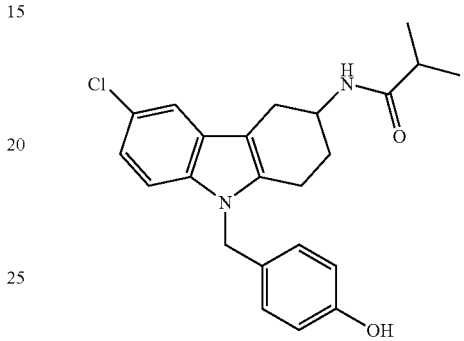

MS (ES): m/z 397, 399 (M+1), 395, 397 (M−1); $^1$H NMR (DMSO-d$_6$): δ 9.36 (s, 1H), 7.84 (d, 1H, J=7.5 Hz), 7.44 (d, 1H, J=2.2 Hz), 7.41 (d, 1H, J=8.4 Hz), 7.04 (dd, 1H, J=8.6, 2.0 Hz), 6.90 (d, 2H, J=8.4 Hz), 6.68 (d, 2H, J=8.4 Hz), 5.21 (s, 2H), 4.01 (m, 1H), 2.93 (dd, 1H, J=15.0, 4.8 Hz), 2.77 (m, 2H), 2.49 (m, 1H), 2.40 (m, 1H), 1.97 (m, 1H), 1.80 (m, 1H), 1.02 (d, 6H, J=6.6 Hz).

Example 104

N-[6-Chloro-9-(2-nitro-benzyl)-2,3,4,9-tetrahydro-1H-carbazol-3-yl]-isobutyramide

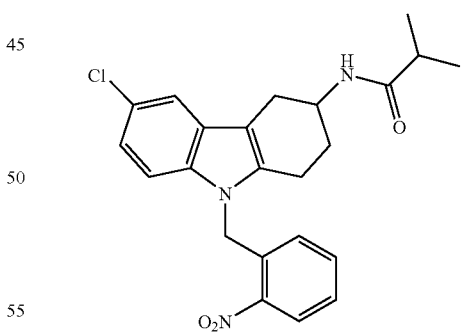

Suspend sodium hydride (60%, 120 mg, 3 mmol) in anhydrous DMF (2.5 mL) under nitrogen and cool in an ice bath. Slowly add N-(6-chloro-2,3,4,9-tetrahydro-1H-carbazol-3-yl)-isobutyramide (prepare essentially as described in Preparation 4)(727 mg, 2.5 mmol) dissolved in DMF (8 mL). After 10 min remove ice bath and allow the reaction to warm to ambient temperature over 1 h. Add DMF (25 mL) and cool in a dry ice/acetone bath. Add dropwise a solution of 2-nitrobenzylbromide (648 mg, 3 mmol) in DMF (2.5 mL). Stir for 18 h, allowing to warm to ambient temperature. Pour into water and extract with ethyl acetate/diethyl ether (100 mL/50 mL). Separate and wash the aqueous portion with ethyl acetate (50 mL). Combine organics and wash with 1N hydrochloric acid (2×100 mL), brine (2×100 mL), dry (MgSO$_4$), and concentrate in vacuo to obtain a yellow solid. Purify by flash chromatography eluting with dichloromethane and then a gradient up to 10% ethyl acetate/dichloromethane to obtain 833 mg (79%) of a yellow solid.

MS (ES): m/z 426, 428 (M+1), 424, 426 (M−1); $^1$H NMR (DMSO-d$_6$): δ 8.21 (dd, 1H, J=7.9, 1.3 Hz), 7.86 (d, 1H, J=7.9 Hz), 7.60-7.51 (m, 3H), 7.40 (d, 1H, J=8.8 Hz), 7.03 (dd, 1H, J=8.6, 2.0 Hz), 6.18 (d, 1H, J=7.0 Hz), 5.75 (s, 2H), 4.05 (m, 1H), 2.99 (dd, 1H, J=15.2, 5.1 Hz), 2.74-2.53 (m, 3H), 2.40 (m, 1H), 1.95 (m, 1H), 1.82 (m, 1H), 1.01 (m, 6H).

Example 105

N-[6-Cyano-9-(2-methoxy-benzyl)-2,3,4,9-tetrahydro-1H-carbazol-3-yl]-isobutyramide

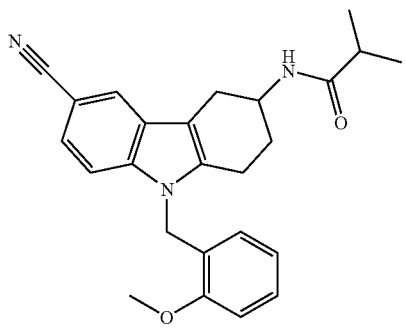

Follow the procedures essentially as described in Example 104, above, using N-(6-cyano-2,3,4,9-tetrahydro-1H-carbazol-3-yl]-isobutyramide (3.38 g, 12 mmol) and treating with sodium hydride (580 mg, 14A mmol). Cool the formed sodium salt in a dry ice/acetonitrile bath and add 2-methoxy-benzylchloride (1.84 mL, 13.2 mmol) in DMF (2 mL) at −35 to −30° C. Remove the bath and allow the reaction to warm to ambient temperature over 3 h with stifling. Add water (250 mL) dropwise, cooling in an ice bath while stirring for 30 min. Filter the resulting precipitate and dry under house vacuum at 45° C. for 18 h. Triturate and sonicate the material in diethyl ether for 1.5 h, filter and dry to provide 3.98 g (83%) of an off-white solid.

MS (ES): m/z 402 (M+1), 400 (M−1); $^1$H NMR(DMSO-d$_6$): δ 7.98 (s, 1H), 7.87 (d, 1H, J=7.5 Hz), 7.50 (d, 1H, J=8.4 Hz), 7.40 (dd, 1H, J=8.3, 1.3 Hz), 7.26 (t, 1H, J=7.9 Hz), 7.06 (d, 1H, J=8.4 Hz), 6.80 (t, 1H, J=7.5 Hz), 6.40 (d, 1H, J=7.5 Hz), 5.34 (s, 2H), 4.03 (m, 1H), 3.87 (s, 3H), 3.02 (dd, 1H, J=15.4, 5.3 Hz), 2.84-2.65 (m, 2H), 2.40 (m, 1H), 2.57 (dd, 1H, J=15.3, 8.6 Hz), 1.98 (m, 1H), 1.82 (m, 1H), 1.02 (m, 6H).

Example 106

N-[9-(2-Amino-benzyl)-6-chloro2,3,4,9-tetrahydro-1H-carbazol-3-yl]-isobutyramide

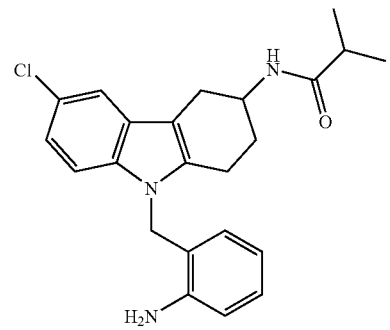

Dissolve tin(II) chloride dihydrate (2.15 g, 9.5 mmol) in absolute ethanol (10 mL) and add it to N-[6-chloro-9-(2-nitro-benzyl)-2,3,4,9-tetrahydro-1H-carbazol-3-yl]-isobutyramide (Example 104) (810 mg, 1.9 mmol) in concentrated hydrochloric acid (10 mL). Heat the reaction at 60° C. for 1.5 h. Allow to cool and add 5N NaOH (27 mL) until pH=11-12. Extract the suspended solids into ethyl acetate (4×). Combine the organic portions and wash with water, brine, dry (MgSO$_4$), and concentrate in vacuo to obtain a solid. Pass over a silica pad eluting with 25% ethyl acetate/dichloromethane to obtain 640 mg (85%). MS (ES): m/z 396, 398 (M+1), 394 (M−1); $^1$H NMR(DMSO-d$_6$): δ 7.86 (d, 1H, J=7.5 Hz), 7.49 (d, 1H, J=1.8 Hz), 7.24 (d, 1H, J=8.8 Hz), 7.04 (dd, 1H, J=8.6, 2.0 Hz), 6.93 (dt, 1H, J=7.5, 1.3 Hz), 6.71 (dd, 1H, J=8.1, 1.1 Hz), 6.37 (dt, 1H, J=7.5, 1.3 Hz), 5.89 (d, 1H, J=7.0 Hz), 5.14 (m, 4H), 4.03 (m, 1H), 2.98 (dd, 1H, J=15.2, 5.1 Hz), 2.75-2.60 (m, 2H), 2.55 (m, 1H), 2.41 (m, 1H), 1.97 (m, 1H), 1.81 (m, 1H), 1.03 (d, 3H, J=4.0 Hz), 1.02 (d, 3H, J=4.4 Hz).

Example 107

N-[6-Cyano-9-(2-hydroxy-benzyl)-2,3,4,9-tetrahydro-1H-carbazol-3-yl]-isobutyrarmide

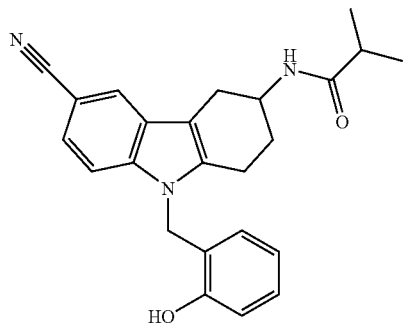

Follow the procedures essentially as described in Example 101, above, using N-[6-cyano-9-(2-methoxy-benzyl)-2,3,4, 9-tetrahydro-1H-carbazol-3-yl]-isobutyramide (Example 105) (3.90 g, 9.71 mmol) to provide, after workup, 4.4 g of a solid. Partially dissolve in dichloromethane/THF/acetone and a small amount of methanol. Filter and dissolve the remaining solids in THF/methanol. Apply the two solutions to a large silica pad and elute with dichloromethane, 25% ethyl acetate/dichloromethane and 50% ethyl acetate/dichloromethane for a total volume of 3-4 L. Concentrate in vacuo to give a brown solid. Triturate the solid in dichloromethane and filter to provide 3.15 g (84%) of a white solid. MS (ES): m/z 388 (M+1), 386 (M−1); $^1$H NMR(DMSO-$d_6$): δ 9.87 (s, 1H), 7.97 (s, 1H), 7.88 (d, 1H, J=7.5 Hz), 7.53 (d, 1H, J=8.8 Hz), 7.40 (m, 1H), 7.08 (t, 1H, J=7.7 Hz), 6.86 (d, 1H, J=7.9 Hz), 6.65 (t, 1H, J=7.3 Hz), 6.40 (d, 1H, J=7.5 Hz), 5.30 (s, 2H), 4.03 (m, 1H), 3.01 (dd, 1H, J=15.4, 4.8 Hz), 2.88-2.68 (m, 2H), 2.56 (m, 1H), 2.40 (m, 1H), 1.98 (m, 1H), 1.82 (m, 1H), 1.02 (m, 6H).

Example 108

N-[6-Cyano-9-(2-nitro-benzyl)-2,3,4,9-tetrahydro-1H-carbazol-3-yl]-isobutyramide

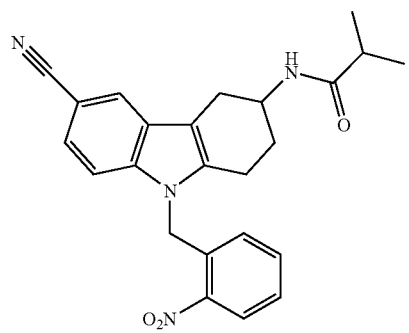

Prepare the title compound by essentially following the procedures as described in Example 104, using N-(6-cyano-2,3,4,9-tetrahydro-1H-carbazol-3-yl)-isobutyramide (Preparation 3) (5.63 g, 20 mmol), sodium hydride (0.96 g, 24 mmol) and 2-nitrobenzyl bromide (5.18 g, 24 mmol). After workup, concentrate the solution in vacuo and when the volume is a slurry, filter and dry under house vacuum to obtain 6.33 g (76%) of a yellow solid which is used without further purification. MS (ES): m/z 417 (M+1), 415 (M−1); $^1$H NMR (DMSO-$d_6$): δ 8.22 (dd, 1H, J=7.3, 2.0 Hz), 8.05 (s, 1H), 7.88 (d, 1H, J=7.5 Hz), 7.62-7.52 (m, 3H), 7.41 (dd, 1H, J=8.4, 1.3 Hz), 6.20 (d, 1H, J=7.0 Hz), 5.83 (s, 2H), 4.07 (m, 1H), 3.05 (dd, 1H, J=15.4, 4.8 Hz), 2.77-2.57 (m, 3H), 2.41 (m, 1H), 1.96 (m, 1H), 1.85 (m, 1H), 1.02 (m, 6H).

Example 109

N-[9-(2-Amino-benzyl)-6-cyano-2,3,4,9-tetrahydro-1H-carbazol-3-yl]-isobutyramide

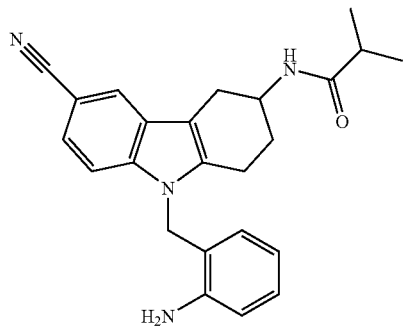

Dissolve tin(II) chloride dihydrate (16.70 g, 74.0 mmol) in absolute ethanol (35 mL) and add it to N-[6-cyano-9-(2-nitrobenzyl)-2,3,4,9-tetrahydro-1H-carbazol-3-yl]-isobutyramide (6.18 g, 14.8 mmol). Add concentrated hydrochloric acid (35 mL) and heat at 60° C. for 2 h. Allow to cool and add 5N NaOH (80 mL). Extract the suspended solids into ethyl acetate (150 mL). Add more 5N NaOH (5 mL) and extract with ethyl acetate (200 mL). Combine the organic portions and wash with water (2×200 mL), brine (150 mL), dry (MgSO$_4$), filter and concentrate in vacuo to obtain 3.45 g. Triturate the material in dichloromethane, filter, and dry under house vacuum to obtain 1.71 g (30%) of a white solid. MS (ES): m/z 387 (M+1); $^1$H NMR(DMSO-$d_6$): δ 8.00 (s, 1H), 7.88 (d, 1H, J=7.9 Hz), 7.42 (m, 2H), 6.94 (t, 1H, J=7.6 Hz), 6.72 (dd, 1H, J=7.9, 0.9 Hz), 6.37 (dt, 1H, J=7.4, 0.9 Hz), 5.90 (d, 1H, J=7.0 Hz), 5.19 (m, 4H), 4.05 (m, 1H), 3.03 (dd, 1H, J=15.2, 5.1 Hz), 2.71 (m, 2H), 2.59 (dd, 1H, J=15.9, 8.4 Hz), 2.41 (m, 1H), 1.98 (m, 1H), 1.83 (m, 1H), 1.03 (d, 3H, J=4.4 Hz), 1.01 (d, 3H, J=4.4 Hz); HPLC: $R_t$=1.95 min, (93%).

Obtain more product by making the aqueous portion basic with 5N NaOH and extracting with two large volumes of ethyl acetate. Combine organic portions, wash with brine, dry (MgSO$_4$), filter, and concentrate in vacuo to obtain 1.36 g off-white solid which was 92.6% by HPLC. Combine with the mother liquor from the above trituration and absorb on silica with THF/dichloromethane and apply to a silica pad. Elute with a large volume of 1 dichloromethane/ethyl acetate, 2 dichloromethane/3 ethyl acetate, 1 dichloromethane/2 ethyl acetate and then straight ethyl acetate to obtain 1.96 g (34%)

Example 110

R-N-[9-(2-Amino-benzyl)-6-cyano-2,3,4,9-tetrahydro-1H-carbazol-3-yl]-isobutyramide

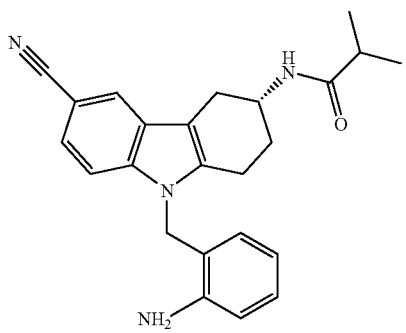

Separate racemic N-[9-(2-amino-benzyl)-6-cyano-2,3,4,9-tetrahydro-1H-carbazol-3-yl]-isobutyramide (1.50 g) by chiral chromatography. Use a Chiralpak AD column of 4.6× 150 mm and elute with heptane/isopropylalcohol (60/40) at a flow rate of 0.6 mL/min with UV detection set at 300 nm. Obtain 640 mg of the titled compound as Isomer 1 with ee=98.4%.

Example 111

S-N-[9-(2-Amino-benzyl)-6-cyano-2,3,4,9-tetrahydro-1H-carbazol-3-yl]-isobutyramide

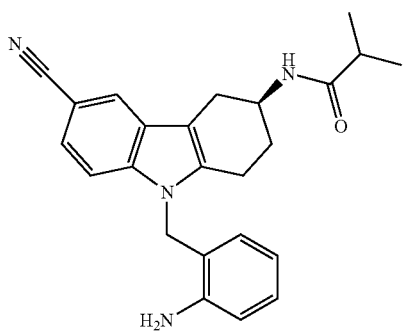

Use conditions in Example 110 to obtain 623 mg of the titled compound as Isomer 2 from chiral chromatography with ee=94.9%.

Example 112

N-[6-Cyano-9-(2-ethylamino-benzyl)-2,3,4,9-tetrahydro-1H-carbazol-3-yl]-isobutyramide

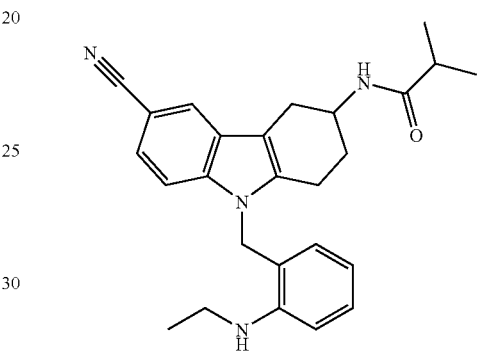

Dissolve N-[9-(2-amino-benzyl)-6-cyano-2,3,4,9-tetrahydro-1H-carbazol-3-yl]-isobutyramide (Example 109) (193 mg, 0.5 mmol) in anhydrous DMF (2 mL) under nitrogen. Add acetaldhyde (0.34 mL, 0.6 mmol), sodium triacetoxyborohydride (191 mg, 0.9 mmol) and acetic acid (0.072 ml, 1.25 mmol) and heat at 40° C. for 6 h. Take TLC (1 hexane/3 ethyl acetate) and observe starting material is still present. Add more acetaldehyde (0.010 mL, 0.18 mmol), sodium triacetoxyborohydride (60 mg, 0.3 mmol) and acetic acid (0.030 mL, 0.5 mmol) and heat at 40° C. for 18 h. Observe TLC which shows the reaction still not complete 1 0 but new by-product is forming. Allow the reaction to cool, dilute with water (20 mL), and extract with ethyl acetate (3×20 mL). Combine the organic portions and wash with brine (40 mL), dry (MgSO$_4$), filter, and concentrate in vacuo to give 416 mg of a brown solid. Absorb on silica with THF and a small amount of methanol and purify by flash chromatography. Elute with dichloromethane, then 10% ethyl acetate/dichloromethane with a gradient up to 50% ethyl acetate/dichloromethane to obtain 103 mg (50%) of a white solid. MS (ES): m/z 415 (M+1), 413 (M−1); $^1$H NMR(DMSO-d$_6$): δ 8.02 (s, 1H), 7.88 (d, 1H, J=7.5 Hz), 7.41 (d, 2H, J=0.9 Hz), 7.07 (t, 1H, J=7.7 Hz), 6.67 (d, 1H, J=7.9 Hz), 6.42 (t, 1H, J=7.6 Hz), 5.85 (d, 1H, J=7.4 Hz), 5.25 (s, 2H), 5.06 (t, 1H, J=5.3 Hz), 4.04 (m, 1H), 3.17 (m, 2H), 3.04 (dd, 1H, J=15.4, 5.3 Hz), 2.74-2.55 (m, 3H), 2.41 (m, 1H), 1.97 (m, 1H), 1.83 (m, 1H), 1.28 (t, 3H, J=7.0 Hz), 1.02 (m, 6H).

Example 113

N-[6-Cyano-9-(2-methanesulfonylamino-benzyl)-2,3,4,9-tetrahydro-1H-carbazol-3-yl]-isobutyramide

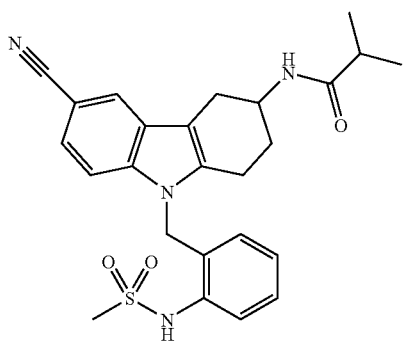

Suspend N-[9-(2-amino-benzyl)-6-cyano-2,3,4,9-tetrahydro-1H-carbazol-3-yl]-isobutyramide (Example 109) (116 mg, 0.3 mmol) in anhydrous dichloromethane (3 mL) under nitrogen. Add methanesulfonyl chloride (0.028 mL, 0.36 mmol) and pyridine (0.032 mL, 0.39 mmol), followed by anhydrous DMF (2 mL) to effect solution. Stir 5.5 h at room temperature. Add additional methanesulfonyl chloride (0.010 mL, 0.13 mmol) and pyridine (0.010 mL, 0.12 mmol) and stir 18 h at room temperature. Dilute with dichloromethane and wash with 1N hydrochloric acid. Backwash the aqueous portion with dichloromethane. Combine the organic portions and wash with brine, dry (MgSO$_4$), filter, and concentrate in vacuo to provide 74 mg of a yellow oil. Absorb the oil on silica with THF and a small amount of methanol and purify by flash chromatography. Elute with a step gradient of 10% ethyl acetate/dichloromethane, 25% ethyl acetate/dichloromethane, and 50% ethyl acetate/dichloromethane to obtain 19 mg (14%) of a light yellow solid. MS (ES): m/z 465 (M+1), 463 (M−1); $^1$H NMR(DMSO-d$_6$): δ 9.43 (s, 1H), 8.02 (s, 1H), 7.88 (d, 1H, J=7.5 Hz), 7.43-7.36 (m, 3H), 7.31 (dt, 1H, J=7.6, 1.0 Hz), 7.12 (dt, 1H, J=7.5, 0.9 Hz), 6.21 (d, 1H, J=7.5 Hz), 5.54 (s, 2H), 4.06 (m, 1H), 3.12 (s, 3H), 3.04 (dd, 1H, J=15.4, 5.3 Hz), 2.70 (m, 2H), 2.59 (dd, 1H, J=15.4, 8.4 Hz), 2.41 (m, 1H), 1.97 (m, 1H), 1.85 (m, 1H), 1.02 (m, 6H).

Example 114

N-[6-Cyano-9-furan-(2-dimethylamino-benzyl)-2,3,4,9-tetrahydro-1H-carbazol-3-yl]-isobutyramide

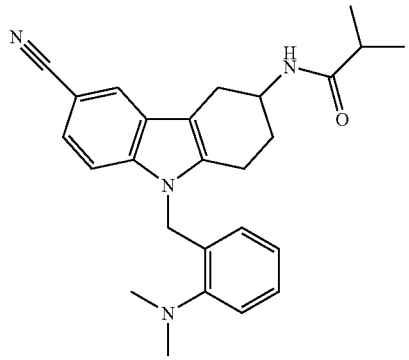

Add sodium cyanoborohydride (0.030 g, 0.48 mmol), to N-[9-(2-aminobenzyl)-6-cyano-2,3,4,9-tetrahydro-1H-carbazol-3-yl]-isobutyramide (Example 109) (0.116 g, 0.3 mmol) and 37% formaldehyde (0.112 ml, 1.5 mmol) in acetonitrile (5 ml ). Stir at ambient temperature for 16 h after addition of acetic acid, one drop after 1 hr, two drops after 1.5 h. Carefully quench the reaction with 1N sodium hydroxide (5 ml). Dilute the reaction with water and extract with ethyl acetate. Wash the ethyl acetate extract with water, dry with magnesium sulfate, filter and evaporate at reduced pressure. Purify the resulting residue with silica gel chromatography, eluting with ethyl acetate/hexanes to obtain product (36 mg, 29% yield). LCMS(Method D): m/z 415 (M+1, APCI). Good for C$_{26}$H$_{30}$N$_4$O, MW 414.56. $^1$H NMR(DMSOd$_6$): δ 7.98 (s, 1H), 7.87 (d, 1H, J=7.9 Hz), 7.42 (m, 2H), 7.22 (m, 2H), 6.87 (m, 1H), 6.30 (d, 1H, J=7.5 Hz), 5.42 (s, 2H), 4.03 (m, 1H), 3.79 (s, 6H), 3.02 (dd, 1H, J=15.2, 5.1 Hz), 2.73-2.56 (m, 3H), 2.40 (m, 1H), 2.00-1.92 (m, 1H), 1.86-1.76 (m, 1H), 1.02 (dd, 6H, J=6.8, 3.7 Hz).

Preparation 12

(4-Bromo-3-fluoro-phenyl)-hydrazine

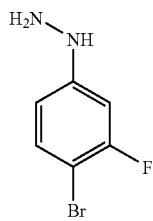

Convert 4-bromo-3-fluoroaniline to the title compound in 71% yield according to the procedure of Street, L. J.; et al. *J. Med. Chem.* (1993) 36, 1529-1538. $^1$H NMR (CDCl$_3$): δ 7.32 (m, 1H), 6.71 (dd, 1H, J=10.8, 2.4 Hz), 6.51 (dd, 1H, J=8.8, 2.6 Hz), 6.51 (dd, 1H, J=8.8, 2.6 Hz), 6.51 (dd, 1H, J=8.5, 2.5 Hz), 5.33 (br s, 1H), 3.62 (br s, 2H); HPLC: R$_t$=1.89 min, (96%)

Prepare the following phenylhydrazines (Preparations 13 to 15) using commercially available anilines by essentially following the procedures of Street et. al., *J. Med. Chem.* (1993) 36, 1529-1538. .

| Commercially available aniline | (Preparation No.) Product Name | Yield | HPLC ($R_t$, %) |
|---|---|---|---|
| 4-amino-3-chlorobenzonitrile | (13) 2-chloro-4-cyanophenylhydrazine | 25% | 1.85 (98%) |
| 2-fluoro-4-bromoaniline | (14) 2-fluoro-4-bromophenylhydrazine | 22% | 2.02 (94%) |
| 4-amino-2-chlorobenzonitrile | (15) 3-chloro-4-cyanophenylhydrazine•(⅓Et₃N•HCl) | 49% | 1.80 (93%) |

Preparation 16

N-(6-Bromo-7-fluoro-2,3,4,9-tetrahydro-1H-carbazol-3-yl)-isobutyramide and N-(6-

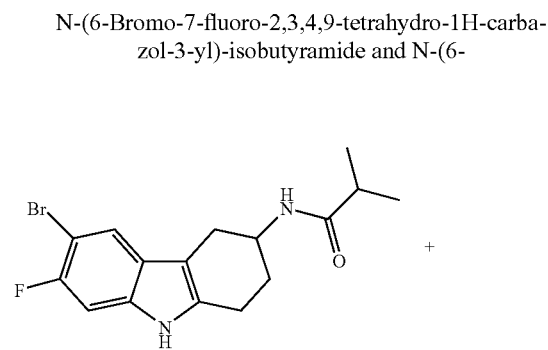

Prepare the title compounds by essentially following the procedure as described in Preparation 4 (Method 2) with (4-bromo-3-fluoro-phenyl)-hydrazine (Preparation 12) and N-(4-oxo-cyclohexyl)-isobutyramide, to obtain a tan solid containing a 65:35 mixture of isomers in 20% overall yield. MS (ES): m/z 353, 355 (M+H), 351, 353 (M−H); HPLC (Method A): $R_t$=2.22 min, (95%).

Preparation 17

N-(7-Chloro-6-cyano-2,3,4,9-tetrahydro-1H-carbazol-3-yl)-isobutyramide and N-(5-chloro-6-cyano-2,3,4,9-tetrahydro-1H-carbazol-3-yl)-isobutyramide

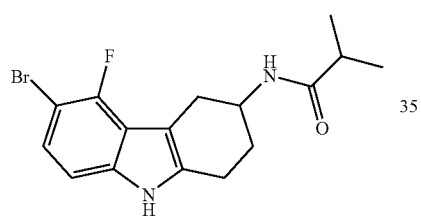

-continued

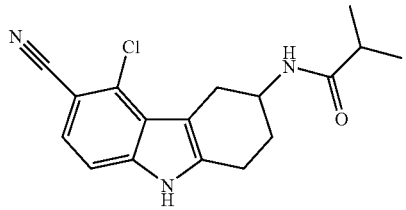

Prepare the title compounds by essentially following the procedure as described in Preparation 4 (Method 2) with 3-chloro-4-cyanophenylhydrazine (⅓ Et₃N.HCl) (Preparation 15) and N-(4-oxo-cyclohexyl)-isobutyramide, to obtain a brown solid containing a 50:50 mixture of isomers in 52% overall yield. MS (ES): m/z 316 (M+H), 314 (M−H); HPLC (Method A): $R_t$=1.83 min, (82%).

Preparation 18

N-(8-Chloro-6-cyano-2,3,4,9-tetrahydro-1H-carbazol-3-yl)-isobutyramide

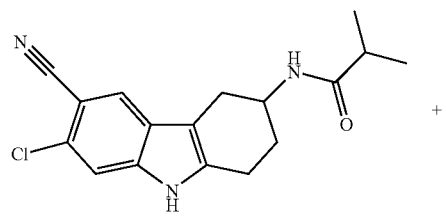

Prepare the title compound by essentially following the procedure as described in Preparation 4 (Method 2) with 2-chloro-4-cyanophenylhydrazine (Preparation 13) and N-(4-oxo-cyclohexyl)-isobutyramide, to obtain the title compound as a pink powder in 50% yield. MS (ES): m/z 316 (M+H), 314 (M−H); HPLC (Method A): $R_t$=1.96, (90%).

Preparation 19

N-(6-Bromo-8-fluoro-2,3,4,9-tetrahydro-1H-carbazol-3-yl)-isobutyramide

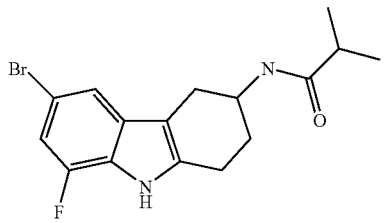

Prepare the tide compound by essentially following the procedure as described in Preparation 4 (Method 2) with 2-fluoro-4-bromophenylhydrazine (Preparation 14) and N-(4-oxo-cyclohexyl)-isobutyramide, to obtain the title compound as a tan foam in 32% yield. MS (ES): m/z 353, 355 (M+H), 351, 353 (M−H); HPLC (Method A): $R_t$=2.34, (89%).

Preparation 20

N-[6-Bromo-7-fluoro-9-(3-fluoro-benzyl)-2,3,4,9-tetrahydro-1H-carbazol-3-yl]-isobutyramide and N-[6-bromo-5-fluoro-9-(3-fluoro-benzyl)-2,3,4,9-tetrahydro-1H-carbazol-3-yl]-isobutyramide

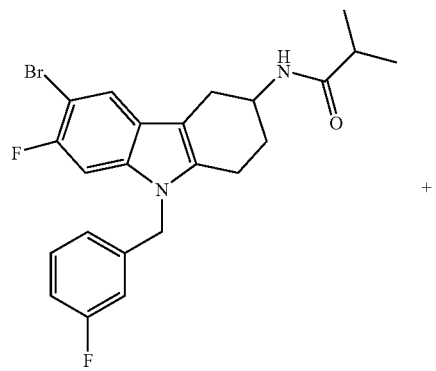

+

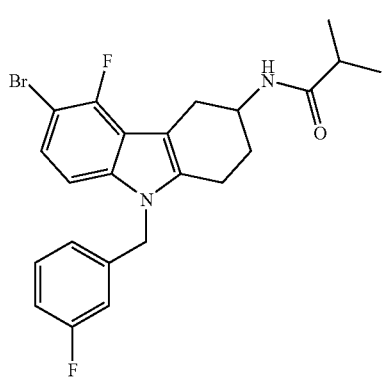

Prepare the title compounds by essentially following procedures as described in Example 96 with N-(6-bromo-7-fluoro-2,3,4,9-tetrahydro-1H-carbazol-3-yl)-isobutyramide and N-(6-bromo-5-fluoro-2,3,4,9-tetrahydro-1H-carbazol-3-yl)-isobutyramide (65:35 mixture) and 3-fluorobenzyl bromide, to obtain a white solid containing a mixture of isomers in 78% overall yield. MS (ES): m/z 461, 463 (M+1), 459, 461 (M−1); HPLC: $R_t$=3.67 min, (59%); $R_t$=3.92 min, (38%).

Example 115

N-[6-Cyano-7-fluoro-9-(3-fluoro-benzyl)-2,3,4,9-tetrahydro-1H-carbazol-3-yl]-isobutyramide

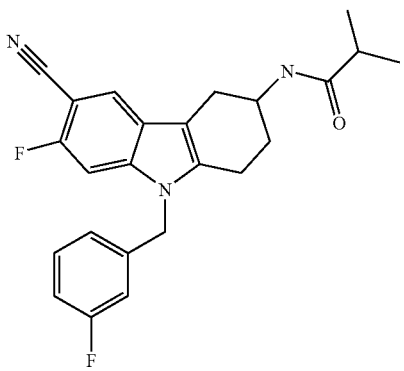

Dissolve a 65:35 mixture of N-[6-bromo-7-fluoro-9-(3-fluoro-benzyl)-2,3,4,9-tetrahydro-1H-carbazol-3-yl]-isobutyramide and N-[6-bromo-5-fluoro-9-(3-fluoro-benzyl)-2,3,4,9-tetrahydro-1H-carbazol-3-yl]-isobutyramide (500 mg, 1.08 mmol; Preparation 20) in N-methylpyrrolidinone (10 mL). Sparge the resulting solution with nitrogen for 30 min, then add copper(I) cyanide (291 mg, 3.25 mmol) and copper (I) iodide (619 mg, 3.25 mmol). Heat to 130° C. for three days, then cool to room temperature. Dilute the reaction mixture with EtOAc (200 mL) and water (100 mL). Add ethylene diamine until all the solids are dissolved (about 20 mL). Separate the layers, then wash the organic layer with water (3×75 mL). Dry the organic portion (MgSO$_4$), filter, and concentrate the organic layer to afford 474 mg of crude product. Separate the title compound from this mixture by silica gel chromatography (0-10% EtOAc/CHCl$_3$), affording the title compound as a white solid in 20% yield. MS (ES): m/z 408 (M+1), 406 (M−1); HPLC: R$_t$=2.51 min, (96%).

Example 116

N-[6-Cyano-5-fluoro-9-(3-fluoro-benzyl)-2,3,4,9-tetrahydro-1H-carbazol-3-yl]-isobutyramide

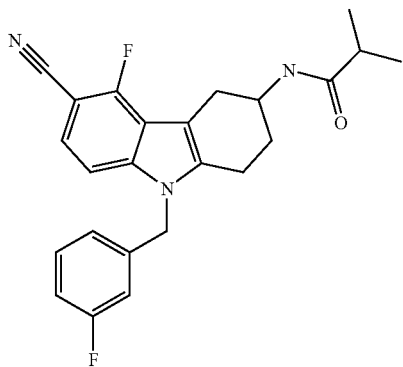

From the mixture obtained in Example 115, separate the title compound by silica gel chromatography (0-10% EtOAc/CHCl$_3$), affording the title compound in 7% yield. MS (ES): m/z 408 (M+1), 406 (M−1); HPLC: R$_t$=2.60 min, (97%).

Example 117

N-[5-Chloro-6-cyano-9-(3-fluoro-benzyl)-2,3,4,9-tetrahydro-1H-carbazol-3-yl]-isobutyramide

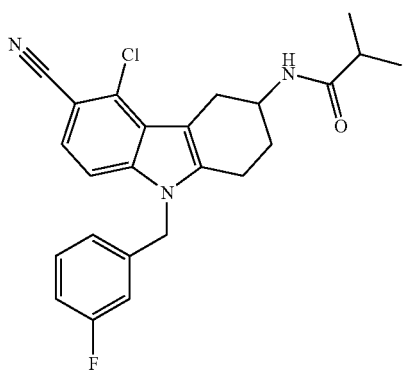

Prepare the title compound by essentially following the procedure as described in Example 96 with N-(7-chloro-6-cyano-2,3,4,9-tetrahydro-1H-carbazol-3-yl)-isobutyramide and N-(5-chloro-6-cyano-2,3,4,9-tetrahydro-1H-carbazol-3-yl)-isobutyramide (50:50 mixture—Preparation 17) and 3-fluorobenzyl bromide, to obtain a mixture of regioisomers. Separate the title compound from this mixture of regioisomers using silica gel chromatography (0-20% EtOAc/CHCl$_3$), to afford the title compound in 5% yield. MS (ES): m/z 424 (M+1), 422 (M−1); HPLC (Method B): R$_t$=6.87 min, (97%).

Example 118

N-[7-Chloro-6-cyano-9-(3-fluoro-benzyl)-2,3,4,9-tetrahydro-1H-carbazol-3-yl]-isobutyramide

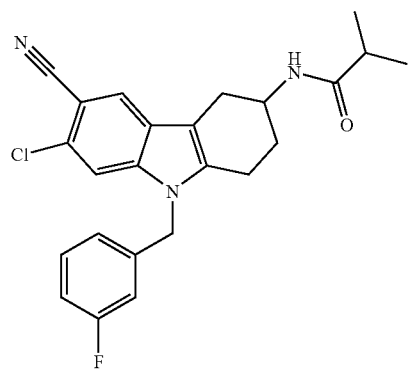

Separate the title compound from the mixture of regioisomers obtained in Example 117 using silica gel chromatography (0-20% EtOAc/CHCl$_3$), to afford the title compound in 3% yield. MS (ES): m/z 424 (M+H), 422 (M−H); HPLC (Method B): R$_t$=7.16 min, (100%).

Example 119

N-[8-Chloro-6-cyano-9-(3-fluoro-benzyl)-2,3,4,9-tetrahydro-1H-carbazol-3-yl]-isobutyramide

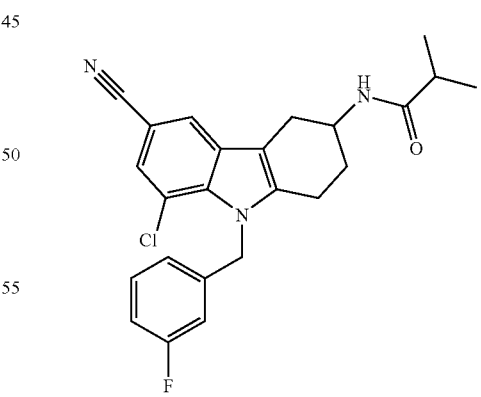

Prepare the title compound by essentially following the procedure as described in Example 96 with N-(8-chloro-6-cyano-2,3,4,9-tetrahydro-1H-carbazol-3-yl)-isobutyramide (Preparation 18) and 3-fluorobenzyl bromide, to obtain the

Example 120

N-[6-Bromo-8-fluoro-9-(3-fluoro-benzyl)-2,3,4,9-tetrahydro-1H-carbazol-3-yl]-isobutyramide

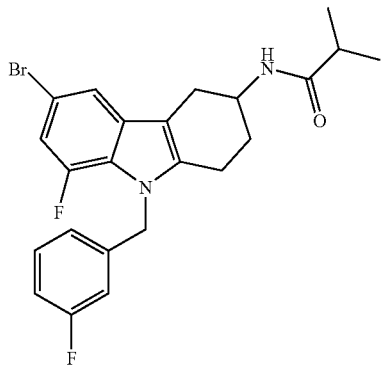

Prepare the title compound by essentially following the procedure as described in Example 96 with N-(6-bromo-8-fluoro-2,3,4,9-tetrahydro-1H-carbazol-3-yl)-isobutyramide (Preparation 19) and 3-fluorobenzyl bromide, to obtain the title compound as a white solid in 36% yield. MS (ES): m/z 461,463 (M+1), 459, 461 (M−1); HPLC (Method A): $R_t$=4.60 (92%).

Example 121

N-[6-Cyano-8-fluoro-9-(3-fluoro-benzyl)-2,3,4,9-tetrahydro-1H-carbazol-3-yl]-isobutyramide

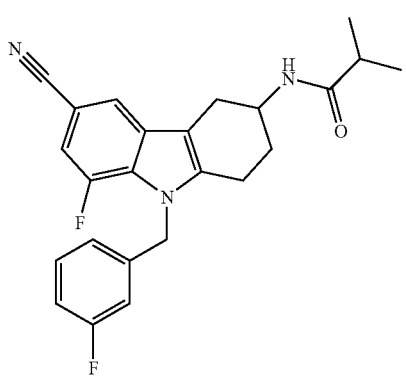

Following procedures essentially as described in Example 115 using N-[6-bromo-8-fluoro-9-(3-fluoro-benzyl)-2,3,4,9-tetrahydro-1H-carbazol-3-yl]-isobutyramide, the title compound is prepared as a white solid in 29% yield. MS (ES) 408 (M+1), 406 (M−1); HPLC (Method A): $R_t$=2.75 (97%).

Preparation 21

(R)-N-(6-Bromo-2,3,4,9-tetrahydro-1H-carbazol-3-yl)isobutyramide

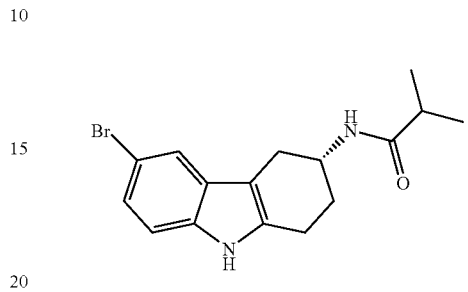

Resolve N-(6-bromo-2,3,4,9-tetrahydro-1H-carbazol-3-yl)isobutyramide via chiral chromatography using a 0.46×15 cm Chiralpak AD-H column eluting with 100% MeOH. Flow rate=0.6 mL/min. Purify using Steady State Recycle (SSR) with dimethylethylamine to improve resolution to afford e.e. >98%. First to elute is Isomer 1 (S isomer) while second isomer to elute gives the R isomer as the title compound. MS (ES): m/z 335 (M+1), 337 (M+1+2).

Example 122

(R)-N-(9-Benzyl-6-bromo-2,3,4,9-tetrahydro-1H-carbazol-3-yl)isobutyramide

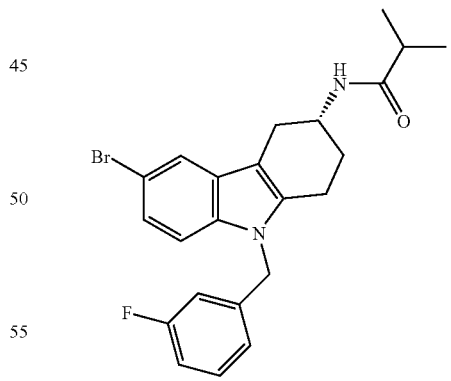

Alkylate (R)-N-(6-Bromo-2,3,4,9-tetrahydro-1H-carbazol-3-yl)isobutyramide with 1-bromomethyl-3-fluorobenzene using procedures essentially as described in Example 1 to give the title compound. MS (ES): m/z 443 (M+1), 445 (M+1+2); m.p.=204-207° C. (Alkylate the S isomer in a similar fashion to obtain (S)-N-(9-Benzyl-6-bromo-2,3,4,9-tetrahydro-1H-carbazol-3-yl)isobutyramide.)

Example 123

(R)-N-(6-Cyano-9-(3-fluorobenzyl)-2,3,4,9-tetrahydro-1H-carbazol-3-yl)isobutyramide

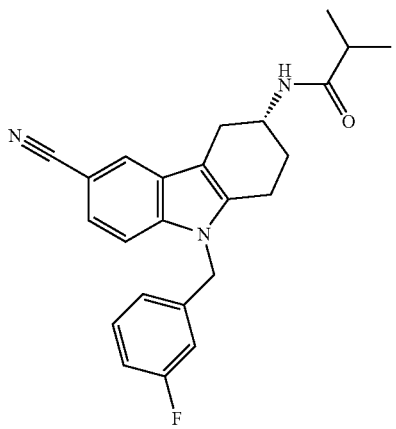

N-(6-Cyano-9-(3-fluorobenzyl)-2,3,4,9-tetrahydro-1H-carbazol-3-yl)isobutyramide (Example 51), is resolved into its enantiomers via chiral chromatography using a 0.46×15 cm Chiralpak AD-H column eluting with EtOH/MeOH/heptanes: 15/10/75. Flow rate=0.6 mL/min. First to elute is Isomer 1 (R), as the title compound with e.e. >99.5%. MS (ES): m/z 390 (M+1); m.p.=223-225° C.

Example 124

(S)-N-(6-Cyano-9-(3-fluorobenzyl)-2,3,4,9-tetrahydro-1H-carbazol-3-yl)isobutyramide

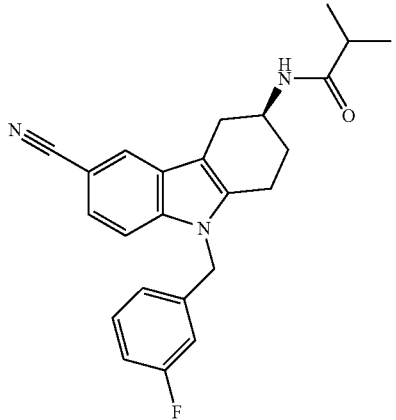

Obtain the title compound from chiral chromatography as described for Example 123. Second isomer to elute is (S) isomer. MS (ES): m/z 390 (M+1); m.p.=223-225° C.

Example 125

N-[6-(5-Amino[1,3,4]thiadiazol-2-yl)-9-(3-fluorobenzyl)-2,3,4,9-tetrahydro-1H-carbazol-3-yl]isobutyramide

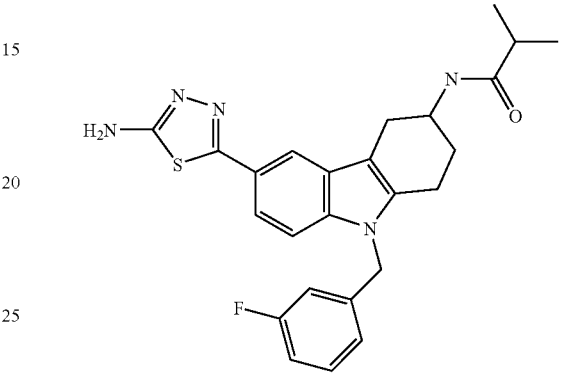

Heat a mixture of N-[6-cyano-9-(3-fluorobenzyl)-2,3,4,9-tetrahydro-1H-carbazol-3-yl]isobutyramide (example 51) (0.500 g, 1.28 mmol) and thiosemicarbazide (0.129 g, 1.41 mmol) in trifluoroacetic acid (5 ml) at 70° C. under nitrogen for 18 h. Pour the mixture onto dilute $NH_4OH$ solution and collect 0.510 g of the resultant precipitate by filtration. Azetrope the precipitate with absolute EtOH and purify by silica chromatography eluting with 0.05% $NH_4OH$ in EtOAc to give 0.10 g of a white solid. MS (ES): m/z 464 (M+1); HPLC: $R_t$=1.89 min, (100%); m.p.=251-254° C.

Example 126

(R)-N-[6-(5-Amino[1,3,4]thiadiazol-2-yl)-9-(3-fluorobenzyl)-2,3,4,9-tetrahydro-1H-carbazol-3-yl]isobutyramide

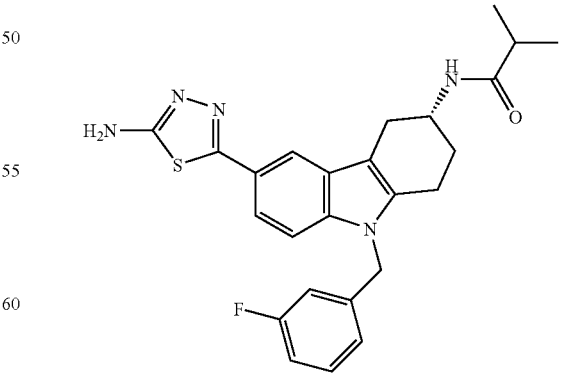

Prepare the title compound in a manner essentially as described for Example 125, starting with (R)-N-(6-cyano-9-(3-fluorobenzyl)-2,3,4,9-tetrahydro-1H-carbazol-3-yl)

isobutyramide (Example 123) to give a white solid. MS (ES): m/z 464 (M+1); HPLC: R$_t$=1.88 min (95.6%).

Example 127

(R)-N-[9-(3-Fluorobenzyl)-6-[1,3,4]thiadiazole-2-yl-2,3,4,9-tetrahydro-1H-carbazol-3-yl]isobutyramide

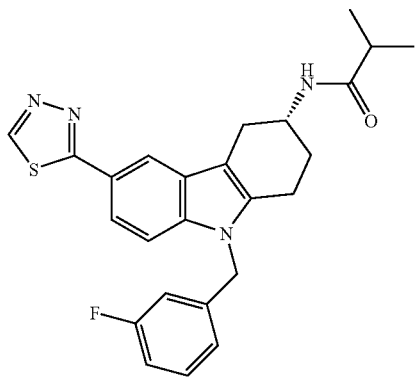

Add (R)-N-[6-(5-Amino[1,3,4]thiadiazole-2-yl)-9-(3-fluorobenzyl)-2,3,4,9-tetrahydro-1H-carbazol-3-yl]isobutyramide (Example 126) (0.104 g, 0.224 mmol) to a solution of isoamylnitrite (0.039 g, 0.337 mmol) in DMF at 60° C. and heat for 1 h. Quench reaction onto water and extract with EtOAc to give 80 mg of a yellow solid. Purify over silica eluting with 25-90% EtOAc/hexanes gradient to give 20 mg (20%). MS (ES) m/z 449 (M+1); $^1$H NMR (DMSO-d$_6$): δ 9.56 (s, 1H), 8.08 (s, 1H), 7.89 (d, 1H), 7.77 (d, 1H), 7.57 (d, 1H), 7.38 (dd, 1H), 7.12 (dd, 2H), 6.84-6.94 (m, 2H), 5.44 (s, 2H), 4.05 (m, 1H), 3.07 (dd, 1H), 2.70-2.84 (m, 2H), 2.63 (m, 2H), 2.41 (septet, 1H), 2.00 (m, 1H), 1.88 (m, 1H), 1.04 (dd, 6H).

Preparation 22

(R)-N-(9-(3-Fluorobenzyl)-6-thiocarbamoyl-2,3,4,9-tetrahydro-1H-carbazol-3-yl)isobutyramide

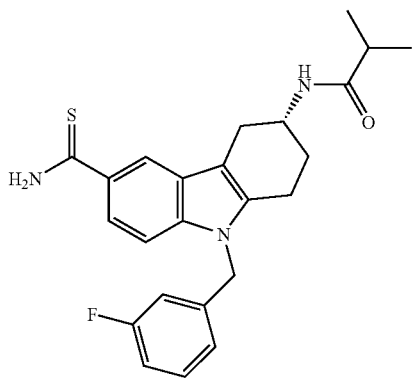

Heat (R)-N-(6-cyano-9-(3-fluorobenzyl)-2,3,4,9-tetrahydro-1H-carbazol-3-yl)isobutyramide (Example 127) (4.00 g, 10.3 mmol) with thioacetamide (1.54 g, 20.5 mmol) at reflux in 4N HCl in dioxane (100 mL) for 16 h. Cool the reaction, pour onto water, and neutralize with NaHCO$_3$. Extract with EtOAc and evaporate to 4.2 g of a red foam. Purify using silica gel chromatography, eluting with 25-100% EtOAc/hexanes gradient to give 2.6 g (60%) of a yellow solid. MS (ES): m/z 424 (M+1); HPLC: R$_t$=1.90 min (95%).

Example 128

(R)-N-[9-(3-Fluorobenzyl)-6-(4-methylthiazol-2-yl)-2,3,4,9-tetrahydro-1H-carbazol-3-yl]isobutyramide

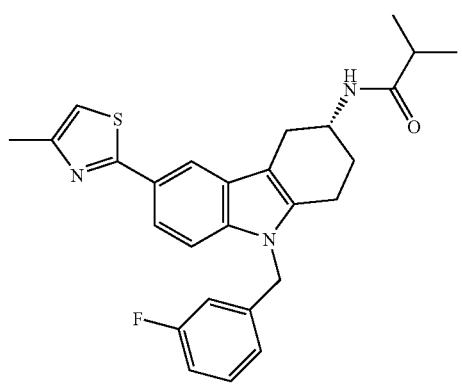

Combine chloroacetone (0.197 g, 2.13 mmol) and (R)-N-(9-(3-fluorobenzyl)-6-thiocarbamoyl-2,3,4,9-tetrahydro-1H-carbazol-3-yl)isobutyramide (Preparation 22) (0.300 g, 0.708 mmol) and heat at 80° C. in DMF under nitrogen for 2.5 h. Upon cooling, dilute the mixture with water and collect the precipitate by filtration. Slurry the precipitate in hot EtOAc to give 0.278 g of a yellow solid. MS (ES): m/z 462 (M+1); HPLC: R$_t$=3.33 min (100%).

Example 129

(R)-N-[9-(3-Fluorobenzyl)-6-(3,4-dimethylthiazol-2-yl)-2,3,4,9-tetrahydro-1H-carbazol-3-yl]isobutyramide

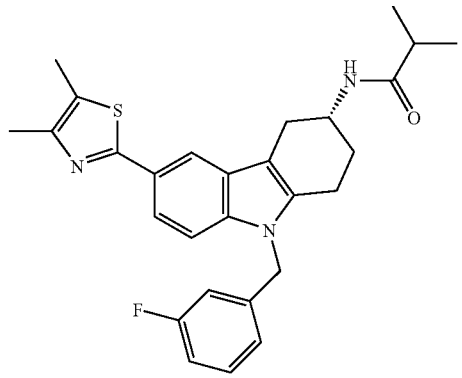

Combine 3-bromo-2-butanone (0.224 g, 1.48 mmol) and (R)-N-(9-(3-fluorobenzyl)-6-thiocarbamoyl-2,3,4,9-tetrahydro-1H-carbazol-3-yl)isobutyramide (Preparation 22) (0.209 g, 0.493 mmol) and heat in DMF at 80° C. under nitrogen for 2 h. Upon cooling, dilute the mixture with water and collect the precipitate by filtration. Recrystallize from absolute EtOH to give yellow crystals: MS (ES): m/z 476 (M+1); HPLC: $R_t$=3.87 min (100%).

Preparation 23

N-[9-(3-Flourobenzyl)-6-(4,4,5,5-tetramethyl[1,3,2]dioxaborolan-2-yl)-2,3,4,9-tetrahydro-1H-carbazol-3-yl]isobutyramide

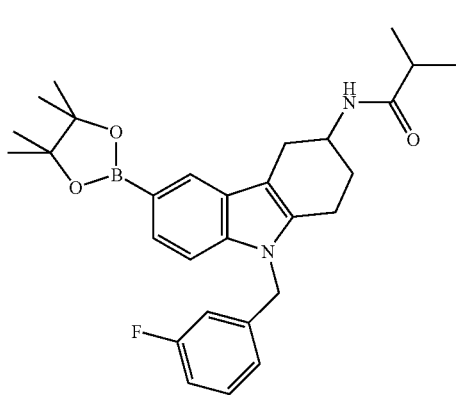

Combine N-[6-bromo-9-(3-fluorobenzyl)-2,3,4,9-tetrahydro-1H-carbazol-3-yl]-isobutyramide (Example 1) (3.00 g, 6.77 mmol), bis(pinacoloto)borane (1.89 g, 7.44 mmol), tricyclophosphine (0.270 g, 0.961 mmol), potassium acetate (1.99 g, 20.3 mmol), tris(benzylideneacetone)dipalladium (0.366 g, 0.399 mmol) in DMSO (15 mL), purge with argon in a sealed tube and heat at 95° C. for 24 h. Upon cooling, pour the mixture onto water and extract with EtOAc. Wash the EtOAc extracts with water and brine, dry (Na₂SO₄), filter, and evaporate. Chromatograph over neutral alumina eluting with 20-40% EtOAc/hexanes to give 2.2 g (66%) of a yellow foam. MS (ES): m/z 491(M+1).

Preparation 24

(R)-N-[9-(3-Flourobenzyl)-6-(4,4,5,5-tetramethyl[1,3,2]dioxaborolan-2-yl)-2,3,4,9-tetrahydro-1H-carbazol-3-yl]isobutyramide

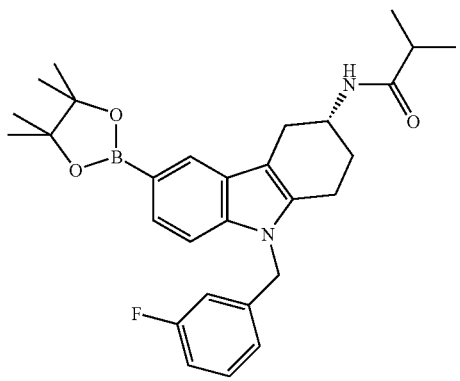

Prepare essentially as described in Preparation 23 from (R)-N-(9-Benzyl-6-bromo-2,3,4,9-tetrahydro-1H-carbazol-3-yl)isobutyramide (Example 122). MS (ES): 491 (M+1); m.p.=93-96° C.;

Example 130

N-[9-(3-Fluorobenzyl)-6-thiazol-2-yl-2,3,4,9-tetrahydro-1H-carbazol-3-yl]isobutyramide

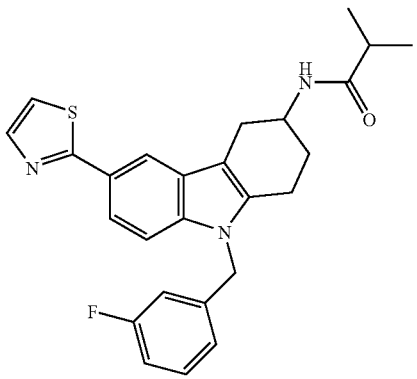

Combine N-[9-(3-fluorobenzyl)-6-(4,4,5,5-tetramethyl[1,3,2]dioxaborolan-2-yl)-2,3,4,9-tetrahydro-1H-carbazol-3-yl]isobutyramide (Preparation 23), 2-bromothiazole (0.0602 g, 0.367 mmol), tetrakis(triphenylphosphine)palladium(0) (0.0353 g, 0.031 mmol), and K₂CO₃ (2 mL of a 2 M solution) in 1,4-dioxane (4 mL), purge with argon, and heat at 95° C. for 18 h. Upon cooling, pour the mixture onto water and extract with EtOAc. Wash EtOAc extracts with brine, dry (Na₂SO₄), filter, and evaporate to give a brown solid. Chromatograph over silica gel with 20-80% EtOAc/hexanes to yield 0.050 g (37%) of an off-white solid. MS (ES): m/z 448; m.p.=221-225° C.

Example 131

N-[9-(3-Fluorobenzyl)-6-pyridin-2-yl-2,3,4,9-tetrahydro-1H-carbazol-3-yl]isobutyramide

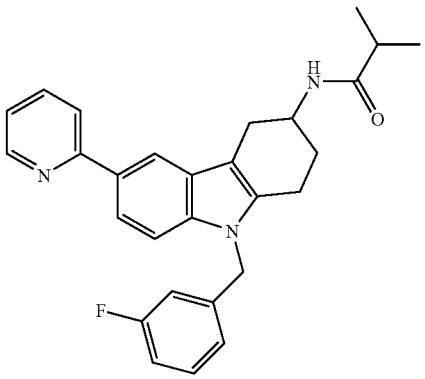

Prepare the title compound essentially as described in Example 130 using N-[9-(3-fluorobenzyl)-6-(4,4,5,5-tetramethyl[1,3,2]dioxaborolan-2-yl)-2,3,4,9-tetrahydro-1H-carbazol-3-yl]isobutyramide (Preparation 23) (0.200 g, 408 mmol), 2-chloropyridine (0.0556 g, 0.489 mmol), tetrakis(triphenyl-phosphine)palladium(0) (0.0471 g, 0.041 mmol), and K₂CO₃ (2 mL of a 2 M solution) in 1,4-dioxane (4 mL), to obtain, after workup and chromatography, 0.039 g (22%) of a beige solid. MS (ES): m/z 442; m.p.=228-230° C.

Examples 132 to 138, contained in the table below, are prepared essentially as described in Example 136, starting with the appropriate haloheteroaryl and N-[9-(3-flourobenzyl)-6-(4,4,5,5-tetramethyl[1,3,2]dioxaborolan-2-yl)-2,3,4,9-tetrahydro-1H-carbazol-3-yl]isobutyramide (Preparation 23) (for Examples 132, 134 to 138) or (R)-N-[9-(3-flourobenzyl)-6-(4,4,5,5-tetramethyl[1,3,2]dioxaborolan-2-yl)-2,3,4,9-tetrahydro-1H-carbazol-3-yl]isobutyramide (Preparation 24) (for Example 133).

| Ex | Structure | MS (ES) | HPLC ($R_t$, %) |
|---|---|---|---|
| 132 | 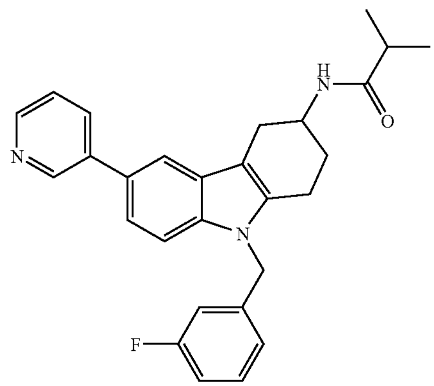 | 442 (M + 1) | 2.47 min (98.1%) |
| 133 | 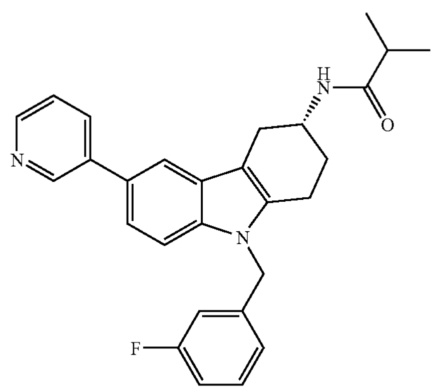 | 442 (M + 1) | 2.56 min (90.3%) |
| 134 | 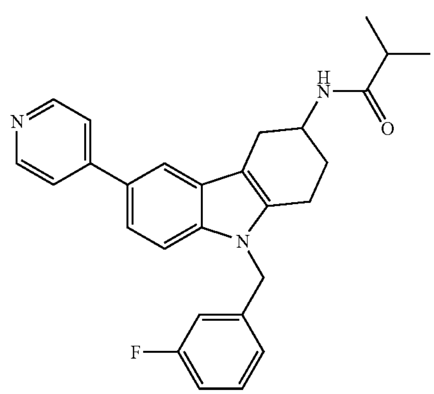 | 442 (M + 1) | 2.32 min (96.2%) |

-continued
| Ex | Structure | MS (ES) | HPLC (R$_t$, %) |
|---|---|---|---|
| 135 | 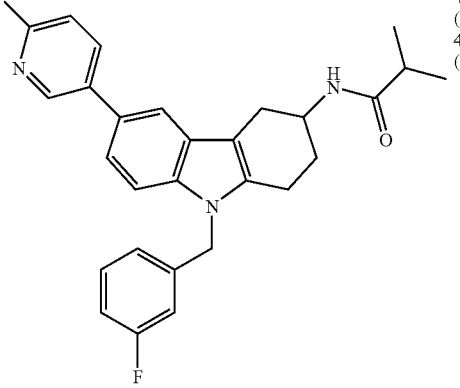 | 460 (M + 1), 458 (M − 1) | 8.92 min (95%) (Method B) |
| 136 | 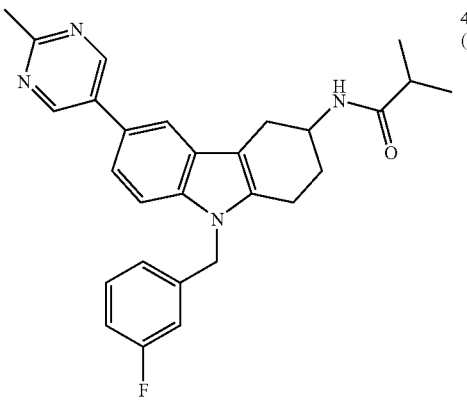 | 457 (M + 1) | 5.07 min (100%) |
| 137 | 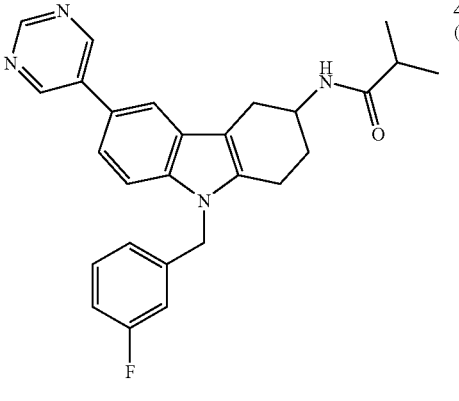 | 443 (M + 1) | 5.52 min (99%) |
| 138 | 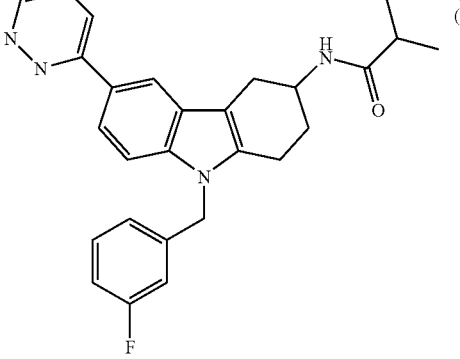 | 443 (M + 1) | 3.32 min (94%) |

Example 139

N-[9-(3-Fluoro-benzyl)-6-(6-methyl-pyridazin-3-yl)-2,3,4,9-tetrahydro-1H-carbazol-3-yl]-isobutyramide

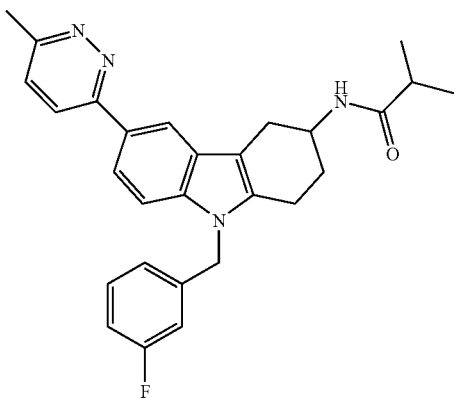

Dissolve N-[9-(3-flourobenzyl)-6-(4,4,5,5-tetramethyl[1,3,2]dioxaborolan-2-yl)-2,3,4,9-tetrahydro-1H-carbazol-3-yl]isobutyramide (Preparation 23) (150 mg, 0.31 mmol) and 3-chloro-6-methylpyridazine (39 mg, 0.31 mmol) in dioxane (2.5 mL) and 2M $Na_2CO_3$ (388 µL). Sparge the solution with nitrogen for 5 min, add dichlorobis(triphenylphosphine)palladium (II) (11 mg, 0.016 mmol) and seal the reaction vessel. Heat to 140° C. in a microwave reactor for 30 min, then dilute with water (20 mL). Extract into EtOAc (3×25 mL), dry organics ($MgSO_4$), filter, and concentrate in-vacuo to give the crude product (179 mg) as a brown solid. Purify the crude product on silica gel (12 g), eluting with 25-70% (4% (2M $NH_3$/MeOH)/$CH_2Cl_2$)/hexanes to afford 35 mg (25%) of the title compound as a white solid. MS (ES): m/z 457 (M+1), 455 (M−1); HPLC (Method B) $R_t$=3.37 min (100%).

Preparation 25

5-Bromo-2-(2,5-dimethylpyrrol-1-yl)thiazole

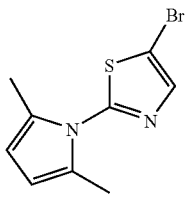

Neutralize 2-amino-5-bromothiazole hydrobromide (2.90 g, 16.2 mmol of free amine) by treating with $Na_2CO_3$ and then add it to a mixture of hexane-2,5-dione (2.04 g, 17.8 mmol) and acetic acid (1.1 mL) in benzene. Heat the mixture for 18 h in a flask equipped with a Dean-Stark trap. Filter and concentrate in vacuo to give a dark oil. Chromatograph the oil over silica eluting with 20-80% EtOAc/hexanes to yield 2.95 g (71%) of a yellow oil. MS (ES): 259 (M+1), 261 (M+H+2).

Preparation 26

N-[9-[2-(2,5-dimethylpyrrol-1-yl)thiazol-5-yl]-9-(3-fluorobenzyl)-2,3,4,9-tetrahydro-1H-carbazol-3-yl]isobutyramide

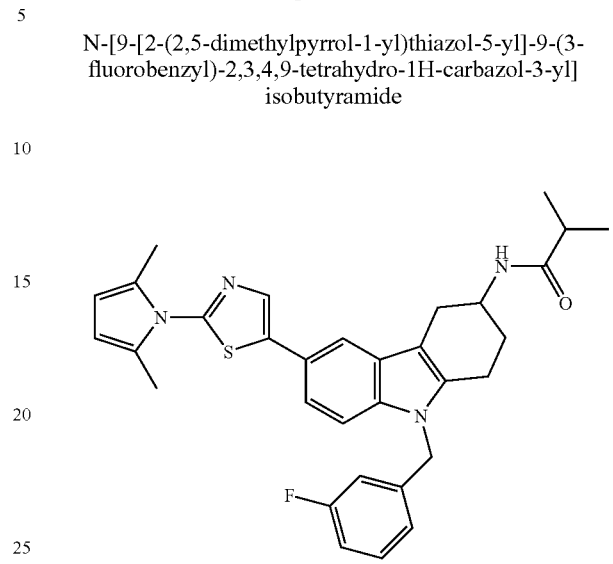

Combine N-[9-(3-flourobenzyl)-6-(4,4,5,5-tetramethyl[1,3,2]-dioxaborolan-2-yl)-2,3,4,9-tetrahydro-1H-carbazol-3-yl]isobutyramide (Preparation 20) (0.458 g, 0.934 mmol), 5-bromo-2-(2,5-dimethylpyrrol-1-yl)thiazole (Preparation 22) (0.312 g, 1.21 mmol), dichloro[1,2-bis(diphenylphosphino)-ferrocene]palladium II dichloromethane complex (0.137 g, 0.168 mmol), 2 M $Na_2CO_3$ (10 mL), and dioxane (12 mL) and purge with argon for five minutes. Heat the mixture at reflux for 18 h. Pour onto water, extract with EtOAc, and chromatograph over silica to give the title compound as a tan solid. MS (ES): m/z 541 (M+1); HPLC $R_t$=5.87 min, (97%).

Example 140

N-[9-[2-(Aminothiazol-5-yl]-9-(3-fluorobenzyl)-2,3,4,9-tetrahydro-1H-carbazol-3-yl]isobutyramide

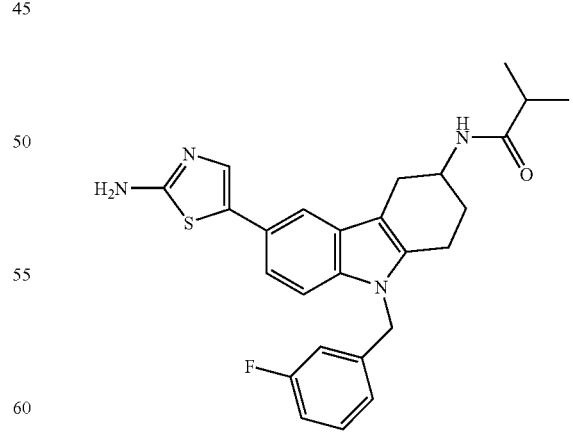

Treat N-[9-[2-(2,5-dimethylpyrrol-1-yl)thiazol-5-yl]-9-(3-fluorobenzyl)-2,3,4,9-tetrahydro-1H-carbazol-3-yl] isobutyramide (Preparation 26) (0.200 g, 0.370 mmol) with hydroxylamine hydrochloride (0.257 g, 3.70 mmol), triethylamine (0.15 mL, 1.1 mmol), and 1 M NaOH (1.1 ml) in absolute EtOH (2 mL) and heat at reflux until complete by TLC (70% EtOAc/hexanes). Extract and evaporate to give the title compound. MS (ES): m/z 463 (M+1).

Example 141

(R)-N-[9-[2-(Aminothiazol-5-yl]-9-(3-fluorobenzyl)-2,3,4,9-tetrahydro-1H-carbazol-3-yl]isobutyramide

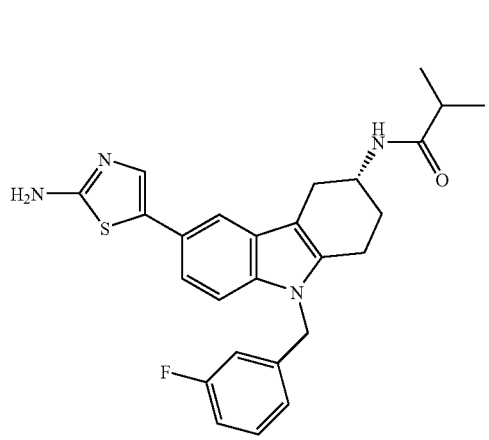

Prepare chiral product essentially as described in Example 140, starting with (R)-N-[9-(3-flourobenzyl)-6-(4,4,5,5-tetramethyl[1,3,2]dioxaborolan-2-yl)-2,3,4,9-tetrahydro-1H-carbazol-3-yl]isobutyramide (Preparation 24). MS (ES): m/z 363 (M+1); HPLC: $R_t$=1.90 min (97%).

Preparation 27

5-Bromo-2-(2,5-dimethylpyrrol-1-yl)pyridine

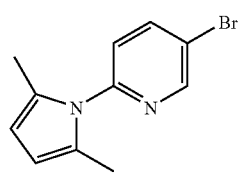

Prepare using procedures essentially as described for 5-bromo-2-(2,5-dimethylpyrrol-1-yl)thiazole (Preparation 25) starting with 2-amino-5-bromopyridine. MS (ES): m/z 252 (M+1).

Preparation 28

N-[6-[6-(2,5-Dimethylpyrrol-1-yl)-pyridin-3-yl]-9-(3-fluorobenzyl)-2,3,4,9-tetrahydro-1H-carbazol-3-yl]isobutyramide

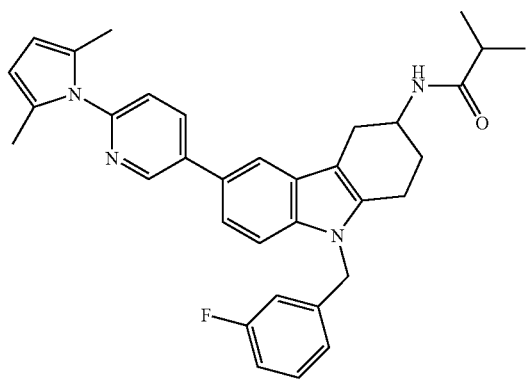

Prepare the title compound using procedures essentially as described in Preparation 26, to give an off-white solid. MS (ES): m/z 535 (M+1); HPLC: $R_t$=4.32 min, (100%).

Example 142

N-[6-(6-(Amino-pyridin-3-yl)-9-(3-fluorobenzyl)-2,3,4,9-tetrahydro-1H-carbazol-3-yl]isobutyramide

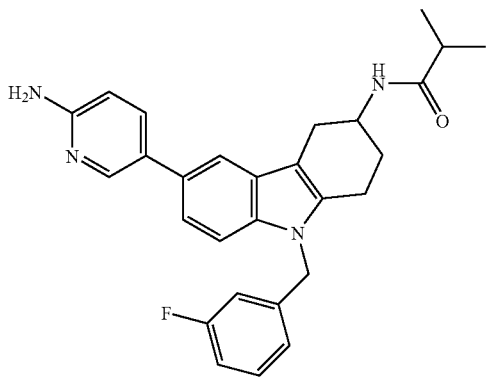

Prepare the title compound from N-[6-[6-(2,5-dimethylpyrrol-1-yl)-pyridin-3-yl]-9-(3-fluorobenzyl)-2,3,4,9-tetrahydro-1H-carbazol-3-yl]isobutyramide (Preparation 28) essentially as described in Example 140, above. MS (ES): m/z 457 (M+1); HPLC: $R_t$=1.79 min, (95%).

Preparation 29

N-(6-methoxy-2,3,4,9-tetrahydro-1H-carbazol-3-yl)-isobutyramide

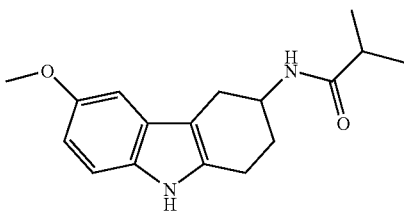

Add acetyl chloride (8.5 mL, 120 mmol) to absolute ethanol (30 mL) and stir for 1 h. Add 4-methoxyphenylhydrazine hydrochloride (1.74 g, 10 mmol) and N-(4-oxo-cyclohexyl)-isobutyramide (Preparation 2) (1.83 g, 120 mmol) and reflux with stirring for 56 h. Cool to room temperature, dilute with ethyl acetate (100 mL) and wash with sodium bicarbonate solution (2×50 mL), and brine. Dry the organic portion (MgSO$_4$), filter, and concentrate in vacuo. Dissolve in dichloromethane and pass over a silica pad, eluting with 20% ethyl acetate/dichloromethane. Obtain 2.32 g of a solid. Triturate the solid in diethyl ether with a small amount of dichloromethane, filter and dry under house vacuum to obtain 2.14 g (75%) of an off-white solid. MS (ES): m/z 287 (M+1)$^+$, 285 (M−1)$^-$; $^1$H NMR(DMSO-d$_6$): δ 10.52 (s, 1H), 7.83 (d, 1H, J=7.5 Hz), 7.13 (d, 1H, J=8.8 Hz), 6.85 (s, 1H), 6.64 (dd, 1H, J=8.8, 2.2 Hz), 4.02 (m, 1H), 3.75 (m, 3H), 2.90 (dd, 1H, J=15.0, 5.3 Hz), 2.78 (m, 2H), 2.42 (m, 2H), 1.96 (m, 1H), 1.79 (m, 1H), 1.03 (d, 6H, J=6.6 Hz),

Example 143

N-(6-methoxy-9-pyridin-2-ylmethyl-2,3,4,9-tetrahydro-1H-carbazol-3-yl)-isobutyramide

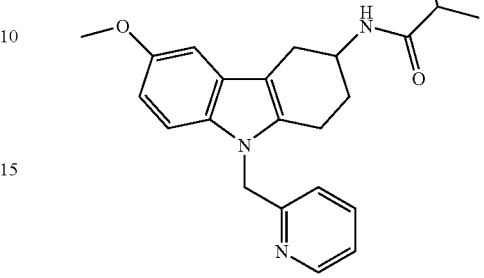

Dissolve N-(6-methoxy-2,3,4,9-tetrahydro-1H-carbazol-3-yl)-isobutyramide (200 mg, 0.70 mmol) in anhydrous tetrahydrofuran (6 mL) under nitrogen. Add dropwise potassium bis(trimethylsilyl)amide (3.2 mL, 1.6 mmol, 0.5M in toluene) and stir 30 min. Add slowly 2-(chloromethyl)pyridine hydrochloride (131 mg, 0.80 mmol) in THF/DMF (0.4 mL/1.3 mL) and stir at ambient temperature for 18 h. Quench with saturated ammonium chloride solution (0.5 mL) and partition between ethyl acetate and water. Separate the two phases and wash the aqueous phase with ethyl acetate (2×). Dry the combined organic portions (MgSO$_4$), filter, and concentrate in vacuo to obtain a residue. Purify the material by silica gel chromatography, eluting with 50% ethyl acetate/dichloromethane with a gradient up to 80% ethyl acetate/dichloromethane to obtain 199 mg (75%) of a light yellow solid. MS (ES): m/z 378 (M+1); $^1$H NMR(DMSO-d$_6$): δ 8.50 (dd, 1H, J=4.8, 0.9 Hz), 7.82 (d, 1H, J=7.5 Hz), 7.65 (dt, 1H, J=7.6, 1.6 Hz), 7.22 (m, 2H), 6.89 (d, 1H, J=2.2 Hz), 6.77 (d, 1H, J=7.9 Hz), 6.63 (dd, 1H, J=8.6, 2.4 Hz), 5.32 (s, 2H), 3.97 (m, 1H), 3.72 (s, 3H), 2.91 (dd, 1H, J=15.0, 5.3 Hz), 2.85-2.76 (m, 1H), 2.74-2.64 (m, 1H), 2.45 (m, 1H), 2.37 (m, 1H), 1.94 (m, 1H), 1.77 (m, 1H), 0.99 (m, 6H).

Examples 144 to 146, in the table below, are prepared essentially as described in Example 143, above, using the following heteromethyl reagents respectively: 3-(chloromethyl)pyridine hydrochloride, 4-(chloromethyl)pyridine hydrochloride, and 2-(chloromethyl)pyridine hydrochloride.

| Ex. | Structure | MS (ES): m/z | HPLC (Method A) (R$_t$, %) |
|---|---|---|---|
| 144 | 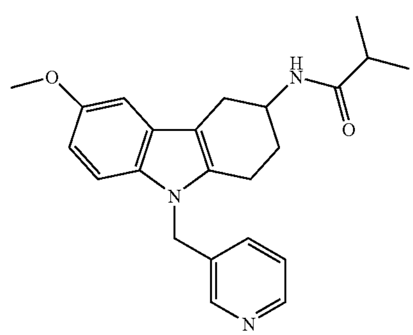 | 378 (M + 1) | 1.91 min, (99.1%) |

| Ex. | Structure | MS (ES): m/z | HPLC (Method A) (R_t, %) |
|---|---|---|---|
| 145 | 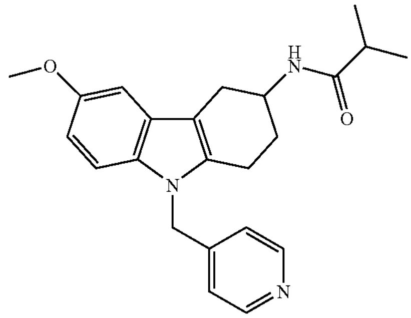 | 378 (M + 1) | 1.90 min, (98.4%) |
| 146 | 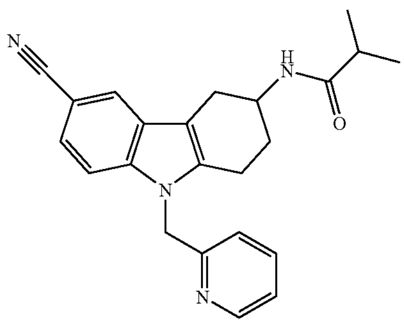 | 373 (M + 1), 371 (M − 1) | (Method B) t = 2.78 min, (100%) |

Preparation 30

(4-Methyl-thiazol-2-yl)-methanol

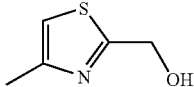

Method A: Dissolve 4-methyl-thiazole-2-carbaldehyde (prepare in 92% yield according to the procedures essentially as described in Khanna, I. K., et al., *J. Med. Chem.* (2000) 43, 3168-3185) (15.0 g, 118 mmol) in EtOH (250 mL) and add sodium borohydride (2.23 g, 59.0 mmol). Stir at room temperature for 1 h, then cautiously add aqueous NH$_4$Cl (50 mL) to the reaction mixture. Concentrate in vacuo at 45° C. to remove EtOH. Dilute with water (50 mL) and extract into EtOAc (3×100 mL). Dry the combined organic portions (MgSO$_4$), filter, and concentrate in vacuo at 45° C. to give 14.39 g (94%) of the title compound as a yellow oil. MS (ES): 130 (M+1); $^1$H NMR (CDCl$_3$): δ 6.88 (s, 1H), 4.94 (s, 2H), 3.16 (s, 1H), 2.46 (s, 3H).

Method B: Alternatively, dissolve 4-methyl-thiazole-2-carboxylic acid ethyl ester (prepare in 27% yield according to the procedures essentially as described in Erlenmeyer, H., et al., *Helv. Chim. Acta* (1944), 27, 1437-1438) (1.52 g, 8.88 mmol) in THF (60 mL) and add lithium borohydride (2.0M solution in THF, 9 mL, 17.8 mmol). Heat at reflux temperature for 18 h. Allow to cool to room temperature and dilute the reaction mixture with water (20 mL). Extract into ethyl acetate (3×50 mL). Dry the combined organic portions (MgSO$_4$), filter, and concentrate in vacuo at 45° C. Purify the crude product on silica gel (40 g) with 40-80% EtOAc/hexanes to give 690 mg (60%) of the title compound as a colorless oil.

Preparation 31

Thiazol-5-yl-methanol

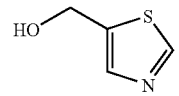

Prepare the title compound according to literature procedures (McElhinney, R. S., et al., *J. Med. Chem.* (1998) 41, 5265-5271).

Preparation 32

(2-Chloro-thiazol-4-yl)-methanol

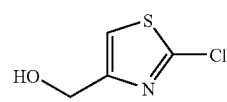

Prepare the title compound by essentially following the procedures as described in Preparation 27 (Method B), using 2-chloro-thiazole-4-carboxylic acid ethyl ester (prepare according to the procedures essentially as reported by Erlenmeyer, H., et al., *Helv. Chim. Acta* (1944) 27, 1432-1436). MS (ES): m/z 150 (M+1); $^1$H NMR (CDCl$_3$): δ 7.16 (t, 1H, J=1.0 Hz), 4.75 (d, 2H, J=0.9 Hz), 2.48 (s, 1H).

Preparation 33

(5-chloro-thiophen-2-yl)-methanol

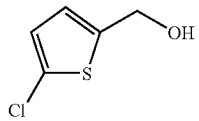

Add dropwise a solution of 5-chloro-thiophene-2-carboxylic acid ethyl ester (5.0 g, 28 mmol) in Et$_2$O (100 mL) to a mixture of lithium aluminum hydride (1.1 g, 28 mmol) in Et$_2$O. Stir at room temperature for 18 h, then quench the reaction with water and 20% aqueous NaOH. Extract into Et$_2$O/EtOAc, dry (Na$_2$SO$_4$), filter, and concentrate the organic portion to give the crude product. Purify by vacuum distillation to give 3.4 g of an oil, boiling point 160° C./20 mm Hg. MS [FD] 148; Anal. Calcd for C$_5$H$_5$ClOS: C, 40.41; H, 3.39. Found: C, 39.59; H, 3.59.

Preparation 34

Methanesulfonic acid 4-methyl-thiazol-2-ylmethyl ester

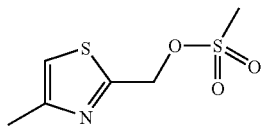

Combine 4-methyl-thiazol-2-yl)-methanol (Preparation 30) (1.00 g, 7.74 mmol) and triethylamine (1.25 g, 1.73 mL, 12.4 mmol) in dichloromethane (30 mL) with stirring and cool to 0° C. under nitrogen. Add methanesulfonyl chloride (931 mg, 633 μL, 8.13 mmol) to the reaction mixture and stir at 0° C. for 30 min. Warm to room temperature over 30 min, then dilute with water (40 mL) and dichloromethane (40 mL). Separate the layers, dry the organic portion (MgSO$_4$), filter, and concentrate in vacuo at 40° C. to afford 1.15 g (72%) of the title compound as a brown oil. MS (ES): m/z 208 (M+1); $^1$H NMR (CDCl$_3$): δ 7.03 (m, 1H), 5.48 (s, 2H), 3.11 (s, 3H), 2.50 (d, 3H, J=0.9 Hz).

Preparation 35

Methanesulfonic acid 2-chloro-thiazol-4-ylmethyl ester

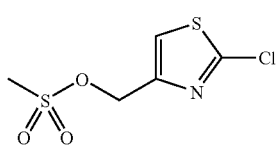

Prepare the title compound by essentially following the procedures as described in Preparation 31, using (2-chloro-thiazol-4-yl)-methanol (Preparation 29) to afford the title compound as a colorless oil. $^1$H NMR (CDCl$_3$): δ 7.39 (s, 1H), 5.27 (d, 2H, J=0.9 Hz), 3.10 (s, 3H).

Preparation 36

2-Bromomethyl-thiazole

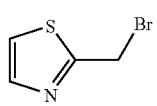

Prepare the title compound according to literature procedures (Yang, L., et al., *Bioorg. Med. Chem. Lett.* (1999) 9, 1761-1766).

Preparation 37

2-Bromomethyl-5-chloro-thiophene

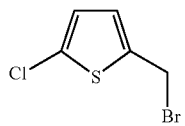

Cool (5-chloro-thiophen-2-yl)-methanol (Preparation 30) (330 mg, 2.22 mmol) to 0° C. and add acetyl bromide (709 mg, 430 μL, 5.76 mmol). Allow to warm to room temperature over 18 h, dilute with EtOAc (10 mL), and cautiously add saturated aqueous NaHCO$_3$ (3 mL). When the carbon dioxide evolution stops, load the mixture onto a Varian Chem Elut CE1005 solid phase extraction cartridge (Varian part number 12198006). Elute with EtOAc, collect, and concentrate about 50 mL to obtain the crude product. Purify on silica gel (12 g) using 0-15% EtOAc/hexanes to afford 250 mg (53%) of the title compound as a yellow oil. MS (EI): 210,212; $^1$H NMR (CDCl$_3$): δ 6.92 (d, 1H, J=3.5 Hz), 6.78 (d, 1H, J=4.0 Hz), 4.66 (s, 2H).

Example 147

N-(6-Cyano-9-thiazol-4-ylmethyl-2,3,4,9-tetrahydro-1H-carbazol-3-yl)-isobutyramide

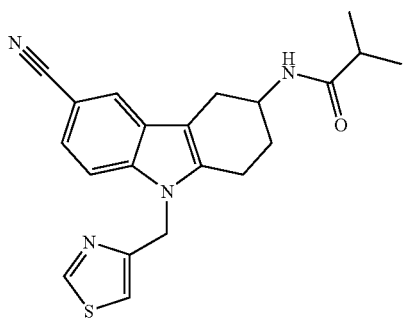

Partition 4-chloromethyl-thiazole hydrochloride (199 mg, 1.17 mmol) between Et$_2$O (20 mL) and saturated aqueous NaHCO$_3$ (20 mL). Separate the layers and dry the ether layer over MgSO$_4$. Add DMF (3 mL) to the ether layer and concentrate in vacuo to remove the ether. Add this solution to a slurry of N-(6-cyano-2,3,4,9-tetrahydro-1H-carbazol-3-yl)-isobutyramide (Preparation 3) (300 mg, 1.07 mmol) and sodium hydride (60% suspension in mineral oil, 47 mg, 1.17 mmol) in DMF (3 mL) which has stirred for 30 min at room temperature. Stir the reaction at room temperature for 2 h, then add aqueous NaHCO$_3$ (30 mL) and EtOAc (50 mL). Separate the layers and wash the organic portion with aqueous NaHCO$_3$ (2×30 mL). Dry the organic layer (MgSO$_4$). Filter and concentrate in vacuo to obtain 487 mg crude yellow solid. Recrystallize the material from boiling toluene (10 mL) to afford 296 mg (73%) of the title compound as a yellow solid. MS (ES): m/z 379 (M+1), 377 (M−1); $^1$H NMR (DMSO-d$_6$): δ 9.01 (d, 1H, J=1.8 Hz), 7.90 (d, 1H, J=1.3 Hz), 7.84 (d, 1H, J=7.9 Hz), 7.69 (d, 1H, J=8.4 Hz), 7.56 (d, 1H, J=1.8 Hz), 7.40 (dd, 1H, J=8.6, 1.5 Hz), 5.47 (s, 2H), 3.99 (m, 1H), 3.03-2.81 (m, 3H), 2.49 (m, 1H), 2.37 (m, 1H), 1.98 (m, 1H), 1.80 (m, 1H), 0.99 (d, 6H, J=7.0 Hz); HPLC (Method A): R$_t$=1.93 min, (97%).

Example 148

N-[9-(5-Chloro-thiophen-2-ylmethyl)-6-cyano-2,3,4,9-tetrahydro-1H-carbazol-3-yl]-isobutyramide

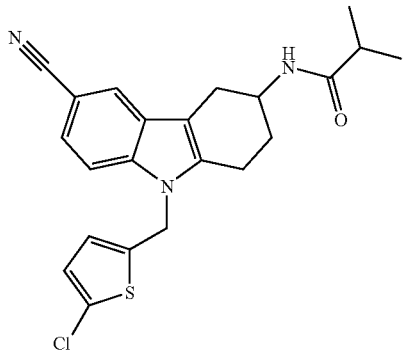

Prepare the title compound by essentially following the procedures as described in Example 147, using 2-bromomethyl-5-chloro-thiophene (Preparation 37). Purify by silica gel chromatography (50-90% EtOAc/hexanes) to give the product in 24% yield as a yellow solid. MS (ES): m/z 412 (M+1), 410 (M−1); HPLC (Method A): R$_t$=2.86 min, (92%).

Example 149

N-(6-Cyano-9-thiazol-2-ylmethyl-2,3,4,9-tetrahydro-1H-carbazol-3-yl)-isobutyramide

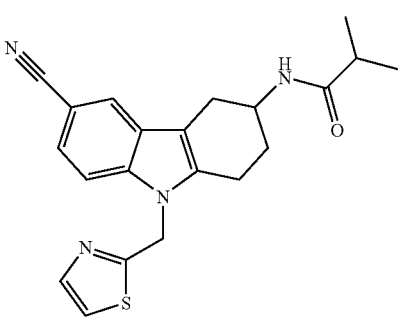

Prepare the title compound by essentially following the procedures as described in Example 147, using 2-bromomethyl-thiazole (Preparation 36). Purify by silica gel chromatography (80-100% EtOAc/Hexanes) to give the product in 55% yield as a white solid. MS (ES): m/z 379 (M+1), 377 (M−1); HPLC (Method A): R$_t$=1.88 min, (100%).

Example 150

N-[6-Cyano-9-(2-methyl-thiazol-4-ylmethyl)-2,3,4,9-tetrahydro-1H-carbazol-3-yl]-isobutyramide

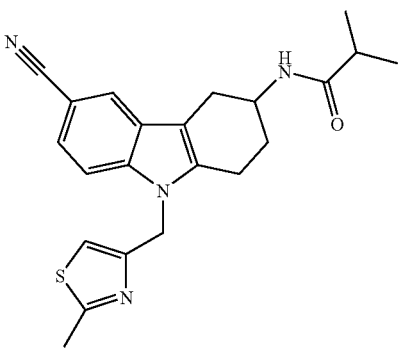

Prepare the title compound by essentially following the procedures as described in Example 147, using 4-chloromethyl-2-methylthiazole hydrochloride. Purify the crude material by recrystillizing from boiling toluene to provide the product in 75% yield. MS (ES): m/z 393 (M+1), 391 (M−1); HPLC (Method A): 2.14 min, (100%).

Example 151

(R)-N-[6-cyano-9-(2-methyl-thiazol-4-ylmethyl)-2,3,4,9-tetrahydro-1H-carbazol-3-yl]-isobutyramide

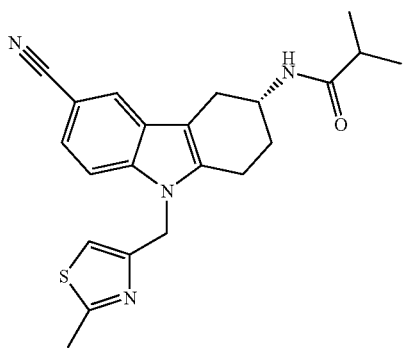

Prepare the title compound by preparative chiral chromatography from racemic N-[6-cyano9-(2-methyl-thiazol-4-ylmethyl)-2,3,4,9-tetrahydro-1H-carbazol-3-yl]-isobutyramide (Example 150) in 97.7% ee using the following conditions: Chiralpak AD (8×30 cm), 75:15:10 heptane:EtOH:MeOH (350 mL/min), 240 nm detection. The title compound elutes first and the other enantiomer (Example 152) elutes second. MS (ES): m/z 393 (M+1), 391 (M−1); $^1$H NMR (CDCl$_3$): δ 7.95 (d, 1H, J=1.1 Hz), 7.88 (d, 1H, J=7.7 Hz), 7.72 (d, 1H, J=8.4 Hz), 7.44 (dd, 1H, J=8.6, 1.5 Hz), 5.40 (s, 2H), 4.04 (m, 1H), 2.95 (m, 3H), 3.05-2.85 (m, 3H), 2.59 (s, 3H), 2.56 (m, 1H), 2.41 (m, 1H), 2.02 (m, 1H), 1.85 (m, 1H), 1.03 (d, 6H, J=6.8 Hz).

Example 152

(S)-N-[6-cyano-9-(2-methyl-thiazol-4-ylmethyl)-2,3,4,9-tetrahydro-1H-carbazol-3-yl]-isobutyramide

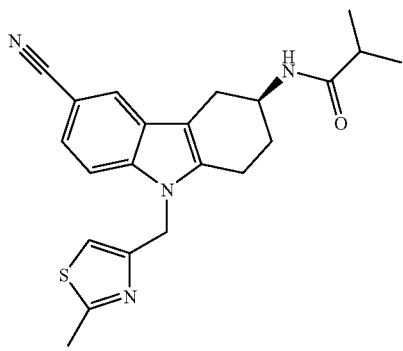

Prepare the title compound by preparative chiral chromatography from racemic N-[6-cyano-9-(2-methyl-thiazol-4-ylmethyl)-2,3,4,9-tetrahydro-1H-carbazol-3-yl]-isobutyramide (Example 154) in 93.6% ee using the following conditions: Chiralpak AD (8×30 cm), 75:15:10 heptane:EtOH:MeOH (350 mL/min), 240 nm detection. The title compound is the second of the two enantiomers to elute. MS (ES): m/z 393 (M+1), 391 (M−1).

Example 153

N-[9-(2-Chloro-thiazol-4-ylmethyl)-6-cyano-2,3,4,9-tetrahydro-1H-carbazol-3-yl]-isobutyramide

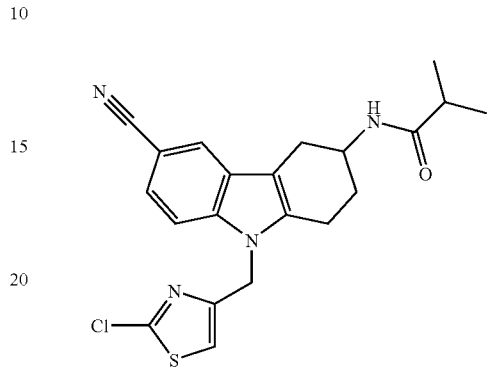

Prepare the title compound by essentially following the procedures as described in Example 143, using methanesulfonic acid 2-chloro-thiazol-4-ylmethyl ester (Preparation 35) (190 mg, 1.0 mmol) and N-(6-cyano-2,3,4,9-tetrahydro-1H-carbazol-3-yl)isobutyramide (Preparation 4) to give the product as a white solid (21%). MS (ES): m/z 413 (M+1), 411 (M−1); HPLC (Method B): R$_t$=4.66 min, (96%).

Preparation 38

(R)-N-(6-Cyano-2,3,4,9-tetrahydro-1H-carbazol-3-yl)-isobutyramide

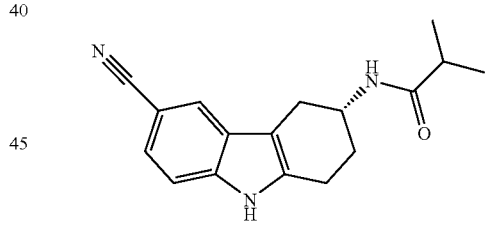

Dissolve (R)-N-(6-bromo-2,3,4,9-tetrahydro-1H-carbazol-3-yl)-isobutyramide (Preparation 21) (1.00 g, 2.98 mmol) in 1-methyl-2-pyrolidinone (30 mL). Sparge the resulting solution with nitrogen for 15 min. Add copper(I) cyanide (801 mg, 8.95 mmol) and copper(I) iodide (1.70 g, 8.95 mmol). Heat to 130° C. for three days, then cool to room temperature. Dilute the reaction mixture with water (100 mL), EtOAc (250 mL), and enough ethylene diamine to dissolve the copper solids (about 70 mL). Separate the layers, then wash the organic layer with water (2×50 mL). Dry the organic portion over MgSO$_4$. Filter, concentrate, and purify on silica gel (80 g) using 50-80% EtOAc/hexanes to afford 530 mg (63%) of the title compound as a white solid. MS (ES): 282 (M+1), 280 (M−1); $^1$H NMR (CDCl$_3$): δ 8.44 (s, 1H), 7.76 (s, 1H), 7.40 (dd, 1H, J=8.4, 1.3 Hz), 7.37 (d, 1H, J=8.5 Hz), 5.64 (d, 1H, J=7.5 Hz), 4.42 (m, 1H), 3.11 (dd, 1H, J=15.2, 5.1 Hz), 2.98-2.80 (m, 2H), 2.59 (dd, 1H, J=15.4, 7.5 Hz), 2.38 (m, 1H), 2.17 (m, 1H), 2.02 (m, 1H), 1.21 (d, 6H, J=7.0 Hz);

Chiral HPLC: Chiralcel OD-H 0.46×15 cm column, 15:85 EtOH/Heptane, 1.0 mL/min, 225 nm detection; $R_t$=7.37 min; >99% ee.

Example 154

(R)-N-[9-(2-Chloro-thiazol-4-ylmethyl)-6-cyano-2,3,4,9-tetrahydro-1H-carbazol-3-yl]-isobutyramide

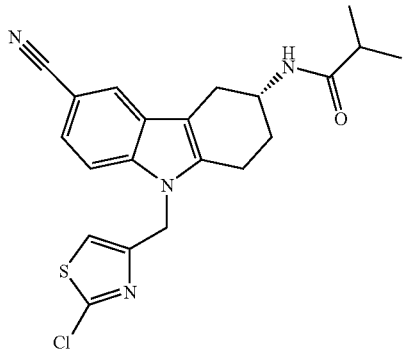

Prepare the title compound by essentially following the procedures as described in Example 147, using (R)-N-(6-cyano-2,3,4,9-tetrahydro-1H-carbazol-3-yl)-isobutyramide (Preparation 38) and methanesulfonic acid 2-chloro-thiazol-4-ylmethyl ester (Preparation 35) to provide the product in 49% yield as a light yellow solid. MS (ES): m/z 413 (M+1), 411 (M−1); $^1$H-NMR (CDCl$_3$): δ 7.82 (d, 1H, J=0.9 Hz), 7.43 (dd, 1H, J=8.6, 1.5 Hz), 7.34 (d, 1H, J=8.4 Hz), 6.59 (s, 1H), 5.59 (d, 1H, J=7.9 Hz), 5.32 (s, 2H), 4.44 (m, 1H), 3.16 (dd, 1H, J=15.4, 4.8 Hz), 2.89 (t, 2H, J=5.9 Hz), 2.64 (dd, 1H, J=15.6, 7.3 Hz), 2.38 (m, 1H), 2.20 (m, 1H), 2.06 (m, 1H), 1.20 (d, 6H, J=7.0 Hz).

Preparation 39

(2-Chloro-thiazol-5-yl)-methanol

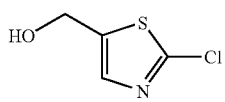

Treat an EtOH solution (10 mL) of 2-chloro-5-thiazolecarboxaldehyde (350 mg, 2.4 mmol) with sodium borohydride (60 mg, 1.6 mmol). After 1 h, carefully quench with saturated ammonium chloride solution and remove the EtOH under reduced pressure. Partition the reaction between EtOAc/water. Dry the organic portion (Na$_2$SO$_4$), filter, and concentrate to give 296 mg (82%) of the title compound as a colorless oil. MS (ES): m/z 150 (M+1); HPLC (Method B): $R_t$=1.86 min (98%).

Preparation 40

Methanesulfonic acid 2-chloro-thiazol-5-ylmethyl ester

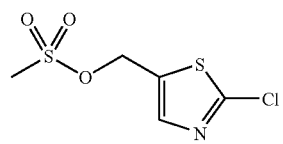

Prepare the title compound by essentially following the procedures as described in Preparation 34, using (2-chloro-thiazol-5-yl)-methanol (200 mg, 1.3 mmol) to provide 277 mg (93%) of the title compound. Use without further purification. $^1$H NMR (CDCl3): δ 7.62 (s,1H), 5.38 (s,2H), 3.05 (s,3H).

Example 155

N-[9-(2-Chloro-thiazol-5-ylmethyl)-6-cyano-2,3,4,9-tetrahydro-1H-carbazol-3-yl]-isobutyramide

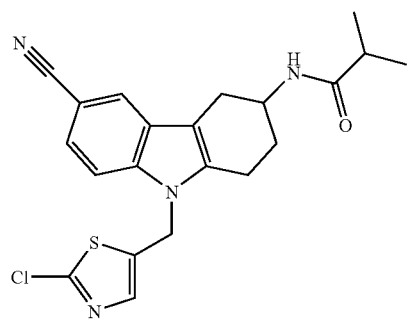

Prepare the title compound by essentially following the procedures as essentially described in Example 143, using methanesulfonic acid 2-chloro-thiazol-5-ylmethyl ester (Preparation 40) (1.3 mmol) and N-(6-cyano-2,3,4,9-tetrahydro-1H-carbazol-3-yl)isobutyramide (Preparation 4) (281 mg, 1.0 mmol) to give the product as a white solid (10%). MS (ES): m/z 413 (M+1), 411 (M−1); HPLC (Method B): $R_t$=3.99 min, (95%).

Example 156

(R)-N-[6-Cyano-9-(4-methyl-thiazol-2-ylmethyl)-2,3,4,9-tetrahydro-1H-carbazol-3-yl]-isobutyramide

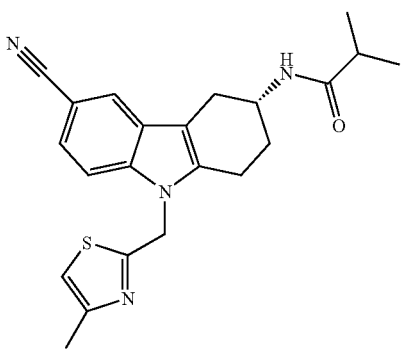

Prepare the title compound by essentially following the procedures as described in Example 147, using (R)-N-(6-cyano-2,3,4,9-tetrahydro-1H-carbazol-3-yl)-isobutyramide (Preparation 38) and methanesulfonic acid 4-methyl-thiazol-2-ylmethyl ester (Preparation 34) to provide the product in 54% yield as a white solid. MS (ES): m/z 393 (M+1), 391 (M−1); $^1$H-NMR (CDCl$_3$): δ 7.83 (d, 1H, J=0.9 Hz), 7.45 (dd, 1H, J=8.6, 1.5 Hz), 7.41 (d, 1H, J=7.9 Hz), 6.82 (d, 1H, J=0.9 Hz), 5.56 (d, 1H, J=7.9 Hz), 5.53 (s, 2H), 4.45 (m, 1H), 3.16 (dd, 1H, J=15.2, 5.1 Hz), 2.98-2.82 (m, 2H), 2.64 (dd, 1H, J=15.9, 7.0 Hz), 2.47 (d, 3H, J=0.9 Hz), 2.36 (m, 1H), 2.20 (m, 1H), 2.08 (m, 1H), 1.19 (dd, 6H, J=7.0, 1.8 Hz).

Example 157

N-(6-Cyano-9-thiophen-3-ylmethyl-2,3,4,9-tetrahydro-1H-carbazol-3-yl)-isobutyramide

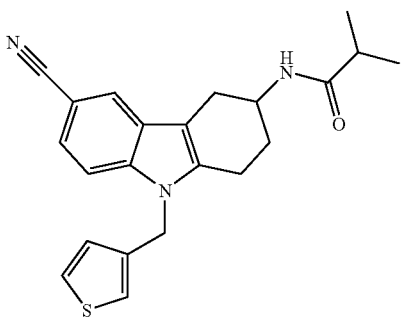

Add sequentially to a slurry of N-(6-cyano-2,3,4,9-tetrahydro-1H-carbazol-3-yl)-isobutyramide (Preparation 3) (100 mg, 0.36 mmol) in THF (2 mL) at 0° C.: trimethylphosphine (1.0 M in toluene, 530 μL, 0.53 mmol), 3-thiophenemethanol (61 mg, 50 μL, 0.53 mmol), and 1,1'-(azodicarbonyl)-dipiperidine (ADDP, 134 mg, 0.53 mmol). Warm up to room temperature and stir in a sealed vial for 18 h. Evaporate the reaction solvent and dissolve the residue in EtOAc (5 ML). Add water (2 mL) and load onto a Varian Chem Elut CE1005 solid-phase extraction cartridge (Varian part number 12198006). Elute with EtOAc, collect, and concentrate (about 50 mL). Purify the crude product on silica gel (12 g) eluting with 30-90% EtOAc/hexanes to give the title compound in 11% yield as a colorless oil. MS (ES): m/z 378 (M+1), 376 (M−1); $^1$H NMR (CDCl$_3$): δ 7.81 (s, 1H), 7.40 (dd, 1H, J=8.4, 1.2 Hz), 7.33 (d, 1H, J=8.4 Hz), 7.30 (m, 1H), 6.86-6.81 (m, 2H), 5.60 (d, 1H, J=7.5 Hz), 5.29 (s, 2H), 4.41 (m, 1H), 3.16 (dd, 1H, J=15.2, 5.1 Hz), 2.90-2.72 (m, 2H), 2.63 (dd, 1H, J=15.4, 7.5 Hz), 2.36 (m, 1H), 2.16 (m, 1H), 2.02 (m, 1H), 1.18 (dd, 7H, J=6.8, 3.7 Hz), 1.18 (dd, 6H, J=6.8, 3.7 Hz).

Example 158

N-(6-Cyano-9-thiophen-2-ylmethyl-2,3,4,9-tetrahydro-1H-carbazol-3-yl)-isobutyramide

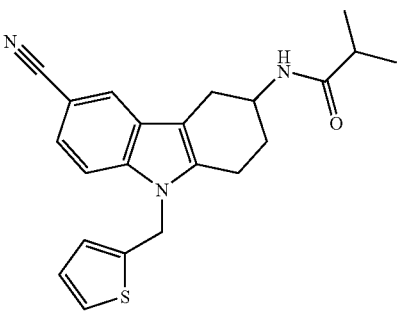

Prepare the title compound by essentially following the procedures as described in Example 157, using 2-thiophenemethanol to give the product in 15% yield as a white solid. MS (ES): m/z 378 (M+1), 376 (M−1); HPLC (Method A): $R_t$=2.34 min, (99%).

Example 159

N-(6-Cyano-9-thiazol-5-ylmethyl-2,3,4,9-tetrahydro-1H-carbazol-3-yl)-isobutyramide

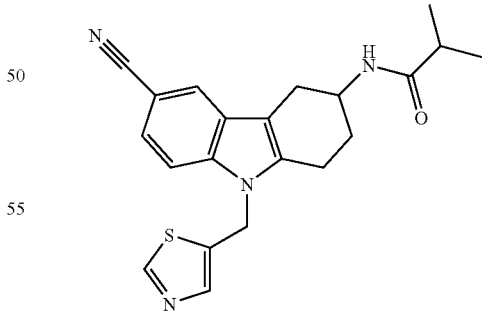

Add potassium hydride (30% w/w in mineral oil, 129 mg, 0.97 mmol) to a slurry of cyanomethyl-trimethyl-phosphonium chloride (prepare according to the procedure essentially as described in Tsunoda, T.; et al., *Tetrahedron Lett.* (1996) 37, 2459-2462) (166 mg, 1.10 mmol) at 0° C. under nitrogen. Allow the reaction mixture to warm to room temperature and stir for 3 h. Add a solution of thiazol-5-ylmethanol (100 mg, 0.87 mmol) in THF (2 mL), then add N-(6-cyano-2,3,4,9-tetrahydro-1H-carbazol-3-yl)-isobutyramide (Preparation 5) (122 mg, 0.44 mmol) and heat at 70° C. for 18 h. Cool to room temperature and dilute with water (40 mL). Extract into EtOAc (3×50 mL) and dry the organic portion (MgSO$_4$). Filter and concentrate to afford the crude product, (340 mg) as a yellow oil. Purify on silica gel (24 g) using 5% (2M NH$_3$/MeOH)/CH$_2$Cl$_2$, and then re-purify on silica gel (40 g) using 80:18:2 EtOAc:hexanes:(2M NH$_3$/MeOH) to afford 70 mg (42%) of the title compound as an orange solid. MS (ES): m/z 379 (M+1), 377 (M−1); $^1$H-NMR (CDCl$_3$): δ 8.78 (s, 1H), 7.83 (d, 1H, J=1.3 Hz), 7.74 (s, 1H), 7.47 (dd, 1H, J=8.6, 1.5 Hz), 7.38 (d, 1H, J=8.4 Hz), 5.53 (d, 1H, J=7.9 Hz), 5.50 (s, 2H), 4.42 (m, 1H), 3.16 (dd, 1H, J=15.4, 5.3 Hz), 2.97-2.80 (m, 2H), 2.62 (dd, 1H, J=15.4, 7.5 Hz), 2.37 (m, 1H), 2.21 (m, 1H), 2.05 (m, 1H), 1.20 (dd, 6H, J=7.0, 1.8 Hz).

Preparation 41 trans-(4-Hydroxy-cyclohexyl)-carbamic acid benzyl ester

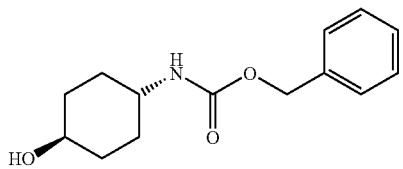

Following procedures essentially as described in the literature (Janda, K. D.; Ashley, J. A. *Synth. Comm.* 1990, 20, 1073-1082) with the exception that the organic layer is repeatedly concentrated under reduced pressure and the resulting precipitate filtered. The reaction mixture is not concentrated to dryness, but only to the point where a significant amount of precipitate has formed. Using this modified protocol, an 80% yield is obtained on a 35.00 g scale.

Preparation 42

(4-Oxo-cyclohexyl)-carbamic acid benzyl ester

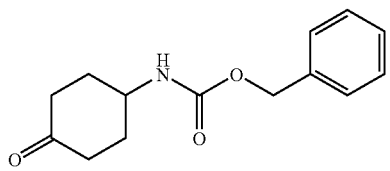

Dissolve oxalyl chloride (18.4 mL, 211 mmol) in CH$_2$Cl$_2$ (1000 mL), cool below −70° C., and add DMSO (18.0 mL, 253 mmol) via syringe pump over 30 min. Stir for 45 min, and then add portionwise a suspension of trans-(4-hydroxy-cyclohexyl)-carbamic acid benzyl ester (35.00 g, 140 mmol) in CH$_2$Cl$_2$ (1000 mL), while maintaining the temperature below −70° C. Add the suspension by removing a stopper from the reaction flask and quickly pouring in as much of the suspension as possible while keeping the temperature below −70° C., resulting in a slightly turbid solution upon complete addition. Stir the reaction for 90 min, then add triethylamine (97.8 mL, 702 mmol) slowly via syringe. Stir for another hour, and allow the reaction to slowly warm to room temperature overnight. Wash sequentially with water (1500 mL), brine (2×1500 mL), and saturated aqueous NaHCO$_3$ (2×1500 mL). Separate the organic portion and dry (MgSO$_4$), filter, and concentrate under reduced pressure. Triturate the crude residue twice with 4:1 Hexane/EtOAc (500 mL, then 250 mL). (Alternatively, triturate with 15% EtOAc/Hexane. Then only one trituration is required.) Filter and collect the solids and dry at 35° C. in a vacuum oven to obtain 26.44 g of the product. Combine the filtrates of the triturations and concentrate under reduced pressure, followed by trituration of the residue in 9:1 hexane/EtOAc (100 mL) to afford a second crop of 5.70 g, for a combined yield of 32.14 g (93%). ESI MS: m/z 248 [C$_{14}$H$_{17}$NO$_3$+H]$^+$; $^1$H NMR (300 MHz, CDCl$_3$): δ 1.63-1.78 (m, 2H), 2.22-2.27 (m, 2H), 2.32-2.49 (m, 4H), 3.95-4.04 (m, 1H), 4.75 (br s, 1H), 5.11 (s, 2H), 7.29-7.42 (m, 5H)

Preparation 43

(6-Trifluoromethoxy-2,3,4,9-tetrahydro-1H-carbazol-3-yl)-carbamic acid benzyl ester

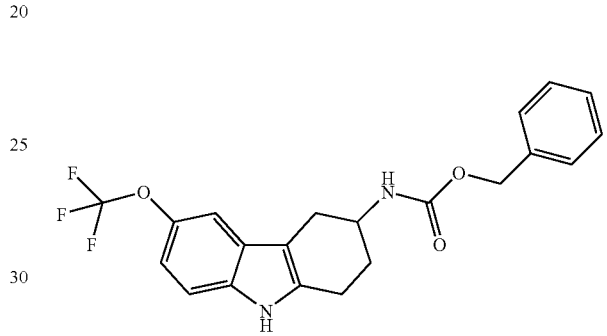

Combine 4-(trifluoromethyl)phenylhydrazine hydrochloride (31.9 g, 140 mmol) and (4-oxo-cyclohexyl)-carbamic acid benzyl ester (Preparation 42) (34.6 g, 140 mmol) and add acetic acid (700 mL). Heat the reaction to 90° C. overnight, cool to room temperature, and concentrate under reduced pressure. Purify the residue by flash chromatography (silica gel, 9:1 chloroform:acetone), and trituration (9:1 hexanes:dichloromethane) to provide 50.9 g (90%) of the title compound as a tan solid, mp 123-126° C. MS (ES): m/z 403 (M−1); $^1$H NMR (CDCl$_3$): δ 7.86 (s, 1H), 7.28-7.36 (m, 5H), 7.26 (m, 1H), 7.23 (d, J=8.8 Hz, 1H), 6.99 (dd, J=1.3, 8.7 Hz, 1H), 5.11 (s, 2H), 4.90-4.92 (m, 1H), 4.18 (m, 1H), 3.08 (dd, J=4.9, 15.4 Hz, 1H), 2.76-2.89 (m, 2H), 2.59 (dd, J=6.8, 15.3 Hz, 1H), 2.08-2.16 (m, 1H), 1.93-2.04 (m, 1H).

Preparation 44

2-Bromomethyl-6-fluoro-pyridine

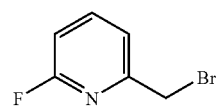

Combine 2-methyl-6-fluoro-pyridine (19.6 g, 176 mmol), 1,1'-azobis-(cyclohexane-carbonitrile) (0.431 g, 1.77 mmol), and freshly recystallized N-bromo-succinimide (32.96 g, 185 mmol) in carbon tetrachloride (200 mL) and stir in a 1000 mL flask while radiating with UV light for 18 h. Allow to cool, then filter to remove succinimide and wash with dilute Na$_2$S$_2$O$_3$ solution. Dry over Na$_2$SO$_4$, filter and evaporate to give an amber oil. Purify by silica gel chromatography, eluting with 0-30% EtOAc/hexanes to obtain 12.3 g (37%) of a clear oil. MS 100% (m/e) 190 (EI); ¹H NMR (DMSO, 400 MHz): δ 8.03-7.95 (m, 1H), 8.03-7.95 (m, 1H), 7.48 (dd, 1H, J=7.5, 2.6 Hz), 7.11 (dd, 1H, J=7.9, 2.6 Hz), 4.63 (s, 2H).

Preparation 45

[9-(6-Fluoro-pyridin-2-ylmethyl)-6-trifluoromethoxy-2,3,4,9-tetrahydro-1H-carbazol-3-yl]-carbamic acid benzyl ester

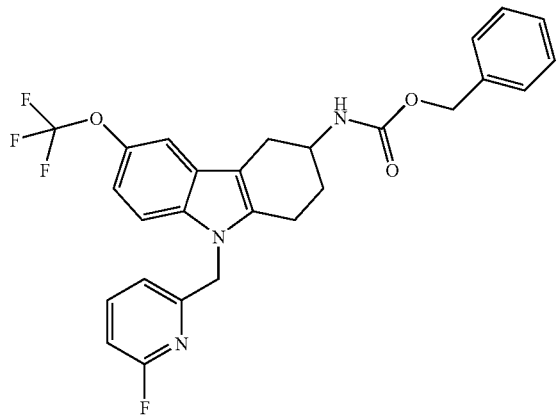

Add Cs$_2$CO$_3$ (6.44 g, 19.8 mmol) to a solution of (6-trifluoromethoxy-2,3,4,9-tetrahydro-1H-carbazol-3-yl)-carbamic acid benzyl ester (Preparation 43) (4.00 g, 9.88 mmol) and 2-bromomethyl-6-fluoropyridine (Preparation 44) (3.11 g, 13.8 mmol) in DMF (40 mL). Heat the resulting mixture to 50° C. for 18 h and then dilute with EtOAc (120 mL). Wash the organics with water (3×40 mL), dry (MgSO$_4$), filter, and concentrate to give the crude product (5.40 g) as a brown oil. Purify the crude product on silica gel (120 g) eluting with 2545% EtOAc/hexanes to afford 2.85 g (56%) of the title compound as a tan oil. MS (ES): m/z 514 (M+1); HPLC (Method A): R$_t$=4.54 min (95%).

Preparation 46

[9-(3-Fluorobenzyl)-6-trifluoromethoxy-2,3,4,9-tetrahydro-1H-carbazol-3-yl]-carbamic acid benzyl ester

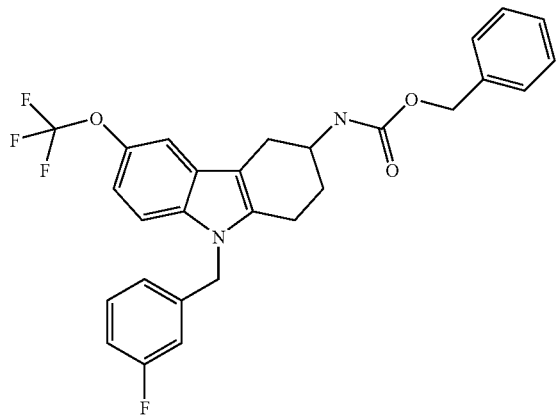

Prepare the title compound by essentially following the procedures as described in Preparation 45, using 3-fluorobenzyl bromide to give 6.15 g (95%) as a pale yellow oil. Purify on silica gel (10-60% EtOAc/hexanes) to give the title compound in 95% yield. MS (ES): m/z 513 (M+1), 513 (M−1); HPLC (Method A): R$_t$=6.23 min (97%).

Example 160

(R)-N-(6-Cyano-9-pyrazin-2-ylmethyl-2,3,4,9-tetrahydro-1H-carbazol-3-yl)-isobutyramide

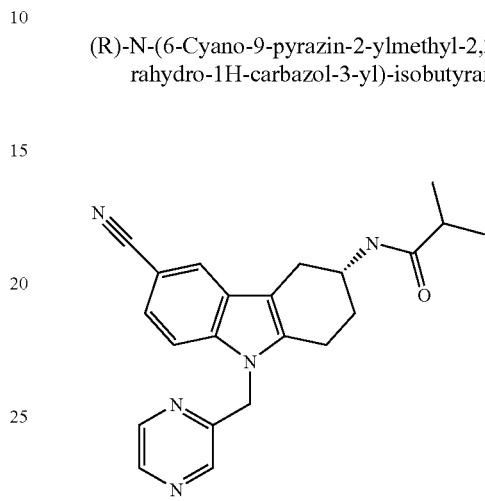

Prepare the title compound by essentially following the procedures as described in Preparation 45, using (R)-N-(6-yano-2,3,4,9-tetrahydro-1H-carbazol-3-yl)-isobutyramide (Preparation 38) and 2-chloromethylpyrazine (prepare according to literature procedure essentially as described in Newkome, G. R.; et. al. *Synthesis* 1984, 8, 676-679). Purify on silica gel (EtOAc) to afford the title compound as a light yellow solid. MS (ES): m/z 374 (M+1), 372 (M−1); HPLC (Method B): R$_t$=2.34 min (98%).

Example 161

(R)-N-(6-cyano-9-pyridin-2-ylmethyl-2,3,4,9-tetrahydro-1H-carbazol-3-yl)-isobutyramide

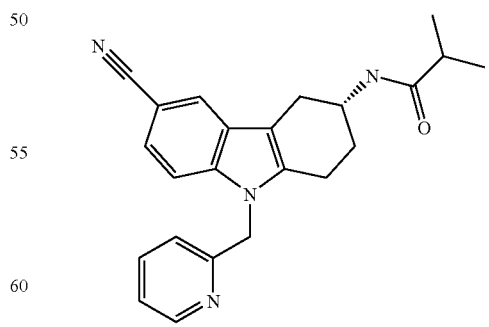

Prepare the title compound by essentially following the procedures as described in Preparation 45, using (R)-N-(6-yano-2,3,4,9-tetrahydro-1H-carbazol-3-yl)-isobutyramide (Preparation 35) and 2-chloromethylpyidine-HCl to afford the title compound as a white solid. MS (ES): m/z 373 (M+1); HPLC (Method B): $R_t$=2.79 min (100%).

Preparation 47

9-(6-Fluoropyridin-2-ylmethyl)-6-trifluoromethoxy-2,3,4,9-tetrahydro-1H-carbazol-3-ylamine

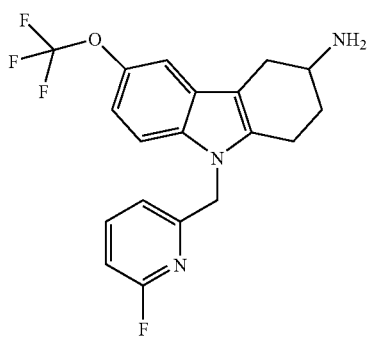

Dissolve [9-(6-fluoro-pyridin-2-ylmethyl)-6-trifluoromethoxy-2,3,4,9-tetrahydro-1H-carbazol-3-yl]-carbamic acid benzyl ester (Preparation 45) (2.73 g, 5.32. mmol) in EtOH (100 mL) and THF (50 mL). Add 10% Pd/C (200 mg) and stir at room temperature under a balloon of hydrogen for 18 h. Filter the reaction through a pad of Celite®, rinse the pad with THF (50 mL), and concentrate the filtrate in vacuo to afford 2.37 g (90%) of the title compound as a dark brown oil. MS (ES): m/z 380 (M+1); HPLC (Method A): $R_t$=1.76 min (89%).

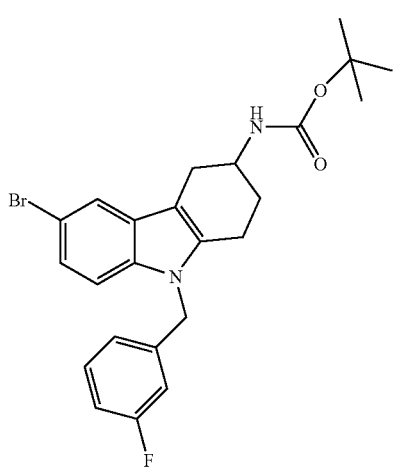

Prepare the title compound by essentially following procedures as described in Example 96, using 6-bromo-2,3,4,9-tetrahydro-1H-carbazol-3-yl)-carbamic acid tert-butyl ester (6.0 g, 16.4 mmol), m-fluorobenzyl bromide (2.2 mL, 18 mmol) and sodium hydride (720 mg of 60%, 18 mmol). Purify by column chromatography using hexane/EtOAc to give 5.95 g (77%). MS (ES): m/z 473, 475 (M+1); HPLC: $R_t$=7.24min, (97%).

Preparation 51

6-Bromo-9-(3-fluoro-benzyl)-2,3,4,9-tetrahydro-1H-carbazol-3-ylamine hydrochloric salt

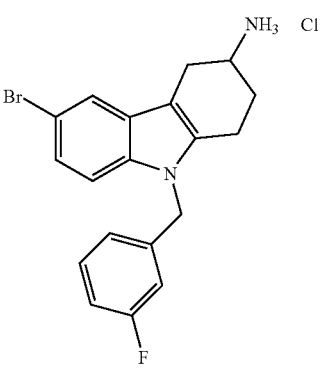

To remove the —BOC protecting group, dissolve [6-bromo-9-(3-fluoro-benzyl)-2,3,4,9-tetrahydro-1H-carbazol-3-yl]-carbamic acid tert-butyl ester (6.0 mg, 12.7 mmol) in 4N HCl in dioxane (100 mL). Stir for 10 min and then add more dioxane (50 mL) to aid in stirring the thick white solid. Collect the solid and wash with diethyl ether to give 5.2 g (99%) 6-bromo-9-(3-fluoro-benzyl)-2,3,4,9-tetrahydro-1H-carbazol-3-ylamine as the HCl salt. MS (ES): m/z 356, 358 (M+1); HPLC: $R_t$=1.84 min, (96%).

Preparation 48

9-(3-Fluorobenzyl)-6-trifluoromethoxy-2,3,4,9-tetrahydro-1H-carbazol-3-ylamine

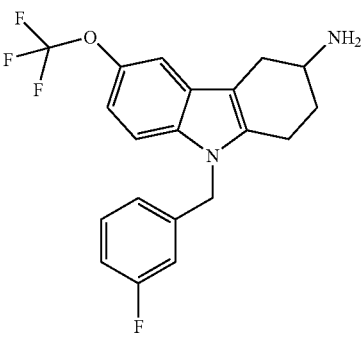

Prepare the title compound by essentially following the procedures as described in Preparation 47 using [9-(3-fluorobenzyl)-6-trifluoromethoxy-2,3,4,9-tetrahydro-1H-carbazol-3-yl]-carbamic acid benzyl ester (Preparation 46) to give 4.08 g (92%) of the title compound as a brown oil. MS (ES): m/z 379 (M+1) weak, 362 (M+1−NH$_3$); HPLC (Method A): $R_t$=1.83 min (89%).

Example 162

N-[9-(6-Fluoro-pyridin-2-ylmethyl)-6-trifluoromethoxy-2,3,4,9-tetrahydro-1H-carbazol-3-yl]-isobutyramide

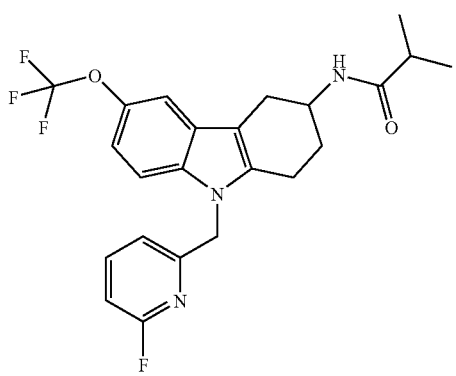

Dissolve 9-(6-fluoro-pyridin-2-ylmethyl)-6-trifluoromethoxy-2,3,4,9-tetrahydro-1H-carbazol-3-ylamine (Preparation 47) (580 mg, 1.53 mmol) and triethylamine (201 mg, 277 µL, 1.99 mmol) in $CH_2Cl_2$ (20 ML). Slowly add isobutyryl chloride (212 mg, 208 µL, 1.99 mmol) and stir at room temperature for 18 h. Dilute the reaction with dilute HCl (10 mL), then load the reaction onto a Varian ChemElut CE1020 solid-phase extraction cartridge (Varian part number 12198008). Elute, collect, and concentrate 125 mL $CH_2Cl_2$ to give the crude product (794 mg) as a brown oil. Purify the crude product on silica gel (40 g), eluting with 35-65% EtOAc/hexanes to afford 358 mg (52%) of the title compound as a yellow foam. MS (ES): m/z 450 (M+1), 448 (M−1); HPLC (Method B): $R_t$=8.21 min (100%).

Examples 163 to 165, in the table below, are prepared essentially as described in Example 162, above, using the following chloroacyl reagents respectively: cyclopropanecarbonyl chloride, methyl chloroformate, and dimethylcarbamylchloride.

| Ex. | Structure | MS (ES): e/z | HPLC ($R_t$, %) |
|---|---|---|---|
| 163 | 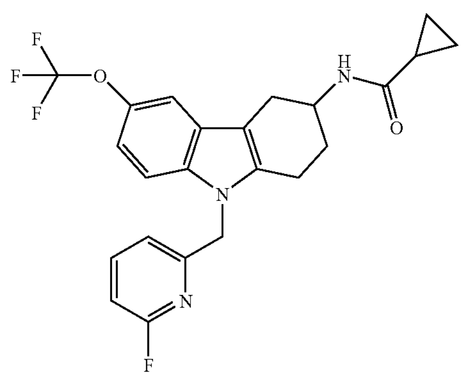 | 448 (M + 1), 446 (M − 1) | 2.76 min (97%) (Method A) |
| 164 | 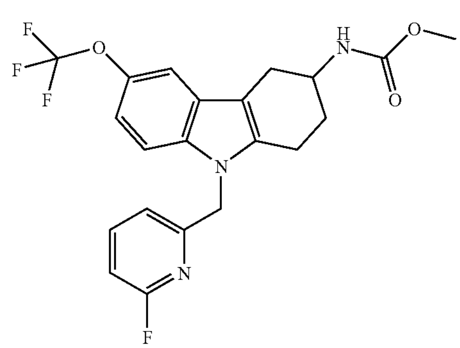 | 438 (M + 1), 482 (M + $HCO_2^-$) | 3.00 min (98%) (Method B) |

| Ex. | Structure | MS (ES): e/z | HPLC (R$_t$, %) |
|---|---|---|---|
| 165 | 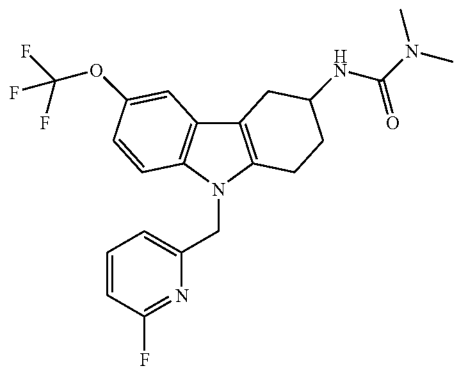 | 451 (M + 1), 449 (M − 1) | 5.74 min (99%) (Method B) |

Examples 166 to 169, in the table below, are prepared essentially as described in Example 162, above, using 9-(3-fluorobenzyl)-6-trifluorometboxy-2,3,4,9-tetrahydro-1H-carbazol-3-ylamine (Preparation 45) and the following chloroacyl reagents respectively: isobutyryl chloride, cyclopropanecarbonyl chloride, methyl chloroformate, and dimethylcarbamylchloride.

| Ex. | Structure | MS (ES): e/z | HPLC (R$_t$, %) (Method A) |
|---|---|---|---|
| 166 | 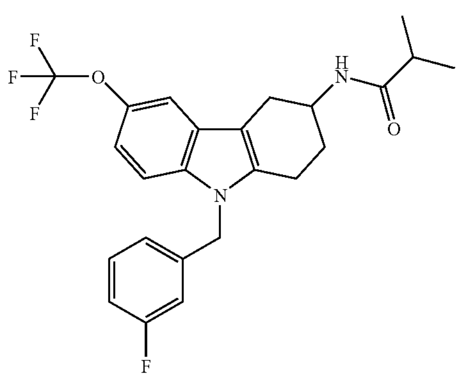 | 449 (M + 1) | 3.79 min (99%) |
| 167 | 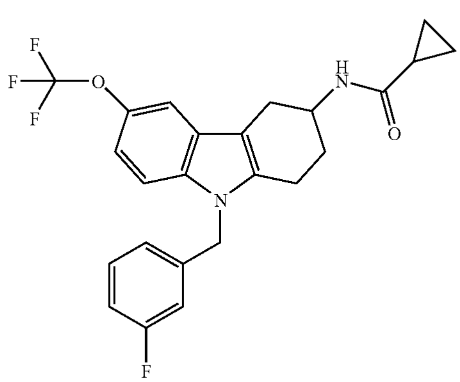 | 447 (M + 1) | 3.49 min (94%) |

-continued
| Ex. | Structure | MS (ES): e/z | HPLC (R$_t$, %) (Method A) |
|---|---|---|---|
| 168 | 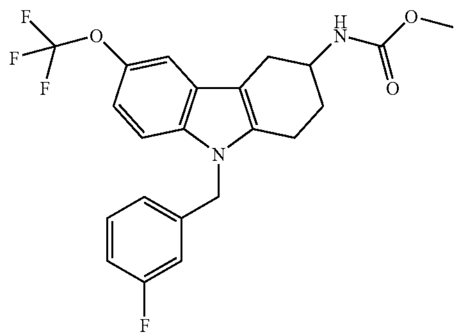 | 437 (M + 1) | 5.79 min (100%) |
| 169 | 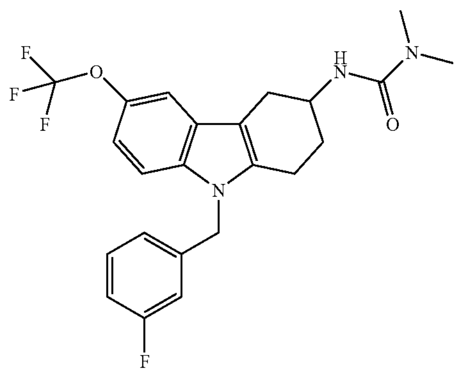 | 450 (M + 1) | 3.24 min (99%) |
Preparation 49
6-Bromo-2,3,4,9-tetrahydro-1H-carbazol-3-yl)-carbamic acid tert-butyl ester
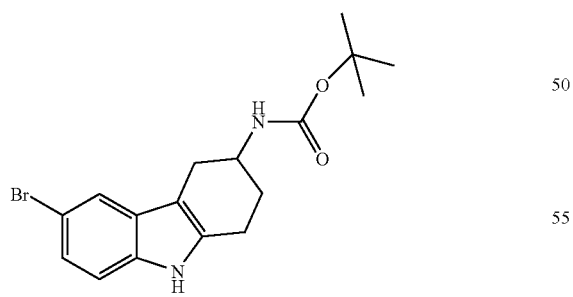
Follow the procedures essentially as described in Preparation 3 (Method 1). Mix p-bromophenylhydrazine hydrochloride (1.99 g, 8.9 mmol) and (4-oxo-cyclohexyl)-carbamic acid tert-butyl ester (1.9 g, 8.9 mmol) in ethanol (50 mL) to give 780 mg (25%) of the title compound after recrystallization from toluene. MS (ES): 363, 365 (M−1); HPLC: $R_t$=3.39 min, (94%).

Preparation 50

[6-Bromo-9-(3-fluoro-benzyl)-2,3,4,9-tetrahydro-1H-carbazol-3-yl]-carbamic acid tert-butyl ester Example 170

Cyclopropanecarboxylic acid [6-bromo-9-(3-fluoro-benzyl)-2,3,4,9-tetrahydro-1H-carbazol-3-yl]-amide

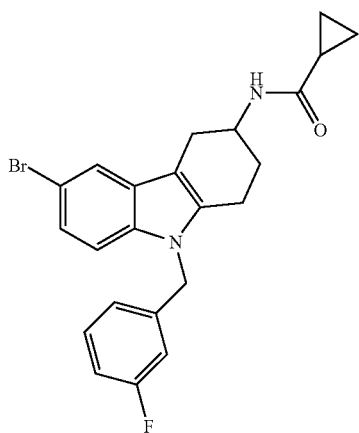

Mix 6-bromo-9-(3-fluoro-benzyl)-2,3,4,9-tetrahydro-1H-carbazol-3-ylamine hydrochloride (195 mg, 0.48 mmol), triethylamine (210 µL, 1.5 mmol), cyclopropanecarbonyl chloride chloride (55 µL, 0.6 mmol) in dichloromethane (10 mL) and stir at room temperature for 18 h. Shake the reaction with dilute HCl/water/EtOAc. Dry (MgSO$_4$) the organic layer and concentrate to give 120 mg crude product. Recrystallize (EtOH) to give 50 mg (24%) of the title compound. MS (ES): m/z 441, 443 (M+1); $^1$H NMR (CDCl$_3$): δ 7.63 (s, 1H), 7.27 (m 2H), 7.08 (d,1H), 6.92 (t, 1H), 6.75 (d, 1H), 6.63 (d, 1H), 5.58 (br d, 1H), 5.23 (s, 2H), 4.44 (br m, 1H), 3.13 (dd, 1H), 2.74 (m, 2H), 2.64 (dd,1H), 2.23 (m,2H), 2.16 (m,1H), 2.02 (m,1H), 1.09 (m,4H); HPLC: $R_t$=3.55 min, (95%).

Examples 171 to 175, in the table below, are prepared following procedures essentially as described in Example 170.

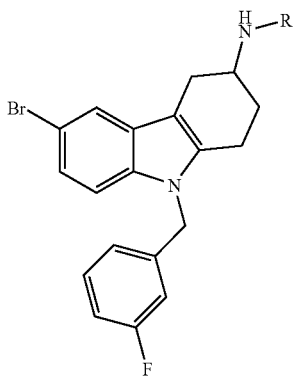

| Ex | R | MS (ES) m/z | HPLC ($R_t$, %) |
|---|---|---|---|
| 171 | ![R group with ketone and ethyl substituent] | 455, 457 (M + 1) | 4.19 min, (93%) |
| 172 | ![R group with ketone and CF3] | 471, 473 (M + 1) | 5.04 min, (93%) |
| 173 | ![R group with ketone and ethyl] | 455, 457 (M + 1) | 4.39 min, (94%) |
| 174 | ![R group with ketone and CF3] | 467, 469 (M + 1) | 4.44 min, (100%) |
| 175 | ![R group with ketone and ethyl] | 429, 431 (M + 1) | 3.46 min, (92%) |

Example 176

3-[6-Bromo-9-(3-fluoro-benzyl)-2,3,4,9-tetrahydro-1H-carbazol-3-yl]-1,1-dimethyl-urea

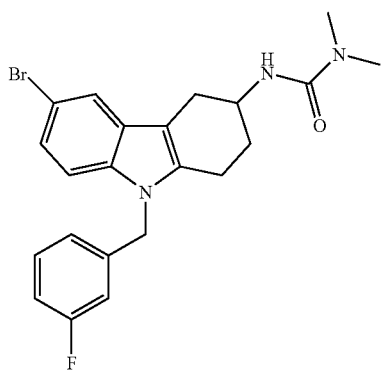

Mix 6-bromo-9-(3-fluoro-benzyl)-2,3,4,9-tetrahydro-1H-carbazol-3-ylamine.HCl (Preparation 51) (200 mg, 0.49 mmol), N,N-dimethylcarbamoyl chloride (54 μL, 63 mg, 0.59 mmol), triethylamine (205 μL, 149 mg, 1.47 mmol), CH$_2$Cl$_2$ (6 mL), and N-methylpyrrolidinone (2 mL). Stir at room temperature for 18 h, then add more N,N-dimethylcarbamoyl chloride (54 μL, 63 mg, 0.59 mmol). Stir at room temperature for 60 h, then evaporate the solvents. Dilute the residue with EtOAc (80 mL) and wash the organic solution with HCl (<1N in water, 40 mL) and aqueous NaHCO$_3$. Dry (MgSO$_4$), filter, and concentrate the organic portion to obtain 308 mg crude product as a brown oil. Purify on silica gel (12 g), eluting with 80-100% EtOAc/hexanes to afford 164 mg (75%) of the title compound as a white foam. MS (ES): 444, 446 (M+1); HPLC: R$_t$=3.27 min, (92%).

Preparation 52

6-Cyano-2,3,4,9-tetrahydro-1H-carbazol-3-yl)-carbamic acid tert-butyl ester

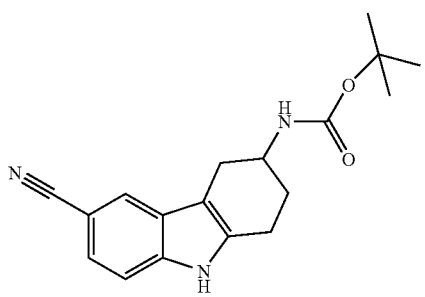

As described in C Chen et al, *J. Org. Chem.* (1997) 62, 2676-2677, mix 3-iodo-4-aminobenzonitrile (T. H. Jonckers, et al, J. Med. Chem. 45 (16) 3497-3508 (2002)) (1.3 g, 5.3 mmol) and (4-oxo-cyclohexyl)-carbamic acid tert-butyl ester (3.4 g, 16 mmol) 1,4-diazobicyclo[2.2.2]octane (DABCO) (1.8 g, 16 mmol), magnesium sulfate (960 mg, 8 mmol) and DMF (30 mL). Sparge the stirred mixture with nitrogen for 10 min and add palladium(II) acetate (58 mg, 0.26 mmol) and place in a 105° C. pre-heated oil bath. After 18 h, cool and dilute with EtOAc. Gravity filter the reaction into a separatory funnel and shake with water/EtOAc. Dry the organic layer (MgSO$_4$) and concentrate to give a dark brown oil. Triturate with hexane (insoluble material is starting ketone). Concentrate the hexane solution and purify by silica gel chromatography (120 g), eluting with methylene chloride (0-40 min), then 10% EtOAc/methylene chloride (40-70 min) to give 550 mg (33%) of an off-white foam. MS (ES): m/z 312 (M+1), 310 (M−1); HPLC: R$_t$=2.30 min, (97%).

Preparation 53

[6-Cyano-9-(3-fluoro-benzyl)-2,3,4,9-tetrahydro-1H-carbazol-3-yl]-carbamic acid tert-butyl ester

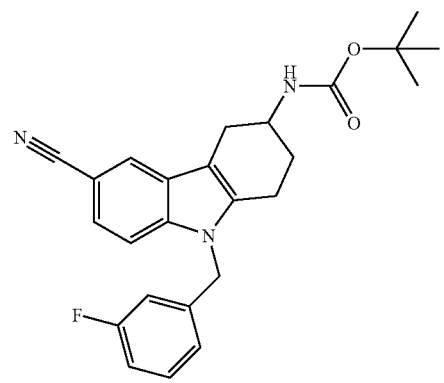

Follow procedures as essentially described in Example 96, using 6-cyano-2,3,4,9-tetrahydro-1H-carbazol-3-yl)-carbamic acid tert-butyl ester (2.0 g, 6.4 mmol), m-fluorobenzyl bromide (0.982 mL, 8 mmol) and 60% NaH (435 mg, 10.9 mmol) in DMF (70 mL) to give 1.41 g (53%) of the title compound after purification by flash chromotagraphy using EtOAc/hexane. MS (ES): m/z 420 (weak) (M+1), 418 (weak) (M−1); HPLC: R$_t$=3.86 min, (100%).

Preparation 54

6-Amino-9-(3-fluoro-benzyl)-6,7,8,9-tetrahydro-5H-carbazole-3-carbonitrile, hydrochloride

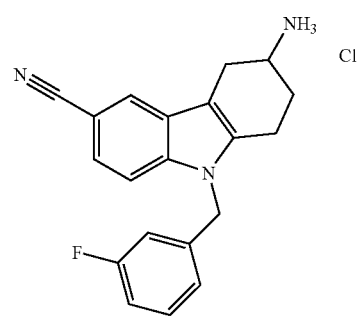

Prepare the title compound by essentially following procedures as described in Preparation 48, starting with [6-cyano-9-(3-fluoro-benzyl)-2,3,4,9-tetrahydro-1H-carbazol-3-yl]-carbamic acid tert-butyl ester (1.38 g, 3.28 mmol) and 4N HCl dioxane (10 mL) to yield 1.02 g (87%). MS (ES): m/z 320 (weak) (M+1); HPLC: $R_f$=1.64 min, (92%).

Example 177

Cyclopropanesulfonic acid[6-cyano-9-(3-fluoro-benzyl)-2,3,4,9-tetrahydro-1H-carbazol-3-yl)-amide

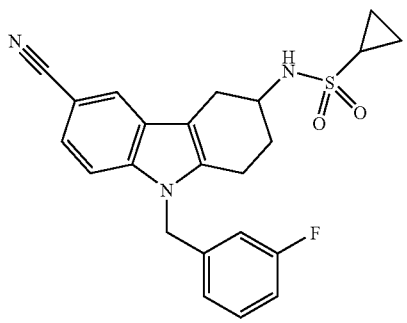

Combine 6-amino-9-(3-fluoro-benzyl)6,7,8,9-tetrahydro-5H-carbazole-3-carbonitrile, hydrochloride salt (Preparation 54) (125 mg, 0.35 mmol) and triethylamine (0.195 mL, 1.4 mmol) in dichloromethane (3 mL) under nitrogen. Add cyclopropylsulfonylchloride (51 mg, 0.36 mmol) in dichloromethane (1 mL). Stir for 18 h at room temperature. Purify the reaction solution directly by flash chromatography, eluting with 20% ethyl acetate/hexane and then a gradient up to 50% ethyl acetate/hexane to obtain 80 mg. Triturate in diethyl ether to obtain 61 mg (41%) of a tan solid. MS (ES): m/z 424 (M+1), 422 (M−1); $^1$H NMR(DMSO-$d_6$): δ 7.98 (d, 1H, J=1.3 Hz), 7.56 (d, 1H, J=8.4 Hz), 7.41 (dd, 1H, J=8.4, 1.3 Hz), 7.36-7.30 (m, 2H), 7.07 (dt, 1H, J=8.7, 2.5 Hz), 6.88 (d, 1H, J=9.7 Hz), 6.83 (d, 1H, J=7.9 Hz), 5.42 (d, 2H, J=5.3 Hz), 3.68 (m, 1H), 3.10 (dd, 1H, J=15.4, 5.3 Hz), 2.90-2.81 (m, 1H), 2.79-2.61 (m, 3H), 2.13 (m, 1H), 1.86 (m, 1H), 0.98-0.91 (m, 4H).

Example 178

3-[6-Cyano-9-(3-fluorobenzyl)-2,3,4,9-tetrahydro-1H-carbazol-3-yl]-1,1-dimethylurea

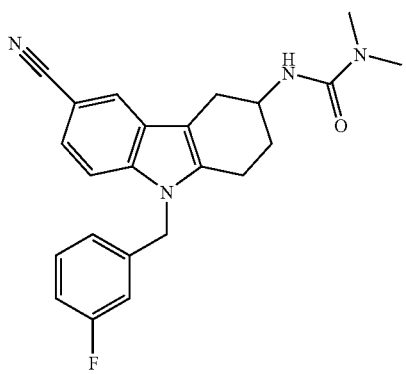

Prepare the title compound by essentially following the procedures as described in Example 162, using 6-amino-9-(3-fluoro-benzyl)-6,7,8,9-tetrahydro-5H-carbazole-3-carbonitrile hydrochloride (Preparation 54) and dimethylcarbamyl chloride. Purify by silica gel chromatography (30-70% (4% (2M NH$_3$/MeOH)/CH$_2$Cl$_2$)/hexanes) to give the title compound in 69% yield as a white solid. MS (ES): m/z 391 (M+1), 389 (M−1); HPLC (Method B): $R_f$=4.11 min (99%).

Preparation 55

[6-Cyano-9-(3-fluorobenzyl)-2,3,4,9-tetrahydro-1H-carbazol-3-yl]-carbamic acid 4-nitrophenyl ester

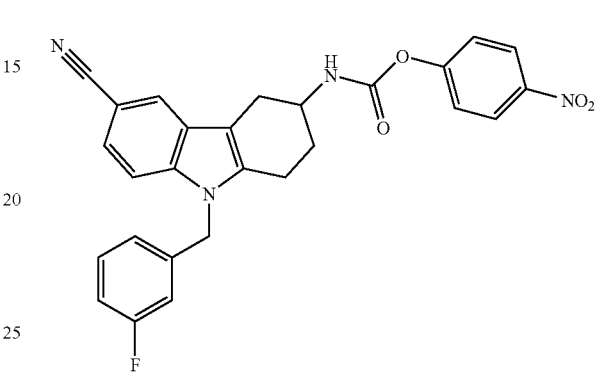

Prepare the title compound by essentially following the procedures as described in Example 162, using 6-amino-9-(3-fluoro-benzyl)-6,7,8,9-tetrahydro-5H-carbazole-3-carbonitrile hydrochloride (Preparation 51) and 4-nitrophenyl chloroformate. Purify by silica gel chromatography (50% (4% (2M NH$_3$/MeOH)/CH$_2$Cl$_2$)/hexanes) to give the title compound in 33% yield as a white solid. MS (ES): m/z 346 (M-p-nitrophenolate); HPLC (Method B): $R_f$=2.23 min (86%).

Example 179

1-[6-Cyano-9-(3-fluorobenzyl)-2,3,4,9-tetrahydro-1H-carbazol-3-yl]-3-methyl-urea

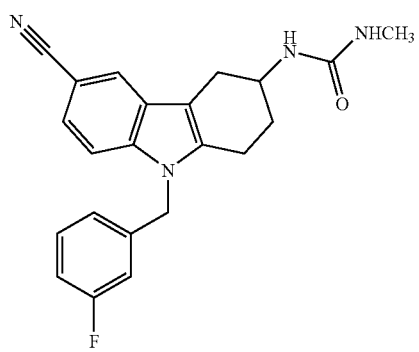

Combine [6-cyano-9-(3-fluorobenzyl)-2,3,4,9-tetrahydro-1H-carbazol-3-yl]-carbamic acid 4-nitrophenyl ester (Preparation 55) (306 mg, 0.63 mmol), methylamine hydrochloride (426 mg, 6.30 mmol), triethylamine (1.40 g, 1.93 mL, 13.9 mmol), and THF (30 mL). Stir the reaction mixture at room temperature for 18 h, then dilute with water (100 mL). Extract into EtOAc (3×65 mL), dry the combined organic portions (MgSO$_4$), filter, and concentrate to give the crude product (310 mg) as a yellow oil. Purify the crude product on 40 g silica gel (50-100% (4% (2M NH$_3$/MeOH)/CH$_2$Cl$_2$)/hexanes) to give 58 mg (24%) of the title compound as a yellow solid. MS (ES): m/z 377 (M+1); HPLC (Method B): R$_t$=3.22 min (98%).

Example 180

3-[6-Cyano-9-(3-fluorobenzyl)-2,3,4,9-tetrahydro-1H-carbazol-3-yl]-1-methoxy-1-methyl-urea

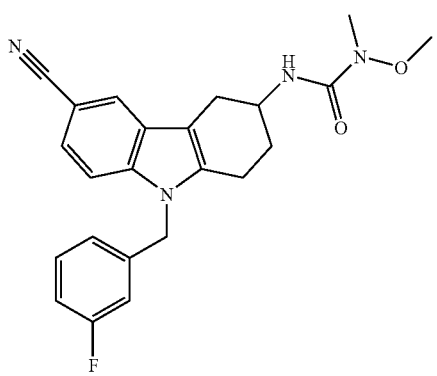

Prepare the title compound by essentially following the procedures as described in Example 179, using N,O-dimethylhydroxylamine hydrochloride. Purify on silica gel (10-30% (2% (2M NH$_3$/MeOH)/CH$_2$Cl$_2$)/hexanes) to give 11 mg (13%) of the title compound as a colorless oil. MS (ES): m/z 407 (M+I), 405 (M−1); HPLC (Method B): R$_t$=5.42 min (88%).

Preparation 56

(5-Fluoro-pyridin-2-yl)-methanol

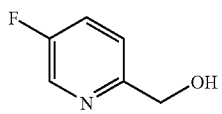

Add butyllithium (10.9 mL, 27.22 mmol, 2.5 M solution in hexanes) to a −78° C. solution of 2-bromo-5-fluoro-pyridine (3.99 g, 22.68 mmol) in toluene (200 mL). Stir the reaction at −78° C. for 90 min and then add N,N-dimethylformamide (2.3 mL, 29.71 mmol) via syringe. Stir the reaction for an additional 2 h at −78° C. and then add sodium borohydride (1.72 g, 45.36 mmol) and allow the reaction to warm to room temperature over a 12 h period. Quench the reaction with saturated aqueous sodium bicarbonate (20 mL) and dilute with ethyl acetate (100 mL). Separate the organic phase and dry (magnesium sulfate), filter and concentrate in vacuo to give a yellow oil. Purify the oil by column chromatography (silica gel; 10% to 50% ethyl acetate in hexanes) to give 1.30 g (45%) as a clear colorless oil. $^1$H NMR (300 MHz, CDCl$_3$): δ 8.41s, 1H), 7.46-7.37 (m, 1H), 7.32-7.27 (m, 1H), 4.75 (s, 2H), 3.64 (br s, 1H).

Preparation 57

2-Chloromethyl-5-fluoro-pyridine hydrochloride salt

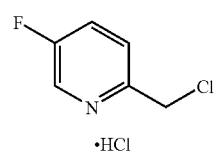

Add thionyl chloride (320 μL, 4.30 mmol) slowly to a 0° C. solution of (5-fluoro-pyridin-2-yl)-methanol (420 mg, 3.31 mmol) in methylene chloride (15 mL). Stir the reaction at 0° C. for 3 h and quench with isopropyl alcohol. Dilute the reaction contents with methylene chloride (50 mL) and then saturated aqueous sodium bicarbonate (20 mL). Separate the organic phase, dry(magnesium sulfate), filter and concentrate in vacuo to give an oil. The oil is treated with hydrochloric acid (10 mL, 3 M solution in dioxane) at room temperature for 30 min. The resultant solid is collected by filtration and washed with a minimal amount of cold diethyl ether to give 200 mg (33%) as a yellow solid. MS (APCI): m/z 146 [C$_6$H$_5$ClFN+H]$^+$; $^1$H NMR (300 MHz, CDCl$_3$): δ 8.42 (s, 1H), 7.56-7.37 (m, 2H), 4.67 (s, 2H).

Example 181

N-[6-Cyano-9-(5-fluoro-pyridin-2-ylmethyl)-2,3,4,9-tetrahydro-1H-carbazol-3-yl]-isobutyramide

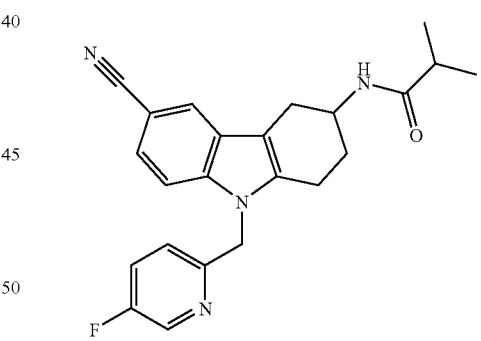

Suspend sodium hydride (60% in oil, 80 mg, 1.99 mmol) in DMF (2 mL) and chill to 0° C. Add a solution of N-(6-cyano-2,3,4,9-tetrahydro-1H-carbazol-3-yl)-isobutyramide (253 mg, 0.90 mmol) in DMF (2 mL) slowly via syringe, and allow to stir 30 min before warming to ambient temperature for 60 min. Add 2-chloromethyl-5-fluoro-pyridine hydrochloride salt (180 mg, 0.99 mmol) and stir the reaction for about 12 h. Quench the reaction with saturated aqueous ammonium chloride (5 mL). Add ethyl acetate (50 mL) and wash the solution with water (50 mL), then brine (2×50 mL). Separate the organic phase and dry over magnesium sulfate, filter, and evaporate under reduced pressure. Titurate the resulting residue with diethyl ether (10 mL) for 5 min and then filter to afford 187 mg (53%) of the title compound as a light yellow solid. mp 235-238° C. (dec); MS (ESI): m/z [391 $C_{23}H_{23}FN_4O+H]^+$; $^1H$ NMR (300 MHz, CDCl$_3$): δ 8.43s, 1H), 7.78 (s, 1H), 7.38-7.25 (m, 3H), 6.67 (dd, J=8.6, 4.2 Hz, 1H), 5.58 (d, J=7.8 Hz, 1H), 5.35 (s, 2H), 4.40 (br s, 1H), 3.14 (dd, J=15.4, 5.0 Hz, 1H), 2.79 (br s, 2H), 2.60 (dd, J=15.4, 7.6 Hz, 1H), 2.34 (pentet, J=6.8 Hz, 1H), 2.15 (br s, 1H), 2.02-1.95 (m, 1H), 1.16 (d, J=6.9 Hz, 6H).

Preparation 58

(6-Bromo-3-fluoro-pyridin-2-yl)-methanol

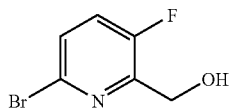

Slowly add n-Butyllithium (2.5 M in hexanes, 9.40 mL, 23.3 mmol) to a −78° C. solution of 2-bromo-5-fluoro-pyridine (3.42 g, 19.4 mmol) and diethyl ether (200 mL). Stir the reaction at −78° C. for 1 h, then add dimethylformamide (2.00 mL, 25.5 mmol) and continue stirring for an additional hour. Warm the reaction to room temperature and remove the solvent under vacuum. Dissolve the crude material in methanol (50 mL) and cool to 0° C. Add sodium borohydride.(1.47 g, 38.9 mmol) and allow the reaction is to slowly warm to room temperature over 12 h. Quench the reaction with saturated aqueous sodium bicarbonate (20 mL) then add ethyl acetate (100 mL). Separate the layers and dry the resultant organic layer with magnesium sulfate, filter, and concentrate under vacuum to give a yellow solid. Purify the crude solid by column chromatography (silica gel; 10% to 50% ethyl acetate in hexanes) to give 1.66 g (42%) of the title compound as a yellow solid. $^1H$ NMR (300 MHz, CDCl$_3$): δ 7.50-7.40m, 1H), 7.35-7.25 (m, 1H), 4.80 (s, 2H), 3.30 (s, 1H).

Preparation 59

(3-Fluoro-pyridin-2-yl)-methanol

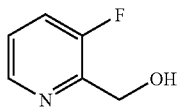

Dissolve (6-bromo-3-fluoro-pyridin-2-yl)-methanol (850 mg, 4.13 mmol) in methanol (40 mL) then purge the solution with nitrogen. Add palladium on carbon (200 mg of 5% wet) and stir the mixture under a hydrogen atmosphere (2 balloons) for 20 h. Filter the mixture through Celite® and wash the filter cake with methanol.

Concentrate the filtrate under reduced pressure and dissolve the resulting residue in chloroform (150 mL). Wash the organics with saturated aqueous sodium bicarbonate (75 mL), dry over magnesium sulfate, filter, and concentrate to give 433 mg (82%) of the title compound which is used without further purification. $^1H$ NMR (300 MHz, CDCl$_3$): δ 8.40 (m, 1H), 7.42-7.36 (m, 1H), 7.29-7.23 (m, 1H), 4.84 (s, 2H), 3.97 (br s, 1H); MS (APCI): m/z 110 $[C_6H_6FNO—H_2O+H]^+$.

Preparation 60

2-Chloromethyl-3-fluoro-pyridine

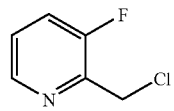

Dissolve (3-fluoro-pyridin-2-yl)-methanol (215 mg, 1.69 mmol) in dichloromethane (10 mL) and cool to 0° C. Add thionyl chloride (160 μL, 2.20 mmol) and stir the reaction for one hour. Add dichloromethane (50 mL) and stir the reaction with saturated aqueous sodium bicarbonate (2×40 mL) and brine (2×40 mL). Separate and dry the organic portion over magnesium sulfate, filter, and concentrate under reduced pressure to provide 198 mg (80%) of product, which is used without further purification. MS: m/z 146, 148 $[C_6H_5ClFN+1]^+$; $^1H$ NMR (300 MHz, CDCl$_3$): δ 8.41-8.44 (m, 1H), 7.41-7.47 (m, 1H), 7.28-7.34 (m, 1H), 4.75 (d, J=2.0 Hz, 2H); $^{19}F$ NMR (282 MHz, CDCl$_3$): δ-123.8.

Example 182

N-[6-Cyano-9-(3-fluoro-pyridin-2-ylmethyl)-2,3,4,9-tetrahydro-1H-carbazol-3-yl]-isobutyramide

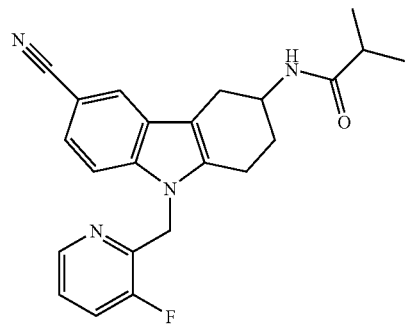

Suspend sodium hydride (60% suspension in mineral oil, 114 mg, 1.64 mmol) in dimethylformamide (7 mL) and cool to 0° C. Add a solution of N-(6-cyano-2,3,4,9-tetrahydro-1H-carbazol-3-yl)-isobutyramide (Preparation 3) (385 mg, 1.37 mmol) in dimethylformamide (3.5 mL). After several minutes, warm the reaction to room temperature, and stir for 30 min, after which time add 2-chloromethyl-3-fluoro-pyridine (Preparation 60). Stir the reaction overnight and then dilute with ethyl acetate (100 mL). Wash the reaction mixture sequentially with brine (3×75 mL), water (75 mL), and brine (75 mL). Separate the organic layer, dry over magnesium sulfate, filter, and concentrate under reduced pressure. Purify using flash chromatography [silica gel, gradient from 0:100 to 20:80 (90:10:1 dichloromethane:methanol:concentrated ammonium hydroxide):dichloromethane] to provide 184 mg (38%) of the title compound as an off-white solid. m.p.=213-216° C.; MS: m/z 391 $[C_{23}H_{23}FN_4O+1]^+$; $^1H$ NMR (300 MHz, DMSO-d$_6$): δ 8.29-8.31 (m, 1H), 7.92 (d, J=1.2 Hz, 1H), 7.84 (d, J=7.6 Hz, 1H), 7.71-7.78 (m, 1H), 7.58 (d, J=8.5 Hz, 1H), 7.38-7.44 (m, 2H), 5.56 (s, 2H), 3.99-4.04 (m, 1H), 2.73-3.00 (m, 3H), 2.49-2.55 (m, 1H), 2.37 (septet, J=6.8 Hz, 1H), 1.96-2.00 (m, 1H), 1.76-1.83 (m, 1H), 1.01 (d, J=6.8 Hz, 6H).

Example 183

(R)-N-[6-Cyano-9-(6-fluoro-pyridin-2-ylmethyl)-2,3,4,9-tetrahydro-1H-carbazol-3-yl]-isobutyramide

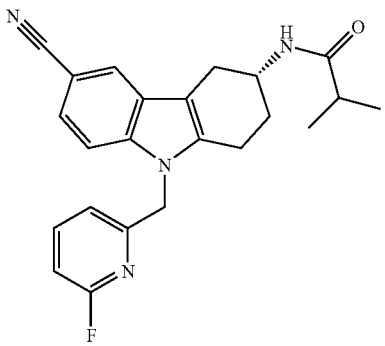

Prepare the title compound by essentially following the procedures as described in Example 147, using N-(6-cyano-2,3,4,9-tetrahydro-1H-carbazol-3-yl)-isobutyramide (Preparation 35) (0.7 mmol, 200 mg), anhydrous dimethylformamide (10 mL), sodium hydride (60% mnineral oil suspension, 1.2 eq., 0.85 mmol, 34 mg), and 2-bromomethyl-6-fluoropyridine (Preparation 41) (0.85 mmol., 162 mg) as a solution in 1 mL anhydrous DMF. Stir the resulting mixture for 30 min at room temperature and then quench the reaction slowly with water (40 mL) to precipitate white solids. Collect the product via filtration and wash the cake with hexanes. Dissolve the filter cake in ethyl acetate and dichloromethane; dry the resulting solution with magnesium sulfate and strip to dryness. Crystallize the product from dichloromethane/hexanes and dry under vacuum at 40° C. to provide 242 mg (87%) white solids. LCMS 100% (m/z) 391 (M+1, APES-pos); $^1$H NMR (DMSO, 400 MHz): δ 7.94 (d, 1H, J=1.3 Hz), 7.90 (dd, 1H, J=15.9, 8.4 Hz), 7.82 (d, 1H, J=7.5 Hz), 7.58 (d, 1H, J=8.4 Hz), 7.40 (dd, 1H, J=8.4, 1.8 Hz), 7.05 (dd, 1H, J=8.1, 2.4 Hz), 6.92 (dd, 1H, J=7.3, 2.4 Hz), 5.44 (s, 2H), 4.06-3.95 (m, 1H), 2.97 (dd, 1H, J=15.2, 5.1 Hz), 2.97 (dd, 1H, J=15.2, 5.1 Hz), 2.88-2.68 (m, 2H), 2.52 (dd, 1H, J=14.9, 8.1 Hz), 2.42-2.31 (m, 1H), 2.00-1.91 (m, 1H), 1.86-1.74 (m, 1H), 0.99 (d, 3H, J=3.1 Hz), 0.98 (d, 3H, J=2.6 Hz)

Preparation 61

(6-Cyano-2,3,4,9-tetrahydro-1H-carbazol-3-yl)-carbamic acid benzyl ester

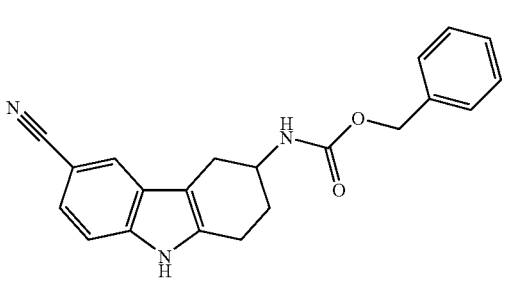

Combine 4-cyanophenylhydrazine hydrochloride (27.4 g, 162 mmol) and (4-oxo-cyclohexyl)-carbamic acid benzyl ester (Preparation 42) (40.0 g, 162 mmol) in acetic acid (800 mL). Heat the reaction to 90° C. overnight, then cool to room temperature and concentrate under reduced pressure. Triturate the residue in dichloromethane and discard the filter cake. Concentrate the filtrate under reduced pressure. Purify the resulting residue by flash chromatography (silica gel, 9:1 chloroform:acetone). Recrystillize the resulting material from benzene to provide 38.8 g (69%) of the title compound. m.p.=141-143° C.; mass spectrum (m/e): 344 [$C_{21}H_{19}N_3O_2$−1]$^-$; $^1$H NMR (300 MHz, CDCl$_3$): δ 8.15 (s, 1H), 7.73 (s, 1H), 7.29-7.38 (m, 7H), 5.12 (s, 2H), 4.89-4.92 (m, 1H), 4.18 (m, 1H), 3.09 (dd, J=5.0, 15.5 Hz, 1H), 2.78-2.91 (m, 2H), 2.59 (dd, J=7.0, 15.5 Hz, 1H), 2.07-2.17 (m, 1H), 1.93-2.05 (m, 1H).

Preparation 62

(R)-(6-Cyano-2,3,4,9-tetrahydro-1H-carbazol-3-yl)-carbamic acid benzyl ester

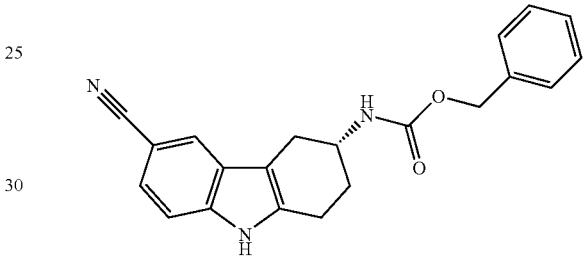

Resolve racemic (6-cyano-2,3,4,9-tetrahydro-1H-carbazol-3-yl)-carbamic acid benzyl ester (Preparation 61) (43.28 g) using preparative HPLC under the following conditions: Chiralcel OD column (8×35 cm), MeOH/0.2% dimethylethyl amine (DMEA) mobile phase at 350 ml/min flow rate with UV detection at 240 nM. Use 20 mL (666 mg) injections in 1:3 CHCl$_3$/MeOH diluent with a runtime of 18.2 min and a stacked recycle injection (2 passes through the column to completely remove both isomers). First isomer to elute is is S isomer (21.34 g) with 98.2% ee. Second isomer to elute is R isomer (20.45 g) with 95.0% ee to give the title compound.

Preparation 63

(R)-6-Amino-6,7,8,9-tetrahydro-5H-carbazole-3-carbonitrile

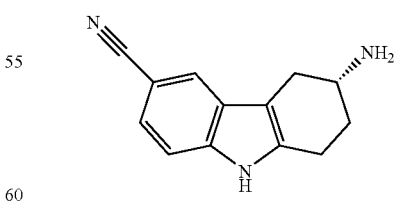

Combine (R)-(6-cyano-2,3,4,9-tetrahydro-1H-carbazol-3-yl)-carbamic acid benzyl ester (Preparation 62) (7.1 mmol, 2.44 g) in anhydrous ethanol (100 mL). To the stirred solution add 5% palladium/carbon (600 mg). Purge and fill the reaction vessel with hydrogen (3×) and stir the reaction mixture under hydrogen at atmospheric pressure for about 18 h. Filter the reaction mixture through a Celite® and wash the cake with methanol. Strip the filtrate to dryness and isolate the first crop via crystallization from ethyl acetate/methanol/hexanes to yield 720 mg of pure product. Strip the crystallization mother liquors to dryness, purify and isolate additional product via flash chromatography (25% methanol/dichloromethane isocratic) for a total yield of 1.17 g (78%). LCMS 100% (m/e) 212 (M+1, APES-pos), 210 (M−1, APES-neg); $^1$H NMR (DMSO, 400 MHz): δ 11.29 (s, 1H), 7.81 (d, 1H, J=0.9 Hz), 7.36 (dd, 1H, J=8.4, 0.9 Hz), 7.30 (dd, 1H, J=8.4, 1.8 Hz), 3.11-3.02 (m, 1H), 2.87 (dd, 1H, J=15.4, 4.8 Hz), 2.79-2.70 (m, 2H), 2.28 (dd, 1H, J=15.4, 8.4 Hz), 1.97-1.89 (m, 1H), 1.78 (s, 2H), 1.66-1.54 (m, 1H)

Preparation 64

6-Amino-6,7,8,9-tetrahydro-5H-carbazole-3-carbonitrile

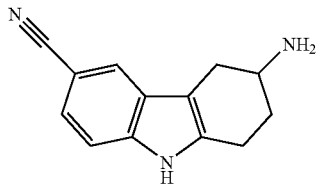

Combine (4-oxocyclohexyl)carbamic acid tert-butyl ester (40.9 g, 192 mmol) and 4-cyanophenylhydrazine hydrochloride (25.0 g, 147 mmol) in concentrated hydrochloric acid (100 mL) and water (200 mL) and heat at reflux for 18 h. Allow to cool and collect the precipitate. Wash with Na$_2$CO$_3$ solution and azetrope with CHCl$_3$, absolute EtOH, and CHCl$_3$ again to obtain 25.5 g of a white solid (82%). MS (ES): m/z 212 (M+1).

Preparation 65

(R)-(6-Cyano-2,3,4,9-tetrahydro-1H-carbazol-3-yl) carbamic acid methyl ester

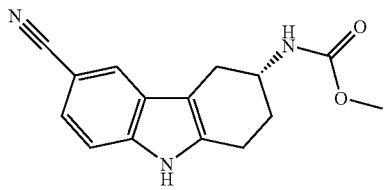

Combine 6-amino-6,7,8,9-tetrahydro-5H-carbazole-3-carbonitrile (2.4 mmol, 0.5 g) and triethylamine (4.7 mmol, 0.66 mL) in DMSO (10 mL) with 15 stirring. Add methyl chloroformate (3.6 mmol, 275 μL) and stir the resulting mixture at room temperature for 5-10 min. Quench with water (35 mL) and dilute the reaction mixture with ethyl acetate (200 mL). Separate the layers and wash the organic layer with brine (100 mL). Back wash the brine layer with ethyl acetate (2×100 mL) and dry the combined organic layers with magnesium sulfate. Filter and concentrate in vacuo to provide crude product that is used without further purification. LCMS of the reaction mixture prior to workup gave masses 270.0 (APCI-pos) and 268.0 (APCI-neg) for the desired product.

Preparation 66

(6-Cyano-2,3,4,9-tetrahydro-1H-carbazol-3-yl)-carbamic acid methyl ester

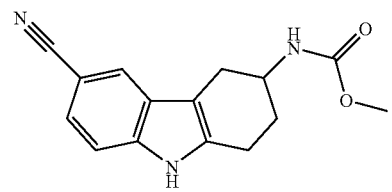

Prepare the title compound by essentially following procedures as described in Preparation 65, using 6-amino-6,7,8,9-tetrahydro-5H-carbazole-3-carbonitrile (Preparation 64) (500 mg, 2.37 mmol), triethyl amine (660 μl, 4.73 mmol) and methyl chloroformate (275 μl, 3.55 mmol) to obtain 460 mg (75%) white solids. $^1$H NMR (DMSO, 400 MHz): δ 11.35 (s, 1H), 7.85 (s, 1H), 7.31-7.39 (m, 3H), 3.72-3.82 (m, 1H), 3.53 (s, 3H), 2.93 (dd, J=4.8, 14.8 Hz, 1H), 2.80-2.82 (m, 2H), 2.45-2.52 (m, 1H), 1.97-2.02 (m, 1H), 1.72-1.79 (m, 1H).

Example 184

[6-Cyano-9-(3-fluoro-benzyl)-2,3,4,9-tetrahydro-1H-carbazol-3-yl]-carbamic acid methyl ester

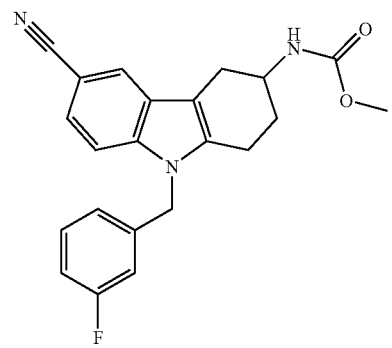

Combine (6-cyano-2,3,4,9-tetrahydro-1H-carbazol-3-yl)-carbamic acid methyl ester (460 mg, 1.7 mmol) and anhydrous dimethylformamide (15 mL) under nitrogen. Chill the mixture to 0° C. and add potassium bis(trimethylsilyl)amide (0.5M toluene solution, 3.4 mL, 1.7 mmol). Stir the resulting mixture for 30 minutes, then add 3-fluorobenzyl bromide (210 μL, 1.7 mmol) and stir the reaction mixture for 4 h allowing slow warming to room temperature. Quench the reaction with water (50 mL) and extract the product with ethyl acetate (2×50 mL). Dry the combined extracts with magnesium sulfate and concentrate in vacuo. Purify the product via flash chromatography (25% ethyl acetate/hexanes isocratic) to afford 475 mg (74%) of a white solid. LCMS (Method E): 100% (m/z) 378 (M+1, APCI-pos); $^1$H NMR (DMSO, 400 MHz): δ 11.33 (s, 1H), 7.85 (s, 1H), 7.46 (d, 1H, J=7.9 Hz), 7.39-7.27 (m, 7H), 5.03 (q, 2H, J=8.8 Hz), 3.87-3.75 (m, 1H), 3.87-3.75 (m, 1H), 2.96 (dd, 1H, J=15.2, 5.1 Hz), 2.85-2.77 (m, 2H), 2.55-2.49 (m, 1H), 2.07-1.97 (m, 1H), 1.85-1.71 (m, 1H).

Example 185

(6(R)-Cyano-9-pyridin-2-ylmethyl-2,3,4,9-tetrahydro-1H-carbazol-3-yl)-carbamic acid methyl ester

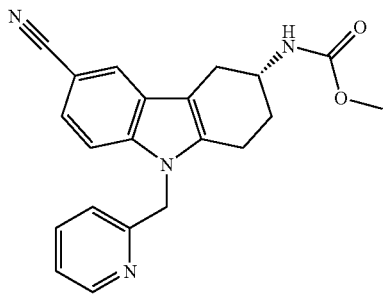

Combine (6-cyano-2,3,4,9-tetrahydro-1H-carbazol-3-yl)-carbamic acid methyl ester (1.4 mmol, 370 mg), anhydrous dimethylformamide (15 mL), cesium carbonate (4.1 mmol, 1.34 g), and 2-chloromethylpyridine hydrochloride (1.8 mmol, 295 mg). Stir the resulting slurry under nitrogen at 50° C. for 24 h. Quench the reaction with slow addition of water (about 50 mL) to allow for base dissolution and product precipitation. Collect the product via filtration and wash the cake with hexanes. Dry the product at 40° C. under vacuum overnight to yield 385 mg (78%). LCMS 93% (m/e) 361 (M+1, APES-pos); $^1$H NMR (DMSO, 400 MHz). δ 8.48 (ddd, 1H, J=4.8, 1.8, 0.9 Hz), 7.92 (d, 1H, J=1.3 Hz), 7.70 (td, 1H, J=10.9, 3.9 Hz), 7.56 (d, 1H, J=8.4 Hz), 7.33 (d, 1H, J=7.5 Hz), 7.25 (ddd, 1H, J=7.5, 4.8, 0.9 Hz), 7.00 (d, 1H, J=7.9 Hz), 5.45 (q, 2H, J=12.4 Hz), 3.82-3.69 (m, 1H), 3.53 (s, 3H), 2.98 (dd, 1H, J=15.6, 5.1 Hz), 2.93-2.84 (m, 1H), 2.80-2.68 (m, 1H), 2.53 (dd, 1H, J=15.4, 9.7 Hz), 2.06-1.97 (m, 1H), 1.82-1.69 (m, 1H).

Example 186

(R)-[6-Cyano-9-(6-fluoro-pyridin-2-ylmethyl)-2,3,4,9-tetrahydro-1H-carbazol-3-yl]-carbamic acid methyl ester

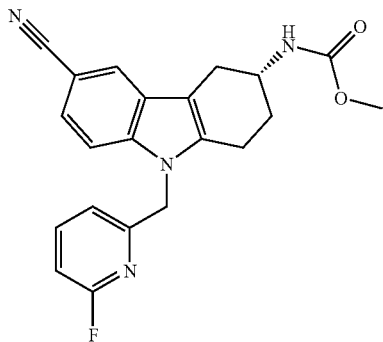

Prepare the title compound by essentially following the procedures as described in Example 147 using (6-cyano-2,3,4,9-tetrahydro-1H-carbazol-3-yl)-carbamic acid methyl ester (700 mg, 2.6 mmol), anhydrous dimethylformamide (30 mL), sodium hydride (60% mineral oil suspension, 12.5 mg, 3.1 mmol), and 2-bromomethyl-6-fluoro-pyridine (Preparation 41) (594 mg, 3.1 mmol) as a solution in 1 mL anhydrous DMF. Stir the resulting mixture for 30 min at room temperature, and then quench the reaction slowly with water (100 mL). Extract the crude product with ethyl acetate (2×100 mL) and wash the combined organic extracts with brine. Dry with magnesium sulfate, filter and concentrate in vacuo. Purify the product via flash chromatography (5% MTBE/dichloromethane for 15 min, step gradient to 10% MTBE). Combine the product fractions and concentrate until solids start crystallizing. Add hexanes as anti-solvent, collect the product via filtration, and wash the cake with hexanes to afford the first crop. Strip the mother liquors and purify additional product as above to afford a total yield of 502 mg (51%) of a white solid. LCMS 100% (mle) 379 (M+1, APES-pos); $^1$H NMR (DMSO, 400 MHz); δ 7.94-7.87 (m, 2H), 7.57 (d, 1H, J=8.4 Hz), 7.39 (dd, 1H, J=8.4, 1.3 Hz), 7.33 (d, 1H, J=7.5 Hz), 7.05 (dd, 1H, J=8.1, 2.4 Hz), 6.91 (dd, 1H, J=7.5, 2.2 Hz), 5.43 (q, 2H, J=12.9 Hz), 3.82-3.70 (m, 1H), 3.53 (s, 3H), 3.53 (s, 3H), 2.99 (dd, 1H, J=15.2, 5.1 Hz), 2.92-2.82 (m, 1H), 2.79-2.67 (m, 1H), 2.53 (dd, 1H, J=15.2, 9.0 Hz), 2.53 (dd, 1H, J=15.2, 9.0 Hz), 2.07-1.98 (m, 1H), 1.83-1.70 (m, 1H).

Example 187

(R)-9-(3-fluorobenzyl)-6-isobutyrylamino-6,7,8,9-tetrahydro-5H-carbazole-3-carboxylic acid methyl ester

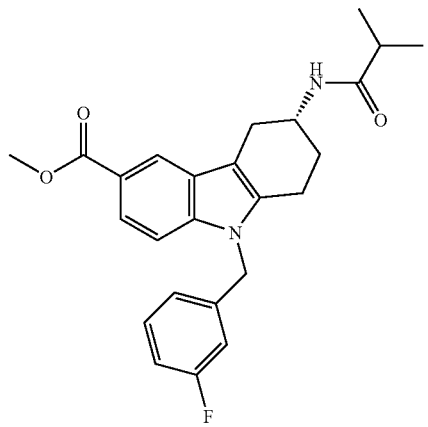

Combine (R)-N-(9-benzyl-6-bromo-2,3,4,9-tetrahydro-1H-carbazol-3-yl)isobutyramide (Example 122) (4.00 g, 9.02 mmol), sodium acetate (2.96 g, 36 mmol), and dichloro[1,1'-bis(diphenyl-phosphino)ferrocene]palladium (II) dichloromethane adduct. (0.368 g, 0.45 mmol) in methanol (36 mL) in a Parr reactor. Charge with carbon monoxide (55 psi) and heat at 95° C. for 20 h. Concentrate and chromatograph over silica eluting with 5-20% EtOAc/CHCl$_3$ to give 3.3 g (87%)

of a white cottony solid that is slurried in diethyl ether for collection by filtration. MS (ES): m/z 423 (M+1); HPLC: $R_f$=1.93 min (100%).

Example 188

(R)-N-(9-Benzyl-6-isobutyrylamino-6,7,8,9-tetrahydro-5H-carbazole-3-carboxylic acid

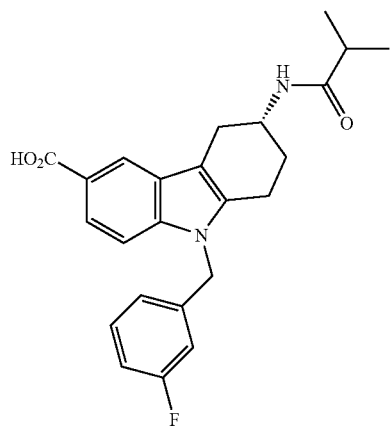

Add (R)-9-(3-fluorobenzyl)-6-isobutyrylamino-6,7,8,9-tetrahydro-5H-carbazole-3-carboxylic acid methyl ester (2.54 g, 6.01 mmol) to a solution of excess LiOH in methanol/water/TBF (33:33:33) and stir for 24 h at 70° C. Concentrate in vacuo, partition between water and EtOAc/Et$_2$O. Make the aqueous layer acidic with aqueous HCl and extract with EtOAc. Wash with brine, filter the solids from the EtOAc layer and slurry in hot EtOAc. Collect by filtration and dry to give 2.35 g (96%) of a white solid. MS (ES): m/z 409 (M+1), HPLC: $R_f$=1.93 (100%).

Example 189

(R)-[9-(3-Fluoro-benzyl)-6-isobutyrylamino-6,7,8,9-tetrahydro-5H-carbazol-3-yl]-carbamic acid ethyl ester

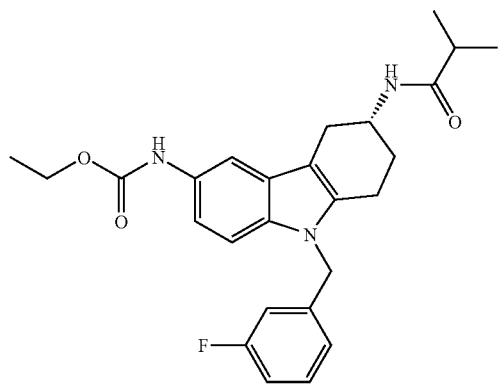

Combine (R)-N-(9-(3-fluorobenzyl)-6-isobutyrylamino-6,7,8,9-tetrahydro-5H-carbazole-3-carboxylic acid (Example 188) (0.281 g, 0.67 mmol) with diphenylphosphorylazide (1.3 ml, 0.67 mmol), and triethylamine (0.73 mL, 0.67 mmol) in benzene (3 mL) and heat at reflux for 18 h. Add absolute ethanol and heat for 4 h longer. Concentrate in vacuo, and partition the resulting residue between EtOAc and water. Separate and dry the EtOAc layer over sodium sulfate. Filter and concentrate in vacuo. Redissolve the resulting residue in a minimal amount of EtOAc and pass through a pad of silica to afford 0.248 g (83%) of the title compound. mp: 169-171° C.; MS (ES): m/z 452 (M+1), HPLC: $R_f$=2.2 min (89%).

Example 190

(R)-[9-(3-Fluorobenzyl)-6-isobutyrylamino-6,7,8,9-tetrahydro-5H-carbazol-3-yl]-carbamic acid methyl ester

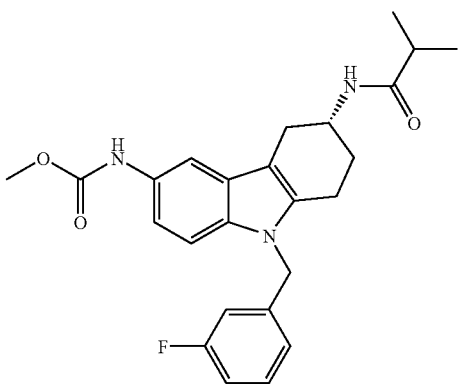

Prepare the title compound from (R)-N-(9-(3-fluorobenzyl)-6-isobutyrylamino-6,7,8,9-tetrahydro-5H-carbazole-3-carboxylic acid (Example 188) (1.00 g, 2.4 mmol) by essentially following procedures as described in Example 189. Purify by silica gel chromatography, eluting with 20-80% EtOAc/hexanes gradient to give 0.35 g (34%) of product. mp: 111-115° C.; MS (ES): m/z 438 (M+1).

Example 191

(R)-N-[6-Acetyl-9-(3-fluoro-benzyl)-2,3,4,9-tetrahydro-1H-carbazol-3-yl]-isobutyramide

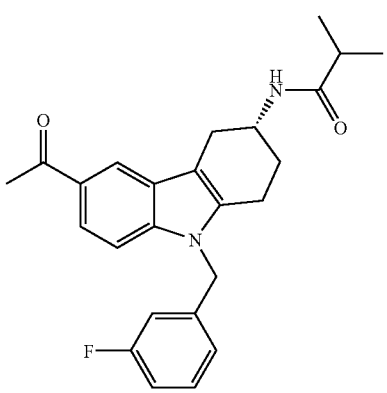

Treat (R)-N-[6-cyano-9-(3-fluorobenzyl)-2,3,4,9-tetrahydro-1H-carbazol-3-yl]isobutyramide (Example 123) (2.07 g, 5.32 mmol) with methyl magnesium bromide (9 mL) in refluxing tetrahydrofuran for 18 h. Quench with MeOH, filter to remove the solids, and concentrate in vacuo. Treat the residue with 1N HCl/THF and reflux for 2 h. Add ethyl acetate, filter to remove insoluable precipitate, and concentrate the filtrate in vacuo to give 2.7 g (74%) of a yellow solid. MS (ES): m/z 407 (M+1); HPLC: $R_t$=2.3 min (97%).

Example 192

(R)-N-[9-(3-Fluoro-benzyl)-6-isoxazol-5-yl-2,3,4,9-tetrahydro-1H-carbazol-3-yl]-isobutyramide

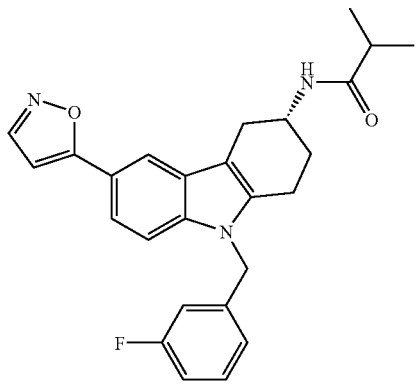

Combine (R)-N-[6-Acetyl-9-(3-fluoro-benzyl)-2,3,4,9-tetrahydro-1H-carbazol-3-yl]-isobutyramide (Example 191) (0.055 g, 0.14 mmol) and dimethylformamide dimethylacetal (0.81 g, 6.8 mmol) and heat at 100° C. for 82 h. Concentrate in vacuo and treat the resulting residue with hydroxylamine hydrochloride (0.012 g, 0.18 mmol) in dioxane at 23° C. for 1 h before warming to 40° C. briefly. Dilute with water and collect 0.029 g of a solid by filtration. Recrystallize from EtOAc/hexanes to yield a light yellow solid. mp: 238-241° C.; MS (ES): m/z 432 (M+1); HPLC: $R_t$=2.59 (85%).

Preparation 67

Cyclopropanecarboxylic acid(4-hydroxycyclohexyl)amide

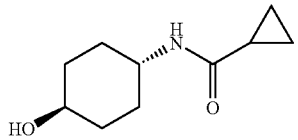

Add cyclopropylcarbonyl chloride (200 g, 1.74 mol) dropwise to trans-4-aminocyclopropylhexanol (272 g, 2.60 mol) and potassium carbonate (360 g, 2.60 mol) in methanol (6.9 liters) in a twelve liter mechanically stirred flask. Stir at room temperature under nitrogen for 18 h. Concentrate in vacuo, re-suspend the residue in MeOH (1 liter) and methylene chloride (3 liters) and filter. Concentrate the filtrate in vacuo, re-suspend in iso-propanol, filter and evaporate again to give 311 g (66%) of an off-white solid. mp: 220-222° C.; MS (ES): m/z 184 (M+1).

Preparation 68

Cyclopropanecarboxylic acid(4-oxocyclohexyl)amide

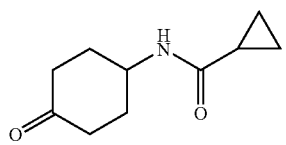

Prepare the title compound from cyclopropanecarboxylic acid(4-hydroxycyclo-hexyl)amide (379 g, 2.07 mmol) by essentially following procedures as described in Preparation 2 to obtain 141 g (38%) of white crystals. mp: 155-157° C.; MS (ES): m/z 182 (M+1).

Preparation 69

Cyclopropanecarboxylic acid(6-cyano-2,3,4,9-tetrahydro-1H-carbazol-3-yl)-amide

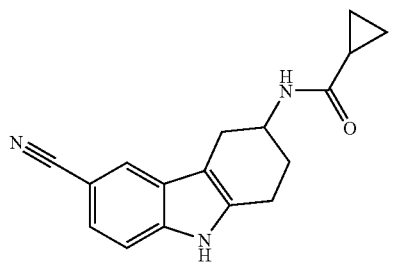

Prepare the title compound from cyclopropanecarboxylic acid(4-oxocyclohexyl)amide (51.3 g, 283 mmol) and 4-cyanophenylhydrazine hydrochloride (48.0 g, 283 mmol) by essentially following procedures as described in Preparation 3 to obtain 57.0 g (72%) of a pale yellow solid. mp: 231-233° C.; MS (ES): m/z 280 (M+1).

Example 193

Cyclopropanecarboxylic acid[6-cyano-9-(3-fluorobenzyl)-2,3,4,9-tetrahydro-1H-carbazol-3-yl]amide

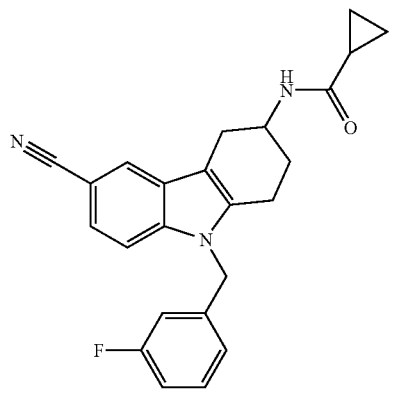

Prepare the title compound from cyclopropanecarboxylic acid(6-cyano-2,3,4,9-tetrahydro-1H-carbazol-3-yl)amide (3.00 g, 10.7 mmol) and 3-fluorobenzyl bromide (2.2 g, 11.8 mmol) by essentially following procedures as described in Example 1 to obtain 1.4 g (34%) of a beige solid. mp: 207-209° C.; MS (ES): m/z 388 (M+1); HPLC: $R_t$=2.28 min (100%).

Example 194

(R)-Cyclopropanecarboxylic acid[6-cyano-9-(3-fluorobenzyl)-2,3,4,9-tetrahydro-1H-carbazol-3-yl]amide

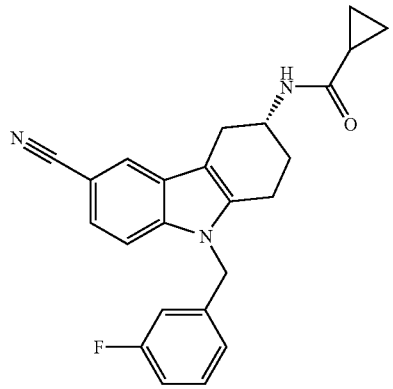

Cyclopropanecarboxylic acid[6-cyano-9-(3-fluorobenzyl)-2,3,4,9-tetrahydro-1H-carbazol-3-yl]amide is resolved into its enantiomers via chiral chromatography as described for Example 123, using iPrOH/MeOH/heptanes as eluent.

First to elute is Isomer 1 (R), as the title compound with e.e. >99.8% mp: 208-210° C.; MS (ES): m/z 389 (M+1).

Example 195

Cyclopropanecarboxylic acid[6-cyano-9-(6-fluoropyridin-2-ylmethyl)-2,3,4,9-tetrahydro-1H-carbazol-3-yl]-amide

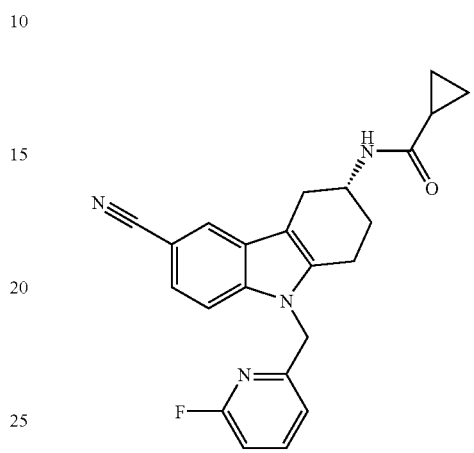

Prepare the title compound from cyclopropanecarboxylic acid(6-cyano-2,3,4,9-tetrahydro-1H-carbazol-3-yl)amide (Preparation 69) (10.0 g, 35.8 mmol) and 2-bromomethyl-6-fluoro-pyridine (Preparation 44) (7.49 g, 39.4 mmol) by essentially following procedures as described in Preparation 45 to obtain 4.30 g (31%) of a salmon colored solid. Resolve the enantiomers using chiral chromatography essentially as described for Example 194, but using 0.2% DMEA/EtOH eluent. (R)-Isomer is first to elute. Slurry the solid in EtOAc and filter to give the title compound. m.p.=243-245° C.; MS (ES): m/z 389 (M+1).

Example 196

Cyclopropanecarboxylic acid[6-cyano-9-(pyridin-2-ylmethyl)-2,3,4,9-tetrahydro-1H-carbazol-3-yl]-amide

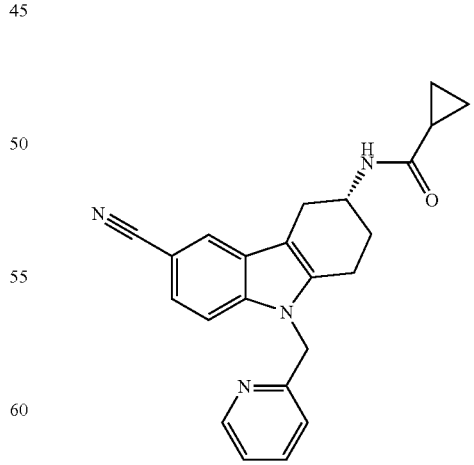

Prepare the title compound from cyclopropanecarboxylic acid(6-cyano-2,3,4,9-tetrahydro-1H-carbazol-3-yl)amide (Preparation 69) (19.0 g, 68.0 mmol), 2-bromomethyl-6-pyridine hydrobromide (22.4 g, 88.4 mmol), and cesium carbonate (57.5 g, 177 mmol) by essentially following procedures as described in Preparation 45. Resolve a portion of the racemic product by essentially following procedures as described in Example 195, but using 100% EtOH as eluent to obtain the R-isomer as 8.56 g of yellow solid. e.e=100%; mp: 239-241° C.; MS (ES): m/z 371 (M+1).

Example 197

N-[9-(3-Fluoro-benzyl)-6-formyl-2,3,4,9-tetrahydro-1H-carbazol-3-yl]-isobutyramide

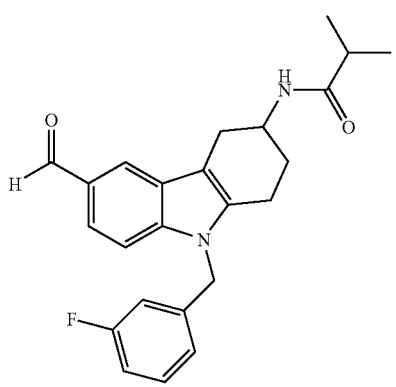

Mix N-(6-cyano-9-(3-fluorobenzyl)-2,3,4,9-tetrahydro-1H-carbazol-3-yl)isobutyramide (Preparation 3) (8.1 g, 20.8 mmol), Al—Ni catalyst (15.0 g, 231 mmol) in 90% formic acid (125 mL). Heat at reflux for 3 h, then dilute with MeOH and filter hot. Concentrate and partition the residue between aqueous NaHCO3/EtOAc. Dry the organic layer (MgSO$_4$) and concentrate to give 5.9 g yellow semi-solid. Purify using silica gel chromatagraphy, eluting with 30-75% EtOAc in hexane to give 3.3 g (40%) as a white solid. MS (ES): m/z 393 (M+1), 391 (M−1); HPLC (Method B): R$_t$=4.41 (100%).

Example 198

N-[6-Difluoromethyl-9-(3-fluoro-benzyl)-2,3,4,9-tetrahydro-1H-carbazol-3-yl]-isobutyramide

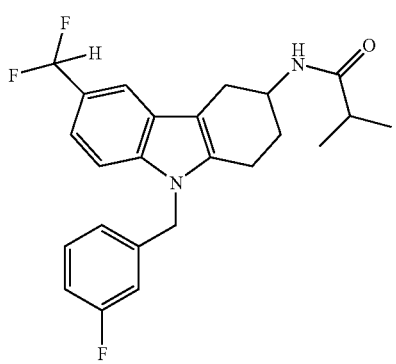

Following procedures as described by Lal, G. S., et. al. (J. Org. Chem. (1999) 64, 7048) combine N-[9-(3-fluoro-benzyl)-6-formyl-2,3,4,9-tetrahydro-1H-carbazol-3-yl]-isobutyramide (1.29 mmol, 506 mg) and bis(2-methoxyethyl)amine sulfur trifluoride (21.9 mmol, 485 mg) in dichloromethane (8 mL). Reflux the stirred reaction mixture under nitrogen for 7 h. Quench the reaction with saturated aqueous sodium bicarbonate and dilute the mixture with ethyl acetate. Separate the layers and wash the organic layer with water, dilute aqueous hydrochloric acid, and water (3×). Dry the organics with sodium sulfate and strip to dryness. Purify the product via flash chromatography (5% ethyl acetate/dichloromethane −25 min., step gradient to 10% ethyl acetate) to yield 175 mg (33%). LCMS 100% (m/e) 415 (M+1, APES-pos); $^1$H NMR (DMSO, 400 MHz); δ 7.64 (s, 1H), 7.31-7.20 (m, 4H), 6.93 (td, 1H, J=11.9, 4.2 Hz), 6.76-6.72 (m, 1H), 6.64-6.59 (m, 1H), 5.50 (d, 1H, J=7.9 Hz), 5.26 (s, 2H), 4.46-4.36 (m, 1H), 3.16 (dd, 1H, J=15.4, 5.3 Hz), 2.81-2.71 (m, 1H), 2.70-2.61 (m, 2H), 2.36-2.25 (m, 1H), 2.15-1.97 (m, 2H), 0.00 (s, 2H), 1.62 (s, 2H), 1.14 (d, 3H, J=5.3 Hz), 1.13 (d, 3H, J=4.8 Hz).

Example 199

N-[9-(3-Fluoro-benzyl)-6-(methoxyimino-methyl)-2,3,4,9-tetrahydro-1H-carbazol-3-yl]-isobutyramide

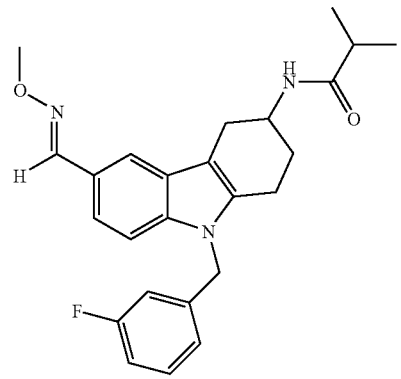

Add N-[9-(3-fluoro-benzyl)-6-formyl-2,3,4,9-tetrahydro-1H-carbazol-3-yl]-isobutyramide (Example 197) (crude, 506 mg, 1.29 mmol) to a suspension of methoxyamine hydrochloride salt (140 mg, 1.48 mmol) and pyridine (10 mL). Stir the reaction at ambient temperature for 12 h. Remove the pyridine under vacuum and dissolve the resultant residue in ethyl acetate (100 mL). Wash with saturated aqueous copper sulfate (2×50 mL) and water (2×50 mL). Separate the organic layer and dry over magnesium sulfate, filter, and concentrate under vacuum to give a greasy yellow solid. The solid was purified with column chromatography (silica gel; 10% to 50% ethyl acetate in hexanes) to give 183 mg (34%) of the title compound as a white solid. mp: 180-182° C.; ESI MS m/z 422 [C$_{25}$H$_{28}$FN$_3$O$_2$+H]$^+$; $^1$H NMR (300 MHz, CDCl$_3$) δ 8.28 (s, 1H), 7.79 (s, 1H), 7.45 (d, J=7.9 Hz, 1H), 7.26-7.17 (m, 2H), 6.93 (t, J=7.1 Hz, 1H), 6.75 (d, J=7.6 Hz, 1H), 6.62 (d, J=9.1 Hz, 1H), 5.49 (br d, J=7.0 Hz, 1H), 5.24 (s, 2H), 4.40 (br s, 1H), 3.97 (s, 3H), 3.15 (dd, J=15.8, 4.7 Hz, 1H), 2.71-2.61 (m, 3H), 2.28 (septet, J=6.8 Hz, 1H), 2.07-2.00 (m, 2H), 1.14 (d, J=6.7 Hz, 3H), 1.12 (d, J=6.7 Hz, 3H).

Example 200

(R)-N-[9-(3-Fluorobenzyl)-6-formyl-2,3,4,9-tetrahydro-1H-carbazol-3-yl]-isobutyramide

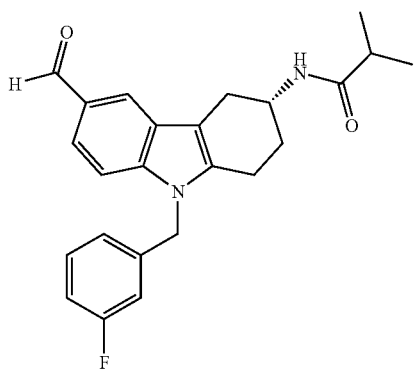

Add Al—Ni catalyst [12635-27-7] (3.0 g) to a solution of (R)-N-(6cyano9-(3-fluorobenzyl)-2,3,4,9-tetrahydro-1H-carbazol-3-yl)isobutyramide (Example 123) (2.50 g, 6.42 mmol) in formic acid (96%, 40 mL) and water (5 mL). Heat the reaction mixture to 90° C. for 18 h, then add 2 g fresh Al—Ni catalyst. Heat to reflux for 18 h, cool to 60° C., dilute with MeOH (30 mL), and resume heating. When reflux has begun, filter the reaction mixture while hot through filter paper. Concentrate the filtrate in-vacuo. Dilute the residue with water (30 mL) and saturated aqueous NaHCO$_3$ (30 mL), then extract into EtOAc (3×150 mL). Dry the organics (MgSO$_4$), filter, and concentrate to give 2.25g (89%) of the title compound as a brown solid. MS (ES): m/z 393 (M+1); HPLC (Method B): R$_t$=4.57 min (91%).

Example 201

(R)-N-[9-(3-Fluorobenzyl)-6-(methoxyimino-methyl)-2,3,4,9-tetrahydro-1H-carbazol-3-yl]-isobutyramide

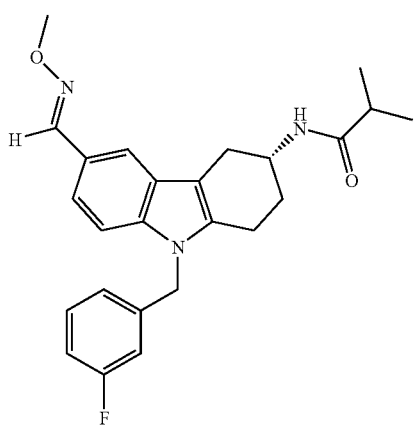

Add methoxyamine hydrochloride (613 mg, 7.34 mmol) to a solution of (R)-N-[9-(3-fluorobenzyl)-6-formyl-2,3,4,9-tetrahydro-1H-carbazol-3-yl]-isobutyramide (Example 200) (2.40 g, 6.11 mmol) in pyridine (40 mL). Stir the reaction mixture at room temperature for 18 h. Concentrate the reaction in-vacuo and dilute with EtOAc (175 mL). Wash the organics with water (3×75 mL), dry (MgSO$_4$), filter, and concentrate to give the crude product (2.22 g) as a brown foam. Purify the crude product on 40 g silica gel (15-80% EtOAc/hexanes) to give 261 mg (10%) of the title compound as a yellow flaky solid. Re-purify the impure fractions on 40 g silica gel (50-80% (1% (2M NH$_3$/MeOH)/CH$_2$Cl$_2$)/hexanes) and combine the purified materials to give 673 mg (26%) of the title compound as a yellow flaky solid. MS (ES): m/z 422 (M+1), 420 (M−1); HPLC (Method B): R$_t$=7.98 min (99%).

Preparation 70

Cyclopropanecarboxylic acid[9-(3-fluorobenzyl)-6-formyl-2,3,4,9-tetrahydro-1H-carbazol-3-yl]-amide

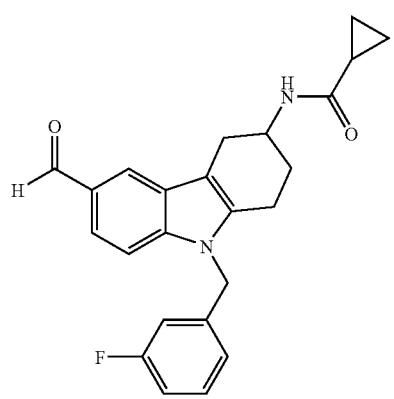

Prepare the title compound by essentially following procedures as described in Example 200, by using cyclopropanecarboxylic acid[6-cyano-9-(3-fluorobenzyl)-2,3,4,9-tetrahydro-1H-carbazol-3-yl]amide (Example 193) (0.500 g, 1.29 mmol) and aluminum-nickel catalyst (1.3 g) in 90% formic acid (10 ml) to obtain 0.32 g (64%) of a light brown solid. MS (ES): m/z 391 (M+1); $^1$H NMR (DMSO-d$_6$): δ 9.90 (s, 1H), 8.19 (d, 1H), 8.04 (s, 1H), 7.61 (d, 1H), 7.57 (d, 1H), 7.37 (dd, 1H), 7.15 (m, 1H), 6.81-6.92 (m, 2H), 5.44 (s, 2H), 4.08 (m, 1H), 3.03 (dd, 1H), 2.57-2.82 (m, 4H), 2.00 (m, 1H), 1.59 (m, 1H), 1.82 (m, 1H), 0.65 (m, 4H).

Example 202

Cyclopropanecarboxylic acid[9-(3-fluorobenzyl)-6-(methoxyimino-methyl)-2,3,4,9-tetrahydro-1H-carbazol-3-yl]-amide

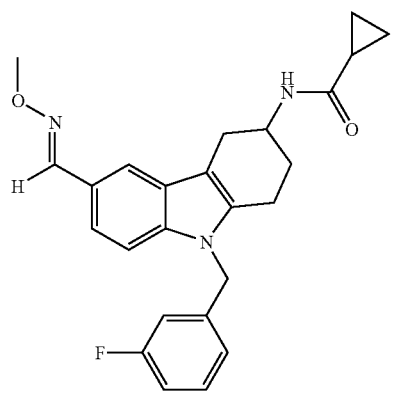

Combine cyclopropanecarboxylic acid[9-(3-fluoro-benzyl)-6-formyl-2,3,4,9-tetrahydro-1H-carbazol-3-yl]-amide (Preparation 70) (0.32 g, 0.82 mmol), methoxylamine (0.21 g, 2.4 mmol), and sodium hydroxide (0.049 g, 1.3 mmol) in EtOH (15 mL). Add enough water to dissolve the sodium hydroxide and stir for 18 h. Dilute with water and extract with EtOAc. Dry EtOAc extracts over Na2SO4 and filter twice through a pad of silica to give 0.21 g (61%) of an off-white solid. MS (ES): m/z 420 (M+1).

Preparation 71

(R)-Cyclopropanecarboxylic acid[9-(3-fluorobenzyl)-6-formyl-2,3,4,9-tetrahydro-1H-carbazol-3-yl]-amide

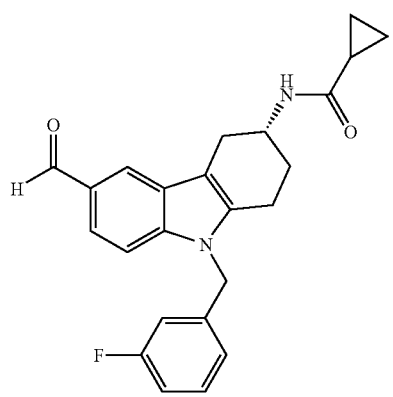

Combine (R)-cyclopropanecarboxylic acid[6-cyano-9-(3-fluorobenzyl)-2,3,4,9-tetrahydro-1H-carbazol-3-yl]amide (Example 194) (3.70 g, 9.55 mmol) and nickel-aluminum catalyst (10.0 g) in 90% formic acid and heat at 90-100° C. for 18 h. Dilute with methanol, filter to remove catalyst, and concentrate the filtrate in vacuo. Neutralize the filtrate by addition of solid NaHCO3 after taking up in ethyl acetate/water. Dry the ethyl acetate portion over Na2SO4, filter, and evaporate to give 3.53 g (95%) of the title compound as a foam. MS (ES): n/z 391 (M+1); $^1$H NMR(DMSO-d$_6$): δ 9.90 (s, 1H), 8.19 (d, 1H), 8.04 (s, 1H), 7.61 (d, 1H), 7.57 (d, 1H), 7.37 (dd, 1H), 7.15 (m, 1H), 6.81-6.92 (m, 2H), 5.44 (s, 2H), 4.08 (m, 1H), 3.03 (dd, 1H), 2.57-2.82 (m, 4H), 2.00 (m, 1H), 1.82 (m, 1H), 1.59 (m, 1H), 0.65 (m, 4H).

Example 203

(R)-Cyclopropanecarboxylic acid[9-(3-fluoro-benzyl)-6-(hydroxyimino-methyl)-2,3,4,9-tetrahydro-1H-carbazol-3-yl]-amide

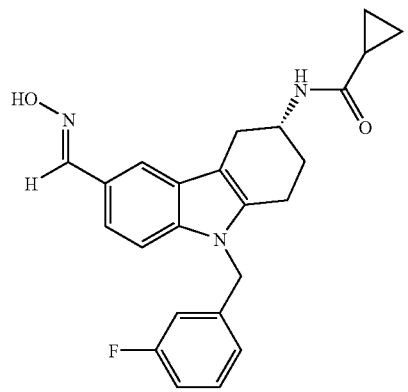

Combine (R)-cyclopropanecarboxylic acid[9-(3-fluorobenzyl)-6-formyl-2,3,4,9-tetrahydro-1H-carbazol-3-yl]-amide (Preparation 71) (1.50 g, 3.82 mmol), hydroxylamine hydrochloride (0.801 g, 11.5 mmol), and sodium hydroxide (0.23 g, 5.76 mmol) and stir under nitrogen for 1.5 h. Dilute with water and extract with EtOAc. Pass the dark residue through a pad of silica eluting with 50% EtOAc/hexanes to give 1.27 g (82%) of the title compound. MS (ES): m/z 406 (M+1).

Example 204

(R)-Cyclopropanecarboxylic acid[9-(3-fluoro-benzyl)-6-(5-methyl-isoxazol-3-yl)-2,3,4,9-tetrahydro-1H-carbazol-3-yl]-amide

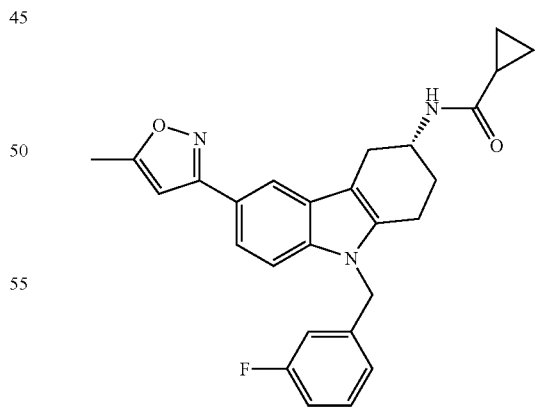

Bubble propyne gas through a solution of (R)-cyclopropanecarboxylic acid[9-(3-fluoro-benzyl)-6-(hydroxyimino-methyl)-2,3,4,9-tetrahydro-1H-carbazol-3-yl]-amide (Example 203) (0.065 g, 0.16 mmol) in methylene chloride and NaOCl solution maintained in a sealed tube. Cap the tube and stir at 23° C. for 16 h. Partition the reaction between methylene chloride and water. Separate and dry the organic portion over Na₂SO₄ to give 0.045 g of a tan solid. Purify by silca gel chromatography, eluting with 20-80% EtOAc/gradient to give an 0.030g (42%) of an off-white solid. mp: 190-192° C.; MS (ES): m/z 444 (M+1).

Example 205

(R)-Cyclopropanecarboxylic acid[9-(3-fluoro-benzyl)-6-(1-methoxyimino-methyl)-2,3,4,9-tetrahydro-1H-carbazol-3-yl]-amide

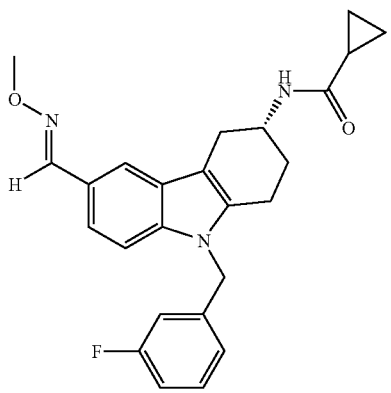

Prepare the title compound from (R)-cyclopropanecarboxylic acid[9-(3-fluorobenzyl)-6-formyl-2,3,4,9-tetrahydro-1H-carbazol-3-yl]-amide (Preparation 71) (3.10 g, 7.94 mmol), methoxylamine hydrochloride (1.99 g, 23.8 mmol), and sodium hydroxide (0.48 g, 11.9 mmol) by essentially following procedures as described in Example 204. Purify using silica gel chromatography eluting with 10% EtOAc/CH₂Cl₂ to provide 1.94 g (58%) of product. mp: 200-203° C.; MS (ES) m/z 420 (M+1).

Example 206

Cyclopropanecarboxylic acid[9-(3-fluorobenzyl)-6-formyl-2,3,4,9-tetrahydro-1H-carbazol-3-yl]-amide

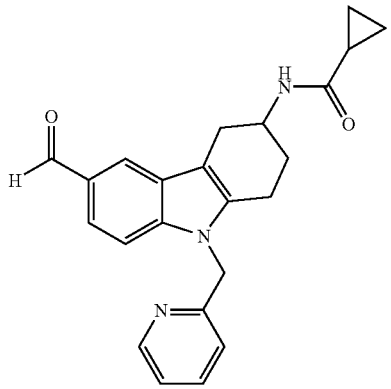

Prepare the title compound from cyclopropanecarboxylic acid[6-cyano-9-(pyridin-2-ylmethyl)-2,3,4,9-tetrahydro-1H-carbazol-3-yl]-amide (Example 196) (1.00 g, 2.70 mmol) and Al-Ni catalyst (3.0 g) by essentially following procedures as described in Example 200 to obtain 0.78 g (77%) of a tan solid. MS (ES): m/z 374 (M+1).

Example 207

Cyclopropanecarboxylic acid[6-(1-methoxyimino-methyl)-9-pyridin-2-ylmethyl-2,3,4,9-tetrahydro-1H-carbazol-3-yl]-amide

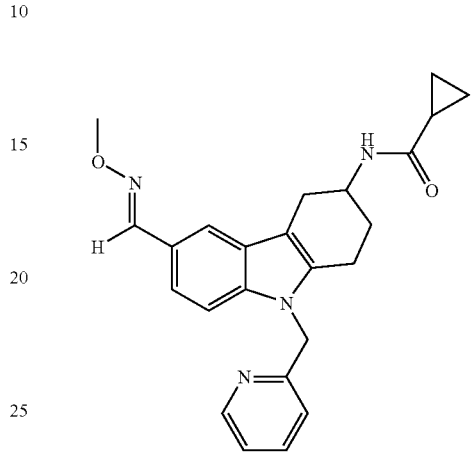

Prepare the title compound from cyclopropanecarboxylic acid[9-(3-fluorobenzyl)-6-formyl-2,3,4,9-tetrahydro-1H-carbazol-3-yl]-amide (Example 206) (0.62 g, 1.66 mmol), methoxylamine hydrochloride (0.416 g, 4.98 mmol), and sodium hydroxide (0.100 g, 2.5 mmol) by essentially following procedures as described in Example 204 to give 0.54 g (81%) of a tan solid. mp: 88-92° C.; MS (ES): m/z 403 (M+1).

Example 208

(R)-Cyclopropanecarboxylic acid[6-(1-methoxy-imino-methyl)-9-pyridin-2-ylmethyl-2,3,4,9-tetrahydro-1H-carbazol-3-yl]-amide

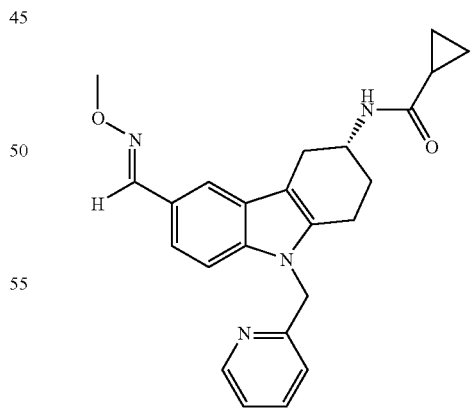

Resolve cyclopropanecarboxylic acid[6-(1-methoxy-imino-ethyl)-9-pyridin-2-ylmethyl-2,3,4,9-tetrahydro-1H-carbazol-3-yl]-amide using chiral chromatography on a Chiralcel OD-H column similarly as described for Example 194, but using 0.2% DMEA/MeOH as eluent. (R)-Isomer is first to elute. Concentrate the eluent and slurry the residue in EtOAc. Collect by filtration to give the title compound. mp: 215-217° C.; MS (ES): m/z 403 (M+1).

Preparation 72

Cyclopropanecarboxylic acid(6-formyl-2,3,4,9-tetrahydro-1H-carbazol-3-yl)-amide

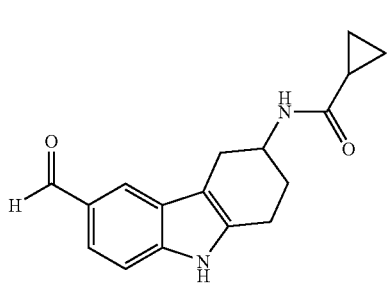

Prepare the title compound from cyclopropanecarboxylic acid(6-cyano-2,3,4,9-tetrahydro-1H-carbazol-3-yl)-amide (10.2 g, 36.5 mmol) and Al—Ni catalyst (20.0 g) by essentially following procedures as described by in Example 205 to obtain 6.80 g (66%) of a yellow-orange solid. MS (ES): m/z 283 (M+1).

Preparation 73

Cyclopropanecarboxylic acid[6-(methoxyimino-methyl)-2,3,4,9-tetrahydro-1H-carbazol-3-yl]-amide

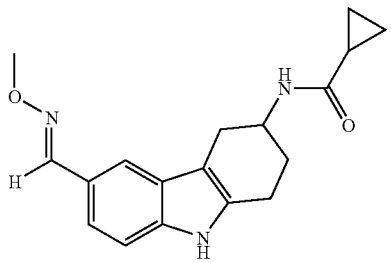

Prepare the title compound from cyclopropanecarboxylic acid(6-formyl-2,3,4,9-tetrahydro-1H-carbazol-3-yl)-amide (Preparation 72) (6.50 g, 57.3 mmol) methoxylamine hydrochloride (4.81 g, 57.6 mmol) and sodium hydroxide (1.84 g, 46.0 mmol), by essentially following procedures as described in Example 202 to obtain 6.00 g (84%) of product. MS (ES): m/z 312 (M+1).

Example 209

Cyclopropanecarboxylic acid [(R)-9-(6-fluoro-pyridin-2ylethyl)-6(methoxyimino-methyl)-2,3,4,9-tetrahydro-1H-carbazol-3-yl]-amide

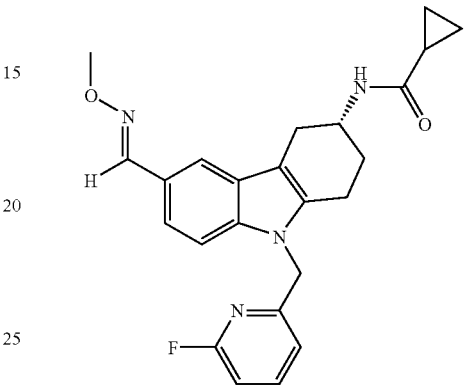

Prepare the title compound from cyclopropanecarboxylic acid[6-(methoxyimino-methyl)-2,3,4,9-tetrahydro-1H-carbazol-3-yl]-amide (Preparation 73) (6.00 g, 19.3 mmol) and 2-bromomethyl-6-fluoro-pyridine (Preparation 44) (4.03 g, 21.2 mmol) by essentially following procedures in Example 1 to obtain 9.2 g of an orange-brown foam. Purify the material by silica gel chromatography, eluting with 20-80% EtOAc/hexanes to give 2.65 g of a yellow solid. Resolve the enantiomers by chiral chromatography on a Chiralcel OD-H column similarly as described for Example 194, but using 0.2% DMEA/MeOH as eluent. (R)-Isomer is first to elute. Concentrate the eluent and slurry the residue in EtOAc. Collect by filtration to give the title compound. mp: 223-225° C.; MS (ES): m/z 421 (M+1).

Preparation 74

N-[6-(2,2,2-Trifluoro-acetyl)-2,3,4,9-tetrahydro-1H-carbazol-3-yl]-isobutyramide

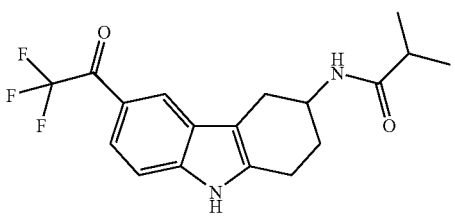

Mix 4-trifluoroacetylphenylhydrazine (prepare essentially as described by Tschirret-Guth, R. A., et. al., *J. Am. Chem. Soc.* (1999) 121, 4731) (2.6 g, 12.7 mmol) and N-(4oxocyclohexyl)isobutyramide (2.2 g, 12 mmol) in EtOH (100 mL) containing concentrated HCl (20 mL). Reflux the reaction for 18 h, cool to ambient temperature and remove the EtOH under vacuum. Extract the product into EtOAc, dry (MgSO₄), filter and concentrate to give 2.0 g yellow semi-solid. Purify by silica gel chromotagraphy (ISCO (120 g) using 50% to 100% EtOAc in hexane over 60 min). Obtain 590 mg (14%) N-[6-(2,2,2-trifluoro-acetyl)-2,3,4,9-tetrahydro-1H-carbazol-3-yl]-isobutyramide as a yellow solid. MS (ES) m/z 353 (M+1), 351 (M−1); HPLC (Method B): R$_t$=3.69 min (98%).

Example 210

N-[9-(3-Fluoro-benzyl)-6-(2,2,2-trifluoro-acetyl)-2,3,4,9-tetrahydro-1H-carbazol-3-yl]-isobutyramide

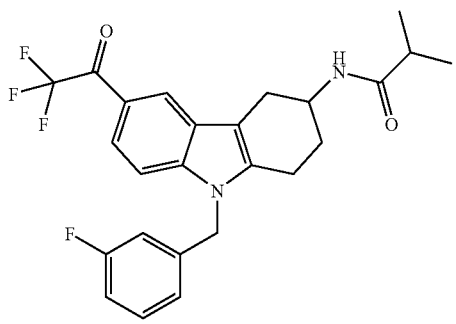

Mix N-[6-(2,2,2-trifluoro-acetyl)-2,3,4,9-tetrahydro-1H-carbazol-3-yl]-isobutyramide (Preparation 74) (428 mg, 0.93 mmol), m-fluorobenzyl bromide (216 mg, 1.11 mmol), Cs$_2$CO$_3$ (650 mg, 2 mmol) and DMF (10 mL). Warm the reaction at 50° C. for 18 h, cool and partition between water/brine/EtOAc. Separate and dry the organic layer (MgSO$_4$), filter and concentrate to give 590 mg of crude product. Purify by silica gel chromatography, using 10% to 60% EtOAc/hexane to obtain 68 mg (16%) of the title compound as a pale yellow solid. MS (ES) m/z 461 (M+1); HPLC: R$_t$=3.43 min (95%).

Example 211

(R)-N-[6-Formyl-9-(2-methyl-thiazol-4-ylmethyl)-2,3,4,9-tetrahydro-1H-carbazol-3-yl]-isobutyramide

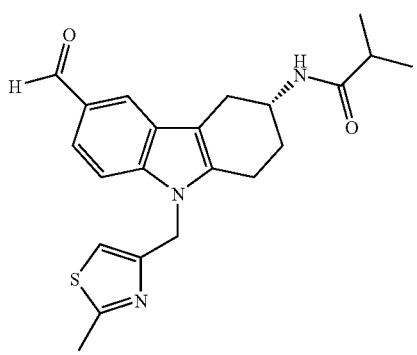

Follow the procedures essentially as described in Example 200, using (R)-N-[6-cyano-9-(2-methyl-thiazol-4-ylmethyl)-2,3,4,9-tetrahydro-1H-carbazol-3-yl]-isobutyramide (Example 151) (134 mg, 0.34 mmol). Purify the crude product on 12 g silica gel {30-70% [4% (2 M NH$_4$/MeOH)/CH$_2$Cl$_2$]/hexanes} to afford 58 mg (43%) of the title compound as a white solid. MS (ES): m/z 396 (M+1), 394 (M−1); $^1$H-NMR (CDCl$_3$): δ 10.01 (s, 1H), 8.01 (d, 1H, J=1.3 Hz), 7.72 (dd, 1H, J=8.4, 1.8 Hz), 7.35 (d, 1H, J=8.4 Hz), 6.47 (s, 1H), 5.57 (d, 1H, J=7.9 Hz), 5.37 (d, 2H, J=2.6 Hz), 4.43 (m, 1H), 3.18 (dd, 1H, J=15.9, 5.3 Hz), 2.86 (t, 2H, J=6.4 Hz), 2.73 (s, 3H), 2.66 (m, 1H), 2.34 (m, 1H), 2.15 (m, 1H), 2.03 (m, 1H), 1.16 (d, 6H, J=7.0 Hz).

Example 212

(R)-N-[6-(Methoxyimino-methyl)-9-(2-methyl-thiazol-4-ylmethyl)-2,3,4,9-tetrahydro-1H-carbazol-3-yl]-isobutyramide

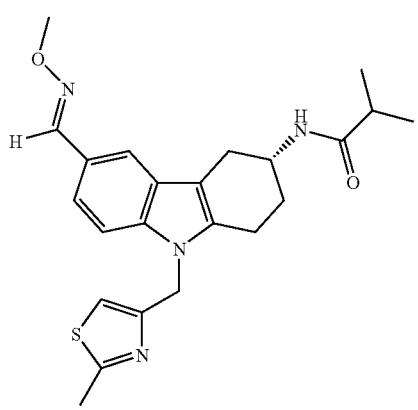

Dissolve (R)-N-[6-formyl-9-(2-methyl-thiazol-4-ylmethyl)-2,3,4,9-tetrahydro-1H-carbazol-3-yl]-isobutyramide (Example 211) (53 mg, 0.13 mmol) and methoxyamine HCl (22 mg, 0.27 mmol) in pyridine (1 mL). Stir the reaction mixture for 18 h at 25° C. Dilute the reaction mixture with water (2 mL), 1N HCl (1 mL), and EtOAc (10 mL). Load the mixture onto a Varian ChemElut CE1005 solid-phase extraction cartridge (Varian part number 12198006), then elute, collect, and concentrate 50 mL EtOAc to give the crude product (59 mg) as a white solid. Purify on 8 g silica gel (50-60% EtOAc/hexanes) to afford 34 mg (62%) of the title compound as a white solid. MS (ES): m/z 425 (M+1), 469 (M+HCO$_2$$^-$); $^1$H NMR (CDCl$_3$): δ 8.16 (s, 1H), 7.63 (d, 1H, J=1.3 Hz), 7.44 (dd, 1H, J=8.6, 1.5 Hz), 7.24 (d, 1H, J=8.5 Hz), 6.36 (s, 1H), 5.55 (d, 1H, J=7.9 Hz), 5.29 (td, 2H, J=24.7, 9.0 Hz), 4.41 (m, 1H), 3.96 (s, 3H), 3.13 (dd, 1H, J=15.4, 4.8 Hz), 2.80 (m, 2H), 2.68 (s, 3H), 2.62 (dd, 1H, J=15.6, 6.8 Hz), 2.30 (m, 1H), 2.14-1.97 (m, 2H), 1.14 (d, 6H, J=6.6 Hz).

Preparation 75

[6-Cyano-9-(3-fluoro-benzyl)-2,3,4,9-tetrahydro-1H-carbazol-3-yl]-carbamic acid benzyl ester

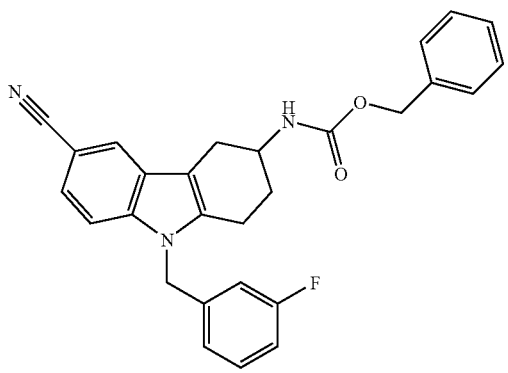

Prepare the title compound by essentially following procedures as described in Example 184 using (6-cyano-2,3,4,9-tetrahydro-1H-carbazol-3-yl)-carbamic acid benzyl ester (Preparation 61) and 3-fluorobenzyl bromide to obtain 1.34 g (51%) of product. LCMS 100% (mle) 454 (M+1, APCI-pos).

Preparation 76

6-Amino-9-(3-fluoro-benzyl)-6,7,8,9-tetrahydro-5H-carbazole-3-carbonitrile

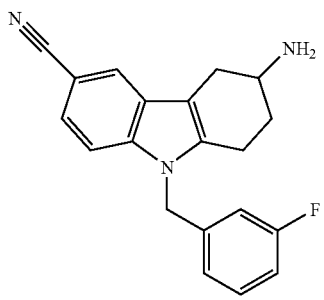

Prepare the title compound by essentially following procedures as described in Preparation 63 using [6-cyano-9-(3-fluoro-benzyl)-2,3,4,9-tetrahydro-1H-carbazol-3-yl]-carbamic acid benzyl ester to obtain crude product. Purify the product via flash chromatography (10 to 25% methanol/dichloromethane) to obtain a thick oil containing ~25% of a co-eluting impurity. Crystallize the product from dichloromethane/hexanes to obtain a small amount (40 mg, 35%) for analysis. LCMS 75% (m/z) 320 (M+1, APCI-pos)

Example 213

N-[6-Cyano-9-(3-fluoro-benzyl)-2,3,4,9-tetrahydro-1H-carbazol-3-yl]-N',N'-dimethylmethanesulfamide

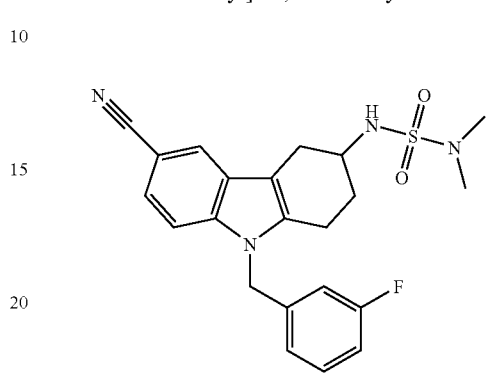

Mix 6-amino-9-(3-fluoro-benzyl)-6,7,8,9-tetrahydro-5H-carbazole-3-carbonitrile (Preparation 76) (900 mg, 2.8 mmol), triethylamine (600 µL, 4.2 mmol) in methylene chloride (15 mL). Add dimethylsulfamoyl chloride (391 µL, 3.64 mmol) and stir overnight at ambient temperature. Shake the reaction with water/methylene chloride and dry the organic layer ($Na_2SO_4$). Concentrate to give 1.44 g tan oil. Purify by silica gel chromatography, using 10% to 60% EtOAc in hexane to give 630 mg (53%) of the title compound as a white solid. MS (ES): m/z 427 (M+1), 425 (M−1); HPLC (Method B): $R_t$=6.14 min (100%).

Preparation 77

Cyclopropanecarboxylic acid(2,2-difluoro-6,7,8,9-tetrahydro-5H-1,3-dioxa-9-aza-cyclopenta[b]fluoren-6-yl)-amide

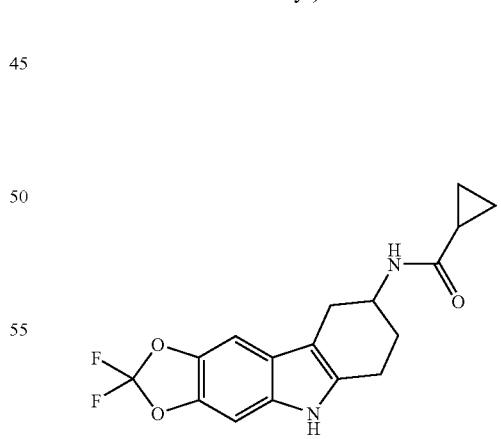

Prepare the title compound by essentially following the procedures as described in Preparation 3, using (2,2-difluoro-benzo[1,3]dioxol-5-yl)-hydrazine hydrochloride salt (Preparation 10) and cyclopropanecarboxylic acid(4-oxocyclohexyl)amide (Preparation 68) to provide 7.12 g (80%) of product.

Example 214

Cyclopropanecarboxylic acid(2,2-difluoro-9-pyridin-2-ylmethyl-6,7,8,9-tetrahydro-5H-1,3-dioxa-9-aza-cyclopenta[b]fluoren-6-yl)-amide

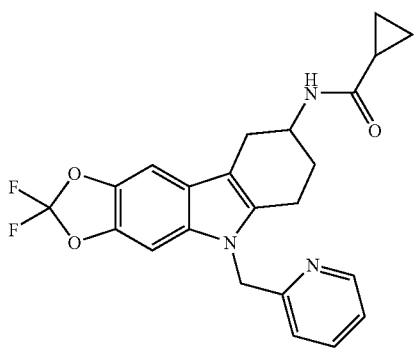

Prepare the title compound by essentially following the procedures as described in Example 1, using cyclopropanecarboxylic acid(2,2-difluoro-6,7,8,9-tetrahydro-5H-1,3-dioxa-9-aza-cyclopenta[b]fluoren-6-yl)-amide and 2-bromomethylpyridine hydrobromide. Purify the crude material by silica gel chromatography eluting with 0-100% EtOAc/dichloromethane. Run a second chromatography eluting with 5-40% EtOAc/dichloromethane to provide 0.42 g (4.7%) of a white solid. MS (ES): m/z 426 (M+1).

Example 215

Cyclopropanecarboxylic acid[2,2-difluoro-9-(6-fluoro-pyridin-2-ylmethyl)-6,7,8,9-tetrahydro-5H-1,3-dioxa-9-aza-cyclopenta[b]fluoren-6-yl]-amide

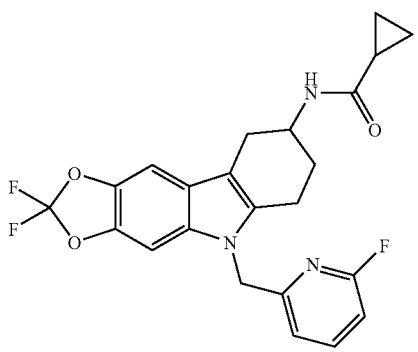

Prepare the title compound by essentially following the procedures as described in Example 1, using cyclopropanecarboxylic acid(2,2-difluoro-6,7,8,9-tetrahydro-5H-1,3-dioxa-9-aza-cyclopenta[b]fluoren-6-yl)-amide and 2-bromomethyl-6-fluoro-pyridine (Preparation 44). Purify the crude material by silica gel chromatography eluting with 5-50% EtOAc/dichloromethane to provide 0.29 g (46%) of a white solid. MS (ES): m/z 444 (M+1).

Biological Data

TABLE I

| Ex | AR binding Ki (nM) | n | C2C12 EC50 (nM) | C2C12 % Efficacy | n |
|---|---|---|---|---|---|
| 1 | 2.6 | 1 | 2.3 | 74.1 | 2 |
| 2 | 17.7 | 2 | 313.1 | 59.4 | 4 |
| 3 | 10.1 | 2 | 194.2 | 66.4 | 4 |
| 4 | 36.6 | 2 | nd | 36.1 | 2 |
| 5 | 24.6 | 1 | nd | 80.3 | 2 |
| 6 | 156.2 | 1 | 1771.5 | 49.7 | 3 |
| 7 | 99.6 | 1 | nd | 35.8 | 2 |
| 8 | 2.5 | 1 | 57.8 | 108.4 | 2 |
| 9 | 7.2 | 1 | 113.1 | 62.3 | 2 |
| 10 | 31.9 | 1 | 192.7 | 40.4 | 2 |
| 11 | 61.5 | 1 | 2176.7 | 36.3 | 2 |
| 12 | 25.0 | 1 | 186.3 | 50.0 | 2 |
| 13 | 33.5 | 1 | 1033.7 | 55.5 | 2 |
| 14 | 81.4 | 1 | 926.7 | 36.4 | 2 |
| 15 | 274.6 | 1 | nd | 15.3 | 2 |
| 16 | 1.9 | 4 | 5.5 | 86.0 | 6 |
| 17 | 8.6 | 1 | 147.9 | 62.1 | 2 |
| 18 | 10.5 | 1 | 152.7 | 82.1 | 2 |
| 19 | 37.8 | 1 | 245.3 | 63.2 | 3 |
| 20 | 9.6 | 1 | 559.9 | 43.2 | 2 |
| 21 | 2.0 | 1 | 20.1 | 81.0 | 2 |
| 22 | 3.5 | 1 | 75.7 | 74.7 | 2 |
| 23 | 4.3 | 1 | 157.4 | 54.4 | 2 |
| 24 | 8.2 | 2 | 304.9 | 48.9 | 2 |
| 25 | 6.0 | 1 | 120.8 | 62.7 | 2 |
| 26 | 16.6 | 1 | 301.4 | 33.0 | 2 |
| 27 | 45.8 | 1 | nd | 23.2 | 2 |
| 28 | 12.8 | 2 | 301.0 | 64.3 | 2 |
| 29 | 2.4 | 1 | 2.7 | 64.0 | 2 |
| 30 | 2.1 | 2 | 3.1 | 87.0 | 2 |
| 31 | 5.3 | 2 | 58.7 | 70.8 | 2 |
| 32 | 10.3 | 2 | 53.3 | 94.3 | 2 |
| 33 | 13.0 | 2 | 433.1 | 87.3 | 2 |
| 34 | 24.9 | 2 | 184.6 | 103.2 | 2 |
| 35 | 2.6 | 1 | 2.3 | 74.1 | 2 |
| 36 | 7.6 | 2 | 20.7 | 99.4 | 2 |
| 37 | 9.1 | 2 | 109.0 | 95.5 | 2 |
| 38 | 9.7 | 2 | 108.0 | 79.5 | 2 |
| 39 | 5.3 | 2 | 28.9 | 76.1 | 2 |
| 40 | 30.9 | 2 | 187.7 | 68.0 | 2 |
| 41 | 43.2 | 2 | 1822.8 | 46.6 | 2 |
| 42 | 63.6 | 1 | 30.4 | 73.0 | 3 |
| 43 | 104.4 | 1 | 461.6 | 69.6 | 2 |
| 44 | 94.2 | 1 | 304.7 | 71.1 | 3 |
| 45 | 121.2 | 1 | 940.8 | 63.6 | 2 |
| 46 | 136.7 | 1 | nd | 40.5 | 2 |
| 47 | 12.1 | 3 | 24.1 | 86.3 | 4 |
| 48 | 9.4 | 1 | 115.5 | 69.5 | 2 |
| 49 | 82.2 | 1 | nd | 71.6 | 2 |
| 50 | 149.7 | 1 | 940.0 | 45.8 | 2* |
| 51 | 1.5 | 2 | 0.6 | 87.5 | 6 |
| 52 | 6.1 | 1 | 5.6 | 73.2 | 2 |
| 53 | 21.6 | 2 | 24.3 | 106.6 | 2 |
| 54 | 5.3 | 2 | 6.2 | 81.1 | 4 |
| 55 | 11.2 | 2 | 2.5 | 82.9 | 2 |
| 56 | 3.8 | 1 | 54.0 | 66.6 | 2 |
| 57 | 25.1 | 1 | 323.4 | 36.5 | 2 |
| 58 | 7.2 | 1 | 258.3 | 62.1 | 2 |
| 59 | 59.0 | 1 | 241.9 | 39.5 | 2 |
| 60 | 35.9 | 1 | 299.1 | 74.2 | 2 |
| 61 | 2.3 | 1 | 3.6 | 83.2 | 4 |
| 62 | 110.2 | 1 | 368.8 | 56.1 | 4 |
| 63 | 39.3 | 2 | 66.9 | 112.8 | 2 |
| 64 | 14.5 | 1 | 9.3 | 89.3 | 4 |
| 65 | 58.4 | 1 | 40.5 | 87.3 | 1 |
| 66 | 6.9 | 1 | 19.2 | 79.8 | 2 |
| 67 | 6.2 | 1 | 18.6 | 96.9 | 1 |
| 68 | 46.2 | 1 | 40.8 | 98.0 | 2 |
| 69 | 34.1 | 1 | 213.0 | 63.3 | 3 |
| 70 | 10.0 | 1 | 39.8 | 63.9 | 3 |
| 71 | 82.5 | 1 | 401.8 | 40.7 | 3 |
| 72 | 152.9 | 1 | 685.5 | 66.4 | 4 |
| 73 | 52.1 | 1 | 226.7 | 54.7 | 3 |
| 74 | 858.8 | 1 | 764.1 | 22.6 | 3 |

TABLE I-continued

| Ex | AR binding Ki (nM) | n | C2C12 EC50 (nM) | C2C12 % Efficacy | n |
|---|---|---|---|---|---|
| 75 | 6.2 | 1 | 18.6 | 96.9 | 1 |
| 76 | 477.7 | 1 | 1709.8 | 58.1 | 2* |
| 77 | 102.7 | 1 | 1195.8 | 74.9 | 2 |
| 78 | 187.2 | 1 | 237.7 | 71.5 | 3 |
| 79 | 28.2 | 1 | 16.4 | 85.7 | 2 |
| 80 | 98.0 | 1 | 108.2 | 59.9 | 2 |
| 81 | 11.3 | 2 | 94.0 | 81.9 | 2 |
| 82 | 6.1 | 2 | 37.1 | 87.3 | 2 |
| 83 | 29.5 | 2 | 85.1 | 93.1 | 2 |
| 84 | 19.7 | 2 | nd | 32.9 | 2 |
| 85 | 4.6 | 1 | 3.8 | 79.8 | 4 |
| 86 | 2.6 | 1 | 36.3 | 93.9 | 4 |
| 87 | 17.7 | 1 | nd | 10.6 | 3 |
| 88 | 4.4 | 1 | 24.3 | 96.1 | 4 |
| 89 | 3.3 | 1 | 1.9 | 78.5 | 2 |
| 90 | 30.5 | 1 | 123.0 | 67.6 | 2 |
| 91 | 11.8 | 1 | 97.1 | 86.9 | 2 |
| 92 | 4.1 | 1 | 3.0 | 73.4 | 2 |
| 93 | 6.8 | 1 | 5.0 | 82.4 | 2 |
| 94 | 38.3 | 2 | 41.0 | 100.6 | 2 |
| 95 | 12.4 | 2 | 18.3 | 79.6 | 4 |
| 96 | 14.7 | 1 | 122.6 | 88.0 | 4 |
| 97 | 4.6 | 1 | 32.8 | 102.4 | 4 |
| 98 | 7.0 | 1 | 40.8 | 104.5 | 3 |
| 99 | 6.2 | 1 | 9.4 | 69.0 | 4 |
| 100 | 8.0 | 1 | 125.8 | 87.6 | 4 |
| 101 | 5.2 | 1 | 4.1 | 65.3 | 2 |
| 102 | 16.8 | 1 | 300.1 | 39.6 | 2 |
| 103 | 51.4 | 1 | 293.5 | 32.8 | 2 |
| 104 | 22.5 | 2 | 555.4 | 71.6 | 2 |
| 105 | 7.7 | 1 | 30.7 | 97.5 | 2 |
| 106 | 8.2 | 1 | 2.3 | 82.1 | 2 |
| 107 | 3.1 | 1 | 0.5 | 86.2 | 2 |
| 108 | 57.3 | 1 | 717.6 | 58.4 | 2 |
| 109 | 15.9 | 1 | 2.3 | 76.9 | 2 |
| 110 | 4.8 | 1 | 1.8 | 110.5 | 4 |
| 111 | 127.2 | 1 | 55.2 | 110.7 | 4 |
| 112 | 12.7 | 1 | 27.2 | 100.8 | 4 |
| 113 | 21.4 | 1 | 35.8 | 97.7 | 4 |
| 114 | 20.8 | 1 | 98.7 | 118.0 | 5 |
| 115 | 3.2 | 1 | 4.3 | 74.7 | 2 |
| 116 | 3.4 | 1 | 2.7 | 78.3 | 2 |
| 117 | 4.5 | 1 | 12.0 | 76.7 | 2 |
| 118 | 5.9 | 1 | 31.7 | 124.3 | 4 |
| 119 | 7.3 | 1 | 34.2 | 99.1 | 2 |
| 120 | 7.0 | 1 | 51.4 | 100.6 | 2 |
| 121 | 2.9 | 1 | 6.2 | 109.7 | 2 |
| 122 | 1.9 | 2 | 43.1 | 96.8 | 8 |
| 123 | 1.0 | 2 | 1.8 | 87.0 | 8 |
| 124 | 195.5 | 1 | 1106.1 | 49.9 | 2 |
| 125 | 55.1 | 1 | 68.5 | 75.8 | 6 |
| 126 | 19.0 | 1 | 31.3 | 87.0 | 4 |
| 127 | 10.4 | 1 | 21.0 | 72.2 | 3 |
| 128 | 43.0 | 1 | 235.9 | 72.5 | 3 |
| 129 | 196.3 | 1 | 73.6 | 65.5 | 7 |
| 130 | 13.6 | 1 | 5.0 | 85.6 | 2 |
| 131 | 118.2 | 1 | 65.2 | 91.3 | 2 |
| 132 | 7.4 | 1 | 5.4 | 83.9 | 2 |
| 133 | 4.6 | 1 | 7.5 | 66.4 | 5 |
| 134 | 380.4 | 1 | 364.5 | 37.6 | 2 |
| 135 | 20.4 | 1 | 62.3 | 66.0 | 2 |
| 136 | 13.8 | 1 | 0.7 | 90.4 | 2 |
| 137 | 16.2 | 1 | 17.5 | 79.4 | 4 |
| 138 | 47.3 | 1 | 31.1 | 86.8 | 6 |
| 139 | 34.9 | 1 | 19.4 | 96.9 | 4 |
| 140 | 29.0 | 1 | 44.0 | 74.6 | 2 |
| 141 | 10.0 | 1 | 41.0 | 101.9 | 2 |
| 142 | 31.8 | 1 | 23.7 | 61.8 | 4 |
| 143 | 361.7 | 1 | 351.0 | 80.3 | 2 |
| 144 | 737.1 | 1 | 274.6 | 41.4 | 2 |
| 145 | 1395.6 | 1 | 2051.9 | 46.6 | 2 |
| 146 | 12.7 | 1 | 15.5 | 86.8 | 2 |
| 147 | 29.2 | 1 | 79.7 | 101.6 | 2 |
| 148 | 7.3 | 1 | 23.8 | 86.7 | 6 |
| 149 | 18.0 | 1 | 17.6 | 91.4 | 4 |
| 150 | 19.6 | 1 | 98.8 | 91.3 | 2 |
| 151 | 12.4 | 1 | 30.4 | 85.6 | 2 |
| 152 | 208.3 | 1 | 409.2 | 61.1 | 2 |
| 153 | 7.8 | 1 | 19.3 | 93.3 | 4 |
| 154 | 2.2 | 1 | 4.4 | 118.8 | 3 |
| 155 | 13.5 | 1 | 101.9 | 54.8 | 3 |
| 156 | 10.8 | 1 | 30.5 | 79.4 | 5 |
| 157 | 5.2 | 1 | 3.0 | 72.3 | 2 |
| 158 | 3.1 | 1 | 4.5 | 124.2 | 2 |
| 159 | 34.4 | 1 | 35.8 | 80.9 | 2 |
| 160 | 19.8 | 1 | 6.3 | 89.5 | 2 |
| 161 | 6.8 | 1 | 3.1 | 95.7 | 2 |
| 162 | 8.6 | 1 | 9.2 | 81.7 | 2 |
| 163 | 12.7 | 1 | 37.3 | 75.2 | 2 |
| 164 | 42.3 | 1 | 1234.1 | 41.8 | 2 |
| 165 | 14.2 | 1 | 15.3 | 74.6 | 2 |
| 166 | 5.3 | 2 | 6.2 | 81.1 | 4 |
| 167 | 7.8 | 1 | 13.7 | 82.4 | 2 |
| 168 | 37.0 | 1 | 279.8 | 56.7 | 2 |
| 169 | 8.3 | 1 | 6.5 | 76.8 | 2 |
| 170 | 5.9 | 1 | 22.4 | 67.2 | 2 |
| 171 | 8.2 | 1 | 410.7 | 63.5 | 2 |
| 172 | 29.7 | 1 | nd | 13.8 | 2 |
| 173 | 9.3 | 1 | 112.0 | 72.3 | 2 |
| 174 | 7.1 | 1 | 88.0 | 65.2 | 2 |
| 175 | 3.2 | 1 | 11.2 | 80.2 | 2 |
| 176 | 7.8 | 1 | 46.0 | 61.5 | 2 |
| 177 | 3.8 | 1 | 102.3 | 75.2 | 2 |
| 178 | 5.9 | 1 | 11.5 | 81.8 | 3 |
| 179 | 14.6 | 1 | 24.1 | 113.8 | 2 |
| 180 | 4.6 | 1 | 2.2 | 97.0 | 4 |
| 181 | 34.6 | 1 | 87.8 | 93.5 | 6 |
| 182 | 28.4 | 1 | 150.5 | 88.7 | 6 |
| 183 | 4.3 | 2 | 0.7 | 95.3 | 4 |
| 184 | 2.8 | 1 | 27.3 | 78.9 | 6 |
| 185 | 23.3 | 1 | 76.0 | 77.5 | 4 |
| 186 | 7.1 | 2 | 17.4 | 102.9 | 6 |
| 187 | 2.3 | 1 | 2.4 | 77.8 | 2 |
| 188 | 952.1 | 2 | 793.8 | 82.4 | 8 |
| 189 | 8.3 | 1 | 1.2 | 52.9 | 2 |
| 190 | 6.7 | 1 | 2.2 | 86.0 | 2 |
| 191 | 3.3 | 1 | 1.2 | 91.2 | 2 |
| 192 | 2.6 | 1 | 7.7 | 66.5 | 2 |
| 193 | 4.3 | 1 | 7.9 | 92.7 | 6 |
| 194 | 1.3 | 1 | 2.0 | 95.5 | 4 |
| 195 | 4.3 | 1 | 2.7 | 96.5 | 2 |
| 196 | 16.1 | 1 | 15.3 | 95.2 | 4 |
| 197 | 4.2 | 1 | 26.8 | 146.9 | 2 |
| 198 | 3.2 | 1 | 11.0 | 102.1 | 4 |
| 199 | 6.6 | 1 | 1.8 | 83.6 | 4 |
| 200 | 2.8 | 1 | 8.1 | 112.2 | 4 |
| 201 | 2.9 | 1 | 5.0 | 79.9 | 4 |
| 202 | 4.7 | 1 | 1.5 | 90.5 | 6 |
| 203 | 12.3 | 1 | 20.2 | 73.1 | 2 |
| 204 | 6.8 | 1 | 2.7 | 90.8 | 2 |
| 205 | 3.0 | 2 | 0.5 | 88.4 | 6 |
| 206 | 99.2 | 2 | 206.4 | 96.1 | 4 |
| 207 | 41.6 | 2 | 11.6 | 93.3 | 4 |
| 208 | 21.1 | 1 | 3.8 | 96.3 | 4 |
| 209 | 7.8 | 1 | 1.1 | 95.7 | 4 |
| 210 | 15.5 | 1 | 17.6 | 71.2 | 2 |
| 211 | 43.7 | 1 | 86.7 | 88.4 | 4 |
| 212 | 16.7 | 1 | 7.8 | 90.4 | 2 |
| 213 | 3.2 | 2 | 40.2 | 95.4 | 7 |

"Ex" = Example Number

"nd" = not determined

"n" = number of trials used to calculate average values

*AR EC50 n = 1

In vivo data of select examples:

TABLE II

| Example | Dose (mg/Kg/d), route | % Efficacy versus control (ANOVA, $p < 0.05$) |
|---|---|---|
| 126 | 3, po | 241% |
| 133 | 3, po | 306% |
| 150 | 3, po | 106% |
| 151 | 3, po | 165% |
| 154 | 30, po | 180% |
| 156 | 3 | 211% |
| 161 | 10, po | 53% |
|  | 10, sc | 160% |
| 183 | 10, po | 170% |
|  | 10, sc | 246% |
| 184 | 10, po | 67% |
|  | 10, sc | 47% |
| 186 | 3, po | 74% |
|  | 10, sc | 140% |
| 194 | 3, po | 98% |
| 201 | 3, po | 58% |
| 205 | 3, po | 97% |
| 209 | 10, sc | 34% |
| 212 | 10, po | 95% |

Seminal vesicle and/or prostate showed no statistical significant weight change compared to castrated vehicle-only control group for the Examples listed in Table II.

We claim:

1. A compound of the formula:

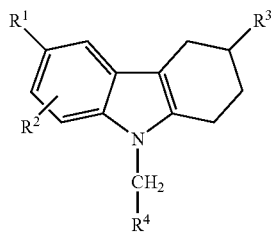

Formula I wherein, $R^1$ represents cyano, fluoro, chloro, bromo, methyl, $CF_3$, $CHF_2$, $OCF_3$, $OCHF_2$, $CH=NOCH_3$, $CH=NOCH_2CH_3$, $C(NOCH_3)CH_3$, $C(NOCH_2CH_3)CH_3$, $COR^{1a}$ wherein $R^{1a}$ represents hydrogen, hydroxyl, amino, methyl, methoxy, ethoxy, or $CF_3$, $OR^{1b}$ wherein $R^{1b}$ represents methyl, ethyl, propyl, isopropyl, cyclopropyl, or cyclopropylmethyl; $SO_2R^{1c}$ wherein $R^{1c}$ represents methyl; or $NHCOR^{1d}$ wherein $R^{1d}$ represents methoxy or ethoxy;

---

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Synthetic Construct

<400> SEQUENCE: 1
ggttcttgga gtact                                             15

<210> SEQ ID NO 2
<211> LENGTH: 15
<212> TYPE: DNA
<213> ORGANISM: Artificial
<220> FEATURE:
<223> OTHER INFORMATION: Synthetic Construct

<400> SEQUENCE: 2
tgtacaggat gttct                                             15

<210> SEQ ID NO 3
<211> LENGTH: 15
<212> TYPE: DNA
<213> ORGANISM: Artificial
<220> FEATURE:
<223> OTHER INFORMATION: Synthetic Construct

<400> SEQUENCE: 3
tgtacaggat gttct                                             15
```

R² represents hydrogen bromo, chloro, fluoro, methyl, or methoxy, or R¹ and R² together represent a group of the formula

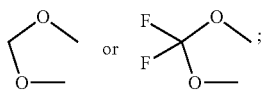

R³ represents NHCOR³ᵃ wherein R³ᵃ represents independently at each occurrence methyl, ethyl, isopropyl, CH(C₂H₅)₂, CH(CH₃)CH₂CH₃, CF₃, methoxy, ethoxy, cyclopropyl, cyclobutyl, NH(CH₃), or N(CH₃)₂; or R³ represents NHSO₂R³ᵇ, wherein R³ᵇ represents independently at each occurrence cyclopropyl, NH(CH₃), N(CH₃)₂, or N(CH₃)OCH₃; and R⁴ represents a phenyl group optionally substituted with a first subsitutent selected from the group consisting of amino, hydroxy, cyano, bromo, chloro, fluoro, nitro, methyl, methoxy, CF₃, CHF₂, OCF₃, OCHF₂, NH(C₂H₅), N(CH₃)₂, NHSO₂CH₃, and COOCH₃ and a second substituent selected from the group consisting of bromo, chloro, fluoro, and methyl, or a pharmaceutically acceptable salt thereof.

2. The compound or salt according to claim 1 wherein R¹ represents cyano, fluoro, chloro, bromo, CH=NOCH₃, CH=NOCH₂CH₃, C(NOCH₃)CH₃, C(NOCH₂CH₃)CH₃, or OR¹ᵇ wherein R¹ᵇ represents methyl, ethyl, propyl, isopropyl, cyclopropyl, or cyclopropylmethyl.

3. The compound or salt according to claim 1 wherein R¹ represents cyano.

4. The compound or salt according to claim 1 wherein R¹ represents fluoro, bromo, or chloro.

5. The compound or salt according to claim 1 wherein R¹ represents CH=NOCH₃, CH=NOCH₂CH₃, C(NOCH₃)CH₃, or C(NOCH₂CH₃)CH₃.

6. The compound or salt according to claim 1 wherein R¹ represents OR¹ᵇ wherein R¹ᵇ represents methyl, ethyl, propyl, isopropyl, cyclopropyl, or cyclopropylmethyl.

7. The compound or salt according to claim 1 wherein R² represents hydrogen, bromo, chloro, or fluoro.

8. The compound or salt according to claim 1 wherein R² represents hydrogen, methyl, or methoxy.

9. The compound or salt according to claim 1 wherein R² represents hydrogen, or R¹ and R² together represent a group of the formula

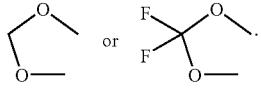

10. The compound or salt according to claim 1 wherein R³ represents NHCOR³ᵃ wherein R³ᵃ represents methyl, ethyl, isopropyl, cyclopropyl, or cyclobutyl.

11. The compound or salt according to claim 1 wherein R³ represents NHCOR³ᵃ wherein R³ᵃ represents isopropyl.

12. The compound or salt according to claim 1 wherein R⁴ represents a phenyl group optionally substituted with a first subsitutent selected from the group consisting of cyano, bromo, chloro, fluoro, methyl, and methoxy, and a second subsitutent that is fluoro.

13. The compound or salt according to claim 1 wherein R⁴ represents a phenyl group optionally substituted with a subsitutent selected from the group consisting of cyano, bromo, chloro, fluoro, methyl, and methoxy.

14. The compound according to claim 1 of the formula

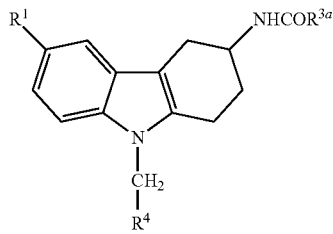

wherein,

R¹ represents a 5 to 6 membered heteroaryl selected from the group consisting of thiazolyl, thiadiazolyl, isoxazolyl, pyridinyl, pyradazinyl, and pyrimidinyl, each optionally substituted with a first substituent selected from the group consisting of amino, methyl, and fluoro, and a second subsitutent that is methyl;

R³ᵃ represents methyl, ethyl, propyl, isopropyl, cyclopropyl, or cyclobutyl; and R⁴ represents a phenyl group optionally substituted with 1 or 2 substituents independently selected from the group consisting of amino, hydroxy, cyano, halo, nitro, (C₁-C₄)alkyl, (C₁-C₄)alkoxy, halo(C₁-C₄)alkyl, halo(C₁-C₄)alkoxy, NH—(C₁-C₄)alkylamine, N,N—(C₁-C₆)dialkylamine, NHSO₂CH₃, and COOCH₃, or a pharmaceutically acceptable salt thereof.

15. The compound or salt according to claim 14 wherein R⁴ represents a phenyl group optionally substituted with 1 or 2 substituents independently selected from the group consisting of cyano, halo, (C₁-C₄)alkyl, and (C₁-C₄)alkoxy.

16. The compound or salt according to claim 14 wherein R⁴ represents a phenyl group optionally substituted with 1 or 2 substituents independently selected from the group consisting of cyano, fluoro, methyl, and methoxy.

17. The compound according to claim 1 that is (S)-N-(6-Cyano-9-(3-fluorobenzyl)-2,3,4,9-tetrahydro-1H-carbazol-3-yl)isobutyramide.

18. A pharmaceutical composition comprising as an active ingredient a compound or salt according to claim 1 in combination with a pharmaceutically acceptable carrier, diluent, or excipient.

19. The composition according to claim 18 comprising as an active ingredient the compound that is (S)-N-(6-Cyano-9-(3-fluorobenzyl)-2,3,4,9-tetrahydro-1H-carbazol-3-yl)isobutyramide, or a pharmaceutically acceptable salt thereof.

* * * * *